US010420813B2

(12) United States Patent
Newell-Rogers et al.

(10) Patent No.: US 10,420,813 B2
(45) Date of Patent: *Sep. 24, 2019

(54) COMPETITIVE INHIBITORS OF INVARIANT CHAIN EXPRESSION AND/OR ECTOPIC CLIP BINDING

(71) Applicant: Regents of the University of Colorado, a body corporate, Denver, CO (US)

(72) Inventors: Martha Karen Newell-Rogers, Holland, TX (US); Evan Newell, Singapore (SG)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/232,856

(22) Filed: Aug. 10, 2016

(65) Prior Publication Data

US 2017/0348377 A1 Dec. 7, 2017

Related U.S. Application Data

(60) Continuation of application No. 14/609,127, filed on Jan. 29, 2015, now abandoned, which is a division of application No. 12/739,459, filed as application No. PCT/US2008/012078 on Oct. 23, 2008, now Pat. No. 8,957,031.

(60) Provisional application No. 61/137,150, filed on Jul. 25, 2008, provisional application No. 61/135,964, filed on Jul. 25, 2008, provisional application No. 61/000,152, filed on Oct. 23, 2007.

(51) Int. Cl.

| | |
|---|---|
| ***A61K 38/00*** | (2006.01) |
| ***C07K 7/06*** | (2006.01) |
| ***A61K 38/08*** | (2019.01) |
| ***A61K 38/10*** | (2006.01) |
| ***C07K 7/08*** | (2006.01) |
| ***G16B 15/00*** | (2019.01) |
| ***G16B 20/00*** | (2019.01) |
| ***G16B 35/00*** | (2019.01) |
| ***G16C 20/60*** | (2019.01) |
| ***A61K 39/00*** | (2006.01) |

(52) U.S. Cl.

CPC .......... *A61K 38/08* (2013.01); *A61K 39/0011* (2013.01); *C07K 7/06* (2013.01); *G16B 15/00* (2019.02); *G16B 20/00* (2019.02); *G16B 35/00* (2019.02); *G16C 20/60* (2019.02); *A61K 38/00* (2013.01); *Y02A 50/401* (2018.01); *Y02A 50/409* (2018.01); *Y02A 50/411* (2018.01)

(58) Field of Classification Search

CPC ...... A61K 38/08; A61K 39/0011; C07K 7/06; C40B 30/02; G06F 19/16

See application file for complete search history.

(56) References Cited

U.S. PATENT DOCUMENTS

| | | | | |
|---|---|---|---|---|
| 4,415,553 | A | 11/1983 | Zhabilov et al. | |
| 4,818,763 | A | 4/1989 | Rusch et al. | |
| 5,616,554 | A | 4/1997 | Beardsley | |
| 5,723,323 | A | 3/1998 | Kauffman et al. | |
| 5,756,666 | A | 5/1998 | Takiguchi et al. | |
| 6,165,493 | A | 12/2000 | Neurath et al. | |
| 6,245,904 | B1 | 6/2001 | Melms et al. | |
| 6,326,465 | B1 | 12/2001 | Hess | |
| 6,734,192 | B1 | 5/2004 | Keller | |
| 6,998,125 | B2 | 2/2006 | Hanna et al. | |
| 7,252,829 | B1 | 8/2007 | Sette et al. | |
| 7,312,318 | B2 | 12/2007 | Hansen et al. | |
| 8,557,764 | B2 * | 10/2013 | Newell | A61K 31/03 514/3.8 |
| 8,906,846 | B2 | 12/2014 | Newell et al. | |
| 8,957,031 | B2 * | 2/2015 | Newell | C07K 7/06 514/21.6 |
| 9,073,985 | B2 | 7/2015 | Newell et al. | |
| 9,359,404 | B2 * | 6/2016 | Newell-Rogers | A61K 38/08 |

(Continued)

FOREIGN PATENT DOCUMENTS

| | | | |
|---|---|---|---|
| CN | 1 458 165 | A | 11/2003 |
| WO | WO 96/34886 | A1 | 11/1996 |

(Continued)

OTHER PUBLICATIONS

Badger et al. Comparative Genomic Evidence for a Close Relationship between the Dimorphic Prosthecate Bacteria *Hyphomonas neptunium* and *Caulobacter crescentus*. J Bacteriol, Oct. 2006, vol. 188, No. 19, pp. 6841-6850.*

(Continued)

*Primary Examiner* — Marcela M Cordero Garcia

(74) *Attorney, Agent, or Firm* — Wolf, Greenfield & Sacks, P.C.

(57) ABSTRACT

The invention relates to methods for modulating the immune function through targeting of CLIP molecules. The result is wide range of new therapeutic regimens for treating, inhibiting the development of, or otherwise dealing with, a multitude of illnesses and conditions, including autoimmune disease, cancer, Alzheimer's disease, allergic disease, transplant and cell graft rejection, HIV infection and other viral, bacterial, and parasitic infection, and AIDS. Methods are also provided for preparing a peptide having the property of being able to displace CLIP by feeding one or more peptide sequences into software that predicts MHC Class II binding regions in an antigen sequence and related products.

12 Claims, 23 Drawing Sheets

Specification includes a Sequence Listing.

(56) References Cited

U.S. PATENT DOCUMENTS

2002/0164685 A1 11/2002 Rosen et al.
2002/0182222 A1 12/2002 Groot
2003/0113798 A1* 6/2003 Burmer ................ C07K 14/705 435/7.1
2003/0157135 A1 8/2003 Tsuji et al.
2004/0018639 A1 1/2004 Zhabilov
2005/0032834 A1 2/2005 Kastan et al.
2005/0048071 A1 3/2005 Bae
2005/0196385 A1 9/2005 Romagne et al.
2005/0271676 A1 12/2005 Sette et al.
2006/0008448 A1 1/2006 Xu et al.
2008/0095798 A1 4/2008 Humphreys et al.
2009/0175838 A1 7/2009 Newell et al.
2009/0258027 A1 10/2009 Newell et al.
2010/0034839 A1 2/2010 Newell et al.
2010/0166782 A1 7/2010 Newell et al.
2010/0166789 A1 7/2010 Keledjian et al.
2011/0118175 A1 5/2011 Newell et al.
2013/0259829 A1 10/2013 Newell et al.
2013/0295047 A1 11/2013 Newell et al.
2014/0220000 A1 8/2014 Newell et al.
2014/0315818 A1 10/2014 Newell et al.
2015/0231195 A1 8/2015 Newell-Rogers et al.

FOREIGN PATENT DOCUMENTS

WO WO 97/025344 A1 7/1997
WO WO 98/18491 A1 5/1998
WO WO 2004/043361 A2 5/2004
WO WO 2004/047719 A2 6/2004
WO WO 2004/108753 A1 12/2004
WO WO2004110349 * 12/2004
WO WO 2005/079523 A2 9/2005
WO WO2006114799 * 11/2006 ............... C07K 7/08
WO WO 07/091240 A2 8/2007
WO WO 08/054635 A2 5/2008
WO WO 2008/094510 A2 8/2008
WO WO 2009/055005 A2 4/2009

OTHER PUBLICATIONS

Kon et al. Antibodies to Different Peptides in Osteopontin Reveal Complexities in the Various Secreted Forms. Journal of Cellular Biochemistry, 2000. vol. 77, pp. 487-498. (Year: 2000).*

Lametschwandtner et al. The Difference in Recognition of Terminal Tripeptides as Peroxisomal Targeting Signal 1 between Yeast and Human is Due to [. . . ] Signal and to Residues Adjacent to it. The Journal of Biological Chemistry, vol. 273, No. 50, pp. 33635-33643. (Year: 1998).*

Badger et al. Comparative Genomic Evidence for a Close Relationship between the Dimorphic Prosthecate Bacteria *Hyphomonas neptunium* and *Caulobacter crescentus*. Journal of Bacteriology, vol. 188, No. 19, pp. 6841-6850 (Year: 2006).*

Adams et al., Biological activity and therapeutic potential of homologs of an Ii peptide which regulates antigenic peptide binding to cell surface MHC class II molecules. Arzneimittelforschung. Sep. 1997;47(9):1069-77.

Alter et al., NK cell function in HIV-1 infection. Curr Mol Med. Sep. 2006;6(6):621-9.

Ayala-Gaytan et al., Diminution of plasma viral load and cultured HIV-infected peripheral blood mononuclear cells in non-responding patients treated with two calf thymus nuclear proteins and conventional antiretrovirals. HIV AIDS Rev. 2004;3(3):8-13.

Badger et al., Comparative genomic evidence for a close relationship between the dimorphic prosthecate bacteria *Hyphomonas neptunium* and *Caulobacter crescentus*. J Bacteriol. Oct. 2006;188(19):6841-50.

Badger et al., Protein Accession No. Q0BZX0. Nov. 28, 2006. 1 page.

Barrera et al., The role of the invariant chain in mucosal immunity. Int Arch Allergy Immunol. Oct. 1998;117(2):85-93.

Belmares et al., Structural factors contributing to DM susceptibility of MHC class II/peptide complexes. J Immunol. Nov. 1, 2002;169(9):5109-17.

Castellino et al., Antigen presentation by MHC class II molecules: invariant chain function, protein trafficking, and the molecular basis of diverse determinant capture. Hum Immunol. May 1997;54(2):159-69. Review.

Chaturvedi et al., The functional role of class II-associated invariant chain peptide (CLIP) in its ability to variably modulate immune responses. Int Immunol. Jun. 2000;12(6):757-65.

Cheng, A novel immunotherapeutic for cancer and autoimmune diseases. Drug Disc Devel. Feb. 22, 2012. Last accessed online via http://www.dddmag.com/articles/2012/02/novel-immunotherapeutic-cancer-and-autoimm . . . on Nov. 19, 2012. 5 pages.

Christie et al., Alzheimer's disease:correlation of the suppression of beta-amyloid peptide secretion from cultured cells with inhibition of the chymotrypsin-like activity of the proteasome. J Neurochem. Jul. 1999;73(1):195-204.

Derdakova et al., Association of genetic variability within the Borrelia burgdorferi sensu lato with the ecology, epidemiology of Lyme borreliosis in Europe. Ann Agric Environ Med. 2005;12(2):165-72.

Dorrell et al., Cytotoxic T lymphocytes recognize structurally diverse, clade-specific and cross-reactive peptides in human immunodeficiency virus type-1 gag through HLA-B53. Eur J Immunol. Jun. 2001;31(6):1747-56.

Frölich et al., The anti-CD74 humanized monoclonal antibody, milatuzumab, which targets the invariant chain of MHC II complexes, alters B-cell proliferation, migration, and adhesion molecule expression. Arthritis Res Ther. Mar. 9, 2012;14(2):R54. doi: 10.1186/ar3767.

Goldsby et al., Chapter 8: Antigen Processing and Presentation. In Immunology, Fifth Edition, Eds. Goldsby et al. W. H. Freeman and Company. 2002; 171-77, 193-6.

Gunther et al., Bidirectional binding of invariant chain peptides to an MHC class II molecule. Proc Natl Acad Sci U S A. Dec. 21, 2010;107(51):22219-24. Epub Nov. 29, 2010.

Hand et al., Calf thymus fractions: enhancement and suppression of immunocompetent cells. Experientia. Jun. 15, 1970;26(6):653-5.

Hand et al., Isolation of a thymus hormone, LSH. Biochem Biophys Res Commun. Jan. 10, 1967;26(1):18-23.

Hillman et al., Generating MHC Class II+/Ii− phenotype after adenoviral delivery of both an expressible gene for MHC Class II inducer and an antisense Ii-RNA construct in tumor cells. Gene Ther. Aug. 2003;10(17):1512-8.

Hitzel et al., The invariant chain derived fragment CLIP is an efficient in vitro inhibitor of peptide binding to MHC class II molecules. Mol Immunol. Jan. 1996;33(1):25-31.

Janeway et al., Chapter 5: Antigen Presentation to T Lymphocytes. In Immunbiology, Fifth Edition, Eds. Janeway et al. Garland Publishing; 2001; p. 175-6.

Kang et al., Low-dose peptide tolerance therapy of lupusgenerates plasmacytoid dendritic cells that cause expansion ofautoantigen-specific regulatory T cells and contraction of inflammatory Th17cells. J Immunol. Jun. 15, 2007;178(12):7849-58.

Kasai et al., CLIP-derived selfpeptides bound to MHC class II molecules of medullary thymic epithelial cells differ from those of cortical thymic epithelial cells in their diversity, length, and C-terminal processing. Eur J Immunol. Dec. 2000;30(12):3542-51.

Lederman et al., Cyclosporin A provides no sustained immunologic benefit to persons with chronic HIV-1 infection starting suppressive antiretroviral therapy: results of a randomized, controlled trial of the AIDS Clinical Trials Group A5138. J Infect Dis. Dec. 15, 2006;194(12):1677-85. Epub Nov. 2, 2006.

Lu et al., Suppression of major histocompatibility complex class II-associated invariant chain enhances the potency of an HIV gp120 DNA vaccine. Immunology. Feb. 2007;120(2):207-16. Epub Nov. 20, 2006.

Lund et al., Web-based tools for vaccine design. Dec. 2002. Last accessed Online Sep. 7, 2012 at www.hiv.lanl.gov/content/immunology/pdf/2002/1/Lund2002.pdf.

Maggio, A renaissance in peptide therapeutics is underway. Drug Delivery Report. Spring/Summer 2006:23-6.

(56) References Cited

OTHER PUBLICATIONS

Mamikonyan et al., Detection of the active components of calf thymus nuclear proteins (TNP), histones that are binding with high affinity to HIV-1 envelope proteins and CD4 molecules. Curr HIV Res. Jun. 2008;6(4):318-26.
Matza et al., Invariant chain, a chain of command. Trends Immunol. May 2003;24(5):264-8.
Montoya et al., Increased IFN-gamma production by NK and CD3+/CD56+ cells in sexually HIV-1-exposed but uninfected individuals. Clin Immunol. Aug. 2006;120(2):138-46. Epub Apr. 19, 2006.
Mozes et al., A novel synthetic peptide for the specific treatment of lupus: clinical effects and mechanism of action. Isr Med Assoc J. Jan. 2008;10(1):40-2.
Nakano et al., Histone H1 vaccine therapy for overcoming acute rejection in experimental organ transplantation. Transplant Proc. Dec. 2006;38(10):3247-8.
Nanno et al.,gammadelta T cells: firefighters or fire boosters in the front lines of inflammatory responses. Immunol Rev. Feb. 2007;215:103-13.
Newell et al., Biochemical characterization of proteins that co-purify with class II antigens of the murine MHC. J Immunol. Mar. 15, 1988;140(6):1930-8.
Newell et al., TLR-mediated B cell activation results in ectopic CLIP expression that promotes B cell-dependent inflammation. J Leukoc Biol. Oct. 2010;88(4):779-789. Epub Jul. 14, 2010.
Noveljic et al., Virological responses of treatment-naïve stage CDC-2 HIV-1 positive subjects receiving VGV-1 injections in a blinded, placebo-controlled, multi-centre clinical trial. Retrovirology. 2006; 3(Suppl 1): p. 73.
Nowell et al., Chloroquine affects biosynthesis of Ia molecules by inhibiting dissociation of invariant (gamma) chains from alpha-beta dimers in B cells. J Exp Med. Oct. 1, 1985;162(4):1371-6.
O'Brien et al., gammadelta T-cell receptors: functional correlations. Immunol Rev. Feb. 2007;215:77-88.
Paulsen et al., Antimicrobial peptides are expressed and produced in healthy and inflamed human synovial membranes. J Pathol. Nov. 2002;198(3):369-77.
Powis, CLIP-region mediated interaction of Invariant chain with MHC class I molecules. FEBS Lett. May 29, 2006;580(13):3112-6. Epub Apr. 27, 2006.
Röhn et al., Upregulation of the CLIP self peptide on mature dendritic cells antagonizes T helper type 1 polarization. Nat Immunol. Sep. 2004;5(9):909-18.
Savarino et al., The anti-HIV-1 activity of chloroquine. J Clin Virol. Feb. 2001;20(3):131-5.
Schindler et al., Nef alleles from children with non-progressive HIV-1 infection modulate MHC-II expression more efficiently than those from rapid progressors. AIDS. May 31, 2007;21(9):1103-7.
Schönbach et al., FIMM, a database of functional molecular immunology. Nucleic Acids Res. Jan. 1, 2000;28(1):222-4.
Singh et al., ProPred: prediction of HLA-DR binding sites. Bioinformatics. Dec. 2001;17(12):1236-7.
Snell et al, "The Nobel Lectures in Immunology. Lecture for the Nobel Prize for Physiology or Medicine," Studies in histocompatibility, Scand J Immunol. Oct.; 36(4):513-26 (1992).
Stein et al., CD74: a new candidate target for the immunotherapy of B-cell neoplasms. Clin Cancer Res. Sep. 15, 2007;13(18 Pt 2):5556s-5563s.
Stumptner et al., Interaction of MHC class II molecules with the invariant chain: role of the invariant chain (81-90) region. EMBO J. Oct. 1, 1997;16(19):5807-18.
Stumptner-Cuvelette et al., HIV-1 Nef impairs MHC class II antigen presentation and surface expression. Proc Natl Acad Sci U S A. Oct. 9, 2001;98(21):12144-9. Epub Oct. 2, 2001.
Van Ham et al., Human histocompatibility leukocyte antigen (HLA)-DM edits peptides presented by HLA-DR according to their ligand binding motifs. J Exp Med. Nov. 1, 1996;184(5):2019-24.
Weber et al., Enhanced dissociation of HLA-DR-bound peptides in the presence of HLA-DM. Science. Oct. 25, 1996;274(5287):618-20.
Wu et al., The MHC class II-associated invariant chain-derived peptide clip binds to the peptide-binding groove of class II molecules. Mol Immunol. Mar.-Apr. 1996;33(4-5):371-7.
Xu et al., Immunotherapy of cancer by antisense inhibition of Ii protein, an immunoregulator of antigen selection by MHC class II molecules. Curr Opin Mol Ther. Apr. 2004;6(2):160-5.
Yamamoto et al., Cloning of the cDNA encoding a novel subtype of histone H1. Gene. Sep. 16, 1996;173(2):281-5.
Zhao et al., Acute and relapsing experimental autoimmuneencephalomyelitis in IL-4- and alpha/beta T cell-deficient C57BL/6 mice. J Neuroimmunol. Jul. 1, 1998;87(1-2):171-8.

* cited by examiner

5uM MKN.6

5uM MKN.8

5uM MKN.10

DMSO CONTROL

T-reg Staining
LIVE CELLS

DAY 6 WITH NO TX

T-reg Staining
LIVE CELLS

DAY 6 WITH MKN.6 TX

T-reg Staining
LIVE CELLS

DAY 6 WITH TNP TX

B Cell Death

Subject Characteristics

| PID | HIV SEROSTATUS | AGE | SEX | RACE | VIRAL LOAD COP/ML | CD4 COUNT #/μl |
|---|---|---|---|---|---|---|
| MD | NEG | 29 | F | ASIAN | | |
| MH | NEG | 34 | F | CAUC | | |
| RS | NEG | 48 | M | CAUC | | |
| M14 | POS | 39 | M | CAUC | 750,000 | 352 |
| M15 | POS | 37 | F | AA | 67,800 | 416 |
| M16 | POS | 47 | M | CAUC | 444,000 | 395 |
| SUB 121 | POS | 36 | M | AA | pending | pending |

FIG. 17C
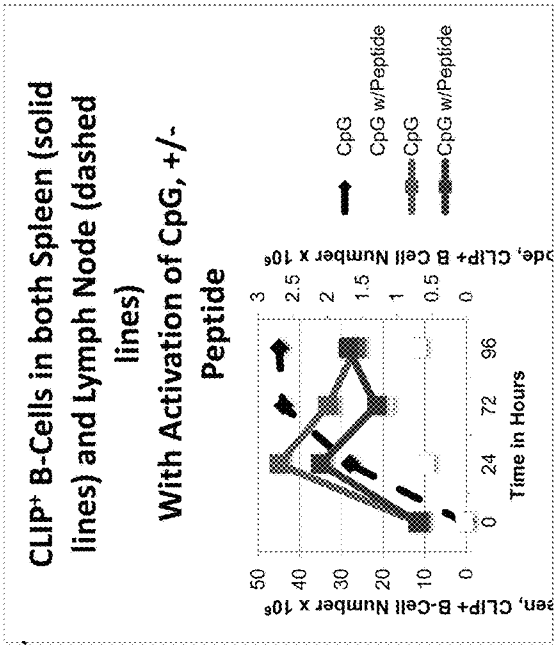
FIG. 17A
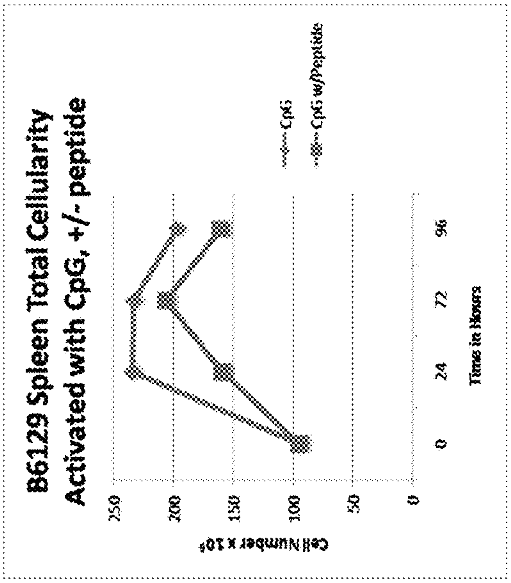
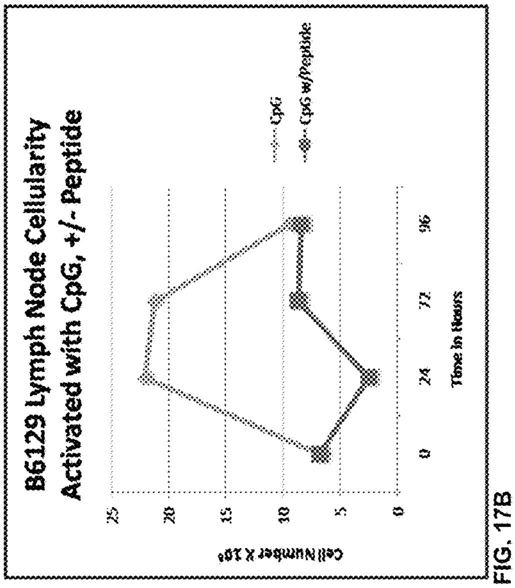
FIG. 17B

COMPETITIVE INHIBITORS OF INVARIANT CHAIN EXPRESSION AND/OR ECTOPIC CLIP BINDING

RELATED APPLICATIONS

This application is a continuation application which claims benefit under 35 U.S.C. § 120 of U.S. application Ser. No. 14/609,127, filed on Jan. 29, 2015, which is a divisional application which claims the benefit under 35 U.S.C. § 120 of U.S. application Ser. No. 12/739,459, filed on Jan. 10, 2011, now U.S. Pat. No. 8,957,031 issued Feb. 17, 2015, entitled "COMPETITIVE INHIBITORS OF INVARIANT CHAIN EXPRESSION AND/OR ECTOPIC CLIP BINDING", which is a National Stage application of PCT/US2008/012078, filed Oct. 23, 2008, which claims the benefit of priority under 35 U.S.C. § 119(e) to U.S. Provisional Application Ser. No. 61/000,152, filed on Oct. 23, 2007, and U.S. Provisional Application Ser. No. 61/135,964, filed on Jul. 25, 2008, both entitled "COMPETITIVE INHIBITORS OF INVARIANT CHAIN EXPRESSION AND/OR ECTOPIC CLIP BINDING," and U.S. Provisional Application Ser. No. 61/137,150, filed on Jul. 25, 2008 and entitled METHODS FOR TREATING VIRAL DISORDERS which are herein incorporated by reference in their entirety.

FIELD OF THE INVENTION

The invention involves computer implemented methods of analysis and methods for identifying binding peptides. The present invention also relates generally to the field of immunology. More particularly, it concerns the ability to modulate immune function using CLIP inhibitors, as well as related products and methods.

BACKGROUND OF INVENTION

The defining characteristic of HIV infection is the depletion of CD4+ T-cells. A number of mechanisms may contribute to killing, including direct killing of the infected CD4+ T-cells by the virus or "classical" killing of HIV-infected cells by cytotoxic CD8+ lymphocytes. The effectiveness of cytotoxic T cell killing is dramatically impaired by down-regulation of class I Major Histocompatiblity Complex (MHC) expression on the surface of the infected cell due to the action of the viral Tat and Nef proteins. However, the same reduction in MHC class I expression that impairs cytotoxic T-cell mediated killing, in conjunction with increased expression of death inducing receptors, could mark cells instead as targets for NK cell killing.

(MHC)-encoded molecules are key components of T cell immunity. The significance of these molecules as tissue compatibility molecules was first observed in the late 1930s. Peter Gorer and George Snell observed that when tumors were transplanted from a genetically non-identical member of the same species, the tumors were always rejected, but when tumors were transplanted between genetically identical members of the same species, the tumor would "take" and would grow in the syngeneic animal. The genetic complex responsible for the rejection was subsequently found to be a series of genes that encode protein products known as Major Histocompatibility molecules. These genes, also known as immune response or IR genes, and their protein products are responsible for all graft rejection. There are two types of MHC molecules: MHC class I and MHC class II. All nucleated cells express cell surface MHC class I. A subset of specialized cells express class II MHC. Included in the specialized, professional antigen-presenting cells (APCs) are B cells, macrophages, microglia, dendritic cells, and Langerhans cells among others.

As stated above, B cells express MHC class II. Once antigen has been bound by the antigen receptor on the B cell, the antigen and its receptor are engulfed into an endosomal compartment. This compartment fuses with another compartment known as the lysosome. The B cell is very efficient at breaking down antigens into smaller parts and loading the parts into MHC class II in the lysosome. The MHC is then trafficked to the cell surface where the B cell can effectively "show" the antigen to a CD4+ T cell. The activated CD4 cell is also called a helper cell and there are two major categories, Th1 and Th2.

The MHC molecules are tightly protected in the endosomal/lysosomal compartments to insure that only antigens for which we need a response get presented to T cells. MHC class II molecules, prior to antigen loading, are associated with a molecule called invariant chain, also known as CD74. The invariant chain is associated with MHC class II (and recently shown to be associated with certain MHC class I molecules) prior to antigen loading into the antigen binding grooves of the MHC molecules. As antigen is processed, the invariant chain gets cleaved by proteases within the compartment. First an end piece is removed, and then another known as CLIP (class II invariant chain associated peptide). CLIP fills the groove that will ultimately hold the antigen until the antigen is properly processed. For a detailed review of the invariant chain, including CLIP, see Matza et al., *Trends Immunol.,* 24(5): 264-268, 2003, incorporated herein in its entirety. Despite the fact that this "chaperone" role for invariant chain and CLIP has been identified, the full impact of these molecules on immune signaling and activation has not been appreciated by the prior art, nor has their been any sense from the prior art that anything useful would be served by inhibiting invariant chain expression or ectopic CLIP binding.

Major Histocompatiblity Complex (MHC)-encoded molecules are key components of T cell immunity. The significance of these molecules as tissue compatibility molecules was first observed in the late 1930s. Peter Gorer and George Snell observed that when tumors were transplanted from a genetically non-identical member of the same species, the tumors were always rejected, but when tumors were transplanted between genetically identical members of the same species, the tumor would "take" and would grow in the syngeneic animal. The genetic complex responsible for the rejection was subsequently found to be a series of genes that encode protein products known as Major Histocompatibility molecules. These genes, also known as immune response or IR genes, and their protein products are responsible for all graft rejection. There are two types of MHC molecules: MHC class I and MHC class II. All nucleated cells express cell surface MHC class I. A subset of specialized cells express class II MHC. Included in the specialized, professional antigen-presenting cells (APCs) are B cells, macrophages, microglia, dendritic cells, and Langerhans cells among others.

As stated above, B cells express MHC class II. Once antigen has been bound by the antigen receptor on the B cell, the antigen and its receptor are engulfed into an endosomal compartment. This compartment fuses with another compartment known as the lysosome. The B cell is very efficient at breaking down antigens into smaller parts and loading the parts into MHC class II in the lysosome. The MHC is then trafficked to the cell surface where the B cell can effectively "show" the antigen to a CD4+ T cell. The activated CD4 cell is also called a helper cell and there are two major categories, Th1 and Th2.

The MHC molecules are tightly protected in the endosomal/lysosomal compartments to insure that only antigens for which we need a response get presented to T cells. MHC class II molecules, prior to antigen loading, are associated with a molecule called invariant chain, also known as CD74. The invariant chain is associated with MHC class II (and recently shown to be associated with certain MHC class I molecules) prior to antigen loading into the antigen binding grooves of the MHC molecules. As antigen is processed, the invariant chain gets cleaved by proteases within the compartment. First an end piece is removed, and then another known as CLIP (class II invariant chain associated peptide). CLIP fills the groove that will ultimately hold the antigen until the antigen is properly processed. For a detailed review of the invariant chain, including CLIP, see Matza et al., *Trends Immunol.,* 24(5): 264-268, 2003, incorporated herein in its entirety. Despite the fact that this "chaperone" role for invariant chain and CLIP has been identified, the full impact of these molecules on immune signaling and activation has not been appreciated by the prior art, nor has their been any sense from the prior art that anything useful would be served by inhibiting invariant chain expression or ectopic CLIP binding

SUMMARY OF INVENTION

The invention involves, in some aspects, computational analysis comparing the binding affinity of peptides to a target protein in a family of proteins having structural similarities, such as multiple alleles. As an example a computational analysis was performed to identify peptides for their ability to displace CLIP from the binding groove of MHC alleles. Using the methods of the invention optimal sequences for peptides that can displace CLIP from the groove of any MHC molecule encoded by any MHC allele were identified.

In some aspects the invention is a computer implemented method for identifying a target protein binding peptide by preparing amino acid prediction matrices of data points for a binding site for at least two target proteins having similar binding sites, wherein the prediction matrices have a first axis representing amino acids and a second axis representing a binding site position number, wherein each data point represents a score for the amino acid at the binding site position number, preparing an average score for each data point in the amino acid prediction matrices for the at least two target proteins, and determining a binding peptide based on the average score for each data point by selecting an amino acid for each site of the binding peptide having a score of zero or greater.

In other aspects the invention is a computer implemented method for identifying a target protein binding peptide by computing an average score for each data point in a set of amino acid prediction matrices for at least two target proteins having similar binding sites, wherein the prediction matrices have a first axis representing amino acids and a second axis representing a binding site position number, wherein each data point represents a score for the amino acid at the binding site position number, and determining a binding peptide based on the average score for each data point by selecting an amino acid for each site of the binding peptide having a score of zero or greater.

The invention in some embodiments involves determining the binding peptide based on the highest average score.

In other embodiments amino acid prediction matrices are prepared for all target proteins having similar binding sites. In yet other embodiments the at least two target proteins correspond to alleles of a gene, for instance, MHC class II or MHC class I.

A predicted peptide binding score may also be generated for the binding peptide and the predicted peptide binding score may be compared with a predicted CLIP binding score, wherein if the predicted peptide binding score is higher than or equivalent to the predicted CLIP binding score then the peptide is a CLIP inhibitor.

In other embodiments the results of the average score for each data point are displayed; thereby outputting an amino acid sequence of at least one binding peptide.

A computer readable medium encoding instructions capable of being executed on one or more processors, the instructions, when executed, performing a method of automatically identifying a target protein binding peptide is provided according to other aspects of the invention. The method involves computing an average score for each data point in a set of amino acid prediction matrices for at least two target proteins having similar binding sites, wherein the prediction matrices have a first axis representing amino acids and a second axis representing a binding site position number, wherein each data point represents a score for the amino acid at the binding site position number, and determining a binding peptide based on the average score for each data point by selecting an amino acid for each site of the binding peptide having a score of zero or greater.

In other aspects the invention is a method for identifying a subject sensitive to treatment with a CLIP inhibitor by determining an MHC class II HLA-DR allele of the subject and determining whether a CLIP inhibitor is effective for displacing CLIP from the MHC class II HLA-DR allele, wherein if the MHC class II HLA-DR allele is associated with a CLIP inhibitor then the subject is sensitive to treatment with the CLIP inhibitor.

A method of treating a subject with a CLIP inhibitor by determining an MHC class II HLA-DR allele of a subject and administering to the subject a CLIP inhibitor in an effective amount to displace CLIP from a surface of a cell is provided according to other aspects of the invention.

A method for identifying a CLIP inhibitor is provided according to other aspects of the invention. The method involves analyzing an amino acid prediction matrix of an MHC class II HLA-DR allele for binding to a peptide to produce a predicted peptide binding score, comparing the predicted peptide binding score with a predicted CLIP binding score, wherein if the predicted peptide binding score is higher than or equivalent to the predicted CLIP binding score then the peptide is a CLIP inhibitor. In some embodiment the method is a method for identifying an MHC specific CLIP inhibitor and a single amino acid prediction matrix is used for a single MHC class II HLA-DR. In other embodiments the method is performed for a set of prediction matrices for multiple MHC class II HLA-DRs and an average predicted peptide score is generated.

According to another aspect a method for identifying a subject specific CLIP inhibitor by determining an MHC class II allele of a subject and determining a peptide that is a CLIP inhibitor based on the MHC class II allele in order to identify the subject specific CLIP inhibitor is provided. In one embodiment the peptide is determined based on a predetermined association of the peptide with the MHC class II allele. In another embodiment the peptide is determined by analyzing a prediction matrix of the MHC class II allele for binding to a peptide to produce a predicted peptide binding score, comparing the predicted peptide binding score with a predicted CLIP binding score, wherein if the predicted peptide binding score is higher than or equivalent to the predicted CLIP binding score then the peptide is identified as the subject specific CLIP inhibitor.

According to yet another aspect of the invention a method for identifying a disease specific CLIP inhibitor is provided. The method involves determining a predominant MHC class II HLA-DR allele for a disease and determining a peptide that is a CLIP inhibitor based on the MHC class II HLA-DR allele in order to identify the disease specific CLIP inhibitor.

In other aspects the invention is based, at least in part, on the discovery that CLIP inhibitors alter immune cell function by promoting activation of regulatory T cells such as Tregs, interfering with activation, expansion or function of effector T cells such as γδT cells and/or induce activity leading to killing of antigen non-specifically activated B cells. The CLIP inhibitors of the invention are useful in the treatment of disorders such as infection, including viral infection e.g. HIV, bacterial infection and parasitic infection, autoimmune disease, cancer, allergic disease, Alzheimer's disease and tissue graft rejection.

The present invention provides effective methods for targeting CLIP by treating a subject with a peptide that substitutes for CLIP in the MHC molecule. The invention provides novel peptides for that purpose but also provides a method for uncovering other peptides capable of displacing CLIP, as discussed above. These peptides can be quite short, allowing for easy synthesis.

In some aspects, the invention is an isolated peptide of $X_1RX_2X_3X_4X_5LX_6X_7$, (SEQ ID NO: 3) wherein each X is an amino acid, wherein R is Arginine, L is Leucine and wherein at least one of $X_2$ and $X_3$ is Methionine, wherein the peptide is not N-MRMATPLLM-C(SEQ ID NO: 4), and wherein the peptide is a CLIP displacer. In some embodiments $X_1$ is Phenylalanine, $X_2$ is Isoleucine, $X_3$ is Methionine, $X_4$ is Alanine, $X_5$ is Valine, $X_6$ is Alanine, and/or $X_7$ is Serine. In other embodiments the peptide further comprises 1-5 amino acids at the N and/or C terminus. For instance the peptide may have 1-5 amino acids at the C terminus of $X_1RX_2X_3X_4X_5LX_6X_7$ (SEQ ID NO: 3) and/or the peptide has 1-5 amino acid at the N terminus of $X_1RX_2X_3X_4X_5LX_6X_7$ (SEQ ID NO: 3). In some embodiments the peptide comprises FRIM $X_4VLX_6S$ (SEQ ID NO: 6), wherein $X_4$ and $X_6$ are any amino acid, wherein $X_4$ and $X_6$ are optionally Alanine. According to other embodiments the peptide comprises FRIMAVLAS (SEQ ID NO: 2) or N-FRIMAVLAS-C(SEQ ID NO: 7). In yet other embodiments the peptide consists essentially of FRIMAVLAS (SEQ ID NO: 2). In other embodiments the peptide consists of FRIMAVLAS (SEQ ID NO: 2). The peptide has a minimum length of 9 amino acids. In some embodiments it has a length of 9-20 amino acids. The peptide may be cyclic or non-cyclic. In some embodiments the peptide is PEGylated.

In other aspects the invention is an isolated peptide comprising FRIMAVLAS (SEQ ID NO: 2).

A composition of a peptide of the invention and a carrier is provided in other aspects. In some embodiments the carrier is a liposome, such as a stealth liposome. In other embodiments the carrier is a particle, for instance, a nanoparticle or a low density particle. In other embodiments the carrier is a transmucosal absorption enhancer.

The invention in some aspects is a method for treating a disorder associated with γδT cell expansion, activation and/or effector function by contacting a CLIP molecule expressing cell with a peptide of the invention in an effective amount to interfere with γδT cell expansion, activation and/or effector function by the CLIP molecule expressing cell. In some embodiments the γδT cell is a vγ9vδ2 T cell. Disorders associated with γδT cell expansion and/or activation include, for instance autoimmune disease, HIV infection, and cell, tissue and graft rejection.

The CLIP molecule expressing cell is a B cell in some embodiments. In other embodiments the CLIP compound expressing cell is a neuron, an oligodendrocyte, a microglial cell, or an astrocyte. In yet other embodiments the CLIP compound expressing cell is a heart cell, a pancreatic beta cell, an intestinal epithelial cell, a lung cell, an epithelial cell lining the uterine wall, and a skin cell. When the cell is a B cell, the method may further involve contacting the B cell with an anti-HLA class I or II antibody in an effective amount to kill the B cell.

A method for treating a disease by administering to a subject a composition of a CLIP inhibitor and a pharmaceutically acceptable carrier is also provided. In some aspects the CLIP inhibitor is a MHC class II CLIP inhibitor. In other embodiments the CLIP inhibitor is a peptide of the invention. In these aspects the disease may be a viral infection, such as HIV, herpes, hepatitis A, B, or C, CMV, EBV, or *Borrelia burgdorferi*, a parasitic infection such as *Leishmania* or malaria, allergic disease, Alzheimer's disease, autoimmune disease or a cell or tissue graft. In these aspects of the invention, the CLIP inhibitor may also be a MHC class I inhibitor. In other aspects wherein the CLIP inhibitor is a MHC class I CLIP inhibitor the disease may be cancer or bacterial infection.

In some embodiments the administration occurs over a period of eight weeks. In other embodiments the administration is bi-weekly which may occur on consecutive days. The administration may also be at least one of oral, parenteral, subcutaneous, intravenous, intranasal, pulmonary, intramuscular and mucosal administration.

In some embodiments the methods involve administering another medicament to the subject, such as an anti-HIV agent, an anti-viral agent, an anti-parasitic agent, an anti-bacterial agent, an anti-cancer agent, an anti allergic medicament, or an autoimmune medicament. In other embodiments the methods involve administering an adjuvant such as aluminum hydroxide or aluminum phosphate, calcium phosphate, nanoparticles, nucleotides ppGpp and pppGpp, killed *Bordetella pertussis* or its components, *Corynebacterium* derived P40 component, killed cholera toxin or its parts and/or killed mycobacteria or its parts.

In some embodiments the methods involve administering any of the compositions described herein.

In some embodiments the autoimmune disease is multiple sclerosis, systemic lupus erythematosus, type 1 diabetes, viral endocarditis, viral encephalitis, inflammatory bowel disease, rheumatoid arthritis, Graves' disease, autoimmune thyroiditis, autoimmune myositis, or discoid lupus erythematosus. In other embodiments the graft tissue or cell is heart, lung, kidney, skin, cornea, liver, neuronal tissue or cell, stem cell, including hematopoietic or embryonic stem cell.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items. As used herein the specification, “a” or “an” may mean one or more. As used herein in the claim(s), when used in conjunction with the word “comprising”, the words “a” or “an” may mean one or more than one. As used herein “another” may mean at least a second or more.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 2A and 2B are dot plots representing flow cytometric analysis of 5 day cultures in which CD40 Ligand activated B cells were co-cultured with autologous PMBCs for 5 days wherein FIG. 2A shows a striking increase in the percentage of activated NK cells in the PBMC culture and FIG. 2B shows a dramatic apoptotic loss of the activated B cells.

FIGS. 3A-1, 3A-2, 3B-1, 3B-2 and 3C depict CLIP displacement from the surface of model B cells lines (Daudi at FIGS. 3A-1 and 3B-1 and Raji at FIGS. 3A-2 and 3B-2) in response to thymic nuclear protein (TNP) mixture. FIGS. 3A-1 and 3A-2 are 3 hour reactions. FIGS. 3B-1 and 3B-2 are 24 hour reactions. FIG. 3C is a 48 hour reaction.

FIG. 12 is a line graph having a double Y axis, on one side depicting % total B cell death (diamonds, representing CpG ODN alone and squares representing CpG ODN+MKN3) and on the other side depicting % CLIP+ B cell death (triangles, representing CpG ODN and CLIP alone and Xs representing CpG ODN+MKN3 and CLIP).

FIG. 13 is a line graph having a double Y axis, on one side depicting % CLIP+B cell numbers in spleen (light gray square with solid lines representing CpG ODN alone and dark gray square with solid lines representing CpG ODN+MKN3) and on the other side depicting % CLIP+ B cell numbers in lymph nodes (diamonds with dashed lines representing CpG ODN alone and light gray square with dashed lines representing CpG ODN+ MKN3).

FIG. 15A is a line graph depicting the amount of CD20+ CLIP+ B cells as mean fluoresce intensity. FIGS. 15B and 15C respectively are bar graphs depicting the percentage of different types of CLIP+ cells in lymph nodes (LN) or peripheral blood (WB).

FIGS. 17A-17C are a set of line graphs depicting an in vivo study to assess the spleen versus lymph node cellularity (up to $250\times10^6$ cells in FIG. 17A and up to $25\times10^6$ cells in FIG. 17B) and CLIP+ B cells upon activation with TLR ligands (FIG. 17C).

DETAILED DESCRIPTION

Figure 1:
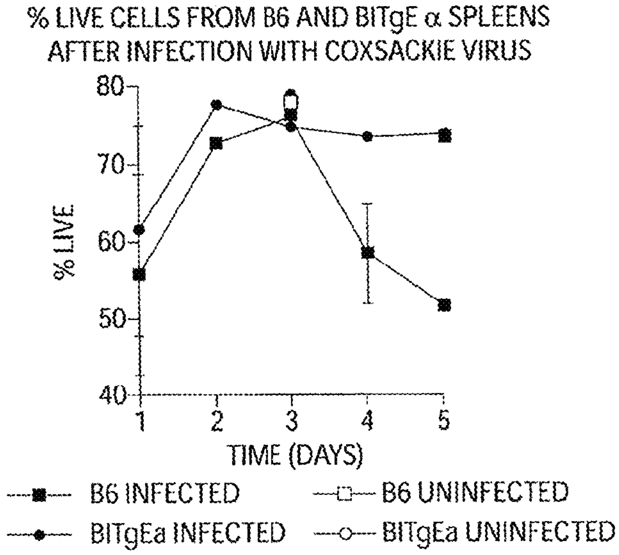
FIG. 1 depicts % B Cell Death in resistant C57B16 versus sensitive Coxsackievirus infected mice from 1 to 5 days post infection.

For clarity of disclosure, and not by way of limitation, the detailed description of the invention is divided into the following subsections:

(i) Methods for Identifying Binding Peptides
(ii) CLIP/Tregs/Disease
(iii) CLIP inhibitors
(iv) Uses of the Compositions of the Invention
(v) Infectious Disease
(vi) Transplant/Graft Rejection
(vii) Autoimmune Disease
(viii) Cancer
(ix) Alzheimer’s Disease
(x) Allergic Disease
(xi) Characterization and Demonstration of CLIP inhibitor activities
(xii) Combinations with Antibodies (xiii) Dosage Regimens (xiv) Administrations, Formulations (xv) Preparation of Peptides (Purification, Recombinant, Peptide Synthesis)

amino acids. Each of the 20 primary amino acids and their commonly known properties are included in the Table 1 below. The first axis may include all of the primary amino acids or it may include less than all of the primary amino acids, for instance it may include 10 or greater.

TABLE 1

| AMINO ACID | SINGLE LETTER CODE | 3 LETTER CODE | SIDE CHAIN | HYDROPHOBICITY | POLARITY | PH |
|---|---|---|---|---|---|---|
| Alanine | A | Ala | $—CH_3$ | X | — | — |
| Cysteine | C | Cys | $—CH_2SH$ | — | — | Acidic |
| Aspartic acid | D | Asp | $—CH_2COOH$ | — | X | Acidic |
| Glutamic acid | E | Glu | $—CH_2CH_2COOH$ | — | X | Acidic |
| Phenylalanine | F | Phe | $—CH_2C_6H_5$ | X | — | — |
| Glycine | G | Gly | —H | — | — | — |
| Histidine | H | His | $—CH_2—C_3H_3N_2$ | — | X | Weak basic |
| Isoleucine | I | Ile | $—CH(CH_3)CH_2CH_3$ | X | — | — |
| Lysine | K | Lys | $—(CH_2)_4NH_2$ | — | X | Basic |
| Leucine | L | Leu | $—CH_2CH(CH_3)_2$ | X | — | — |
| Methionine | M | Met | $—CH_2CH_2SCH_3$ | X | — | — |
| Asparagine | N | Asn | $—CH_2CONH_2$ | — | X | — |
| Proline | P | Pro | $—CH_2CH_2CH_2—$ | X | — | — |
| Glutamine | Q | Gln | $—CH_2CH_2CONH_2$ | — | X | — |
| Arginine | R | Arg | $—(CH_2)_3NH—C(NH)NH_2$ | — | X | Strong basic |
| Serine | S | Ser | $—CH_2OH$ | — | X | — |
| Threonine | T | Thr | $—CH(OH)CH_3$ | — | X | Weak acidic |
| Valine | V | Val | $—CH(CH_3)_2$ | X | — | — |
| Tryptophan | W | Trp | $—CH_2C_8H_6N$ | X | — | — |
| Tyrosine | Y | Tyr | $—CH_2—C_6H_4OH$ | — | X | — |

(xvi) Articles of Manufacture (xvii) Therapeutic Monitoring (i) Methods for Identifying Binding Peptides Methods for identifying peptides which have ideal binding properties involving computational analysis are provided herein. The methods involve comparing the binding affinity of putative peptides to a target protein in a family of proteins having structural similarities, such as multiple alleles. The methods involve a computer assisted comparison of the affinity of a binding site for a particular amino acid at each amino acid in the binding site for each of the target proteins to identify an ideal binder for all of the examined target proteins. The target proteins are proteins having similar binding sites. "Proteins having similar binding sites" are proteins that have different primary structure, but that bind to the same binding partner as one another. Preferably these proteins share at least 80% homology in a binding site for the binding partner. In some embodiments these proteins share at least 85%, 90%, 95%, 96,%, 97%, 98%, or 99% homology in a binding site for the binding partner. The target proteins having similar binding sites may be proteins produced from allelic variants. For instance, MHC class I and II are multi-allelic genes that produce target proteins having similar binding sites.

The target protein binding peptides may be identified using amino acid prediction matrices of data points for a binding site. An amino acid prediction matrix is a table having a first and a second axis defining data points. An example of a prediction matrix is shown in Table 4/Appendix A following the Examples. The Table 4/Appendix A is reproduced from Singh, H. and Raghava, G. P. S. (2001), "ProPred: prediction of HLA-DR binding sites." Bioinformatics, 17(12), 1236-37) and is not part of the invention.

The first axis, which may be the x or y axis, represents each amino acid in a group. The group of amino acids may include all or less than all of the 20 primary or standard The amino acids may be naturally occurring amino acids as well as non-naturally occurring amino acids. Naturally occurring amino acids are generally α-amino acids because the amino group is attached to the first carbon atom after the COOH group.

The second axis represents a binding site position number. A binding site position number refers to the amino acid position number in a putative binding peptide. Conventionally a peptide is numbered from the N terminal to C terminal end. The position number in the prediction matrix, however, can refer to the amino acid number reading either from the N terminus or the C terminus.

The intersection of the first axis and the second axis produces a data point. Each data point in the prediction matrix represents a score for the amino acid at the binding site position number. The score may be a positive or a negative number or it may be zero. A positive score reflects a good binding prediction for the amino acid in that position of the binding peptide with the target peptide. A negative score indicates that the amino acid in that position of the binding peptide may interfere with the binding interaction. A score of zero reflects an amino acid that is neutral in that position with respect to binding between the two peptides.

An average score is then prepared for each data point in the amino acid prediction matrices. The average score is generated by adding each data point at a specific intersection on the prediction matrices for all of the target proteins and dividing by the total number of prediction matrices/target proteins being analyzed. The result of the averaging can be displayed in another prediction matrix, referred to as the average prediction matrix. The average prediction matrix includes a first axis and a second axis with data points. Each data point therein reflects an average score for all of the target proteins.

A binding peptide can then be determined based on the average score for each data point by selecting an amino acid for each site of the binding peptide having a score of zero or greater. In some instances it might be desirable to select the highest score for each amino acid binding site to select the peptide that has the highest likelihood of being a specific binder. However it is not necessary that the selected peptide have the highest score. It may be desirable to select multiple peptides or all possible binding peptides based on the data points having a score of zero or higher.

The analysis can be performed on a set of target proteins. The set may include all of the target proteins having similar binding sites. However, it may include less than all of the target proteins having similar binding sites. In fact it may have as few as two target proteins in the set.

The average score for each data point may be displayed in a physical format, such as on a computer screen, although it is not necessary to display the results. If the results are not displayed they can be further processed by the computer. If the results are displayed outputting an amino acid sequence of at least one binding peptide is apparent from the display.

In a particular example a computational analysis was performed to identify peptides for their ability to displace CLIP from the binding groove of MHC alleles. Using the methods of the invention optimal sequences for peptides that can displace CLIP from the groove of any MHC molecule encoded by any MHC allele were identified. A predicted peptide binding score may also be generated for the binding peptide and the predicted peptide binding score may be compared with a predicted CLIP binding score, wherein if the predicted peptide binding score is higher than or equivalent to the predicted CLIP binding score then the peptide is a CLIP inhibitor.

In the outlined example of CLIP it is not necessary that a set of target proteins be analyzed. The computational method can be performed using a single MHC peptide and the identified binding peptides can be compared to the binding of CLIP to the MHC peptide.

It should be appreciated from the foregoing, there are numerous aspects of the present invention described herein that can be used independently of one another or in any combination. In particular, any of the herein described operations may be employed in any of numerous combinations and procedures. In addition, aspects of the invention can be used in connection with a variety of types of images or any dimensionality. Moreover, one or more automatic operations can be used in combination with one or more manual operations, as the aspects of the invention are not limited in this respect. The results, however obtained, may be used to facilitate the characterization of any peptide binding sites using any of the herein described techniques, alone or in combination.

The herein-described embodiments of the present invention can be implemented in any of numerous ways. For example, the embodiments of automatic peptide analysis may be implemented using hardware, software or a combination thereof. When implemented in software, the software code can be executed on any suitable processor or collection of processors, whether provided in a single computer or distributed among multiple computers. It should be appreciated that any component or collection of components that perform the functions described herein can be generically considered as one or more controllers that control the herein-discussed functions. The one or more controllers can be implemented in numerous ways, such as with dedicated hardware, or with general purpose hardware (e.g., one or more processors) that is programmed using microcode or software to perform the functions recited herein.

It should be appreciated that the various methods outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code. In this respect, it should be appreciated that one embodiment of the invention is directed to a computer-readable medium or multiple computer-readable media (e.g., a computer memory, one or more floppy disks, compact disks, optical disks, magnetic tapes, etc.) encoded with one or more programs that, when executed, on one or more computers or other processors, perform methods that implement the various embodiments of the invention discussed herein. The computer-readable medium or media can be transportable, such that the program or programs stored thereon can be loaded onto one or more different computers or other processors to implement various aspects of the present invention as discussed herein.

It should be understood that the term "program" is used herein in a generic sense to refer to any type of computer code or set of instructions that can be employed to program a computer or other processor to implement various aspects of the present invention as discussed herein. Additionally, it should be appreciated that according to one aspect of this embodiment, one or more computer programs that, when executed, perform methods of the present invention need not reside on a single computer or processor, but may be distributed in a modular fashion amongst a number of different computers or processors to implement various aspects of the present invention.

(ii) CLIP/Tregs/Disease

New insights into the role of invariant chain (CD74) and CLIP in disease have been discovered. The invention thus involves novel approaches to modulating immune function through targeting of invariant chain/CD74 and CLIP as well as related products. A role for CLIP in a number of diseases has been discovered. The result is wide range of new therapeutic regimens for treating or inhibiting the development or progression of a multitude of illnesses and conditions, including autoimmune disease, cancer, Alzheimer's disease, allergic disease, transplant and cell graft rejection, and infection.

B cells, in addition to producing antibodies, can also be activated in a somewhat antigen non-specific, bystander fashion. For example, during a viral or bacterial infection, non-antigen specific B cells in the area of the antigen-specific B cell that were in close proximity to an inflammatory or inciting lesion could manage to become activated in a bystander fashion. In those cases, CLIP would remain in the groove and get transported to the cell surface of the B cell. The presence of CLIP on the cell surface is dangerous because if CLIP gets removed from the groove by a self antigen, the B cell would be in a position to present self antigens to self-reactive T cells, a process that could lead to autoreactivity and autoimmune disease. For some B cells this may result in death to the B cell by a nearby killer cell, perhaps a natural killer (NK) cell. However, if this doesn't remove the potentially autoreactive B cell and it encounters a CD4+ T cell that can recognize that antigen (most likely one that was not in the thymus) the CLIP might be removed, in which case the B cell might receive additional help from a T cell specific for the antigen that now begins to occupy the groove (antigen binding location in the MHC molecule). Alternatively, a nearby cell whose job it is to detect damaged self cells, may become activated by the self antigen-presenting B cell. Such a damage detecting cell is, for example, a gamma delta-cell, also referred to as a γδT cell (γδ refers to the chains of its receptor), which can then seek out other sites of inflammation (for example in the brain in MS, in the heart for autoimmune myocarditis, in the pancreas in the case of Type I Diabetes). Alternatively, the γδT cell might attempt to kill the CD4 T cell that may respond to self antigens. In either event, activation of a γδT cell may not be desirable.

An example of the necessity for selective B cell death when the antigen receptor has not been bound by a real bona fide antigen is in Coxsackievirus. Most people that contract Coxsackievirus get a flu-like disease and then they recover, but in a genetic manner, some people (especially young men) contract Coxsackievirus and then go on to develop autoimmune myocarditis. In some genetically inbred strains of mice, the mice are resistant to myocarditis post-infection; in other strains of mice, the mice succumb. One difference was that the mice that were susceptible had a particular isoform of MHC class II. Mice on the resistant background having the other isoform of class II inserted, both artificially and genetically, showed susceptibility simply on the basis of the isoform, and it was shown that susceptibility depended on the presence of γδT cells (Huber et al., 1999).

Moreover, it was observed that in the mice that did not develop autoimmune disease, during the course of infection, all of their B cells died. Even with such B cell death, the animals survive as new B cells are produced continually. However, the animals susceptible to autoimmune disease had no B cell death. Further support for this notion is the γδ knock-out mice (they genetically have no γδT cells) do not get EAE, the mouse version of multiple sclerosis, nor do they get Type 1 diabetes. NK cell knock-out animals get worse disease in both cases. In addition, the invariant chain knock-out animals are resistant to the animal models of autoimmune diseases as well. Although not bound by mechanism, it is believed according to the invention that removal of γδT cells is a therapeutic treatment for MS, and that NK cells kill the antigen non-specific B cells in normal people and animals, thereby preventing disease. There appears to be a reciprocity of function between these two regulatory cell types.

Many therapies to block autoimmune and transplant disease involve eliminating or inhibiting B cells. The mechanism by which these B cell depleting therapies improve therapeutic outcome are unknown. The inventor has observed that γδT cell activation is often associated with proteins that have been lipid modified. It turns out the invariant chain is fatty acid acylated (e.g., palmitoylated). Antigen non-specifically activated human B cells treated with anti-CLIP antibodies express cell surface CLIP. The inventor recognized that B cell surface expression of CLIP is likely how γδT cells get activated. For example, if there is inflammation at a given site, the long-lived γδT cell kills the type of CD4 helper T cell that could improve disease (the Th2 CD4+ T cells; these likely also express CLIP on their surfaces, making them a target for γδT cells), at the site of injury. They attack the inflamed tissue as well as kill the Th2 cells, leaving behind B cells that can now present self antigens (that load the CLIP binding site) to Th1 cells. The Th1 cells go on to activate additional CD8 killer cells and to attack the tissues as well. Once the γδT cell is activated, it searches for damaged tissue. Importantly, CLIP can preferentially associate with certain isoforms of MHC class II (I-E in mouse, HLA-DR in humans) and to certain MHC class I's (for example, but not limited to, CD1). Interestingly, many autoimmune diseases map to the same HLA-DR alleles and not to the other isoforms.

(iii) CLIP Inhibitors

The invention involves the discovery of a number of molecules that are able to displace CLIP as well as methods for generating a large number of molecules that have the ability to displace CLIP. For instance, analysis of the binding interaction between MHC class I or II and CLIP or the MHC class I or II binding pocket provides information for identifying other molecules that may bind to MHC class I or II and displace CLIP. One method to achieve this involves the use of software that predicts MHC Class II binding regions in an antigen sequence using quantitative matrices and comparing the binding of the peptides with MHC class II to that the binding of CLIP with MHC class II. Software for predicting MHC Class II binding regions in an antigen sequence using quantitative matrices is described for instance in Singh, H. and Raghava, G. P. S. (2001), "ProPred: prediction of HLA-DR binding sites." Bioinformatics, 17(12), 1236-37. Peptide sequences having an equivalent or better binding affinity for MHC class II than CLIP should bind to MHC class II and displace CLIP.

Examples of "ideal" MHC class II binding peptides were generated according to the invention. Because MHC class II HLA-DR can bind to peptides of varying length an analysis of MHC class II HLA-DR-CLIP binding was performed. The methods are described in more detail in the Examples. HLA-DR is the human version of MHC Class II and is homologous to mouse I-E. Since the alpha chain is much less polymorphic than the beta chain of HLA-DR, the HLA-DR beta chain (hence, HLA-DRB) was studied in more detail. A review of HLA alleles is at Cano, P. et al, "Common and Well-Documented HLA Alleles", Human Immunology 68, 392-417 (2007), which is incorporated herein by reference. Peptide binding data for 51 common alleles is publicly available.

Prediction matrices based on peptide binding data for each of the 51 common HLA-DRB alleles are available. The matrices can be obtained from www.imtech.res.in/raghava/propred/page4.html and are presented in Table 4/Appendix A to this application. These matrices weight the importance of each amino acid at each position of the peptide. Critical anchor residues require a very restricted set of amino acids for binding. Other positions are less important but still may influence MHC binding. A couple of the positions do not appear to influence binding at all. The analysis may be accomplished using an available open source MHC Class II binding peptide prediction server, which can be obtained online at: www.imtech.res.in/raghava/propred.

In order to develop a CLIP inhibitor that is an effective CLIP displacer an algorithm was developed and used. The peptide binding score matrix for each allele is a 20 by 9 matrix, although other size matrices can be used as discussed above. One axis represents the binding position on MHC these are positions 1-9. The other axis represents the amino acid (20 different amino acid possibilities). At each position in this 20×9 matrix a score is given. A zero score means that the amino acid does not contribute to binding or inhibit binding. A positive score means that the amino acid contributes to binding and a negative score means that the amino acid inhibits binding if it is in that position. The matrices for the 51 alleles examined is shown below in Table 4/Appendix A. To choose the best amino acid at each position, and thus determine the sequence of the ideal binder, the scores of each amino acid at each position for all MHC alleles were averaged. This average matrix was also a 20×9 matrix (as shown in Table 2). To choose the best amino acid for each position, the amino acid with the highest average score was chosen. For some positions, the average score was zero for all amino acids. For those positions, alanine was used. The highest scoring amino acid at each position was then selected to obtain: FRIM[Any]VL[Any]S (SEQ ID NO: 6). "Any" refers to any amino acid. In order to simplify further analysis Alanine was used in both positions referred to as Any for further characterization. The resultant peptide has the sequence in the one-letter system: FRIMAVLAS (SEQ ID NO: 2), and in three-letter abbreviation as: Phe Arg Ile Met Ala Val Leu Ala Ser (SEQ ID NO: 2). The "Any" positions as well as other positions in the peptide could be optimized for other purposes such as solubility.

TABLE 2

| Averages | P1 | P2 | P3 | P4 | P5 | P6 | P7 | P8 | P9 |
|---|---|---|---|---|---|---|---|---|---|
| A: | −999 | 0 | 0 | 0 | | 0 | 0 | | 0 |
| D: | −999 | −1.3 | −1.3 | −0.67143 | | −2.06531 | −1.48163 | | −1.10408 |
| E: | −999 | 0.1 | −1.2 | −1.03673 | | −1.64898 | −0.82449 | | −0.93265 |
| F: | −0.46939 | 0.8 | 0.8 | 0.34 | | −1.3 | 0.153061 | | −0.2449 |
| G: | −999 | 0.5 | 0.2 | −1.08367 | | −0.72041 | −0.80612 | | −0.46327 |
| H: | −999 | 0.8 | 0.2 | 0.081633 | | −0.49592 | −0.03061 | | 0.053469 |
| I: | −0.5102 | 1.1 | 1.5 | 0.413878 | | 0.288776 | 0.246122 | | 0.208163 |
| K: | −999 | 1.1 | 0 | −0.2449 | | 0.25102 | −0.34898 | | −0.43469 |
| L: | −0.5102 | 1 | 1 | 0.514286 | | −0.19592 | 0.67551 | | −0.25429 |
| M: | −0.5102 | 1.1 | 1.4 | 0.873469 | | −0.92857 | 0.642449 | | 0.216327 |
| N: | −999 | 0.8 | 0.5 | −0.11265 | | −0.25918 | 0.03551 | | −0.85306 |
| P: | −999 | −0.5 | 0.3 | −1.29592 | | 0.293878 | −0.42469 | | −0.9898 |
| Q: | −999 | 1.2 | 0 | −0.1551 | | −0.66531 | −0.31633 | | 0.222449 |
| R: | −999 | 2.2 | 0.7 | −0.42653 | | 0.15102 | −0.0902 | | −0.57347 |
| S: | −999 | −0.3 | 0.2 | −0.30816 | | 0.114286 | −0.46776 | | 0.630612 |
| T: | −999 | 0 | 0 | −0.68163 | | 0.745306 | −0.53714 | | −0.73469 |
| V: | −0.5102 | 2.1 | 0.5 | −0.01633 | | 0.818367 | −0.10245 | | −0.24082 |
| W: | −0.4898 | −0.1 | 0 | −0.19286 | | −1.30612 | −0.26041 | | −0.82653 |
| Y: | −0.4898 | 0.9 | 0.8 | 0.028571 | | −1.29796 | −0.1898 | | −0.41429 |
| MAX: | −0.46939 | 2.2 | 1.5 | 0.873469 | | 0.818367 | 0.67551 | | 0.630612 |
| Position: | 4 | 14 | 7 | 10 | | 17 | 9 | | 15 |
| | F | R | I | M | Any | V | L | Any | S |

The ability of peptide of the invention to bind to MHC class II and displace CLIP was examined by comparing the predicted binding values for the peptide with those of CLIP. Table 3, shows the results of the comparison of predicted MHC Class II binding regions of FRIMAVLAS (SEQ ID NO: 2) to predicted MHC Class II binding regions of CLIP for each MHC class II allele studied. The amino acid sequence of the CLIP peptide that is part of the human invariant chain for HLA-DR is SEQ ID NO: 1, which has the sequence in the one-letter system: MRMATPLLM (SEQ ID NO: 1), and in three-letter abbreviation as: Met Arg Met Ala Thr Pro Leu Leu Met (SEQ ID NO: 1). This peptide is binds many HLA-DR alleles. A typical MHC binding peptide will bind a few alleles well and others not as well. This is consistent with the fact that natural peptides being loaded into MHC class II only need to be compatible with a given allele, rather than being polymorphic like DR alleles The immunology of MHC polymorphism and evolutionary selection provides particular alleles in different populations.

TABLE 3

| MHC CLASS II HLA-DR ALLELE | SCORE FOR CLIP (MRMATPLLM) (SEQ ID NO: 1) | SCORE FOR FRIMAVLAS (SEQ ID NO: 2) |
|---|---|---|
| DRB1_0101 | 3.78 | 3.4 |
| DRB1_0102 | 3.78 | 3.4 |

TABLE 3-continued

| MHC CLASS II HLA-DR ALLELE | SCORE FOR CLIP (MRMATPLLM) (SEQ ID NO: 1) | SCORE FOR FRIMAVLAS (SEQ ID NO: 2) |
|---|---|---|
| DRB1_0301 | 5.4 | 5.2 |
| DRB1_0305 | 2.9 | 5.8 |
| DRB1_0306 | 4.4 | 5.3 |
| DRB1_0307 | 4.4 | 5.3 |
| DRB1_0308 | 4.4 | 5.3 |
| DRB1_0309 | 4.4 | 6.2 |
| DRB1_0311 | 4.4 | 5.3 |
| DRB1_0401 | 2.9 | 6.9 |
| DRB1_0402 | 4.2 | 5.9 |
| DRB1_0404 | 3.5 | 6.4 |
| DRB1_0405 | 3.6 | 7.4 |
| DRB1_0408 | 2.5 | 7.4 |
| DRB1_0410 | 4.6 | 6.4 |
| DRB1_0421 | 4.4 | 7.3 |
| DRB1_0423 | 3.5 | 6.4 |
| DRB1_0426 | 2.9 | 6.9 |
| DRB1_0701 | 6.3 | 5.3 |
| DRB1_0703 | 6.3 | 5.3 |

TABLE 3-continued

| MHC CLASS II HLA-DR ALLELE | SCORE FOR CLIP (MRMATPLLM) (SEQ ID NO: 1) | SCORE FOR FRIMAVLAS (SEQ ID NO: 2) |
|---|---|---|
| DRB1_0801 | 3.5 | 6.7 |
| DRB1_0802 | 2.4 | 6.7 |
| DRB1_0804 | 3.4 | 5.7 |
| DRB1_0806 | 4.5 | 5.7 |
| DRB1_0813 | 3 | 7.3 |
| DRB1_0817 | 5.3 | 8.5 |
| DRB1_1101 | 4.2 | 8.1 |
| DRB1_1102 | 4.1 | 5.8 |
| DRB1_1104 | 5.2 | 7.1 |
| DRB1_1106 | 5.2 | 7.1 |
| DRB1_1107 | 3.9 | 4.8 |
| DRB1_1114 | 3.1 | 6.8 |
| DRB1_1120 | 4.6 | 7.2 |
| DRB1_1121 | 4.1 | 5.8 |
| DRB1_1128 | 5.7 | 8.5 |
| DRB1_1301 | 5.6 | 6.2 |
| DRB1_1302 | 4.6 | 7.2 |
| DRB1_1304 | 5.2 | 5.8 |
| DRB1_1305 | 5.7 | 8.5 |
| DRB1_1307 | 2.4 | 6.3 |
| DRB1_1311 | 5.2 | 7.1 |
| DRB1_1321 | 5.3 | 8.1 |
| DRB1_1322 | 4.1 | 5.3 |
| DRB1_1323 | 3.1 | 6.8 |
| DRB1_1327 | 5.6 | 6.2 |
| DRB1_1328 | 5.6 | 6.2 |
| DRB1_1501 | 5.38 | 5 |
| DRB1_1502 | 4.38 | 6 |
| DRB1_1506 | 5.38 | 5 |
| DRB1_5_0101 | 3.9 | 5.4 |
| DRB1_5_0105 | 3.9 | 5.4 |

Each row of Table 3 represents an HLA-DR allele and the score for each peptide is given. The alleles where FRIMAVLAS (SEQ ID NO: 2) had a higher score than CLIP (SEQ ID NO: 1) have been highlighted. The average score across all alleles was also calculated. For CLIP, it is 4.3156862275 and for FRIMAVLAS (SEQ ID NO: 2), it is 6.266666667, showing that FRIMAVLAS (SEQ ID NO: 2) is capable of displacing CLIP.

A CLIP inhibitor as used herein refers to a compound that interacts with MHC class II or produces a compound that interacts with MHC class II and inhibits CLIP associated activity. CLIP inhibitors include for instance but are not limited to competitive CLIP fragments, MHC class II binding peptides and peptide mimetics.

Thus, the invention includes peptides and peptide mimetics that bind to MHC class II and displace CLIP. For instance, an isolated peptide comprising $X_1RX_2X_3X_4X_5LX_6X_7$ (SEQ ID NO: 3), wherein each X is an amino acid, wherein R is Arginine, L is Leucine and wherein at least one of $X_2$ and $X_3$ is Methionine, wherein the peptide is not N-MRMATPLLM-C (SEQ ID NO: 4), and wherein the peptide is a CLIP displacer is provided according to the invention. X refers to any amino acid, naturally occurring or modified. In some embodiments the Xs referred to the in formula $X_1RX_2X_3X_4X_5LX_6X_7$ (SEQ ID NO: 8) have the following values:

$X_1$ is Ala, Phe, Met, Leu, Ile, Val, Pro, or Trp
$X_2$ is Ala, Phe, Met, Leu, Ile, Val, Pro, or Trp
$X_3$ is Ala, Phe, Met, Leu, Ile, Val, Pro, or Trp.
wherein $X_4$ is any
$X_5$ is Ala, Phe, Met, Leu, Ile, Val, Pro, or Trp
$X_6$ is any
$X_7$ is Ala, Cys, Thr, Ser, Gly, Asn, Gln, Tyr.

The peptide preferably is FRIM $X_4VLX_6S$ (SEQ ID NO: 6), such that $X_4$ and $X_6$ are any amino acid and may be Ala. Such a peptide is referred to as FRIMAVLAS (SEQ ID NO: 2).

The minimal peptide length for binding HLA-DR is 9 amino acids. However, there can be overhanging amino acids on either side of the open binding groove. For some well studied peptides, it is known that additional overhanging amino acids on both the N and C termini can augment binding. Thus the peptide may be 9 amino acids in length or it may be longer. For instance, the peptide may have additional amino acids at the N and/or C terminus. The amino acids at either terminus may be anywhere between 1 and 100 amino acids. In some embodiments the peptide includes 1-50, 1-20, 1-15, 1-10, 1-5 or any integer range there between. When the peptide is referred to as "N-FRIMAVLAS-C" (SEQ ID NO: 7) or "N-$X_1RX_2X_3X_4X_5LX_6X_7$-C" (SEQ ID NO: 9) the —C and —N refer to the terminus of the peptide and thus the peptide is only 9 amino acids in length. However the 9 amino acid peptide may be linked to other non-peptide moieties at either the —C or —N terminus or internally.

The peptide may be cyclic or non-cyclic. Cyclic peptides in some instances have improved stability properties. Those of skill in the art know how to produce cyclic peptides.

The peptides may also be linked to other molecules. The two or more molecules may be linked directly to one another (e.g., via a peptide bond); linked via a linker molecule, which may or may not be a peptide; or linked indirectly to one another by linkage to a common carrier molecule, for instance.

Thus, linker molecules ("linkers") may optionally be used to link the peptide to another molecule. Linkers may be peptides, which consist of one to multiple amino acids, or non-peptide molecules. Examples of peptide linker molecules useful in the invention include glycine-rich peptide linkers (see, e.g., U.S. Pat. No. 5,908,626), wherein more than half of the amino acid residues are glycine. Preferably, such glycine-rich peptide linkers consist of about 20 or fewer amino acids.

Linker molecules may also include non-peptide or partial peptide molecules. For instance the peptide may be linked to other molecules using well known cross-linking molecules such as glutaraldehyde or EDC (Pierce, Rockford, Ill.). Bifunctional cross-linking molecules are linker molecules that possess two distinct reactive sites. For example, one of the reactive sites of a bifunctional linker molecule may be reacted with a functional group on a peptide to form a covalent linkage and the other reactive site may be reacted with a functional group on another molecule to form a covalent linkage. General methods for cross-linking molecules have been reviewed (see, e.g., Means and Feeney, *Bioconjugate Chem.,* 1: 2-12 (1990)).

Homobifunctional cross-linker molecules have two reactive sites which are chemically the same. Examples of homobifunctional cross-linker molecules include, without limitation, glutaraldehyde; N,N'-bis(3-maleimido-propionyl-2-hydroxy-1,3-propanediol (a sulfhydryl-specific homobifunctional cross-linker); certain N-succinimide esters (e.g., di scuccinimyidyl suberate, dithiobis(succinimidyl propionate), and soluble bis-sulfonic acid and salt thereof (see, e.g., Pierce Chemicals, Rockford, Ill.; Sigma-Aldrich Corp., St. Louis, Mo.).

Preferably, a bifunctional cross-linker molecule is a heterobifunctional linker molecule, meaning that the linker has at least two different reactive sites, each of which can be separately linked to a peptide or other molecule. Use of such heterobifunctional linkers permits chemically separate and stepwise addition (vectorial conjunction) of each of the reactive sites to a selected peptide sequence. Heterobifunctional linker molecules useful in the invention include, without limitation, m-maleimidobenzoyl-N-hydroxysuccinimide ester (see, Green et al., *Cell,* 28: 477-487 (1982); Palker et al., *Proc. Natl. Acad. Sci* (*USA*), 84: 2479-2483 (1987)); m-maleimido-benzoylsulfosuccinimide ester; γ-maleimidobutyric acid N-hydroxysuccinimide ester; and N-succinimidyl 3-(2-pyridyl-dithio)propionate (see, e.g., Carlos et al., *Biochem. J.,* 173: 723-737 (1978); Sigma-Aldrich Corp., St. Louis, Mo.).

The carboxyl terminal amino acid residue of the peptides described herein may also be modified to block or reduce the reactivity of the free terminal carboxylic acid group, e.g., to prevent formation of esters, peptide bonds, and other reactions. Such blocking groups include forming an amide of the carboxylic acid group. Other carboxylic acid groups that may be present in polypeptide may also be blocked, again provided such blocking does not elicit an undesired immune reaction or significantly alter the capacity of the peptide to specifically function.

The peptide for instance, may be linked to a PEG molecule. Such a molecule is referred to as a PEGylated peptide.

The peptides useful herein are isolated peptides. As used herein, the term "isolated peptides" means that the peptides are substantially pure and are essentially free of other substances with which they may be found in nature or in vivo systems to an extent practical and appropriate for their intended use. In particular, the peptides are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in living systems.

Suitable biologically active variants of native or naturally occurring CLIP can be fragments, analogues, and derivatives of that polypeptide. By "analogue" is intended an analogue of either the native polypeptide or of a fragment of the native polypeptide, where the analogue comprises a native polypeptide sequence and structure having one or more amino acid substitutions, insertions, or deletions. A CLIP fragment is a peptide that is identical to or at least 90% homologous to less than the full length CLIP peptide, referred to herein as a portion of CLIP. The portion of CLIP is representative of the full length CLIP polypeptide. A fragment is representative of the full length CLIP polypeptide if it includes at least 2 amino acids (contiguous or non-contiguous) of the CLIP polypeptide and binds to MHC class II. In some embodiments the portion is less than 90% of the entire native human CLIP polypeptide. In other embodiments the portion is less than 50%, 45%,40%, 35%, 30%, 25%, 20%, 15%, 10%, or 5% of the entire native human CLIP polypeptide. By "derivative" is intended any suitable modification of the polypeptide of interest, of a fragment of the polypeptide, or of their respective analogues, such as glycosylation, phosphorylation, polymer conjugation (such as with polyethylene glycol), or other addition of foreign moieties, so long as the desired biological activity of the CLIP inhibitor is retained. Methods for making polypeptide fragments, analogues, and derivatives are generally available in the art.

Amino acid sequence variants of a polypeptide can be prepared by mutations in the cloned DNA sequence encoding the native polypeptide of interest. Methods for mutagenesis and nucleotide sequence alterations are well known in the art. See, for example, Walker and Gaastra, eds. (1983) Techniques in Molecular Biology (MacMillan Publishing Company, New York); Kunkel (1985) Proc. Natl. Acad. Sci. USA 82:488-492; Kunkel et al. (1987) Methods Enzymol. 154:367-382; Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly,Ala; Val,Ile,Leu; Asp,Glu; Lys,Arg; Asn,Gln; and Phe, Trp,Tyr.

The determination of percent identity between any two sequences can be accomplished using a mathematical algorithm. One preferred, non-limiting example of a mathematical algorithm utilized for the comparison of sequences is the algorithm of Myers and Miller (1988) CABIOS 4:11-17. Such an algorithm is utilized in the ALIGN program (version 2.0), which is part of the GCG sequence alignment software package. A PAM120 weight residue table, a gap length penalty of 12, and a gap penalty of 4 can be used with the ALIGN program when comparing amino acid sequences. Another preferred, nonlimiting example of a mathematical algorithm for use in comparing two sequences is the algorithm of Karlin and Altschul (1990) Proc. Natl. Acad. Sci. USA 87:2264, modified as in Karlin and Altschul (1993) Proc. Natl. Acad. Sci. USA 90:5873-5877. Such an algorithm is incorporated into the NBLAST and) XBLAST programs of Altschul et al. (1990) J. Mol. Biol. 215:403. BLAST nucleotide searches can be performed with the NBLAST program, score=100, wordlength=12, to obtain nucleotide sequences homologous to a nucleotide sequence encoding the polypeptide of interest. BLAST protein searches can be performed with the XBLAST program, score=50, wordlength=3, to obtain amino acid sequences homologous to the polypeptide of interest. To obtain gapped alignments for comparison purposes, Gapped BLAST can be utilized as described in Altschul et al. (1997) Nucleic Acids Res. 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g.,) (BLAST and NBLAST) can be used. See http://www.ncbi.nlm.nih.gov. Also see the ALIGN program (Dayhoff (1978) in Atlas of Protein Sequence and Structure 5: Suppl. 3 (National Biomedical Research Foundation, Washington, D.C.)) and programs in the Wisconsin Sequence Analysis Package, Version 8 (available from Genetics Computer Group, Madison, Wis.), for example, the GAP program, where default parameters of the programs are utilized.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Myers and Miller (1988) Computer Applic. Biol. Sci. 4:11-17.

In addition to the peptides described herein, CLIP inhibitors include peptide mimetics, which may in some instances have more favorable pharmacological properties than peptides. A CLIP peptide mimetic is an organic compound that is structurally similar to CLIP or a CLIP fragment. Thus peptide mimetics ideally mimic the function of a CLIP peptide or fragment thereof but have improved cellular transport properties, low toxicity, few side effects and more rigid structures as well as protease resistance.

Various methods for the development of peptide mimetics, including computational and screening methods, are know in the art. Review articles on such methods include for instance, Zutshi R, et al Inhibiting the assembly of protein-protein interfaces. *Cur Open Chem. Biol* 1998, 2:62-6, Cochran AG: Antagonists of protein-protein interactions. *Chem Biol* 2000, 7:R85-94, and Toogood PL: Inhibition of protein-protein association by small molecules: approaches and progress. *J Med Chem* 2002, 45:1543-58. Another approach, referred to as the supermimetic method, detects peptide mimetics directly using a known protein structure and a mimetic structure. Goede A. et al *BMC Bioinformatics* 2006, 7:11. In that method, specific atomic positions are defined in both structures and then compared with respect to their spatial conformations. In this way, organic compounds that fit into the backbone of a protein can be identified. Conversely, it is possible to find protein positions where a specific mimetic could be inserted. Using such methods it is possible to find organic compounds or design artificial peptides that imitate the binding site and hence the functionality of a protein. Programs for enabling such methods can be downloaded from the SuperMimic website (http://bioinformatics.charite.de/supermimic).

Methods for identifying peptide mimetics and other molecules that bind to a target have been described. For instance, U.S. Pat. No. 6,230,102 to Tidor et al describe a computer implemented system involving a methodology for determining properties of ligands which in turn can be used for designing ligands for binding with protein or other molecular targets. The methods involve defining the electrostatic complement for a given target site and geometry. The electrostatic complement may be used with steric complement for the target site to discover ligands through explicit construction and through the design or bias of combinatorial libraries. The methods lead to the identification of molecules having point charges that match an optimum charge distribution, which can be used to identify binding molecules.

(iv) Uses of the Compositions of the Invention

The instant invention is based at least in part on the discovery that specific peptides are CLIP inhibitors and are useful in the methods of the invention. The invention, thus, involves treatments for infectious disease, cancer, autoimmune disease, allergic disease, Alzheimer's disease and graft rejection by administering to a subject in need thereof a CLIP inhibitor. The invention also involved methods for promoting Treg development.

A subject shall mean a human or vertebrate mammal including but not limited to a dog, cat, horse, goat and primate, e.g., monkey. Thus, the invention can also be used to treat diseases or conditions in non human subjects. Preferably the subject is a human.

As used herein, the term treat, treated, or treating when used with respect to a disorder refers to a prophylactic treatment which increases the resistance of a subject to development of the disease or, in other words, decreases the likelihood that the subject will develop the disease as well as a treatment after the subject has developed the disease in order to fight the disease, prevent the disease from becoming worse, or slow the progression of the disease compared to in the absence of the therapy.

When used in combination with the therapies of the invention the dosages of known therapies may be reduced in some instances, to avoid side effects.

The CLIP inhibitor can be administered in combination with other therapeutic agents and such administration may be simultaneous or sequential. When the other therapeutic agents are administered simultaneously they can be administered in the same or separate formulations, but are administered at the same time. The administration of the other therapeutic agent and the CLIP inhibitor can also be temporally separated, meaning that the therapeutic agents are administered at a different time, either before or after, the administration of the CLIP inhibitor. The separation in time between the administration of these compounds may be a matter of minutes or it may be longer.

For instance the CLIP inhibitor may be administered in combination with an antibody such as an anti-MHC antibody or an anti-CLIP antibody. The purpose of exposing a cell to an anti-MHC class II antibody, for instance, is to prevent the cell, once CLIP has been removed, from picking up a self antigen, which could be presented in the context of MHC, if the cell does not pick up the CLIP inhibitor right away. A also an anti-MHC class II antibody may engage a B cell and kill it. Once CLIP has been removed, the antibody will be able to interact with the MHC and cause the B cell death. This prevents the B cell with an empty MHC from picking up and presenting self antigen or from getting another CLIP molecule in the surface that could lead to further γδ T cell expansion and activation.

The methods may also involve the removal of antigen non-specifically activated B cells and/or γδT cells from the subject to treat the disorder. The methods can be accomplished as described above alone or in combination with known methods for depleting such cells.

(v) Infectious Disease

Infectious diseases that can be treated or prevented by the methods of the present invention are caused by infectious agents including, but not limited to, viruses, bacteria, fungi, protozoa and parasites.

The present invention provides methods of preventing or treating an infectious disease, by administering to a subject in need thereof a composition comprising CLIP inhibitor alone or in combination with one or more prophylactic or therapeutic agents other than the CLIP inhibitor. Any agent or therapy which is known to be useful, or which has been used or is currently being used for the prevention or treatment of infectious disease can be used in combination with the composition of the invention in accordance with the methods described herein.

Viral diseases that can be treated or prevented by the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papolomavirus, cytomegalovirus, echinovirus, arbovirus, huntavirus, coxsackie virus, mumps virus, measles virus, rubella virus, and polio virus. In accordance with the some preferred embodiments of the invention, the disease that is treated or prevented by the methods of the present invention is caused by a human immunodeficiency virus (human immunodeficiency virus type I (HIV-I), or human immunodeficiency virus type II (HIV-II); e.g., the related disease is AIDS). In other embodiments the disease that is treated or prevented by the methods of the present invention is caused by a Herpes virus, Hepatitis virus, *Borrelia* virus, Cytomegalovirus, or Epstein Barr virus.

AIDS or HIV Infection

According to an embodiment of the invention, the methods described herein are useful in treating AIDS or HIV infections. HIV stands for human immunodeficiency virus, the virus that causes AIDS. HIV is different from many other viruses because it attacks the immune system, and specifically white blood cell (T cells or CD4 cells) that are important for the immune system to fight disease. In a specific embodiment, treatment is by introducing one or more CLIP inhibitors into a subject infected with HIV. In particular, HIV intracellular entry into T cells can be blocked by treatment with the peptides of the invention.

Both B cell and T cell populations undergo dramatic changes following HIV-infection. During the early stages of HIV infection, peripheral B-cells undergo aberrant polyclonal activation in an antigen-independent manner[Lang, K. S., et al., *Toll-like receptor engagement converts T-cell autoreactivity into overt autoimmune disease*. Nat Med, 2005. 11(2): p. 138-45.], perhaps as a consequence of their activation by HIV gp120 (He, B., et al., *HIV-*1 *envelope triggers polyclonal Ig class switch recombination through a CD*40*-independent mechanism involving BAFF and C-type lectin receptors*. J Immunol, 2006. 176(7): p. 3931-41.). At early stages, the B cells appear to be resistant to T cell-mediated cytotoxicity [Liu, J. and M. Roederer, *Differential susceptibility of leukocyte subsets to cytotoxic T cell killing: implications for HIV immunopathogenesis*. Cytometry A, 2007. 71(2): p. 94-104]. However, later in infection, perhaps as a direct consequence of their antigen-independent activation [Cambier, J. C., et al., *Differential transmembrane signaling in B lymphocyte activation*. Ann N Y Acad Sci, 1987. 494: p. 52-64. Newell, M. K., et al., *Ligation of major histocompatibility complex class II molecules mediates apoptotic cell death in resting B lymphocytes*. Proc Natl Acad Sci USA, 1993. 90(22): p. 10459-63], B-cells become primed for apoptosis [Ho, J., et al., *Two overrepresented B cell populations in HIV-infected individuals undergo apoptosis by different mechanisms*. Proc Natl Acad Sci USA, 2006. 103(51): p. 19436-41]. The defining characteristic of HIV infection is the depletion of CD4+ T-cells. A number of mechanisms may contribute to killing, including direct killing of the infected CD4+ T-cells by the virus or "conventional" killing of HIV-infected cells by cytotoxic CD8+ lymphocytes. The effectiveness of cytotoxic T cell killing is dramatically impaired by down-regulation of class I MHC expression on the surface of the infected cell due to the action of the viral Tat and Nef proteins[Joseph, A. M., M. Kumar, and D. Mitra, *Nef: "necessary and enforcing factor" in HIV infection*. Curr HIV Res, 2005. 3(1): p. 87-94.].

However, the same reduction in MHC class I expression that impairs cytotoxic T-cell mediated killing, in conjunction with increased expression of death inducing receptors, could mark infected cells, such as $CD4^+$ macrophages and $CD4^+$ T cells, instead as targets for NK or γδ T cell killing.

Recent work suggests that HIV-1 infection leads to a broad level of chronic activation of the immune system including changes in cytokines, redistribution of lymphocyte subpopulations, immune cell dysfunctions, and cell death [Biancotto, A., et al., *Abnormal activation and cytokine spectra in lymph nodes of people chronically infected with HIV*-1. Blood, 2007. 109(10): p. 4272-9.]. Our early work demonstrated that CD4 engagement prior to T cell receptor recognition of antigen and MHC class by $CD4^+$ T cells primes $CD4^+$ T cells for apoptotic cell death [Newell, M. K., et al., Death of mature T cells by separate ligation of CD4 and the T-cell receptor for antigen. Nature, 1990. 347(6290): p. 286-9]. As the $CD4^+$T cell levels decline, the ability to fight off minor infections declines, viremia increases, and symptoms of illness appear.

B cell activation is typically an exquisitely well-regulated process that requires interaction of the resting B cell with specific antigen. However, during the course of HIV infection, (and certain autoimmune diseases) peripheral B cells become polyclonally activated by an antigen-independent mechanism. Paradoxically, and in contrast to the polyclonal B cell activation and consequent hypergammaglobulinemia that is characteristic of early HIV infection, patients are impaired in their B cell response to immunological challenges, such as vaccination [Mason, R. D., R. De Rose, and S. J. Kent, *CD4+ T-cell subsets: what really counts in preventing HIV disease*? Expert Rev Vaccines, 2008. 7(2): p. 155-8]. At these early stages, the B cells appear to be resistant to T cell mediated cytotoxicity. At later stages in the course of infection, B cells from HIV infected patients become primed for apoptosis. The pathological role of polyclonal activated B cells and late stage B cell death in HIV is not known.

There have been conflicting reports on the role of Tregs in HIV infection. Some argue that Tregs prevent an adequate CD4 T cell response to infections and that diminished Tregs may contribute directly, or indirectly to the loss of CD4 T cells. Others have recognized a positive correlation between decreases in Tregs and viremia and advancing disease. These seemingly opposing functions of Tregs can likely be reconciled by the fact that HIV infection renders Tregs dysfunctional at two stages of disease: early Treg dysfunction prevents B cell death of polyclonally activated B cells and, in late stage disease, HIV-induced death of Treg correlates with late stage conventional CD4 T cell activation and activation induced cell death resulting in loss of activated, conventional CD4T cells. Therefore an important therapeutic intervention of the invention involves reversal of Treg dysfunction in both early and late stages of disease. These methods may be accomplished using the CLIP inhibitors of the invention. Although Applicant is not bound by a proposed mechanism of action, it is believed that the CLIP inhibitors may be peptide targets for Treg activation. Therefore, polyclonally activated B cells, having self antigens in the groove of MHC class I or II, may serve as antigen presenting cells for the targeted peptides (CLIP inhibitors) such that the targeted peptides replace CLIP. This results in the activation of Tregs.

Susceptibility or resistance to many diseases appears to be determined by the genes encoding Major Histocompatibilty Complex (MHC) molecules. Often referred to as immune response genes (or IR genes), these molecules are the key players in restricting T cell activation. T cells, both CD8 and CD4 positive T cells, recognize antigens only when the antigen is presented to the T cell in association with MHC class I (expressed on all nucleated cells) or MHC class II molecules (expressed on cells that present antigens to CD4+ T cells), respectively. MHC molecules are highly polymorphic, meaning there are many possible alleles at a given MHC locus. The polymorphism of MHC accounts for the great variations in immune responses between individual members of the same species. The ability of an antigen to bind to the MHC molecules is therefore genetically dependent on the MHC alleles of the individual person.

Viral Genetics Inc. has conducted six human clinical trials outside of the United States testing the safety and efficacy of a TNP extract (TNP-1, referred to as VGV-1 in the trials) in patients infected with HIV. In all 6 studies, subjects received 8 mg VGV-1 as an intramuscular injection of 2.0 mL of a 4.0 mg/mL suspension of TNP, twice a week for 8 weeks for a total of 16 doses. The studies are described in detail in the Examples section. The data suggested that TNP-1 treatment in HIV-1 infected patients was safe and well tolerated in human trials. There was a decrease in CD4 cells observed in the trials which trended consistently with the natural progression of disease. However, changes in HIV-1 RNA observed were less than expected during a natural course of HIV-1 infection.

The South African study demonstrated efficacy of TNP in various subsets of HIV/AIDS patients while providing additional verification of the compound being well-tolerated. In brief, TNP appeared to have a meaningful effect on levels of HIV virus in subsets of patients with more heavily damaged immune systems. The discoveries of the invention, specifically relating to CLIP inhibitors are consistent with and provide an explanation for some of the observations arising in the trials. For instance, the fact that TNP which has long been believed to be an immune-based drug, showed superior results in patients with a more damaged immune system was difficult to reconcile. However, the results of the invention specifically related to the ability of CLIP inhibitors to reverse Treg dysfunction in HIV disease, as discussed above.

Additionally, the transient, short-term anti-HIV effect of TNP in the clinical trials was difficult to explain. The results of the instant invention demonstrate that these results appears to be a simple dosing problem. The formulation used in the clinical trials was not the ideal dosage and the number of times it is administered was also likely not optimal. By extending the period of time TNP is dosed and increasing the dosage, it appears likely it can achieve a longer-lasting effect.

Another phenomena observed in the clinical trial related to the fact that TNP appeared to work in 25-40% of patients. The discoveries of the invention provide an explanation for this. It has been discovered that TNP includes several protein compounds that should be able to treat HIV in certain subgroups of human patients but not all of them. This is based on the specific MHC of the patient. The invention also relates to the discovery of subgroups of peptides that are MHC matched that will provide more effective treatment for a much larger group of patients. The differential binding affinity of the TNP peptides to widely variant MHC molecules between individuals may account for the variation in the ability of TNP peptides to modulate disease between various HIV-infected people. MHC polymorphisms may also account for the wide range that describes time between first infection with HIV and the time to onset of full-blown AIDS.

Because TNP is derived from the thymus, the epitopes in the TNP mixtures could be involved in Treg selection. The B cell would not be recognized by the Tregs until TNP peptides (CLIP inhibitors), or other appropriate self peptides, competitively replace the endogenous peptide in the groove of B cell MHC class II. The TNP peptides are likely enriched for the pool that selects Tregs in the thymus and these peptides are processed and presented in B cells differentially depending on disease state. Therefore, the partial success in reducing the HIV viral load that was observed in patients treated with the VGV-1 targeted peptide treatment is explained by the following series of observations: 1) gp120 from HIV polyclonally activates B cells that present conserved self antigens via MHC class II (or potentially MHC class I) and the activated B cells stimulate gamma delta T cells, 2) the VGV-1 targeted peptides bind with stronger affinity to the MHC molecules of the polyclonally activated B cell, 3) the consequence is activation and expansion of Tregs whose activation and expansion corresponds with decreased viral load, diminished $\gamma\delta$ T cell activation, and improvement as a result of inhibition of activation-induced cell death of non-Treg (referred to as conventional) CD4+ T cells.

The discoveries of the invention suggest that the success of TNP extract treatment in HIV patients involves binding of targeted peptides from the TNP mixture to cell surface Major Histocompatibility Complex (MHC) molecules on the activated B cell surface. MHC molecules are genetically unique to individuals and are co-dominantly inherited from each parent. MHC molecules serve to display newly encountered antigens to antigen-specific T cells. According to our model, if the MHC molecules bind a targeted peptide that has been computationally predicted to bind the individual's MHC molecules with greater affinity than the peptide occupying the groove of the MHC molecules on the activated B cell surface, the consequence will be activation of Treg cells that can dampen an inflammatory response. Tregs usually have higher affinity for self and are selected in the thymus. Because TNP is derived from the thymus, it is reasonable to suggest that these epitopes could be involved in Treg selection. Aberrantly activated B cells have switched to expression of non-thymically presented peptides. The TNP peptides may be represented in the pool that selects Tregs in the thymus. Loading of the thymic derived peptides onto activated B cells then provides a unique B cell/antigen presenting cell to activate the Treg.

In accordance with another embodiment, the methods of this invention can be applied in conjunction with, or supplementary to, the customary treatments of AIDS or HIV infection. Historically, the recognized treatment for HIV infection is nucleoside analogs, inhibitors of HIV reverse transcriptase (RT). Intervention with these antiretroviral agents has led to a decline in the number of reported AIDS cases and has been shown to decrease morbidity and mortality associated with advanced AIDS. Prolonged treatment with these reverse transcriptase inhibitors eventually leads to the emergence of viral strains resistant to their antiviral effects. Recently, inhibitors of HIV protease have emerged as a new class of HIV chemotherapy. HIV protease is an essential enzyme for viral infectivity and replication. Protease inhibitors have exhibited greater potency against HIV in vitro than nucleoside analogs targeting HIV-1 RT. Inhibition of HIV protease disrupts the creation of mature, infectious virus particles from chronically infected cells. This enzyme has become a viable target for therapeutic intervention and a candidate for combination therapy.

Knowledge of the structure of the HIV protease also has led to the development of novel inhibitors, such as saquinovir, ritonavir, indinivir and nelfinavir. NNRTIs (non-nucleoside reverse transcriptase inhibitors) have recently gained an increasingly important role in the therapy of HIV infection. Several NNRTIs have proceeded onto clinical development (i.e., tivirapine, loviride, MKC-422, HBY-097, DMP 266). Nevirapine and delaviridine have already been authorized for clinical use. Every step in the life cycle of HIV replication is a potential target for drug development.

Many of the antiretroviral drugs currently used in chemotherapy either are derived directly from natural products, or are synthetics based on a natural product model. The rationale behind the inclusion of deoxynucleoside as a natural based antiviral drugs originated in a series of publications dating back as early as 1950, wherein the discovery and isolation of thymine pentofuranoside from the air-dried sponges (*Cryptotethia crypta*) of the Bahamas was reported. A significant number of nucleosides were made with regular bases but modified sugars, or both acyclic and cyclic derivatives, including AZT and acyclovir. The natural spongy-derived product led to the first generation, and subsequent second-third generations of nucleosides (AZT, DDI, DDC, D4T, 3TC) antivirals specific inhibitors of HIV-1 RT.

A number of non-nucleoside agents (NNRTIs) have been discovered from natural products that inhibit RT allosterically. NNRTIs have considerable structural diversity but share certain common characteristics in their inhibitory profiles. Among NNRTIs isolated from natural products include: calanoid A from calophylum langirum; Triterpines from Maporonea African a. There are publications on natural HIV integrase inhibitors from the marine ascidian alkaloids, the lamellarin.

Lyme's Disease is a tick-borne disease caused by bacteria belonging to the genus *Borrelia. Borrelia burgdorferi* is a predominant cause of Lyme disease in the US, whereas *Borrelia afzelii* and *Borrelia garinii* are implicated in some European countries. Early manifestations of infection may include fever, headache, fatigue, and a characteristic skin rash called erythema migrans. Long-term the disease involves malfuncctions of the joints, heart, and nervous system. Currently the disease is treated with antibiotics. The antibiotics generally used for the treatment of the disease are doxycycline (in adults), amoxicillin (in children), and ceftriaxone. Late, delayed, or inadequate treatment can lead to late manifestations of Lyme disease which can be disabling and difficult to treat.

A vaccine, called Lymerix, against a North American strain of the spirochetal bacteria was approved by the FDA and leter removed from the market. It was based on the outer surface protein A (OspA) of *B. burgdorferi*. It was discovered that patients with the genetic allele HLA-DR4 were susceptible to T-cell cross-reactivity between epitopes of OspA and lymphocyte function-associated antigen in these patients causing an autoimmune reaction.

It is believed according to the invention that *Borrelia* Bergdorf also produces a Toll ligand for TLR2. Replacement of the CLIP on the surface of the B cell by treatment with a CLIP inhibitor with high affinity for the MHC fingerprint of a particular individual, would result in activation of the important Tregs that can in turn cause reduction in antigen-non-specific B cells. Thus treatment with CLIP inhibitors could reactivate specific Tregs and dampen the pathological inflammation that is required for the chronic inflammatory condition characteristic of Lyme Disease. With the appropriate MHC analysis of the subject, a specific CLIP inhibitor can be synthesized to treat that subject. Thus individuals with all different types of MHC fingerprints could effectively be treated for Lymes disease.

Chronic Lyme disease is sometimes treated with a combinatin of a macrolide antibiotic such as clarithromycin (biaxin) with hydrochloroquine (plaquenil). It is thought that the hydroxychloroquine raises the pH of intracellular acidic vacuoles in which *B. burgdorferi* may reside; raising the pH is thought to activate the macrolide antibiotic, allowing it to inhibit protein synthesis by the spirochete.

At least four of the human herpes viruses, including herpes simplex virus type 1 (HSV-1), herpes simplex virus type 2 (HSV-2), cytomegalovirus (CMV), Epstein-Barr virus (EBV), and varicella zoster virus (VZV) are known to infect and cause lesions in tissues of certain infected individuals. Infection with the herpes virus is categorized into one of several distinct disorders based on the site of infection. For instance, together, these four viruses are the leading cause of infectious blindness in the developed world. Oral herpes, the visible symptoms of which are referred to as cold sores, infects the face and mouth. Infection of the genitals, commonly known as, genital herpes is another common form of herpes. Other disorders such as herpetic whitlow, herpes gladiatorum, ocular herpes (keratitis), cerebral herpes infection encephalitis, Mollaret's meningitis, and neonatal herpes are all caused by herpes simplex viruses. Herpes simplex is most easily transmitted by direct contact with a lesion or the body fluid of an infected individual. Transmission may also occur through skin-to-skin contact during periods of asymptomatic shedding.

HSV-1 primarily infects the oral cavity, while HSV-2 primarily infects genital sites. However, any area of the body, including the eye, skin and brain, can be infected with either type of HSV. Generally, HSV is transmitted to a non-infected individual by direct contact with the infected site of the infected individual.

VZV, which is transmitted by the respiratory route, is the cause of chickenpox, a disease which is characterized by a maculopapular rash on the skin of the infected individual. As the clinical infection resolves, the virus enters a state of latency in the ganglia, only to reoccur in some individuals as herpes zoster or "shingles". The reoccurring skin lesions remain closely associated with the dermatome, causing intense pain and itching in the afflicted individual.

CMV is more ubiquitous and may be transmitted in bodily fluids. The exact site of latency of CMV has not been precisely identified, but is thought to be leukocytes of the infected host. Although CMV does not cause vesicular lesions, it does cause a rash. Human CMVs (HCMV) are a group of related herpes viruses. After a primary infection, the viruses remain in the body in a latent state. Physical or psychic stress can cause reactivation of latent HCMV. The cell-mediated immune response plays an important role in the control and defense against the HCMV infection. When HCMV-specific $CD8^{+}$T cells were transferred from a donor to a patient suffering from HCMV, an immune response against the HCMV infection could be observed (P. D. Greenberg et al., 1991, Development of a treatment regimen for human cytomegalovirus (CMV) infection in bone marrow transplantation recipients by adoptive transfer of donor-derived CMV-specific T cell clones expanded in vitro. Ann. N.Y. Acad. Sci., Vol.: 636, pp 184 195). In adults having a functional immune system, the infection has an uneventful course, at most showing non-specific symptoms, such as exhaustion and slightly increased body temperature. Such infections in young children are often expressed as severe respiratory infection, and in older children and adults, they are expressed as anicteric hepatitis and mononucleosis. Infection with HCMV during pregnancy can lead to congenital malformation resulting in mental retardation and deafness. In immunodeficient adults, pulmonary diseases and retinitis are associated with HCMV infections.

Epstein-Barr virus frequently referred to as EBV, is a member of the herpesvirus family and one of the most common human viruses. The virus occurs worldwide, and most people become infected with EBV sometime during their lives. Many children become infected with EBV, and these infections usually cause no symptoms or are indistinguishable from the other mild, brief illnesses of childhood. When infection with EBV occurs during adolescence or young adulthood, it can cause infectious mononucleosis. EBV also establishes a lifelong dormant infection in some cells of the body's immune system. A late event in a very few carriers of this virus is the emergence of Burkitt's lymphoma and nasopharyngeal carcinoma, two rare cancers that are not normally found in the United States. EBV appears to play an important role in these malignancies, but is probably not the sole cause of disease.

No treatment that can eradicate herpes virus from the body currently exists. Antiviral medications can reduce the frequency, duration, and severity of outbreaks. Antiviral drugs also reduce asymptomatic shedding. Antivirals used against herpes viruses work by interfering with viral replication, effectively slowing the replication rate of the virus and providing a greater opportunity for the immune response to intervene. Antiviral medicaments for controlling herpes simplex outbreaks, include aciclovir (Zovirax), valaciclovir (Valtrex), famciclovir (Famvir), and penciclovir. Topical lotions, gels and creams for application to the skin include Docosanol (Avanir Pharmaceuticals), Tromantadine, and Zilactin.

Various substances are employed for treatment against HCMV. For example, Foscarnet is an antiviral substance which exhibits selective activity, as established in cell cultures, against human herpes viruses, such as herpes simplex, varicella zoster, Epstein-Barr and cytomegaloviruses, as well as hepatitis viruses. The antiviral activity is based on the inhibition of viral enzymes, such as DNA polymerases and reverse transcriptases.

Hepatitis refers to inflammation of the liver and hepatitis infections affect the liver. The most common types are hepatitis A, hepatitis B, and hepatitis C. Hepatitis A is caused by the hepatitis A virus (HAV) and produces a self-limited disease that does not result in chronic infection or chronic liver disease. HAV infection is primarily transmitted by the fecal-oral route, by either person-to-person contact or through consumption of contaminated food or water. Hepatitis B is a caused by hepatitis B virus (HBV) and can cause acute illness, leading to chronic or lifelong infection, cirrhosis (scarring) of the liver, liver cancer, liver failure, and death. HBV is transmitted through percutaneous (puncture through the skin) or mucosal contact with infectious blood or body fluids. Hepatitis C is caused by the hepatitis C virus (HCV) that sometimes results in an acute illness, but most often becomes a silent, chronic infection that can lead to cirrhosis, liver failure, liver cancer, and death. Chronic HCV infection develops in a majority of HCV-infected persons. HCV is spread by contact with the blood of an infected person.

Presently, the most effective HCV therapy employs a combination of alpha-interferon and ribavirin. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load.

Examples of antiviral agents that can be used in combination with CLIP inhibitor to treat viral infections include, but not limited to, amantadine, ribavirin, rimantadine, acyclovir, famciclovir, foscarnet, ganciclovir, trifluridine, vidarabine, didanosine (ddI), stavudine (d4T), zalcitabine (ddC), zidovudine (AZT), lamivudine, abacavir, delavirdine, nevirapine, efavirenz, saquinavir, ritonavir, indinavir, nelfinavir, amprenavir, lopinavir and interferon.

Parasitic diseases that can be treated or prevented by the methods of the present invention are caused by parasites including, but not limited to, *leishmania*, and malaria. Hisaeda H. et al Escape of malaria parasites from host immunity requires $CD4^+CD25^+$ regulatory T cells *Nature Medicine* 10, 29-30 (2004) describes a study designed to understand why infection with malaria parasites frequently induced total immune suppression. Such immune suppression presents a challenge to the host in maintaining long-lasting immunity. Hisaeda et al demonstrated that depletion of $T_{reg}$s protected mice from death when infected with a lethal strain of *Plasmodium yoelii*, and that this protection was associated with an increased T-cell responsiveness against parasite-derived antigens. The authors concluded that "activation of $Tr_{eg}$ cells contributes to immune suppression during malaria infection, and helps malaria parasites to escape from host immune responses." Suffia I. J., et al Infected site-restricted $Foxp3^+$ natural regulatory T cells are specific for microbial antigens, JEM, Volume 203, Number 3, 777-788 (2006) describe the finding that natural Treg cells are able to respond specifically to *Leishmania*. The majority of natural Treg cells at the infected site were *Leishmania* specific. The findings suggest that *Leishmania* induces Tregs to help dampen the immune response of the subject upon infection. Thus the methods of the invention are useful for treating parasitic infection by activating Tregs and preventing the immune suppression caused by such parasites.

Parasiticides are agents that kill parasites directly. Such compounds are known in the art and are generally commercially available. Examples of parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide.

Bacterial diseases that can be treated or prevented by the methods of the present invention are caused by bacteria including, but not limited to, mycobacteria, *rickettsia, mycoplasma, neisseria, Borrelia* and *legionella.*

Although Applicant is not bound by a specific mechanism of action it is believed that the CLIP inhibitors of the invention displace CLIP from MHC class I and cause down regulation of Treg activity and/or activation of effector T cells such as γδ T cells. Downregulation of regulatory function of Treg activity prevents suppression of the immune response and enables the subject to mount an effective or enhanced immune response against the bacteria. At the same time the Treg cell may shift to an effector function, producing an antigen specific immune response. Thus, replacement of CLIP with a peptide of the invention results in the promotion of an antigen specific CD8+ response against the bacteria, particularly when the peptide is administered in conjunction with a tumor specific antigen. Activation of effector T cells also enhances the immune response against the bacteria, leading to a more effective treatment.

One component of the invention involves promoting an enhanced immune response against the bacteria by administering the compounds of the invention. The compounds may be administered in conjunction with an antigen to further promote a bacterial specific immune response. A "bacterial antigen" as used herein is a compound, such as a peptide or carbohydrate, associated with a bacteria surface and which is capable of provoking an immune response when expressed on the surface of an antigen presenting cell in the context of an MHC molecule. Preferably, the antigen is expressed at the cell surface of the bacteria.

The compounds of the invention may be used in combination with anti-bacterial agents. Examples of such agents to treat bacterial infections include, but are not limited to, folate antagonists (e.g., mafenide, silver sulfadiazine, succinylsulfathiazole, sulfacetamide, sulfadiazine, sulfamethoxazole, sulfasalazine, sulfisoxazole, pyrimethoamine, trimethoprim, co-trimoxazole), inhibitors of cell wall synthesis (e.g., penicillins, cephalosporins, carbapenems, monobactams, vacomycin, bacitracin, clavulanic acid, sulbactam, tazobactam), protein synthesis inhibitors (e.g., tetracyclines, aminoglycosides, macrolides, chloramphenicol, clindamycin), fluoroquinolones (e.g., ciproloxacin, enoxacin, lomefloxacin, norfloxacin, ofloxacin), nalidixic acid, methenamine, nitrofurantoin, aminosalicylic acid, cycloserine, ethambutol, ethionamide, isoniazid, pyrazinamide, rifampin, clofazimine, and dapsone.

(vi) Transplant/Graft Rejection

According to an embodiment of the invention, the methods described herein are useful in inhibiting cell graft or tissue graft rejection. Thus, the methods are useful for such grafted tissue as heart, lung, kidney, skin, cornea, liver, neuronal tissue or cell, or with stem cells, including hematopoietic or embryonic stem cells, for example.

The success of surgical transplantation of organs and tissue is largely dependent on the ability of the clinician to modulate the immune response of the transplant recipient. Specifically the immunological response directed against the transplanted foreign tissue must be controlled if the tissue is to survive and function. Currently, skin, kidney, liver, pancreas, lung and heart are the major organs or tissues with which allogeneic transplantations are performed. It has long been known that the normally functioning immune system of the transplant recipient recognizes the transplanted organ as "non-self" tissue and thereafter mounts an immune response to the presence of the transplanted organ. Left unchecked, the immune response will generate a plurality of cells and proteins that will ultimately result in the loss of biological functioning or the death of the transplanted organ.

This tissue/organ rejection can be categorized into three types: hyperacute, acute and chronic. Hyperacute rejection is essentially caused by circulating antibodies in the blood that are directed against the tissue of the transplanted organ (transplant). Hyperacute rejection can occur in a very short time and leads to necrosis of the transplant. Acute graft rejection reaction is also immunologically mediated and somewhat delayed compared to hyperacute rejection. The chronic form of graft rejection that can occur years after the transplant is the result of a disease state commonly referred to as Graft Arterial Disease (GAD). GAD is largely a vascular disease characterized by neointimal proliferation of smooth muscle cells and mononuclear infiltrates in large and small vessels. This neointimal growth can lead to vessel fibrosis and occlusion, lessening blood flow to the graft tissue and resulting in organ failure. Current immunosuppressant therapies do not adequately prevent chronic rejection. Most of the gains in survival in the last decade are due to improvements in immunosuppressive drugs that prevent acute rejection. However, chronic rejection losses remain the same and drugs that can prevent it are a critical unmet medical need.

A clinical trial testing the use of Tregs obtained from umbilical cord blood to decrease the risk of immune reactions common in patients undergoing blood and marrow transplantation was recently initiated. It is expected that therapy will improve overall survival rates for blood cancer patients as well as offer a potential new mode for treating autoimmune diseases.

In a transplant situation, donor T-regs may suppress the recipient's immune system so that the healthy donor's blood-forming stem cells and immune cells can grow, helping ward off life-threatening graft-versus-host-disease (GVHD). GVHD occurs when the immune cells within the donated cells attack the body of the transplant recipient. In a recent study (Xia et al. *Ex vivo-expanded natural CD4+ CD25+ regulatory T cells synergize with host T-cell depletion to promote long-term survival of allografts. Am J Transplant.* 2008 February; 8(2):298-306) the question of therapeutic utilization of T regulatory cells was asked in an animal model of heart transplantation. It was discovered that Tregs were capable of extending allograft survival in a donor specific manner.

The methods of the invention involve the specific activation of Tregs by replacement of the cell surface CLIP with a CLIP inhibitor of the invention. This activation should result in a dampening of the immune system to suppress rejection of the graft.

The methods of treating transplant/graft rejection can be applied in conjunction with, or supplementary to, the customary treatments of transplant/graft rejection. Tissue graft and organ transplant recipients are customarily treated with one or more cytotoxic agents in an effort to suppress the transplant recipient's immune response against the transplanted organ or tissue. Current immunosuppressant drugs include: cyclosporin, tacrolimus (FK506), sirolimus (rapamycin), methotrexate, mycophenolic acid (mycophenolate mofetil), everolimus, azathiprine, steroids and NOX-100. All of these drugs have side effects (detailed below) that complicate their long-term use. For example, cyclosporin (cyclosporin A), a cyclic polypeptide consisting of 11 amino acid residues and produced by the fungus species *Tolypocladium inflatum* Gams, is currently the drug of choice for administration to the recipients of allogeneic kidney, liver, pancreas and heart (i.e., wherein donor and recipient are of the same species of mammals) transplants. However, administration of cyclosporin is not without drawbacks as the drug can cause kidney and liver toxicity as well as hypertension. Moreover, use of cyclosporin can lead to malignancies (such as lymphoma) as well as opportunistic infection due to the "global" nature of the immunosuppression it induces in patients receiving long term treatment with the drug, i.e., the hosts normal protective immune response to pathogenic microorganisms is downregulated thereby increasing the risk of infections caused by these agents. FK506 (tacrolimus) has also been employed as an immunosuppressive agent as a stand-alone treatment or in combination. Although its immunosuppressive activity is 10-100 times greater than cyclosporin, it still has toxicity issues. Known side effects include kidney damage, seizures, tremors, high blood pressure, diabetes, high blood potassium, headache, insomnia, confusion, seizures, neuropathy, and gout. It has also been associated with miscarriages. Methotrexate is commonly added to the treatment of the cytotoxic agent. Methotrexate is given in small doses several times after the transplant. Although the combination of cyclosporin and methotrexate has been found to be effective in decreasing the severity of transplant rejection, there are side effects, such as mouth sores and liver damage. Severe transplant rejection can be treated with steroids. However, the side effects of steroids can be extreme, such as weight gain, fluid retention, elevated blood sugar, mood swings, and/or confused thinking.

Rapamycin, a lipophilic macrolide used as an anti-rejection medication can be taken in conjunction with other anti-rejection medicines (i.e., cyclosporin) to reduce the amount of toxicity of the primary cytotoxic agent, but it too has specific side effects, such as causing high cholesterol, high triglycerides, high blood pressure, rash and acne. Moreover, it has been associated with anemia, joint pain, diarrhea, low potassium and a decrease in blood platelets.

(vii) Autoimmune Disease

According to an embodiment of the invention, the methods described herein are useful in inhibiting the development of an autoimmune disease in a subject by administering a CLIP inhibitor to the subject. Thus, the methods are useful for such autoimmune diseases as multiple sclerosis, systemic lupus erythematosus, type 1 diabetes, viral endocarditis, viral encephalitis, rheumatoid arthritis, Graves' disease, autoimmune thyroiditis, autoimmune myositis, and discoid lupus erythematosus.

In autoimmune disease non-specifically activated B cells that do not undergo apoptosis are present. Although not being bound by a specific mechanism, it is believed that the CLIP inhibitors of the invention result in activation of Tregs and reduction in these non-specific activated B cells. While, at first glance, it might seem immunologically dangerous to lose a majority of B cells for instance during an infection, it is noted that B cells continually mature in the bone marrow and new B cells continually to exit to the periphery at least until old age. Collectively it is believed that a common feature in the development of autoimmune disease may be dysfunctional Tregs and a consequent failure of antigen non-specific B cells to die. Thus, the compounds of the invention produce a therapeutic result by activating Tregs and killing antigen non-specific B cells. It is also believed that, according to an aspect of the invention, cells having CLIP on the surface in the context of MHC may cause the expansion and/or activation of these cells. Once the γδT cells are activated they may recognize CLIP in the context of MHC on host tissue such as neurons, pancreatic B cells and heart tissue. The result of that recognition may be the killing of the host cell. The γδT cells may also cause further production of antigen non-specific B cells which are capable of picking up host antigen and further producing a host specific immune response.

"Autoimmune Disease" refers to those diseases which are commonly associated with the nonanaphylactic hypersensitivity reactions (Type II, Type III and/or Type IV hypersensitivity reactions) that generally result as a consequence of the subject's own humoral and/or cell-mediated immune response to one or more immunogenic substances of endogenous and/or exogenous origin. Such autoimmune diseases are distinguished from diseases associated with the anaphylactic (Type I or IgE-mediated) hypersensitivity reactions.

(viii) Cancer

In some embodiments, the present invention provides a method of treating a cancer comprising administering to a subject in whom such treatment is desired a therapeutically effective amount of a composition comprising a CLIP inhibitor. A composition of the invention may, for example, be used as a first, second, third or fourth line cancer treatment. In some embodiments, the invention provides methods for treating a cancer (including ameliorating a symptom thereof) in a subject refractory to one or more conventional therapies for such a cancer, said methods comprising administering to said subject a therapeutically effective amount of a composition comprising a CLIP inhibitor. A cancer may be determined to be refractory to a therapy when at least some significant portion of the cancer cells are not killed or their cell division are not arrested in response to the therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced, or has increased.

Although Applicant is not bound by a specific mechanism of action it is believed that the CLIP inhibitors of the invention displace CLIP from MHC class I and cause down regulation of Treg activity and/or activation of effector T cells such as γδ T cells. Downregulation of regulatory function of Treg activity prevents suppression of the immune response and enables the subject to mount an effective or enhanced immune response against the cancer. At the same time the Treg cell may shift to an effector function, producing an antigen specific immune response. Thus, replacement of CLIP with a peptide of the invention results in the promotion of an antigen specific CD8+ response against the tumor, particularly when the peptide is administered in conjunction with a tumor specific antigen. Activation of effector T cells also enhances the immune response against the cancer, leading to a more effective treatment.

The invention provides methods for treating a cancer (including ameliorating one or more symptoms thereof) in a subject refractory to existing single agent therapies for such a cancer, said methods comprising administering to said subject a therapeutically effective amount of a composition comprising a CLIP inhibitor and a therapeutically effective amount of one or more therapeutic agents other than the CLIP inhibitor. The invention also provides methods for treating cancer by administering a composition comprising a CLIP inhibitor in combination with any other anti-cancer treatment (e.g., radiation therapy, chemotherapy or surgery) to a patient who has proven refractory to other treatments. The invention also provides methods for the treatment of a patient having cancer and immunosuppressed by reason of having previously undergone one or more other cancer therapies. The invention also provides alternative methods for the treatment of cancer where chemotherapy, radiation therapy, hormonal therapy, and/or biological therapy/immunotherapy has proven or may prove too toxic, i.e., results in unacceptable or unbearable side effects, for the subject being treated.

Cancers that can be treated by the methods encompassed by the invention include, but are not limited to, neoplasms, malignant tumors, metastases, or any disease or disorder characterized by uncontrolled cell growth such that it would be considered cancerous. The cancer may be a primary or metastatic cancer. Specific cancers that can be treated according to the present invention include, but are not limited to, those listed below (for a review of such disorders, see Fishman et al., 1985, Medicine, 2d Ed., J. B. Lippincott Co., Philadelphia).

Cancers include, but are not limited to, biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma;

intraepithelial neoplasms including Bowen's disease and Paget's disease; liver cancer;

lung cancer; lymphomas including Hodgkin's disease and lymphocytic lymphomas;

neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer.

The compositions of the invention also can be administered to prevent progression to a neoplastic or malignant state. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68-79.). Hyperplasia is a form of controlled cell proliferation involving an increase in cell number in a tissue or organ, without significant alteration in structure or function. Endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of the composition of the invention. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

The prophylactic use of the compositions of the invention is also indicated in some viral infections that may lead to cancer. For example, human papilloma virus can lead to cervical cancer (see, e.g., Hernandez-Avila et al., Archives of Medical Research (1997) 28: 265-271), Epstein-Barr virus (EBV) can lead to lymphoma (see, e.g., Herrmann et al., J Pathol (2003) 199(2): 140-5), hepatitis B or C virus can lead to liver carcinoma (see, e.g., El-Serag, J Clin Gastroenterol (2002) 35(5 Suppl 2): S72-8), human T cell leukemia virus (HTLV)-I can lead to T-cell leukemia (see e.g., Mortreux et al., Leukemia (2003) 17(1): 26-38), and human herpesvirus-8 infection can lead to Kaposi's sarcoma (see, e.g., Kadow et al., Curr Opin Investig Drugs (2002) 3(11): 1574-9).

In other embodiments, a patient which exhibits one or more of the following predisposing factors for malignancy is treated by administration of an effective amount of a composition of the invention: a chromosomal translocation associated with a malignancy (e.g., the Philadelphia chromosome for chronic myelogenous leukemia, t(14; 18) for follicular lymphoma, etc.), familial polyposis or Gardner's syndrome (possible forerunners of colon cancer), benign monoclonal gammopathy (a possible forerunner of multiple myeloma), a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W.B. Saunders Co., Philadelphia, pp. 112-113) etc.), and exposure to carcinogens (e.g., smoking, and inhalation of or contacting with certain chemicals).

In one set of embodiments, the invention includes a method of treating a subject susceptible to or exhibiting symptoms of cancer. The cancer may be primary, metastatic, recurrent or multi-drug resistant. In some cases, the cancer is drug-resistant or multi-drug resistant. As used herein, a "drug-resistant cancer" is a cancer that is resistant to conventional commonly-known cancer therapies. Examples of conventional cancer therapies include treatment of the cancer with agents such as methotrexate, trimetrexate, adriamycin, taxotere, doxorubicin, 5-flurouracil, vincristine, vinblastine, pamidronate disodium, anastrozole, exemestane, cyclophosphamide, epirubicin, toremifene, letrozole, trastuzumab, megestrol, tamoxifen, paclitaxel, docetaxel, capecitabine, goserelin acetate, etc. A "multi-drug resistant cancer" is a cancer that resists more than one type or class of cancer agents, i.e., the cancer is able to resist a first drug having a first mechanism of action, and a second drug having a second mechanism of action.

One component of the invention involves promoting an enhanced immune response against the cancer by administering the compounds of the invention. The compounds may be administered in conjunction with a cancer antigen to further promote an cancer specific immune response. A "cancer antigen" as used herein is a compound, such as a peptide or carbohydrate, associated with a tumor or cancer cell surface and which is capable of provoking an immune response when expressed on the surface of an antigen presenting cell in the context of an WIC molecule. Preferably, the antigen is expressed at the cell surface of the cancer cell. Even more preferably, the antigen is one which is not expressed by normal cells, or at least not expressed to the same level as in cancer cells. For example, some cancer antigens are normally silent (i.e., not expressed) in normal cells, some are expressed only at certain stages of differentiation and others are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. The differential expression of cancer antigens in normal and cancer cells can be exploited in order to target cancer cells. As used herein, the terms "cancer antigen" and "tumor antigen" are used interchangeably.

Cancer antigens, such as those present in cancer vaccines or those used to prepare cancer immunotherapies, can be prepared from crude cancer cell extracts, as described in Cohen, et al., 1994, *Cancer Research,* 54:1055, or by partially purifying the antigens, using recombinant technology, or de novo synthesis of known antigens. Cancer antigens can be used in the form of immunogenic portions of a particular antigen or in some instances a whole cell (killed) can be used as the antigen. Such antigens can be isolated or prepared recombinantly or by any other means known in the art.

Examples of cancer antigens include but are not limited to MAGE, MART-1/Melan-A, gp100, dipeptidyl peptidase IV (DPPIV), adenosine deaminase-binding protein (ADAbp), cyclophilin b, colorectal associated antigen (CRC)-0017-1A/GA733, carcinoembryonic antigen (CEA) and its immunogenic epitopes CAP-1 and CAP-2, etv6, amll, prostate specific antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAIVIE, NY-ESO-1, cdc27, adenomatous polyposis coli protein (APC), fodrin, Connexin 37, Ig-idiotype, p15, gp75, GM2 and GD2 gangliosides, viral products such as human papillomavirus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2. This list is not meant to be limiting.

Another form of anti-cancer therapy involves administering an antibody specific for a cell surface antigen of, for example, a cancer cell. In one embodiment, the antibody may be selected from the group consisting of Ributaxin, Herceptin, Rituximab, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egfr3, ior c5, BABS, anti-FLK-2, MDX-260, ANA Ab, SMART 1D10 Ab, SMART ABL 364 Ab and ImmuRAIT-CEA. Other antibodies include but are not limited to anti-CD20 antibodies, anti-CD40 antibodies, anti-CD19 antibodies, anti-CD22 antibodies, anti-HLA-DR antibodies, anti-CD80 antibodies, anti-CD86 antibodies, anti-CD54 antibodies, and anti-CD69 antibodies. These antibodies are available from commercial sources or may be synthesized de novo.

In one embodiment, the methods of the invention can be used in conjunction with one or more other forms of cancer treatment, for example, in conjunction with an anti-cancer agent, chemotherapy, radiotherapy, etc. (e.g., simultaneously, or as part of an overall treatment procedure). The term "cancer treatment" as used herein, may include, but is not limited to, chemotherapy, radiotherapy, adjuvant therapy, vaccination, or any combination of these methods. Parameters of cancer treatment that may vary include, but are not limited to, dosages, timing of administration or duration or therapy; and the cancer treatment can vary in dosage, timing, or duration. Another treatment for cancer is surgery, which can be utilized either alone or in combination with any of the previously treatment methods. Any agent or therapy (e.g., chemotherapies, radiation therapies, surgery, hormonal therapies, and/or biological therapies/immunotherapies) which is known to be useful, or which has been used or is currently being used for the prevention or treatment of cancer can be used in combination with a composition of the invention in accordance with the invention described herein. One of ordinary skill in the medical arts can determine an appropriate treatment for a subject.

Examples of such agents (i.e., anti-cancer agents) include, but are not limited to, DNA-interactive agents including, but not limited to, the alkylating agents (e.g., nitrogen mustards, e.g. Chlorambucil, Cyclophosphamide, Isofamide, Mechlorethamine, Melphalan, Uracil mustard; Aziridine such as Thiotepa; methanesulphonate esters such as Busulfan; nitroso ureas, such as Carmustine, Lomustine, Streptozocin; platinum complexes, such as Cisplatin, Carboplatin; bioreductive alkylator, such as Mitomycin, and Procarbazine, Dacarbazine and Altretamine); the DNA strand-breakage agents, e.g., Bleomycin; the intercalating topoisomerase II inhibitors, e.g., Intercalators, such as Amsacrine, Dactinomycin, Daunorubicin, Doxorubicin, Idarubicin, Mitoxantrone, and nonintercalators, such as Etoposide and Teniposide; the nonintercalating topoisomerase II inhibitors, e.g., Etoposide and Teniposde; and the DNA minor groove binder, e.g., Plicamydin; the antimetabolites including, but not limited to, folate antagonists such as Methotrexate and trimetrexate; pyrimidine antagonists, such as Fluorouracil, Fluorodeoxyuridine, CB3717, Azacitidine and Floxuridine; purine antagonists such as Mercaptopurine, 6-Thioguanine, Pentostatin; sugar modified analogs such as Cytarabine and Fludarabine; and ribonucleotide reductase inhibitors such as hydroxyurea; tubulin Interactive agents including, but not limited to, colcbicine, Vincristine and Vinblastine, both alkaloids and Paclitaxel and cytoxan; hormonal agents including, but note limited to, estrogens, conjugated estrogens and Ethinyl Estradiol and Diethylstilbesterol, Chlortrianisen and Idenestrol; progestins such as Hydroxyprogesterone caproate, Medroxyprogesterone, and Megestrol; and androgens such as testosterone, testosterone propionate; fluoxymesterone, methyltestosterone; adrenal corticosteroid, e.g., Prednisone, Dexamethasone, Methylprednisolone, and Prednisolone; leutinizing hormone releasing hormone agents or gonadotropin-releasing hormone antagonists, e.g., leuprolide acetate and goserelin acetate; antihormonal antigens including, but not limited to, antiestrogenic agents such as Tamoxifen, antiandrogen agents such as Flutamide; and antiadrenal agents such as Mitotane and Aminoglutethimide; cytokines including, but not limited to, IL-1.alpha., IL-1β, IL-2, IL-3, IL-4, IL-5, IL-6, IL-7, IL-8, IL-9, IL-10, IL-11, IL-12, IL-13, IL-18, TGF-β, GM-CSF, M-CSF, G-CSF, TNF-α, TNF-β, LAF, TCGF, BCGF, TRF, BAF, BDG, MP, LIF, OSM, TMF, PDGF, IFN-α, IFN-β, IFN-γ, and Uteroglobins (U.S. Pat. No. 5,696,092); anti-angiogenics including, but not limited to, agents that inhibit VEGF (e.g., other neutralizing antibodies (Kim et al., 1992; Presta et al., 1997; Sioussat et al., 1993; Kondo et al., 1993; Asano et al., 1995, U.S. Pat. No. 5,520,914), soluble receptor constructs (Kendall and Thomas, 1993; Aiello et al., 1995; Lin et al., 1998; Millauer et al., 1996), tyrosine kinase inhibitors (Siemeister et al., 1998, U.S. Pat. Nos. 5,639,757, and 5,792,771), antisense strategies, RNA aptamers and ribozymes against VEGF or VEGF receptors (Saleh et al., 1996; Cheng et al., 1996; Ke et al., 1998; Parry et al., 1999); variants of VEGF with antagonistic properties as described in WO 98/16551; compounds of other chemical classes, e.g., steroids such as the angiostatic 4,9(11)-steroids and C21-oxygenated steroids, as described in U.S. Pat. No. 5,972,922; thalidomide and related compounds, precursors, analogs, metabolites and hydrolysis products, as described in U.S. Pat. Nos. 5,712,291 and 5,593,990; Thrombospondin (TSP-1) and platelet factor 4 (PF4); interferons and metalloproteinsase inhibitors; tissue inhibitors of metalloproteinases (TIMPs); anti-Invasive Factor, retinoic acids and paclitaxel (U.S. Pat. No. 5,716,981); AGM-1470 (Ingber et al., 1990); shark cartilage extract (U.S. Pat. No. 5,618,925); anionic polyamide or polyurea oligomers (U.S. Pat. No. 5,593,664); oxindole derivatives (U.S. Pat. No. 5,576,330); estradiol derivatives (U.S. Pat. No. 5,504,074); thiazolopyrimidine derivatives (U.S. Pat. No. 5,599,813); and LM609 (U.S. Pat. No. 5,753,230); apoptosis-inducing agents including, but not limited to, bcr-abl, bcl-2 (distinct from bcl-1, cyclin Dl; GenBank accession numbers M14745, X06487; U.S. Pat. Nos. 5,650,491; and 5,539,094) and family members including Bcl-x1, Mcl-1, Bak, A1, A20, and antisense nucleotide sequences (U.S. Pat. Nos. 5,650,491; 5,539,094; and 5,583,034); Immunotoxins and coaguligands, tumor vaccines, and antibodies.

Specific examples of anti-cancer agents which can be used in accordance with the methods of the invention include, but not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interieukin II, or rIL2), interferon alpha-2a; interferon alpha-2b; interferon alpha-n1; interferon alpha-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; angiogenesis inhibitors; anti-dorsalizing morphogenetic protein-1; ara-CDP-DL-PTBA; BCR/ABL antagonists; CaRest M3;

CARN 700; casein kinase inhibitors (ICOS); clotrimazole; collismycin A; collismycin B; combretastatin A4; crambescidin 816; cryptophycin 8; curacin A; dehydrodidemnin B; didemnin B; dihydro-5-azacytidine; dihydrotaxol, duocarmycin SA; kahalalide F; lamellarin-N triacetate; leuprolide+estrogen+progesterone; lissoclinamide 7; monophosphoryl lipid A+myobacterium cell wall sk; N-acetyldinaline; N-substituted benzamides; O6-benzylguanine; placetin A; placetin B; platinum complex; platinum compounds; platinum-triamine complex; rhenium Re 186 etidronate; RII retinamide; rubiginone B 1; SarCNU; sarcophytol A; sargramostim; senescence derived inhibitor 1; spicamycin D; tallimustine; 5-fluorouracil; thrombopoietin; thymotrinan; thyroid stimulating hormone; variolin B; thalidomide; velaresol; veramine; verdins; verteporfin; vinorelbine; vinxaltine; vitaxin; zanoterone; zeniplatin; and zilascorb.

The invention also encompasses administration of a composition comprising CLIP inhibitor in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radioactive source is placed inside the body close to cancer cells or a tumor mass.

In specific embodiments, an appropriate anti-cancer regimen is selected depending on the type of cancer. For instance, a patient with ovarian cancer may be administered a prophylactically or therapeutically effective amount of a composition comprising CLIP inhibitor in combination with a prophylactically or therapeutically effective amount of one or more other agents useful for ovarian cancer therapy, including but not limited to, intraperitoneal radiation therapy, such as $P^{32}$ therapy, total abdominal and pelvic radiation therapy, cisplatin, the combination of paclitaxel (Taxol) or docetaxel (Taxotere) and cisplatin or carboplatin, the combination of cyclophosphamide and cisplatin, the combination of cyclophosphamide and carboplatin, the combination of 5-FU and leucovorin, etoposide, liposomal doxorubicin, gemcitabine or topotecan. In a particular embodiment, a prophylactically or therapeutically effective amount of a composition of the invention is administered in combination with the administration of Taxol for patients with platinum-refractory disease. A further embodiment is the treatment of patients with refractory cancer including administration of: ifosfamide in patients with disease that is platinum-refractory, hexamethylmelamine (HMM) as salvage chemotherapy after failure of cisplatin-based combination regimens, and tamoxifen in patients with detectable levels of cytoplasmic estrogen receptor on their tumors.

Cancer therapies and their dosages, routes of administration and recommended usage are known in the art and have been described in such literature as the *Physician's Desk Reference* ($56^{th}$ ed., 2002).

(ix) Alzheimer's Disease

The thymic derived peptides of the invention are also useful in treating Alzheimer's disease. Alzheimer's disease is a degenerative brain disorder characterized by cognitive and noncognitive neuropsychiatric symptoms, which accounts for approximately 60% of all cases of dementia for patients over 65 years old. Psychiatric symptoms are common in Alzheimer's disease, with psychosis (hallucinations and delusions) present in many patients. It is possible that the psychotic symptoms of Alzheimer's disease involve a shift in the concentration of dopamine or acetylcholine, which may augment a dopaminergic/cholinergic balance, thereby resulting in psychotic behavior. For example, it has been proposed that an increased dopamine release may be responsible for the positive symptoms of schizophrenia. This may result in a positive disruption of the dopaminergic/cholinergic balance. In Alzheimer's disease, the reduction in cholinergic neurons effectively reduces acetylcholine release resulting in a negative disruption of the dopaminergic/cholinergic balance. Indeed, antipsychotic agents that are used to relieve psychosis of schizophrenia are also useful in alleviating psychosis in Alzheimer's patients.

(x) Allergic Disease

The thymic derived peptides of the invention are also useful in treating Allergic disease. A "subject having an allergic condition" shall refer to a subject that is currently experiencing or has previously experienced an allergic reaction in response to an allergen. An "allergic condition" or "allergy" refers to acquired hypersensitivity to a substance (allergen). Allergic conditions include but are not limited to eczema, allergic rhinitis or coryza, hay fever, allergic conjunctivitis, asthma, pet allergies, urticaria (hives) and food allergies, other atopic conditions including atopic dermatitis; anaphylaxis; drug allergy; and angioedema.

Allergy is typically an episodic condition associated with the production of antibodies from a particular class of immunoglobulin, IgE, against allergens. The development of an IgE-mediated response to common aeroallergens is also a factor which indicates predisposition towards the development of asthma. If an allergen encounters a specific IgE which is bound to an IgE Fc receptor (FcεR) on the surface of a basophil (circulating in the blood) or mast cell (dispersed throughout solid tissue), the cell becomes activated, resulting in the production and release of mediators such as histamine, serotonin, and lipid mediators.

An allergic reaction occurs when tissue-sensitizing immunoglobulin of the IgE type reacts with foreign allergen. The IgE antibody is bound to mast cells and/or basophils, and these specialized cells release chemical mediators (vasoactive amines) of the allergic reaction when stimulated to do so by allergens bridging the ends of the antibody molecule. Histamine, platelet activating factor, arachidonic acid metabolites, and serotonin are among the best known mediators of allergic reactions in man. Histamine and the other vasoactive amines are normally stored in mast cells and basophil leukocytes. The mast cells are dispersed throughout animal tissue and the basophils circulate within the vascular system. These cells manufacture and store histamine within the cell unless the specialized sequence of events involving IgE binding occurs to trigger its release.

Recently a role for mast cells in Treg-dependent peripheral tolerance has been suggested. Li-Fan Lu et al, *Nature* Mast cells are essential intermediaries in regulatory T-cell tolerance 442, 997-1002 (31 Aug. 2006). It has been proposed that the immune response to allergens in health and disease is the result of a balance between allergen-specific $T_{Reg}$ cells and allergen-specific $T_H2$ cells. Deviation to $T_{Reg}$ cells suppresses the production of $T_H2$-type pro-inflammatory cytokines, induces the production of allergen-specific IgG4 and IgA antibodies, and suppresses effector cells of allergy. The compounds of the invention are useful for regulating Treg activity and thus are useful in the treatment of allergy and asthma.

Symptoms of an allergic reaction vary, depending on the location within the body where the IgE reacts with the antigen. If the reaction occurs along the respiratory epithelium, the symptoms generally are sneezing, coughing and asthmatic reactions. If the interaction occurs in the digestive tract, as in the case of food allergies, abdominal pain and diarrhea are common. Systemic allergic reactions, for example following a bee sting or administration of penicillin to an allergic subject, can be severe and often life-threatening.

"Asthma" as used herein refers to an allergic disorder of the respiratory system characterized by inflammation and narrowing of the airways, and increased reactivity of the airways to inhaled agents. Symptoms of asthma include recurrent episodes of wheezing, breathlessness, chest tightness, and coughing, resulting from airflow obstruction. Airway inflammation associated with asthma can be detected through observation of a number of physiological changes, such as, denudation of airway epithelium, collagen deposition beneath basement membrane, edema, mast cell activation, inflammatory cell infiltration, including neutrophils, eosinophils, and lymphocytes. As a result of the airway inflammation, asthma patients often experience airway hyper-responsiveness, airflow limitation, respiratory symptoms, and disease chronicity. Airflow limitations include acute bronchoconstriction, airway edema, mucous plug formation, and airway remodeling, features which often lead to bronchial obstruction. In some cases of asthma, sub-basement membrane fibrosis may occur, leading to persistent abnormalities in lung function.

Asthma likely results from complex interactions among inflammatory cells, mediators, and other cells and tissues resident in the airways. Mast cells, eosinophils, epithelial cells, macrophage, and activated T cells all play an important role in the inflammatory process associated with asthma. Djukanovic R et al. (1990) *Am Rev Respir Dis* 142:434-457. It is believed that these cells can influence airway function through secretion of preformed and newly synthesized mediators which can act directly or indirectly on the local tissue. It has also been recognized that subpopulations of T lymphocytes (Th2) play an important role in regulating allergic inflammation in the airway by releasing selective cytokines and establishing disease chronicity. Robinson D S et al. (1992) *N Engl J Med* 326:298-304.

Asthma is a complex disorder which arises at different stages in development and can be classified based on the degree of symptoms as acute, subacute, or chronic. An acute inflammatory response is associated with an early recruitment of cells into the airway. The subacute inflammatory response involves the recruitment of cells as well as the activation of resident cells causing a more persistent pattern of inflammation. Chronic inflammatory response is characterized by a persistent level of cell damage and an ongoing repair process, which may result in permanent abnormalities in the airway.

A "subject having asthma" is a subject that has a disorder of the respiratory system characterized by inflammation and narrowing of the airways and increased reactivity of the airways to inhaled agents. Factors associated with initiation of asthma include, but are not limited to, allergens, cold temperature, exercise, viral infections, and $SO_2$.

The composition of the invention may also be administered in conjunction with an anti-allergy therapy. Conventional methods for treating or preventing allergy have involved the use of allergy medicaments or desensitization therapies. Some evolving therapies for treating or preventing allergy include the use of neutralizing anti-IgE antibodies. Anti-histamines and other drugs which block the effects of chemical mediators of the allergic reaction help to regulate the severity of the allergic symptoms but do not prevent the allergic reaction and have no effect on subsequent allergic responses. Desensitization therapies are performed by giving small doses of an allergen, usually by injection under the skin, in order to induce an IgG-type response against the allergen. The presence of IgG antibody helps to neutralize the production of mediators resulting from the induction of IgE antibodies, it is believed. Initially, the subject is treated with a very low dose of the allergen to avoid inducing a severe reaction and the dose is slowly increased. This type of therapy is dangerous because the subject is actually administered the compounds which cause the allergic response and severe allergic reactions can result.

Allergy medicaments include, but are not limited to, anti-histamines, corticosteroids, and prostaglandin inducers. Anti-histamines are compounds which counteract histamine released by mast cells or basophils. These compounds are well known in the art and commonly used for the treatment of allergy. Anti-histamines include, but are not limited to, acrivastine, astemizole, azatadine, azelastine, betatastine, brompheniramine, buclizine, cetirizine, cetirizine analogues, chlorpheniramine, clemastine, CS 560, cyproheptadine, desloratadine, dexchlorpheniramine, ebastine, epinastine, fexofenadine, HSR 609, hydroxyzine, levocabastine, loratidine, methscopolamine, mizolastine, norastemizole, phenindamine, promethazine, pyrilamine, terfenadine, and tranilast. Corticosteroids include, but are not limited to, methylprednisolone, prednisolone, prednisone, beclomethasone, budesonide, dexamethasone, flunisolide, fluticasone propionate, and triamcinolone.

The composition of the invention may also be administered in conjunction with an asthma therapy. Conventional methods for treating or preventing asthma have involved the use of anti-allergy therapies (described above) and a number of other agents, including inhaled agents. Medications for the treatment of asthma are generally separated into two categories, quick-relief medications and long-term control medications. Asthma patients take the long-term control medications on a daily basis to achieve and maintain control of persistent asthma. Long-term control medications include anti-inflammatory agents such as corticosteroids, chromolyn sodium and nedocromil; long-acting bronchodilators, such as long-acting $\beta_2$-agonists and methylxanthines; and leukotriene modifiers. The quick-relief medications include short-acting $\beta_2$ agonists, anti-cholinergics, and systemic corticosteroids. Asthma medicaments include, but are not limited, PDE-4 inhibitors, bronchodilator/beta-2 agonists, K+ channel openers, VLA-4 antagonists, neurokin antagonists, thromboxane A2 (TXA2) synthesis inhibitors, xanthines, arachidonic acid antagonists, 5 lipoxygenase inhibitors, TXA2 receptor antagonists, TXA2 antagonists, inhibitor of 5-lipox activation proteins, and protease inhibitors. Bronchodilator/$\beta_2$ agonists are a class of compounds which cause bronchodilation or smooth muscle relaxation. Bronchodilator/$\beta_2$ agonists include, but are not limited to, salmeterol, salbutamol, albuterol, terbutaline, D2522/formoterol, fenoterol, bitolterol, pirbuerol methylxanthines and orciprenaline.

(xi) Characterization and Demonstration of CLIP Inhibitor Activity

The activity of the CLIP inhibitors used in accordance with the present invention can be determined by any method known in the art. In one embodiment, the activity of a CLIP inhibitor is determined by using various experimental animal models, including but not limited to, cancer animal models such as scid mouse model or nude mice with human tumor grafts known in the art and described in Yamanaka, 2001, Microbiol Immunol 2001; 45(7): 507-14, which is incorporated herein by reference, animal models of infectious disease or other disorders.

Various in vitro and in vivo assays that test the activities of a CLIP inhibitor are used in purification processes of a CLIP inhibitor. The protocols and compositions of the invention are also preferably tested in vitro, and then in vivo, for the desired therapeutic or prophylactic activity, prior to use in humans.

For instance, the CLIP inhibitor binds to MHC, preferably in a selective manner. As used herein, the terms "selective binding" and "specific binding" are used interchangeably to refer to the ability of the peptide to bind with greater affinity to MHC and fragments thereof than to unrelated proteins.

Peptides can be tested for their ability to bind to MHC using standard binding assays known in the art or the assays experimental and computational described in the examples. As an example of a suitable assay, MHC can be immobilized on a surface (such as in a well of a multi-well plate) and then contacted with a labeled peptide. The amount of peptide that binds to the MHC (and thus becomes itself immobilized onto the surface) may then be quantitated to determine whether a particular peptide binds to MHC. Alternatively, the amount of peptide not bound to the surface may also be measured. In a variation of this assay, the peptide can be tested for its ability to bind directly to a MHC-expressing cell.

Compounds for use in therapy can be tested in suitable animal model systems prior to testing in humans, including but not limited to in rats, mice, chicken, cows, monkeys, rabbits, etc. The principle animal models for cancer known in the art and widely used include, but not limited to, mice, as described in Hann et al., 2001, Curr Opin Cell Biol 2001 December; 13(6): 778-84.

In one embodiment, the S-180 cell line (ATCC CCL 8, batch F4805) is chosen as the tumor model because the same line is capable of growing both in animals and in culture (in both serum-containing and serum-free conditions). Tumors are established in mice (BALB/c) by injection of cell suspensions obtained from tissue culture. Approximately $1\times10^6$ to $3\times10^6$ cells are injected intra-peritoneally per mouse. The tumor developed as multiple solid nodules at multiple sites within the peritoneal cavity and cause death in most of the animals within 10 to 15 days. In addition to monitoring animal survival, their condition is qualitatively assessed as tumor growth progressed and used to generate a tumor index as described in the following paragraph.

To establish an estimate of drug activity in tumor model experiments, an index can be developed that combines observational examination of the animals as well as their survival status. For example, mice are palpated once or twice weekly for the presence, establishment and terminal progression of the intraperitoneal S180 tumor. Tumor development and progression is assessed in these mice according to the following scale: "0"—no tumor palpated; "1"—initial tumor appears to be present; small in size (~1 mm); no distended abdomen; "2"—tumor appears to be established; some distension of the abdomen; no apparent cachexia; "3"—tumor is well established, marked abdominal distension, animal exhibits cachexia; and, "4"—animal is dead. The index value for a treatment group is the average of the individual mouse indices in the group.

In vitro and animal models of HIV have also been described. For instance some animal models are described in McCune J. M., AIDS RESEARCH: Animal Models of HIV-1 Disease *Science* 19 Dec. 1997:Vol. 278. no. 5346, pp. 2141-2142 and K Uberla et al PNAS Animal model for the therapy of acquired immunodeficiency syndrome with reverse transcriptase inhibitors Aug. 29, 1995 vol. 92 no. 18 8210-8214. Uberla et al describes the development of an animal model for the therapy of the HIV-1 infection with RT inhibitors. In the study the RT of the simian immunodeficiency virus (SIV) was replaced by the RT of HIV-1. It was demonstrated that macaques infected with this SIV/HIV-1 hybrid virus developed AIDS-like symptoms and pathology. The authors concluded that "infection of macaques with the chimeric virus seems to be a valuable model to study the in vivo efficacy of new RT inhibitors, the emergence and reversal of drug resistance, the therapy of infections with drug-resistant viruses, and the efficacy of combination therapy."

Further, any assays known to those skilled in the art can be used to evaluate the prophylactic and/or therapeutic utility of the combinatorial therapies disclosed herein for treatment or prevention of cancer and/or infectious diseases.

(xii) Combinations with Antibodies and Other CLIP Inhibitors

In some aspects, the invention provides methods and kits that include anti-CLIP and anti-HLA binding molecules as well as B-cell binding molecules. Binding molecules include peptides, antibodies, antibody fragments and small molecules in addition to the peptides of the invention. CLIP and HLA binding molecules bind to CLIP molecules and HLA respectively on the surface of cells. The binding molecules are referred to herein as isolated molecules that selectively bind to molecules such as CLIP and HLA. A molecule that selectively binds to CLIP and HLA as used herein refers to a molecule, e.g, small molecule, peptide, antibody, fragment, that interacts with CLIP and HLA. In some embodiments the molecules are peptides.

The peptides minimally comprise regions that bind to CLIP and HLA. CLIP and HLA-binding regions, in some embodiments derive from the CLIP and HLA-binding regions of known or commercially available antibodies, or alternatively, they are functionally equivalent variants of such regions.

Antibodies that bind to other B cell surface molecules such as CD20 are also encompassed within this aspect of the invention. An anti-CD20 antibody approved for use in humans is a chimeric anti-CD20 antibody C2B8 (Rituximab; RITUXAN, DEC Pharmaceuticals, San Diego, Calif.; Genentech, San Francisco, Calif). Although not wishing to be bound by a mechanism, it is believed that such antibodies are good adjunctive therapies of the invention because they assist in killing the B cells.

The term "antibody" herein is used in the broadest sense and specifically covers intact monoclonal antibodies, polyclonal antibodies, multi specific antibodies (e.g. bispecific antibodies) formed from at least two intact antibodies, antibody fragments, so long as they exhibit the desired biological activity, and antibody like molecules such as scFv. A native antibody usually refers to heterotetrameric glycoproteins composed of two identical light (L) chains and two identical heavy (H) chains. Each heavy and light chain has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

Numerous CLIP and HLA antibodies are available commercially for research purposes. Certain portions of the variable domains differ extensively in sequence among antibodies and are used in the binding and specificity of each particular antibody for its particular antigen. However, the variability is not evenly distributed throughout the variable domains of antibodies. It is concentrated in three or four segments called "complementarity-determining regions" (CDRs) or "hypervariable regions" in both in the light-chain and the heavy-chain variable domains. The more highly conserved portions of variable domains are called the framework (FR). The variable domains of native heavy and light chains each comprise four or five FR regions, largely adopting a β-sheet configuration, connected by the CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., NIH Publ. No. 91-3242, Vol. I, pages 647-669 (1991)). The constant domains are not necessarily involved directly in binding an antibody to an antigen, but exhibit various effector functions, such as participation of the antibody in antibody-dependent cellular toxicity.

A hypervariable region or CDR as used herein defines a subregion within the variable region of extreme sequence variability of the antibody, which form the antigen-binding site and are the main determinants of antigen specificity. According to one definition, they can be residues (Kabat nomenclature) 24-34 (L1), 50-56 (L2) and 89-97 (L3) in the light chain variable region and residues (Kabat nomenclature 31-35 (H1), 50-65 (H2), 95-102 (H3) in the heavy chain variable region. Kabat et al., Sequences of Proteins of Immunological Interest, 5th Ed. Public Health Service, National Institute of Health, Bethesda, Md. [1991]).

An "intact" antibody is one which comprises an antigen-binding variable region as well as a light chain constant domain ($C_L$) and heavy chain constant domains, $C_{H1}$, $C_{H2}$ and $C_{H3}$. The constant domains may be native sequence constant domains (e.g. human native sequence constant domains) or amino acid sequence variant thereof. Preferably, the intact antibody has one or more effector functions.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. For example, the antibody fragments can be isolated from antibody phage libraries. Alternatively, Fab'-SH fragments can be directly recovered from *E. coli* and chemically coupled to form $F(ab')_2$ fragments (Carter et al., Bio/Technology 10:163-167 (1992)). According to another approach, $F(ab')_2$ fragments can be isolated directly from recombinant host cell culture.

"Antibody fragments" comprise a portion of an intact antibody, preferably the antigen binding or variable region of the intact antibody. Examples of antibody fragments include Fab, Fab', $F(ab')_2$, and Fv fragments; diabodies; single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

The "hinge region," and variations thereof, as used herein, includes the meaning known in the art, which is illustrated in, for example, Janeway et al., Immuno Biology: the immune system in health and disease, (Elsevier Science Ltd., NY) (4th ed., 1999)

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The "light chains" of antibodies (immunoglobulins) from any vertebrate species can be assigned to one of two clearly distinct types, called kappa (K) and lambda (λ), based on the amino acid sequences of their constant domains.

The peptides useful herein are isolated peptides. As used herein, the term "isolated" means that the referenced material is removed from its native environment, e.g., a cell. Thus, an isolated biological material can be free of some or all cellular components, i.e., components of the cells in which the native material is occurs naturally (e.g., cytoplasmic or membrane component). The isolated peptides may be substantially pure and essentially free of other substances with which they may be found in nature or in vivo systems to an extent practical and appropriate for their intended use. In particular, the peptides are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in living systems.

The term "purified" in reference to a protein or a nucleic acid, refers to the separation of the desired substance from contaminants to a degree sufficient to allow the practioner to use the purified substance for the desired purpose. Preferably this means at least one order of magnitude of purification is achieved, more preferably two or three orders of magnitude, most preferably four or five orders of magnitude of purification of the starting material or of the natural material. In specific embodiments, a purified thymus derived peptide is at least 60%, at least 80%, or at least 90% of total protein or nucleic acid, as the case may be, by weight. In a specific embodiment, a purified thymus derived peptide is purified to homogeneity as assayed by, e.g., sodium dodecyl sulfate polyacrylamide gel electrophoresis, or agarose gel electrophoresis.

The CLIP and HLA binding molecules bind to CLIP and HLA, preferably in a selective manner. As used herein, the terms "selective binding" and "specific binding" are used interchangeably to refer to the ability of the peptide to bind with greater affinity to CLIP and HLA and fragments thereof than to non-CLIP and HLA derived compounds. That is, peptides that bind selectively to CLIP and HLA will not bind to non-CLIP and HLA derived compounds to the same extent and with the same affinity as they bind to CLIP and HLA and fragments thereof, with the exception of cross reactive antigens or molecules made to be mimics of CLIP and HLA such as peptide mimetics of carbohydrates or variable regions of anti-idiotype antibodies that bind to the CLIP and HLA-binding peptides in the same manner as CLIP and HLA. In some embodiments, the CLIP and HLA binding molecules bind solely to CLIP and HLA and fragments thereof "Isolated antibodies" as used herein refer to antibodies that are substantially physically separated from other cellular material (e.g., separated from cells which produce the antibodies) or from other material that hinders their use either in the diagnostic or therapeutic methods of the invention. Preferably, the isolated antibodies are present in a homogenous population of antibodies (e.g., a population of monoclonal antibodies). Compositions of isolated antibodies can however be combined with other components such as but not limited to pharmaceutically acceptable carriers, adjuvants, and the like.

In one embodiment, the CLIP and HLA peptides useful in the invention are isolated intact soluble monoclonal antibodies specific for CLIP and HLA. As used herein, the term "monoclonal antibody" refers to a homogenous population of immunoglobulins that specifically bind to an identical epitope (i.e., antigenic determinant).

In other embodiments, the peptide is an antibody fragment. As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford; and Pier G B, Lyczak J B, Wetzler L M, (eds). Immunology, Infection and Immunity (2004) 1$^{st}$ Ed. American Society for Microbiology Press, Washington D.C.). The pFc' and Fc regions of the antibody, for example, are effectors of the complement cascade and can mediate binding to Fc receptors on phagocytic cells, but are not involved in antigen binding. An antibody from which the pFc' region has been enzymatically cleaved, or which has been produced without the pFc' region, designated an $F(ab')_2$ fragment, retains both of the antigen binding sites of an intact antibody. An isolated $F(ab')_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', $F(ab')_2$ and Fv are employed with either standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology,* 7th Ed., (Blackwell Scientific Publications, Oxford); and Pier G B, Lyczak J B, Wetzler L M, (eds). Immunology, Infection and Immunity (2004) 1$^{st}$ Ed. American Society for Microbiology Press, Washington D.C.].

The anti-CLIP and HLA antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biot, 2:593-596 (1992)].

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody.

As an alternative to humanization, human antibodies can be generated. A "human antibody" is one which possesses an amino acid sequence which corresponds to that of an antibody produced by a human and/or has been made using any techniques for making human antibodies. This definition of a human antibody specifically excludes a humanized antibody comprising non-human antigen-binding residues. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369 and 5,545,807.

Human monoclonal antibodies also may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, new York, 1987), and Boerner el al., *J. Immunol.,* 147: 86-95 (1991).

The invention also encompasses the use of single chain variable region fragments (scFv). Single chain variable region fragments are made by linking light and/or heavy chain variable regions by using a short linking peptide. Any peptide having sufficient flexibility and length can be used as a linker in a scFv. Usually the linker is selected to have little to no immunogenicity. An example of a linking peptide is multiple GGGGS residues, which bridge the carboxy terminus of one variable region and the amino terminus of another variable region. Other linker sequences may also be used.

All or any portion of the heavy or light chain can be used in any combination. Typically, the entire variable regions are included in the scFv. For instance, the light chain variable region can be linked to the heavy chain variable region. Alternatively, a portion of the light chain variable region can be linked to the heavy chain variable region, or portion thereof. Also contemplated are scFvs in which the heavy chain variable region is from the antibody of interest, and the light chain variable region is from another immunoglobulin.

The scFvs can be assembled in any order, for example, $V_H$-linker-$V_L$ or $V_L$-linker-$V_H$. There may be a difference in the level of expression of these two configurations in particular expression systems, in which case one of these forms may be preferred. Tandem scFvs can also be made, such as (X)-linker-(X)-linker-(X), in which X are polypeptides form the antibodies of interest, or combinations of these polypeptides with other polypeptides. In another embodiment, single chain antibody polypeptides have no linker polypeptide, or just a short, inflexible linker. Possible configurations are $V_L$-$V_H$ and $V_H$-$V_L$. The linkage is too short to permit interaction between $V_L$ and $V_H$ within the chain, and the chains form homodimers with a $V_L/V_H$ antigen binding site at each end. Such molecules are referred to in the art as "diabodies".

Single chain variable regions may be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*, and the expressed protein may be isolated using standard protein purification techniques.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad Sci. USA, 90: 6444-6448 (1993).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

Peptides, including antibodies, can be tested for their ability to bind to CLIP and HLA using standard binding assays known in the art. As an example of a suitable assay, CLIP and HLA can be immobilized on a surface (such as in a well of a multi-well plate) and then contacted with a labeled peptide. The amount of peptide that binds to the CLIP and HLA (and thus becomes itself immobilized onto the surface) may then be quantitated to determine whether a particular peptide binds to CLIP and HLA. Alternatively, the amount of peptide not bound to the surface may also be measured. In a variation of this assay, the peptide can be tested for its ability to bind directly to a CLIP and HLA-expressing cell.

The invention also encompasses small molecules that bind to CLIP and HLA. Such binding molecules may be identified by conventional screening methods, such as phage display procedures (e.g. methods described in Hart et al., *J. Biol. Chem.* 269:12468 (1994)). Hart et al. report a filamentous phage display library for identifying novel peptide ligands. In general, phage display libraries using, e.g., M13 or fd phage, are prepared using conventional procedures such as those described in the foregoing reference. The libraries generally display inserts containing from 4 to 80 amino acid residues. The inserts optionally represent a completely degenerate or biased array of peptides. Ligands having the appropriate binding properties are obtained by selecting those phage which express on their surface a ligand that binds to the target molecule. These phage are then subjected to several cycles of reselection to identify the peptide ligand expressing phage that have the most useful binding characteristics. Typically, phage that exhibit the best binding characteristics (e.g., highest affinity) are further characterized by nucleic acid analysis to identify the particular amino acid sequences of the peptide expressed on the phage surface in the optimum length of the express peptide to achieve optimum binding. Phage-display peptide or antibody library is also described in Brissette R et al Curr Opin Drug Discov Devel. 2006 May; 9(3):363-9.

Alternatively, binding molecules can be identified from combinatorial libraries. Many types of combinatorial libraries have been described. For instance, U.S. Pat. No. 5,712,171 (which describes methods for constructing arrays of synthetic molecular constructs by forming a plurality of molecular constructs having the scaffold backbone of the chemical molecule and modifying at least one location on the molecule in a logically-ordered array); U.S. Pat. No. 5,962,412 (which describes methods for making polymers having specific physiochemical properties); and U.S. Pat. No. 5,962,736 (which describes specific arrayed compounds).

Other binding molecules may be identified by those of skill in the art following the guidance described herein. Library technology can be used to identify small molecules, including small peptides, which bind to CLIP and HLA and interrupt its function. One advantage of using libraries for antagonist identification is the facile manipulation of millions of different putative candidates of small size in small reaction volumes (i.e., in synthesis and screening reactions). Another advantage of libraries is the ability to synthesize antagonists which might not otherwise be attainable using naturally occurring sources, particularly in the case of non-peptide moieties.

Small molecule combinatorial libraries may also be generated. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A "compound array" as used herein is a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in PCT published patent application W095/18972, published Jul. 13, 1995 and U.S. Pat. No. 5,712,171 granted Jan. 27, 1998 and its corresponding PCT published patent application W096/22529, which are hereby incorporated by reference.

The CLIP and HLA binding molecules described herein can be used alone or in conjugates with other molecules such as detection or cytotoxic agents in the detection and treatment methods of the invention, as described in more detail herein.

Typically, one of the components usually comprises, or is coupled or conjugated to a detectable label. A detectable label is a moiety, the presence of which can be ascertained directly or indirectly. Generally, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin, and enzyme tags such as horseradish peroxidase, β-galactosidase, etc. The label may be bound to a peptide during or following its synthesis. There are many different labels and methods of labeling known to those of ordinary skill in the art. Examples of the types of labels that can be used in the present invention include enzymes, radioisotopes, fluorescent compounds, colloidal metals, chemiluminescent compounds, and bioluminescent compounds. Those of ordinary skill in the art will know of other suitable labels for the peptides described herein, or will be able to ascertain such, using routine experimentation. Furthermore, the coupling or conjugation of these labels to the peptides of the invention can be performed using standard techniques common to those of ordinary skill in the art.

Another labeling technique which may result in greater sensitivity consists of coupling the molecules described herein to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

Conjugation of the peptides including antibodies or fragments thereof to a detectable label facilitates, among other things, the use of such agents in diagnostic assays. Another category of detectable labels includes diagnostic and imaging labels (generally referred to as in vivo detectable labels) such as for example magnetic resonance imaging (MRI): Gd(DOTA); for nuclear medicine: $^{201}$T1, gamma-emitting radionuclide 99mTc; for positron-emission tomography (PET): positron-emitting isotopes, (18)F-fluorodeoxyglucose ((18)FDG), (18)F-fluoride, copper-64, gadodiamide, and radioisotopes of Pb(II) such as 203Pb; 111In.

The conjugations or modifications described herein employ routine chemistry, which chemistry does not form a part of the invention and which chemistry is well known to those skilled in the art of chemistry. The use of protecting groups and known linkers such as mono- and hetero-bifunctional linkers are well documented in the literature and will not be repeated here.

As used herein, "conjugated" means two entities stably bound to one another by any physiochemical means. It is important that the nature of the attachment is such that it does not impair substantially the effectiveness of either entity. Keeping these parameters in mind, any covalent or non-covalent linkage known to those of ordinary skill in the art may be employed. In some embodiments, covalent linkage is preferred. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The conjugates also include an antibody conjugated to a cytotoxic agent such as a chemotherapeutic agent, toxin (e.g. an enzymatically active toxin of bacterial, fungal, plant or animal origin, or fragments thereof, or a small molecule toxin), or a radioactive isotope (i.e., a radioconjugate). Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). Enzymatically active toxins and fragments thereof which can be used in the conjugates include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes.

For selective destruction of the cell, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99}m$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail. Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

Additionally the peptides of the invention may be administered in combination with a glycolytic inhibitor and or a halogenated alky ester. The glycolytic inhibitor and or a halogenated alky ester also function as CLIP activity inhibitors that displace CLIP from the MHC on the cell surface. Preferred glycolytic inhibitors are 2-deoxyglucose compounds, defined herein as 2-deoxy-D-glucose, and homologs, analogs, and/or derivatives of 2-deoxy-D-glucose. While the levo form is not prevalent, and 2-deoxy-D-glucose is preferred, the term "2-deoxyglucose" is intended to cover inter alia either 2-deoxy-D-glucose and 2-deoxy-L-glucose, or a mixture thereof.

Examples of 2-deoxyglucose compounds useful in the invention are: 2-deoxy-D-glucose, 2-deoxy-L-glucose; 2-bromo-D-glucose, 2-fluoro-D-glucose, 2-iodo-D-glucose, 6-fluoro-D-glucose, 6-thio-D-glucose, 7-glucosyl fluoride, 3-fluoro-D-glucose, 4-fluoro-D-glucose, 1-O-propyl ester of 2-deoxy-D-glucose, 1-O-tridecyl ester of 2-deoxy-D-glucose, 1-O-pentadecyl ester of 2-deoxy-D-glucose, 3-O-propyl ester of 2-deoxy-D-glucose, 3-O-tridecyl ester of 2-deoxy-D-glucose, 3-O-pentadecyl ester of 2-deoxy-D-glucose, 4-O-propyl ester of 2-deoxy-D-glucose, 4-O-tridecyl ester of 2-deoxy-D-glucose, 4-O-pentadecyl ester of 2-deoxy-D-glucose, 6-O-propyl ester of 2-deoxy-D-glucose, 6-O-tridecyl ester of 2-deoxy-D-glucose, 6-O-pentadecyl ester of 2-deoxy-D-glucose, and 5-thio-D-glucose, and mixtures thereof.

Glycolytic inhibitors particularly useful herein can have the formula:

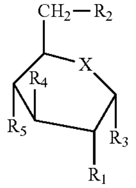

wherein: X represents an O or S atom; $R_1$ represents a hydrogen atom or a halogen atom; $R_2$ represents a hydroxyl group, a halogen atom, a thiol group, or CO-$R_6$; and $R_3$, $R_4$, and $R_5$ each represent a hydroxyl group, a halogen atom, or CO—$R_6$ wherein $R_6$ represents an alkyl group of from 1 to 20 carbon atoms, and wherein at least two of $R_3$, $R_4$, and $R_5$ are hydroxyl groups. The halogen atom is preferably F, and $R_6$ is preferably a $C_3$-$C_{15}$ alkyl group. A preferred glycolytic inhibitor is 2-deoxy-D-glucose. Such glycolytic inhibitors are described in detail in application Ser. No. 10/866,541, filed Jun. 11, 2004, by M. K. Newell et al., the disclosure of which is incorporated herein by reference.

In some embodiments of the invention, one can remove CLIP by administering as a pharmacon a combination of a glycolytic inhibitor and a halogenated alky ester. The combination is preferably combined as a single bifunctional compound acting as a prodrug, which is hydrolyzed by one or more physiologically available eterases. Because of the overall availability of the various esterases in physiological conditions, one can form an ester by combining the glycolytic inhibitor and the halogenated alkyl ester. The prodrug will be hydrolyzed by a physiologically available esterase into its two functional form.

In other particular embodiments, the halogenated alkyl ester has the formula: $R^7{}_mCH_{1-m}X_2R^8{}_nCOOY$ where $R^7$ is methyl, ethyl, propyl or butyl, m and n are each is 0 or 1, $R^8$ is CH or CHCH, X is a halogen, for example independently selected from chlorine, bromine, iodine and fluorine. When used as a separate compound, Y is an alkali metal or alkaline earth metal ion such as sodium, potassium, calcium, and magnesium, ammonium, and substituted ammonium where the substituent is a mono- or di-lower alkyl radical of 1-4 carbon atoms and ethylene diammonium. When used combined with the glycolytic inhibitor as a prodrug. Y is esterified with the glycolytic inhibitor as described in the Methods and Materials section below.

Preferred prodrugs are those prepared by esterification of dichloroacetic acid, exemplified by the following structures:

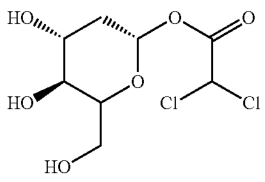

(2S,4R,5S)-4,5-dihydroxy-6-(hydroxymethyl)tetrahydro-2 H-pyran-2-yl dichloroacetate

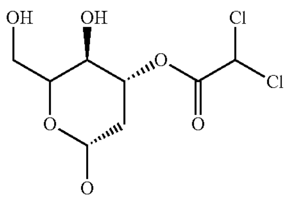

(3S,4R,6R)-3,6-dihydroxy-2-(hydroxymethyl)tetrahydro-2 H-pyran-4-yl dichloroacetate

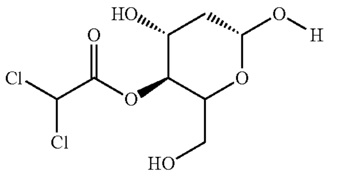

(3S,4R,6R)-4,6-dihydroxy-2-(hydroxymethyl)tetrahydro-2 H-pyran-3-yl dichloroacetate -continued

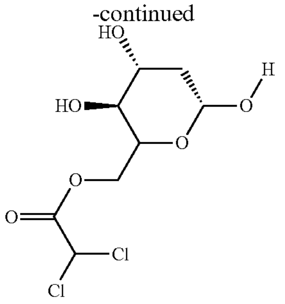

[(3S,4R,6R)-3,4,6-trihydroxytetrahydro-2 H-pyran-2-yl]methyl dichloroacetate

In certain embodiments, the method for treating a subject involves administering to the subject in addition to the peptides described herein an effective amount of a nucleic acid such as a small interfering nucleic acid molecule such as antisense, RNAi, or siRNA oligonucleotide to reduce the level of CLIP molecule, HLA-DO, or HLA-DM expression. The nucleotide sequences of CLIP molecules, HLA-DO, and HLA-DM are all well known in the art and can be used by one of skill in the art using art recognized techniques in combination with the guidance set forth below to produce the appropriate siRNA molecules. Such methods are described in more detail below.

The invention features the use of small nucleic acid molecules, referred to as small interfering nucleic acid (siNA) that include, for example: microRNA (miRNA), small interfering RNA (siRNA), double-stranded RNA (dsRNA), and short hairpin RNA (shRNA) molecules. An siNA of the invention can be unmodified or chemically-modified. An siNA of the instant invention can be chemically synthesized, expressed from a vector or enzymatically synthesized as discussed herein. The instant invention also features various chemically-modified synthetic small interfering nucleic acid (siNA) molecules capable of modulating gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity. The siNA molecules of the instant invention provide useful reagents and methods for a variety of therapeutic applications.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al, 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. (All these publications are hereby incorporated by reference herein).

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'amino, 2'-C-allyl, 2'-flouro, 2'-O-methyl, 2'-H, nucleotide base modifications (for a review see Usman and Cedergren, 1992, TIM. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565 568; Pieken et al. Science, 1991, 253, 314317; Usman and Cedergren, Trends in Biochem. Sci., 1992, 17, 334 339; Usman et al. International Publication PCT No. WO 93/15187; Sproat, U.S. Pat. No. 5,334,711 and Beigelman et al., 1995, *J. Biol. Chem.,* 270, 25702; Beigelman et al., International PCT publication No. WO 97/26270; Beigelman et al., U.S. Pat. No. 5,716,824; Usman et al., molecule comprises one or more chemical modifications.

In one embodiment, one of the strands of the double-stranded siNA molecule comprises a nucleotide sequence that is complementary to a nucleotide sequence of a target RNA or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In another embodiment, each strand of the siNA molecule comprises about 19 to about 23 nucleotides, and each strand comprises at least about 19 nucleotides that are complementary to the nucleotides of the other strand.

In some embodiments an siNA is an shRNA, shRNA-mir, or microRNA molecule encoded by and expressed from a genomically integrated transgene or a plasmid-based expression vector. Thus, in some embodiments a molecule capable of inhibiting mRNA expression, or microRNA activity, is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems.

In some embodiments, a small interfering nucleic acid of the invention is expressed in mammalian cells using a mammalian expression vector. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the myosin heavy chain promoter, albumin promoter, lymphoid-specific promoters, neuron specific promoters, pancreas specific promoters, and mammary gland specific promoters. Developmentally-regulated promoters are also encompassed, for example the murine hox promoters and the a-fetoprotein promoter.

Other inhibitor molecules that can be used include ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., *J. Biol. Chem.* 269(46):28543-6, 1994; Dosaka-Akita et al., Am. J. Clin. Pathol. 102(5):660-4, 1994; Feng et al., Cancer Res. 55(10):2024-8, 1995; Quattrone et al., Cancer Res. 55(1):90-5, 1995; Lewin et al., Nat Med. 4(8):967-71, 1998). For example, neoplastic reversion was obtained using a ribozyme targeted to an H-Ras mutation in bladder carcinoma cells (Feng et al., Cancer Res. 55(10): 2024-8, 1995). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6):643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9,1996). Multitarget ribozymes (connected or shotgun) have been suggested as a means of improving efficiency of ribozymes for gene suppression (Ohkawa et al., Nucleic Acids Symp Ser. (29):121-2, 1993).

Triple helix approaches have also been investigated for sequence-specific gene suppression. Triple helix forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Hanvey et al., Antisense Res. Dev. 1(4): 307-17, 1991; Knudsen and Nielson Nucleic Acids Res. 24(3):494-500, 1996; Taylor et al., Arch. Surg. 132(11): 1177-83, 1997). Minor-groove binding polyamides can bind in a sequence-specific manner to DNA targets and hence may represent useful small molecules for future suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). In some cases suppression strategies have led to a reduction in RNA levels without a concomitant reduction in proteins, whereas in others, reductions in RNA have been mirrored by reductions in protein.

The diverse array of suppression strategies that can be employed includes the use of DNA and/or RNA aptamers that can be selected to target, for example CLIP or HLA-DO. Suppression and replacement using aptamers for suppression in conjunction with a modified replacement gene and encoded protein that is refractory or partially refractory to aptamer-based suppression could be used in the invention.

(xiii) Dosage Regimens

Toxicity and efficacy of the prophylactic and/or therapeutic protocols of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

Subject doses of the compounds described herein typically range from about 0.1 μg to 10,000 mg, more typically from about 1 μg/day to 8000 mg, and most typically from about 10 μg to 100 μg. Stated in terms of subject body weight, typical dosages range from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the molecules of the invention are also contemplated. In some instances, when the molecules of the invention are administered with another therapeutic, for instance, an anti-HIV agent a sub-therapeutic dosage of either the molecules or the an anti-HIV agent, or a sub-therapeutic dosage of both, is used in the treatment of a subject having, or at risk of developing, HIV. When the two classes of drugs are used together, the an anti-HIV agent may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of a an anti-HIV agent is one which would not produce the desired therapeutic result in the subject in the absence of the administration of the molecules of the invention. Therapeutic doses of an anti-HIV agents are well known in the field of medicine for the treatment of HIV. These dosages have been extensively described in references such as Remington's Pharmaceutical Sciences; as well as many other medical references relied upon by the medical profession as guidance for the treatment of infectious disease, cancer, autoimmune disease, Alzheimer's disease and graft rejection. Therapeutic dosages of peptides have also been described in the art.

xiv) Administrations, Formulations

The CLIP inhibitors described herein can be used alone or in conjugates with other molecules such as detection or cytotoxic agents in the detection and treatment methods of the invention, as described in more detail herein.

Typically, one of the components usually comprises, or is coupled or conjugated to a detectable label. A detectable label is a moiety, the presence of which can be ascertained directly or indirectly. Generally, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin, and enzyme tags such as horseradish peroxidase, β-galactosidase, etc. The label may be bound to a peptide during or following its synthesis. There are many different labels and methods of labeling known to those of ordinary skill in the art. Examples of the types of labels that can be used in the present invention include enzymes, radioisotopes, fluorescent compounds, colloidal metals, chemiluminescent compounds, and bioluminescent compounds. Those of ordinary skill in the art will know of other suitable labels for the peptides described herein, or will be able to ascertain such, using routine experimentation. Furthermore, the coupling or conjugation of these labels to the peptides of the invention can be performed using standard techniques common to those of ordinary skill in the art.

Another labeling technique which may result in greater sensitivity consists of coupling the molecules described herein to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

Conjugation of the peptides to a detectable label facilitates, among other things, the use of such agents in diagnostic assays. Another category of detectable labels includes diagnostic and imaging labels (generally referred to as in vivo detectable labels) such as for example magnetic resonance imaging (MRI): Gd(DOTA); for nuclear medicine: $^{201}$Tl, gamma-emitting radionuclide 99mTc; for positron-emission tomography (PET): positron-emitting isotopes, (18)F-fluorodeoxyglucose ((18)FDG), (18)F-fluoride, copper-64, gadodiamide, and radioisotopes of Pb(II) such as 203Pb; 111In.

The conjugations or modifications described herein employ routine chemistry, which chemistry does not form a part of the invention and which chemistry is well known to those skilled in the art of chemistry. The use of protecting groups and known linkers such as mono- and hetero-bifunctional linkers are well documented in the literature and will not be repeated here.

As used herein, "conjugated" means two entities stably bound to one another by any physiochemical means. It is important that the nature of the attachment is such that it does not impair substantially the effectiveness of either entity. Keeping these parameters in mind, any covalent or non-covalent linkage known to those of ordinary skill in the art may be employed. In some embodiments, covalent linkage is preferred. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The conjugates also include a peptide conjugated to another peptide such as CD4, gp120 or gp21. CD4, gp120 and gp21 peptides are all known in the art.

The active agents of the invention are administered to the subject in an effective amount for treating disorders such as autoimmune disease, viral infection, bacterial infection, HIV infection, Alzheimer's disease, graft rejection, and cancer. An "effective amount", for instance, is an amount necessary or sufficient to realize a desired biologic effect. An "effective amount for treating HIV", for instance, could be that amount necessary to (i) prevent HIV uptake by the host cell and/or (ii) inhibit the further development of the HIV infection, i.e., arresting or slowing its development. That amount necessary for treating autoimmune disease may be an amount sufficient to prevent or inhibit a decrease in $T_H$ cells compared to the levels in the absence of peptide treatment. According to some aspects of the invention, an effective amount is that amount of a compound of the invention alone or in combination with another medicament, which when combined or co-administered or administered alone, results in a therapeutic response to the disease, either in the prevention or the treatment of the disease. The biological effect may be the amelioration and or absolute elimination of symptoms resulting from the disease. In another embodiment, the biological effect is the complete abrogation of the disease, as evidenced for example, by the absence of a symptom of the disease.

The effective amount of a compound of the invention in the treatment of a disease described herein may vary depending upon the specific compound used, the mode of delivery of the compound, and whether it is used alone or in combination. The effective amount for any particular application can also vary depending on such factors as the disease being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards. The compounds are generally suitable for administration to humans. This term requires that a compound or composition be nontoxic and sufficiently pure so that no further manipulation of the compound or composition is needed prior to administration to humans.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The agent may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences (1990), incorporated herein by reference). In a particular embodiment, intraperitoneal injection is contemplated.

In any case, the composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The composition of the invention can be used directly or can be mixed with suitable adjuvants and/or carriers. Suitable adjuvants include aluminum salt adjuvants, such as aluminum phosphate or aluminum hydroxide, calcium phosphate nanoparticles (BioSante Pharmaceuticals, Inc.), ZADAXIN™, nucleotides ppGpp and pppGpp, killed *Bordetella pertussis* or its components, *Corynebacterium* derived P40 component, cholera toxin and mycobacteria whole or parts, and ISCOMs (DeVries et al., 1988; Morein et al., 199&, Lovgren: al., 1991). The skilled artisan is familiar with carriers appropriate for pharmaceutical use or suitable for use in humans.

The following is an example of a CLIP inhibitor formulation, dosage and administration schedule. The individual is administered an intramuscular or subcutaneous injection containing 8 mg of the composition (preferably 2 ml of a formulation containing 4 mg/ml of the composition in a physiologically acceptable solution) or 57 μg of CLIP inhibitor per 1 kg body weight of the patient. Each treatment course consists of 16 injections; with two injections on consecutive days per week for 8 weeks. The patient's disease condition is monitored by means described below. Three months after the last injection, if the patient is still suffering from the disease, the treatment regimen is repeated. The treatment regimen may be repeated until satisfactory result is obtained, e.g. a halt or delay in the progress of the disease, an alleviation of the disease or a cure is obtained.

The composition may be formulated alone or in combination with an antigen specific for the disease state and optionally with an adjuvant. Adjuvants include for instance adjuvants that create a depo effect, immune stimulating adjuvants, and adjuvants that create a depo effect and stimulate the immune system and may be systemic or mucosal adjuvants. Adjuvants that creates a depo effect include, for instance, aluminum hydroxide, emulsion-based formulations, mineral oil, non-mineral oil, water-in-oil emulsions, oil-in-water emulsions, Seppic ISA series of Montanide adjuvants, MF-59 and PROVAX. Adjuvants that are immune stimulating adjuvants include for instance, CpG oligonucleotides, saponins, PCPP polymer, derivatives of lipopolysaccharides, MPL, MDP, t-MDP, OM-174 and *Leishmania* elongation factor. Adjuvants that creates a depo effect and stimulate the immune system include for instance, ISCOMS, SB-AS2, SB-AS4, non-ionic block copolymers, and SAF (Syntex Adjuvant Formulation). An example of a final formulation: 1 ml of the final composition formulation can contain: 4 mg of the composition, 0.016 M $AlPO_4$ (or 0.5 mg $A1^{3+}$) 0.14 M NaCl, 0.004 M CH3COONa, 0.004 M KCl, pH 6.2.

The composition of the invention can be administered in various ways and to different classes of recipients.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

According to the methods of the invention, the compound may be administered in a pharmaceutical composition. In general, a pharmaceutical composition comprises the compound of the invention and a pharmaceutically-acceptable carrier. Pharmaceutically-acceptable carriers for peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients, e.g., the ability of the peptide to bind to the target, ie HIV surface molecules.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application serial no. 213,668, filed Mar. 15, 1994). WO 95/24929 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic diseases or recurrent cancer. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Therapeutic formulations of the peptides or antibodies may be prepared for storage by mixing a peptide or antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The peptide may be administered directly to a cell or a subject, such as a human subject alone or with a suitable carrier. Alternatively, a peptide may be delivered to a cell in vitro or in vivo by delivering a nucleic acid that expresses the peptide to a cell. Various techniques may be employed for introducing nucleic acid molecules of the invention into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. For certain uses, it is preferred to target the nucleic acid molecule to particular cells. In such instances, a vehicle used for delivering a nucleic acid molecule of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid molecule delivery vehicle. Especially preferred are monoclonal antibodies. Where liposomes are employed to deliver the nucleic acid molecules of the invention, proteins that bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acid molecules into cells, as is known by those skilled in the art. Such systems even permit oral delivery of nucleic acid molecules.

The peptide of the invention may also be expressed directly in mammalian cells using a mammalian expression vector. Such a vector can be delivered to the cell or subject and the peptide expressed within the cell or subject. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the myosin heavy chain promoter, albumin promoter, lymphoid-specific promoters, neuron specific promoters, pancreas specific promoters, and mammary gland specific promoters. Developmentally-regulated promoters are also encompassed, for example the murine hox promoters and the α-fetoprotein promoter.

As used herein, a "vector" may be any of a number of nucleic acid molecules into which a desired sequence may be inserted by restriction and ligation for expression in a host cell. Vectors are typically composed of DNA although RNA vectors are also available. Vectors include, but are not limited to, plasmids, phagemids and virus genomes. An expression vector is one into which a desired DNA sequence may be inserted by restriction and ligation such that it is operably joined to regulatory sequences and may be expressed as an RNA transcript. In some embodiments, a virus vector for delivering a nucleic acid molecule is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., Virology 219:220-227, 1996; Eloit et al., J. Virol. 7:5375-5381, 1997; Chengalvala et al., Vaccine 15:335-339, 1997), a modified retrovirus (Townsend et al., J. Virol. 71:3365-3374, 1997), a nonreplicating retrovirus (Irwin et al., J. Virol. 68:5036-5044, 1994), a replication defective Semliki Forest virus (Zhao et al., Proc. Natl. Acad. Sci. USA 92:3009-3013, 1995), canarypox virus and highly attenuated vaccinia virus derivative (Paoletti, Proc. Natl. Acad. Sci. USA 93:11349-11353, 1996), non-replicative vaccinia virus (Moss, Proc. Natl. Acad. Sci. USA 93:11341-11348, 1996), replicative vaccinia virus (Moss, Dev. Biol. Stand. 82:55-63, 1994), Venzuelan equine encephalitis virus (Davis et al., J. Virol. 70:3781-3787, 1996), Sindbis virus (Pugachev et al., Virology 212:587-594, 1995), and Ty virus-like particle (Allsopp et al., Eur. *J. Immunol* 26:1951-1959, 1996). In preferred embodiments, the virus vector is an adenovirus.

Another preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Clifton, N.J. (1991). In addition to delivery through the use of vectors, nucleic acids of the invention may be delivered to cells without vectors, e.g., as "naked" nucleic acid delivery using methods known to those of skill in the art.

(xv) Preparation of Peptides (Purification, Recombinant, Peptide Synthesis)

Purification Methods

The CLIP inhibitors of the invention can be purified, e.g., from thymus tissue. Any techniques known in the art can be used in purifying a CLIP inhibitor, including but are not limited to, separation by precipitation, separation by adsorption (e.g., column chromatography, membrane adsorbents, radial flow columns, batch adsorption, high-performance liquid chromatography, ion exchange chromatography, inorganic adsorbents, hydrophobic adsorbents, immobilized metal affinity chromatography, affinity chromatography), or separation in solution (e.g., gel filtration, electrophoresis, liquid phase partitioning, detergent partitioning, organic solvent extraction, and ultrafiltration). See Scopes, PROTEIN PURIFICATION, PRINCIPLES AND PRACTICE, 3rd ed., Springer (1994), the entire text is incorporated herein by reference.

As mentioned above TNPs are typically purified from the thymus cells of freshly sacrificed, i.e., 4 hours or less after sacrifice, mammals such as monkeys, gorillas, chimpanzees, guinea pigs, cows, rabbits, dogs, mice and rats. Such methods can also be used to prepare a preparation of peptides of the invention. The nuclei from the thymus cells are isolated using methods known in the art. Part of their lysine-rich histone fractions are extracted using the pepsin degradation method of U.S. Pat. No. 4,415,553, which is hereby incorporated by reference. Other degradative methods such as trypsin degradation, papain degradation, BrCN degradation appear ineffective in extracting the CLIP inhibitors. The protein rich fragment of the isolate is purified by cation exchange chromatography. For instance, the CLIP inhibitors can be isolated by conducting a size exclusion procedure on an extract from the thymus of any mammal such as calf, sheep, goat, pig, etc. using standard protocols. For example, thymus extract can be obtained using the protocol of Hand et al. (1967) Biochem. BioPhys. Res. Commun. 26:18-23; Hand et al. (1970) Experientia 26:653-655; or Moudjou et al (2001) J Gen Virol 82:2017-2024. Size exclusion chromatography has been described in, for example, Folta-Stogniew and Williams (1999) 1. Biomolec. Tech. 10:51-63 and Brooks et al. (2000) Proc. Natl. Acad. Sci. 97:7064-7067. Similar methods are described in more detail in the Examples section.

The CLIP inhibitors are purified from the resulting size selected protein solution via successive binding to at least one of CD4, gp 120 and gp41. Purification can be accomplished, for example, via affinity chromatography as described in Moritz et al. (1990) FEBS Lett. 275:146-50; Hecker et al. (1997) Virus Res. 49:215-223; McInerney et al. (1998) J. Virol. 72:1523-1533 and Poumbourios et al. (1992) AIDS Res. Hum. Retroviruses 8:2055-2062.

Further purification can be conducted, if necessary, to obtain a composition suitable for administration to humans. Examples of additional purification methods are hydrophobic interaction chromatography, ion exchange chromatography, mass spectrometry, isoelectric focusing, affinity chromatography, HPLC, reversed-phase chromatography and electrophoresis to name a few. These techniques are standard and well known and can be found in laboratory manuals such as Current Protocols in Molecular Biology, Ausubel et al (eds), John Wiley and Sons, New York.; Protein Purification: Principles, High Resolution Methods, and Applications, 2nd ed., 1998, Janson and Ryden (eds.) Wiley-VCH; and Protein Purification Protocols, 2nd ed., 2003, Cutler (ed.) Humana Press.

Recombinant Production of the Peptides

Methods known in the art can be utilized to recombinantly produce CLIP inhibitor. A nucleic acid sequence encoding CLIP inhibitor can be inserted into an expression vector for propagation and expression in host cells.

An expression construct, as used herein, refers to a nucleotide sequence encoding CLIP inhibitor or a fragment thereof operably associated with one or more regulatory regions which enable expression of CLIP inhibitor in an appropriate host cell. "Operably-associated" refers to an association in which the regulatory regions and the CLIP inhibitor sequence to be expressed are joined and positioned in such a way as to permit transcription, and ultimately, translation.

The regulatory regions necessary for transcription of the CLIP inhibitor can be provided by the expression vector. In a compatible host-construct system, cellular transcriptional factors, such as RNA polymerase, will bind to the regulatory regions on the expression construct to effect transcription of the modified CLIP inhibitor sequence in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

In order to attach DNA sequences with regulatory functions, such as promoters, to the CLIP inhibitor or to insert the CLIP inhibitor into the cloning site of a vector, linkers or adapters providing the appropriate compatible restriction sites may be ligated to the ends of the cDNAs by techniques well known in the art (Wu et al., 1987, Methods in Enzymol, 152: 343-349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

An expression construct comprising a CLIP inhibitor sequence operably associated with regulatory regions can be directly introduced into appropriate host cells for expression and production of CLIP inhibitor without further cloning. See, e.g., U.S. Pat. No. 5,580,859. The expression constructs can also contain DNA sequences that facilitate integration of the CLIP inhibitor sequence into the genome of the host cell, e.g., via homologous recombination. In this instance, it is not necessary to employ an expression vector comprising a replication origin suitable for appropriate host cells in order to propagate and express CLIP inhibitor in the host cells.

A variety of expression vectors may be used including, but not limited to, plasmids, cosmids, phage, phagemids or modified viruses. Such host-expression systems represent vehicles by which the coding sequences of interest may be produced and subsequently purified, but also represent cells which may, when transformed or transfected with the appropriate nucleotide coding sequences, express CLIP inhibitor in situ. These include, but are not limited to, microorganisms such as bacteria (e.g., *E. coli* and *B. subtilis*) transformed with recombinant bacteriophage DNA, plasmid DNA or cosmid DNA expression vectors containing CLIP inhibitor coding sequences; yeast (e.g., *Saccharomyces, Pichia*) transformed with recombinant yeast expression vectors containing CLIP inhibitor coding sequences; insect cell systems infected with recombinant virus expression vectors (e.g., baculovirus) containing CLIP inhibitor coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing CLIP inhibitor coding sequences; or mammalian cell systems (e.g., COS, CHO, BHK, 293, NSO, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli* and eukaryotic cells, especially for the expression of whole recombinant CLIP inhibitor molecule, are used for the expression of a recombinant CLIP inhibitor molecule. For example, mammalian cells such as Chinese hamster ovary cells (CHO) can be used with a vector bearing promoter element from major intermediate early gene of cytomegalovirus for effective expression of CLIP inhibitors (Foecking et al., 1986, Gene 45: 101; and Cockett et al., 1990, Bio/Technology 8: 2).

In bacterial systems, a number of expression vectors may be advantageously selected depending upon the use intended for the CLIP inhibitor molecule being expressed. For example, when a large quantity of such a CLIP inhibitor is to be produced, for the generation of pharmaceutical compositions of a CLIP inhibitor molecule, vectors which direct the expression of high levels of fusion protein products that are readily purified may be desirable. Such vectors include, but are not limited to, the *E. coli* expression vector pCR2.1 TOPO (Invitrogen), in which the CLIP inhibitor coding sequence may be directly ligated from PCR reaction and may be placed in frame to the lac Z coding region so that a fusion protein is produced; pIN vectors (Inouye & Inouye, 1985, Nucleic Acids Res. 13: 3101-3109; Van Heeke & Schuster, 1989*, J. Biol. Chem.* 24: 5503-5509) and the like. Series of vectors like pFLAG (Sigma), pMAL (NEB), and pET (Novagen) may also be used to express the foreign polypeptides as fusion proteins with FLAG peptide, malE-, or CBD-protein. These recombinant proteins may be directed into periplasmic space for correct folding and maturation. The fused part can be used for affinity purification of the expressed protein. Presence of cleavage sites for specific protease like enterokinase allows to cleave off the APR. The pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, many vectors to express foreign genes can be used, e.g., *Autographa californica* nuclear polyhedrosis virus (AcNPV) can be used as a vector to express foreign genes. The virus grows in cells like *Spodoptera frugiperda* cells. The CLIP inhibitor coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the CLIP inhibitor coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing CLIP inhibitor in infected hosts (see, e.g., Logan & Shenk, 1984, Proc. Natl. Acad. Sci. USA 81: 355-359). Specific initiation signals may also be required for efficient translation of inserted CLIP inhibitor coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153: 51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript and post-translational modification of the gene product, e.g., glycosylation and phosphorylation of the gene product, may be used. Such mammalian host cells include, but are not limited to, PC12, CHO, VERY, BHK, Hela, COS, MDCK, 293, 3T3, WI 38, BT483, Hs578T, HTB2, BT20 and T47D, NSO (a murine myeloma cell line that does not endogenously produce any immunoglobulin chains), CRL7030 and HsS78Bst cells. Expression in a bacterial or yeast system can be used if post-translational modifications turn to be non-essential for the activity of CLIP inhibitor.

For long term, high yield production of properly processed CLIP inhibitor, stable expression in cells is preferred. Cell lines that stably express CLIP inhibitor may be engineered by using a vector that contains a selectable marker. By way of example but not limitation, following the introduction of the expression constructs, engineered cells may be allowed to grow for 1-2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while CLIP inhibitor is expressed continuously.

A number of selection systems may be used, including but not limited to, antibiotic resistance (markers like Neo, which confers resistance to geneticine, or G-418 (Wu and Wu, 1991, Biotherapy 3: 87-95; Tolstoshev, 1993, Ann. Rev. Pharmacol. Toxicol. 32: 573-596; Mulligan, 1993, Science 260: 926-932; and Morgan and Anderson, 1993, Ann. Rev. Biochem. 62: 191-217; May, 1993, T113 TECH 11 (5): 155-2 15); Zeo, for resistance to Zeocin; Bsd, for resistance to blasticidin, etc.); antimetabolite resistance (markers like Dhfr, which confers resistance to methotrexate, Wigler et al., 1980, Natl. Acad. Sci. USA 77: 357; O'Hare et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072); and hygro, which confers resistance to hygromycin (Santerre et al., 1984, Gene 30: 147). In addition, mutant cell lines including, but not limited to, tk-, hgprt- or aprt-cells, can be used in combination with vectors bearing the corresponding genes for thymidine kinase, hypoxanthine, guanine- or adenine phosphoribosyltransferase. Methods commonly known in the art of recombinant DNA technology may be routinely applied to select the desired recombinant clone, and such methods are described, for example, in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds), Current Protocols in Human Genetics, John Wiley & Sons, N Y (1994); Colberre-Garapin et al., 1981, J. Mol. Biol. 150: 1.

The recombinant cells may be cultured under standard conditions of temperature, incubation time, optical density and media composition. However, conditions for growth of recombinant cells may be different from those for expression of CLIP inhibitor. Modified culture conditions and media may also be used to enhance production of CLIP inhibitor. Any techniques known in the art may be applied to establish the optimal conditions for producing CLIP inhibitor.

Peptide Synthesis

An alternative to producing CLIP inhibitor or a fragment thereof by recombinant techniques is peptide synthesis. For example, an entire CLIP inhibitor, or a peptide corresponding to a portion of CLIP inhibitor can be synthesized by use of a peptide synthesizer. Conventional peptide synthesis or other synthetic protocols well known in the art may be used.

Peptides having the amino acid sequence of CLIP inhibitor or a portion thereof may be synthesized by solid-phase peptide synthesis using procedures similar to those described by Merrifield, 1963, J. Am. Chem. Soc., 85: 2149. During synthesis, N-α-protected amino acids having protected side chains are added stepwise to a growing polypeptide chain linked by its C-terminal and to an insoluble polymeric support, i.e., polystyrene beads. The peptides are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile. Details of appropriate chemistries, resins, protecting groups, protected amino acids and reagents are well known in the art and so are not discussed in detail herein (See, Atherton et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting CLIP inhibitor or a fragment thereof is accomplished using conventional procedures, such as preparative HPLC using gel permeation, partition and/or ion exchange chromatography. The choice of appropriate matrices and buffers are well known in the art and so are not described in detail herein.

(xvi) Articles of Manufacture

The invention also includes articles, which refers to any one or collection of components. In some embodiments the articles are kits. The articles include pharmaceutical or diagnostic grade compounds of the invention in one or more containers. The article may include instructions or labels promoting or describing the use of the compounds of the invention.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of infections, cancer, autoimmune disease, graft rejection or Alzheimer's disease. "Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kits, in one set of embodiments, may comprise a carrier means being compartmentalized to receive in close confinement one or more container means such as vials, tubes, and the like, each of the container means comprising one of the separate elements to be used in the method. For example, one of the containers may comprise a positive control for an assay. Additionally, the kit may include containers for other components, for example, buffers useful in the assay.

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In a preferred embodiment, the unit dosage form is suitable for intravenous, intramuscular or subcutaneous delivery. Thus, the invention encompasses solutions, preferably sterile, suitable for each delivery route.

In another preferred embodiment, compositions of the invention are stored in containers with biocompatible detergents, including but not limited to, lecithin, taurocholic acid, and cholesterol; or with other proteins, including but not limited to, gamma globulins and serum albumins. More preferably, compositions of the invention are stored with human serum albumins for human uses, and stored with bovine serum albumins for veterinary uses.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures (such as methods for monitoring mean absolute lymphocyte counts, tumor cell counts, and tumor size) and other monitoring information.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising a needle or syringe, preferably packaged in sterile form, for injection of the formulation, and/or a packaged alcohol pad.

In a specific embodiment, an article of manufacture comprises packaging material and a pharmaceutical agent and instructions contained within said packaging material, wherein said pharmaceutical agent is a CLIP inhibitor or a derivative, fragment, homolog, analog thereof and a pharmaceutically acceptable carrier, and said instructions indicate a dosing regimen for preventing, treating or managing a subject with cancer, infectious disease, e.g. HIV, autoimmune disease, graft rejection, or Alzheimer's disease. In another embodiment, an article of manufacture comprises packaging material and a pharmaceutical agent and instructions contained within said packaging material, wherein said pharmaceutical agent is a CLIP inhibitor or a derivative, fragment, homolog, analog thereof, a prophylactic or therapeutic agent other than a CLIP inhibitor or a derivative, fragment, homolog, analog thereof, and a pharmaceutically acceptable carrier, and said instructions indicate a dosing regimen for preventing, treating or managing a subject with a cancer, infectious disease, e.g. HIV, autoimmune disease, graft rejection, or Alzheimer's disease. In another embodiment, an article of manufacture comprises packaging material and two pharmaceutical agents and instructions contained within said packaging material, wherein said first pharmaceutical agent is a CLIP inhibitor or a derivative, fragment, homolog, analog thereof and a pharmaceutically acceptable carrier, and said second pharmaceutical agent is a prophylactic or therapeutic agent other than a CLIP inhibitor or a derivative, fragment, homolog, analog thereof, and said instructions indicate a dosing regimen for preventing, treating or managing a subject with a cancer, infectious disease, e.g. HIV, autoimmune disease, graft rejection, or Alzheimer's disease.

(xvii) Therapeutic Monitoring

The adequacy of the treatment parameters chosen, e.g. dose, schedule, adjuvant choice and the like, is determined by taking aliquots of serum from the patient and assaying for antibody and/or T cell titers during the course of the treatment program. T cell titer may be monitored by conventional methods. For example, T lymphocytes can be detected by E-rosette formation as described in Bach, F., Contemporary Topics in *Immunology*, Vol. 2: Thymus Dependency, p. 189, Plenum Press, New York, 1973; Hoffman, T. & Kunkel, H. G., and Kaplan, M. E., et al., both papers are in In vitro Methods in Cell Mediated and Tumor Immunity, B. R. Bloom & R. David eds., Academic Press, New York (1976). Additionally viral load can be measured.

In addition, the clinical condition of the patient can be monitored for the desired effect, e.g. increases in T cell count and/or weight gain. If inadequate effect is achieved then the patient can be boosted with further treatment and the treatment parameters can be modified, such as by increasing the amount of the composition of the invention and/or other active agent, or varying the route of administration.

The effect of immunotherapy with a CLIP inhibitor compositions of the invention on development and progression of neoplastic diseases can be monitored by any methods known to one skilled in the art, including but not limited to measuring: a) delayed hypersensitivity as an assessment of cellular immunity; b) activity of cytolytic T-lymphocytes in vitro; c) levels of tumor specific antigens, e.g., carcinoembryonic (CEA) antigens; d) changes in the morphology of tumors using techniques such as a computed tomographic (CT) scan; e) changes in levels of putative biomarkers of risk for a particular cancer in subjects at high risk, and f) changes in the morphology of tumors using a sonogram.

Although it may not be possible to detect unique tumor antigens on all tumors, many tumors display antigens that distinguish them from normal cells. The monoclonal antibody reagents have permitted the isolation and biochemical characterization of the antigens and have been invaluable diagnostically for distinction of transformed from nontransformed cells and for definition of the cell lineage of transformed cells. The best-characterized human tumor-associated antigens are the oncofetal antigens. These antigens are expressed during embryogenesis, but are absent or very difficult to detect in normal adult tissue. The prototype antigen is carcinoembryonic antigen (CEA), a glycoprotein found on fetal gut and human colon cancer cells, but not on normal adult colon cells. Since CEA is shed from colon carcinoma cells and found in the serum, it was originally thought that the presence of this antigen in the serum could be used to screen patients for colon cancer. However, patients with other tumors, such as pancreatic and breast cancer, also have elevated serum levels of CEA. Therefore, monitoring the fall and rise of CEA levels in cancer patients undergoing therapy has proven useful for predicting tumor progression and responses to treatment.

Several other oncofetal antigens have been useful for diagnosing and monitoring human tumors, e.g., alpha-fetoprotein, an alpha-globulin normally secreted by fetal liver and yolk sac cells, is found in the serum of patients with liver and germinal cell tumors and can be used as a marker of disease status.

CT remains the choice of techniques for the accurate staging of cancers. CT has proved more sensitive and specific than any other imaging techniques for the detection of metastases.

The levels of a putative biomarker for risk of a specific cancer are measured to monitor the effect of the molecular complex of the invention. For example, in subjects at enhanced risk for prostate cancer, serum prostate-specific antigen (PSA) is measured by the procedure described by Brawer, M. K., et. al., 1992*, J. Urol.,* 147: 841-845, and Catalona, W. J., et al., 1993*, JAMA,* 270: 948-958; or in subjects at risk for colorectal cancer, CEA is measured as described above in Section 5.10.3; and in subjects at enhanced risk for breast cancer, 16-hydroxylation of estradiol is measured by the procedure described by Schneider, J. et al., 1982*, Proc. Natl. Acad. Sci. USA,* 79: 3047-3051.

A sonogram remains an alternative choice of technique for the accurate staging of cancers.

Any adverse effects during the use of a CLIP inhibitor alone or in combination with another therapy (including another therapeutic or prophylactic agent) are preferably also monitored. Examples of adverse effects of chemotherapy during a cancer treatment or treatment of an infectious disease include, but are not limited to, gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney failure, as well as constipation, nerve and muscle effects, temporary or permanent damage to kidneys and bladder, flu-like symptoms, fluid retention, and temporary or permanent infertility. Adverse effects from radiation therapy include, but are not limited to, fatigue, dry mouth, and loss of appetite. Other adverse effects include gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney failure. Adverse effects from biological therapies/immunotherapies include, but are not limited to, rashes or swellings at the site of administration, flu-like symptoms such as fever, chills and fatigue, digestive tract problems and allergic reactions. Adverse effects from hormonal therapies include but are not limited to nausea, fertility problems, depression, loss of appetite, eye problems, headache, and weight fluctuation. Additional undesired effects typically experienced by patients are numerous and known in the art. Many are described in the *Physicians' Desk Reference* ($56^{th}$ ed., 2002).

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1: Identification of CLIP Inhibitors

Peptide that are able to displace CLIP were identified using computer based analysis. Thus, examples of "ideal" MHC class II binding peptides were generated according to the invention. Analysis of the binding interaction between MHC class II and CLIP was used to identify other molecules that may bind to MHC class II and displace CLIP. The methods described herein are based on feeding peptide sequences into software that predicts MHC Class II binding regions in an antigen sequence using quantitative matrices as described in Singh, H. and Raghava, G. P. S. (2001), "ProPred: prediction of HLA-DR binding sites." *Bioinformatics,* 17(12), 1236-37.

Because MHC class II HLA-DR can bind to peptides of varying length an analysis of MHC class II HLA-DR-CLIP binding was performed. Since the alpha chain of HLA-DR is much less polymorphic than the beta chain of HLA-DR, the HLA-DR beta chain (hence, HLA-DRB) was studied in more detail. Peptide binding data for 51 common alleles is publicly available. A review of HLA alleles is at Cano, P. et al, "Common and Well-Documented HLA Alleles", *Human Immunology* 68, 392-417 (2007). Based on peptide binding data, prediction matrices were produced for each of the 51 common HLA-DRB alleles. The matrices can be obtained from www.imtech.res.in/raghava/propred/page4.html and are reproduced from the web site in Table 4/Appendix A. The analysis methods are accomplished using an available MHC Class II binding peptide prediction server (Open Source), which can also be obtained online at: www.imtech.res.in/raghava/propred. A summary of the algorithms as described in this web site is described in Sturniolo. T et al (Sturniolo. T., Bono. E., Ding. J., Raddrizzani. L., Tuereci. O., Sahin. U., Braxenthaler. M., Gallazzi. F., Protti. M. P., Sinigaglia. F., Hammer. J., Generation of tissue-specific and promiscuous HLA ligand database using DNA microarrays and virtual HLA class II matrices. *Nat. Biotechnol.* 17. 555-561(1999).). The following matrices were used for the analysis

HLA-DR1: HLA-DRB1*0101; HLA-DRB1*0102

HLA-DR3: HLA-DRB1*0301; HLA-DRB1*0305; HLA-DRB1*0306; HLA-DRB1*0307; HLA-DRB1*0308; HLA-DRB1*0309; HLA-DRB1*0311

HLA-DR4; HLA-DRB1*0401; HLA-DRB1*0402; HLA-DRB1*0404; HLA-DRB1*0405; HLA-DRB1*0408; HLA-DRB1*0410; HLA-DRB1*0423; HLA-DRB1*0426

HLA-DR7: HLA-DRB1*0701; HLA-DRB1*0703;

HLA-DRB8: HLA-DRB1*0801, A-DRB1*0802; HLA-DRB1*0804; HLA-DRB1*0806; HLA-DRB1*0813; HLA-DRB1*0817

HLA-DR11: A-DRB1*1101; HLA-DRB1*1102 HLA-DRB1*1104; HLA-DRB1*1106; HLA-DRB1*1107 A-DRB1*1114; HLA-DRB1*1120; HLA-DRB1*1121 HLA-DRB1*1128

HLA-DR13: HLA-DRB1*1301; HLA-DRB1*1302; HLA-DRB1*1304; HLA-DRB1*1305; HLA-DRB1*1307; HLA-DRB1*1311, HLA-DRB1*1321; HLA-DRB1*1322; HLA-DRB1*1323, HLA-DRB1*1327, HLA-DRB1*1328

HLA-DR2: HLA-DRB1*1501; HLA-DRB1*1502; HLA-DRB1*1506; HLA-DRB5*0101; HLA-DRB5"0105

These matrices weight the importance of each amino acid at each position of the peptide. Critical anchor residues require a very restricted set of amino acids for binding. Other positions are less critical but still influence MHC binding. A couple positions do not appear to influence binding at all.

A database of human MHC molecule is included on a web site by ImMunoGeneTics (http://www.ebi.ac.uk/imgt). The site includes a collection of integrated databases specializing in MHC of all vertebrate species. IMGT/HLA is a database for sequences of the human MHC, referred to as HLA. The IMGT/HLA database includes all the official sequences for the WHO Nomenclature Committee For Factors of the HLA System.

Referring to Table 3, a comparison is shown of predicted MHC Class II binding regions in a peptide of this invention to predicted MHC Class II binding regions of CLIP. For the 9 mer (minimal length), the start is the first position. CLIP has a few overhanging amino acids. The amino acid sequence of the CLIP peptide that is part of the human invariant chain for HLA-DR is (SEQ ID NO: 1), which has the sequence in the one-letter system: MRMATPLLM, and in three-letter abbreviation as: Met Arg Met Ala Thr Pro Leu Leu Met. This peptide is a kind of "jack of all trades" in terms of binding HLA-DR alleles. A typical peptide will bind a handful of the alleles well and others very poorly. This makes good sense considering that it is not polymorphic like the DR alleles but needs to be compatible with whichever alleles it is given. The immunology of MHC polymorphism and evolutionary selection provides particular alleles in different populations.

The minimal peptide length for binding HLA-DR is 9 amino acids. However, there can be overhanging amino acids on either side of the open binding groove. For some well studied peptides, it is known that additional overhanging amino acids on both the N and C termini can augment binding. The prediction matrices used herein do not take these into consideration, however it is an aspect of this invention to add various amino acids to each side of the 9 -mer peptide.

Based on peptide binding data, prediction matrices have been produced for each of the 51 common HLA-DRB alleles. These matrices weight the importance of each amino acid at each position of the peptide. Critical anchor residues require a very restricted set of amino acids for binding. Other positions are less critical but still influence MHC binding. Finally, a couple positions do not appear to influence binding at all.

To make a rough prediction of an ideal peptide, the 51 alleles were averaged and then the best amino acid at each position was selected to obtain: FRIM[Any]VL[Any]S (SEQ ID NO: 6). To run the algorithm and compare such a peptide to CLIP, I used alanine in both [any] positions to yield (SEQ ID NO:1), which has the sequence in the one-letter system: FRIMAVLAS (SEQ ID NO: 2), and in three-letter abbreviation as: Phe Arg Ile Met Ala Val Leu Ala Ser (SEQ ID NO: 2). In general, alanine is a good choice for substitution because it is harmless. These positions could be optimized for other purposes such as solubility.

Referring again to Table 3, each row represents an HLA-DR allele and the score for each peptide is given. The alleles where FRIMAVLAS (SEQ ID NO: 2) had a higher score than CLIP (SEQ ID NO: 1) are apparent. The average score across all alleles is given to the right of the sequence. For CLIP, it is 4.3156862275 and for the displacing peptide, (SEQ ID NO: 2), it is 6.266666667, showing the (SEQ ID NO: 2) is quite capable of displacing CLIP.

Examples 2-9 are reproduced from U.S. Ser. No. 12/011,643 filed on Jan. 28, 2008, naming Karen Newell, Evan Newell and Joshua Cabrera as inventors. It is included here solely to provide a background context to the invention. The experiments reflect the invention of Karen Newell and Evan Newell who are named as inventors on the instant application.

Example 2: B-Cell Apoptosis after Coxsackievirus Infection

During the course of Coxsackievirus infection, animals that recover from the virus without subsequent autoimmune sequelae have high percentages of splenic B cell apoptosis during the infection in vivo (FIG. 1). Those animals susceptible to Coxsackievirus-mediated autoimmune disease have non-specifically activated B cells that do not undergo apoptosis, at least not during acute infection, nor during the time period prior to autoimmune symptoms indicating that a common feature in the development of autoimmune disease is failure of non-specifically activated B cells to die.

Example 3: Activated B Cells in HIV Disease Mediate NK Cell Activation

Figure 2A:
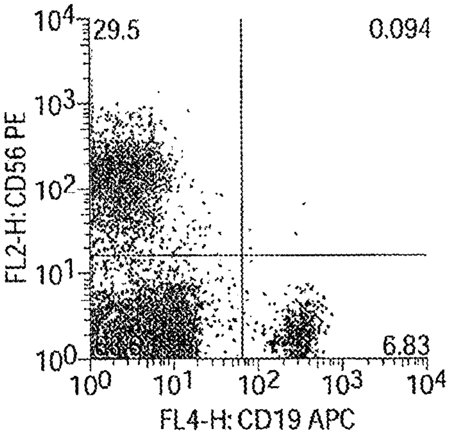
Figure 2B:
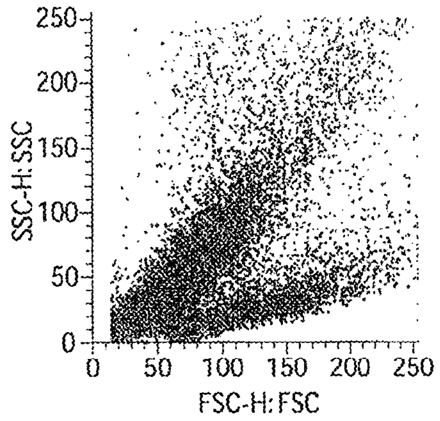
Figures 1, 3A:
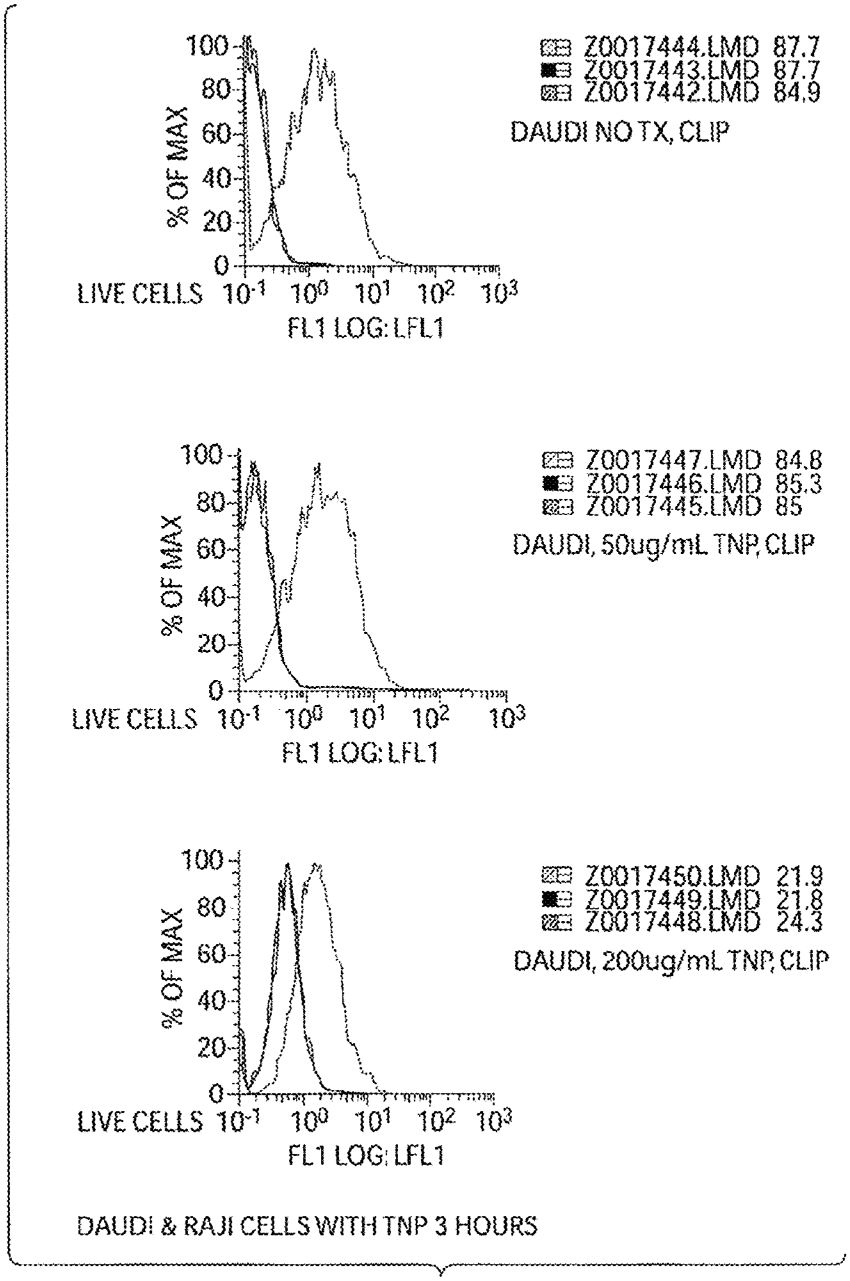
Figures 2, 3A:
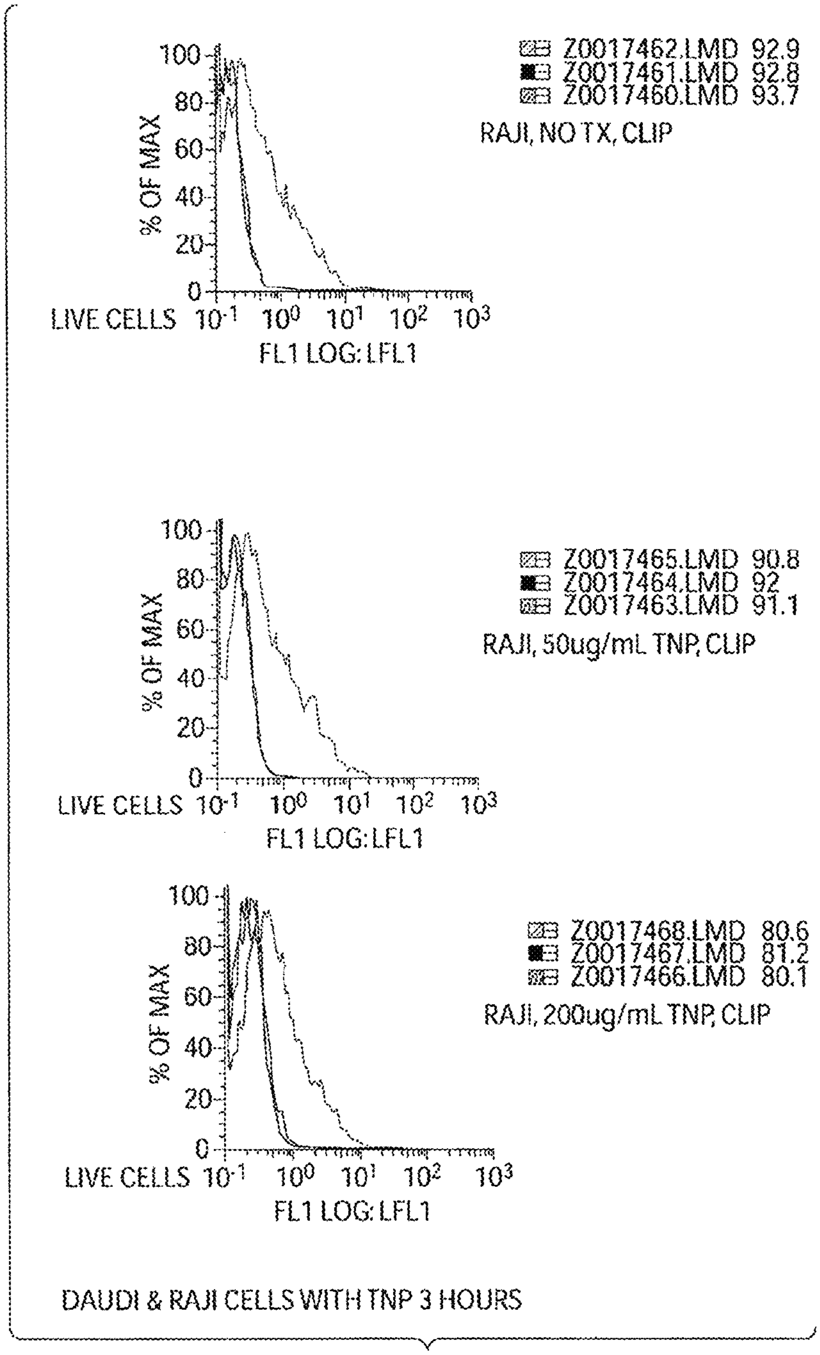
Figures 1, 3B:
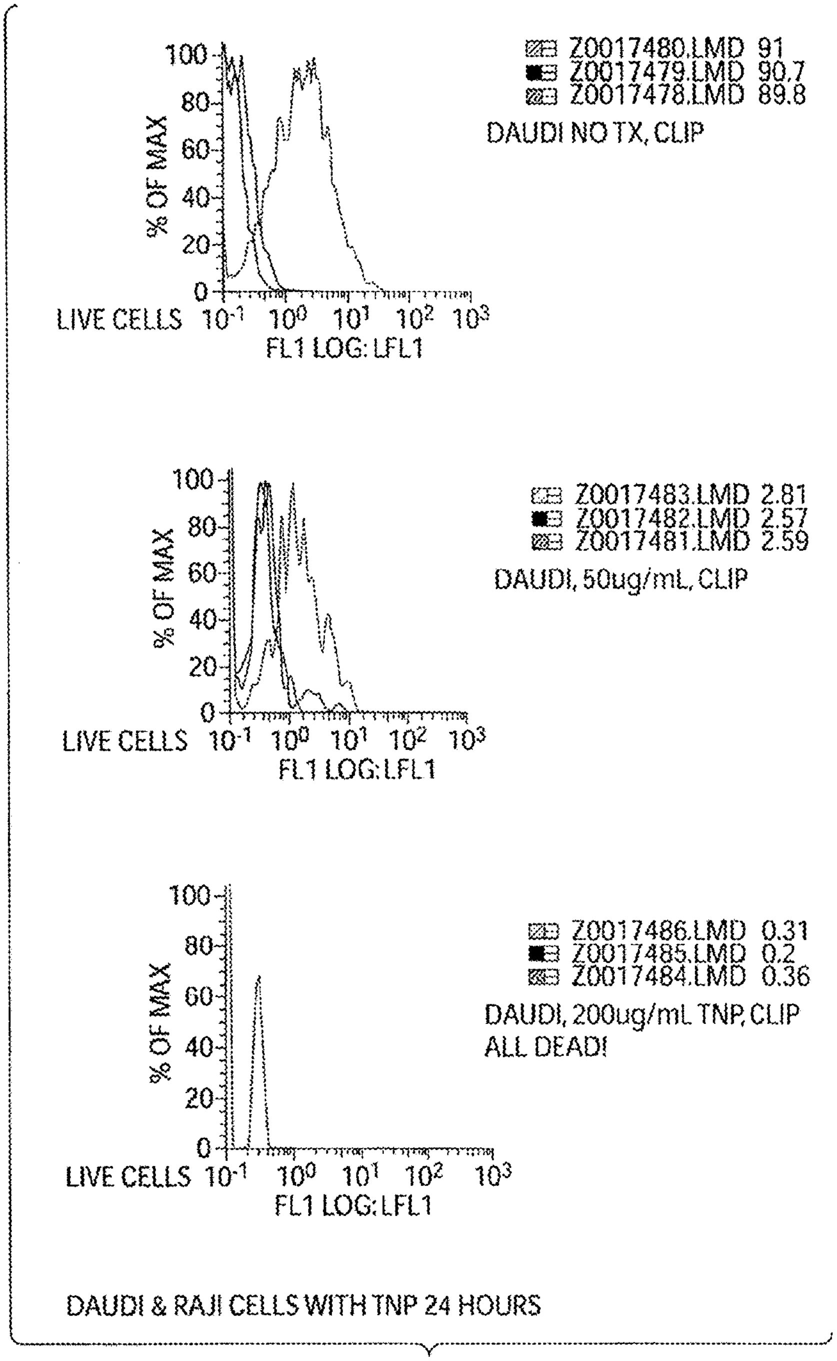
Figures 2, 3B:
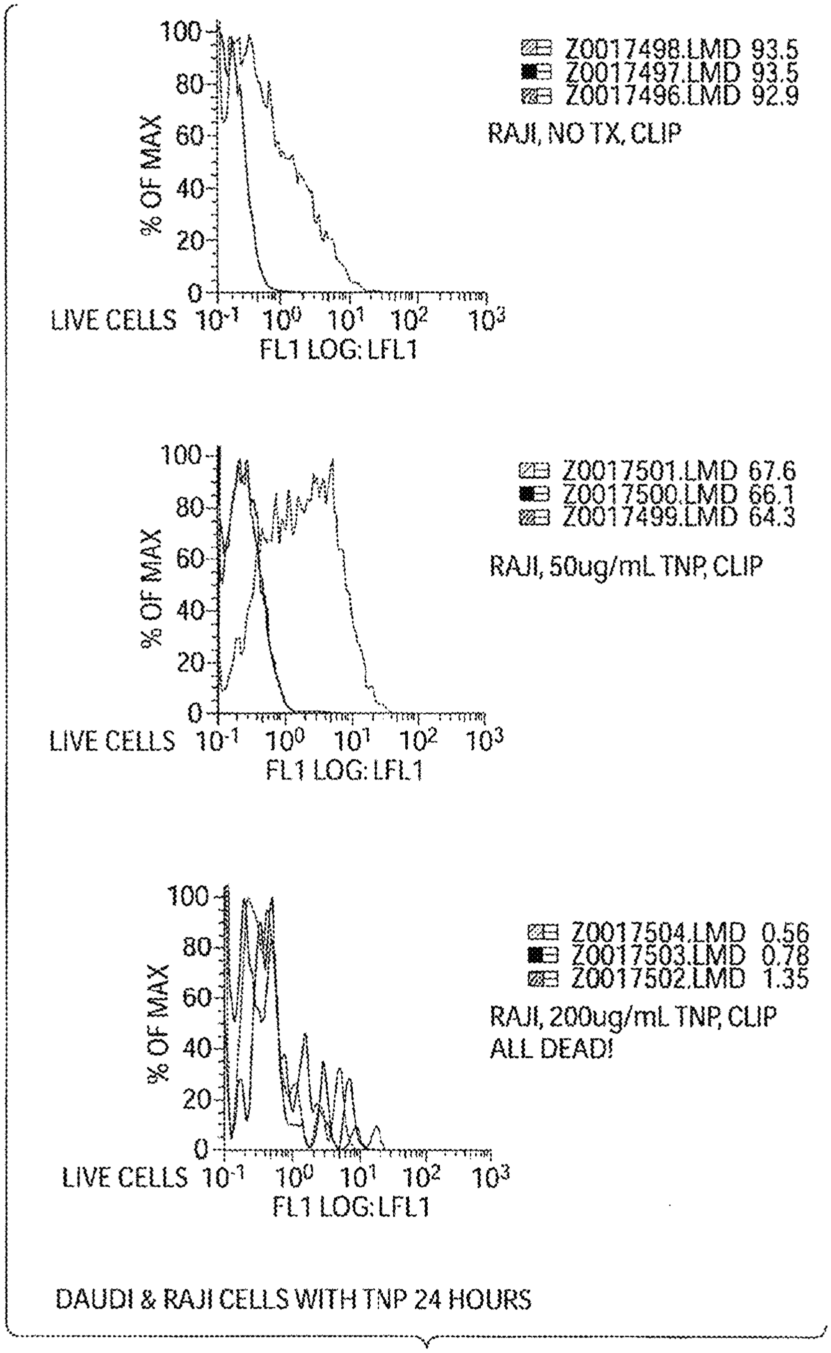
Figure 3C:
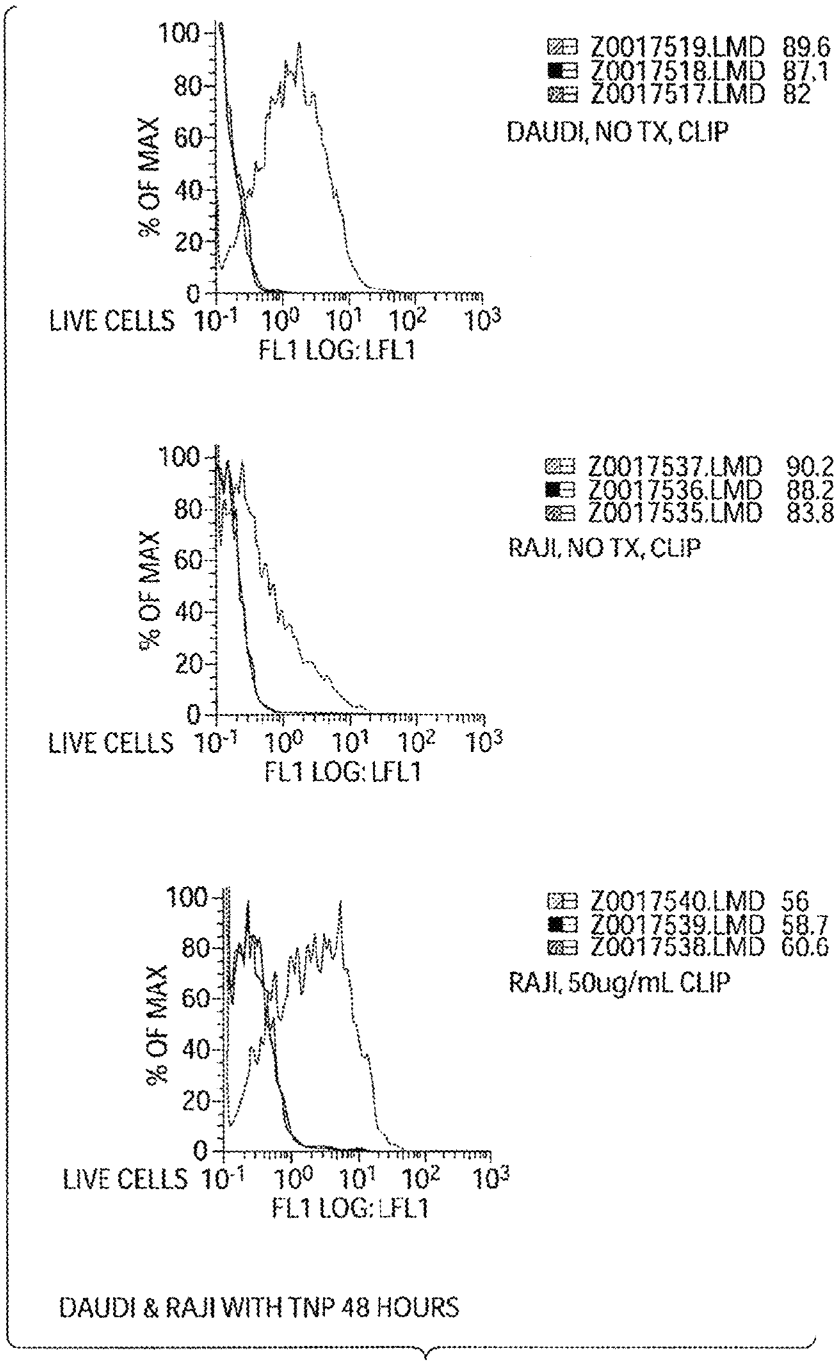

We experimentally induced polyclonal activation of peripheral blood human B cells in an antigen-independent fashion using a combination of CD40 engagement (CD40Ligand bearing fibroblasts) and culture in recombinant IL-4. We isolated the activated B cells and return them to co-culture with autologous peripheral blood mononuclear cells (PBMCs). After five days of co-culture, we observed a striking increase in the percentage of activated NK cells in the PBMC culture (NK cells accounting for up to 25-50%, FIG. 2*a*, of the surviving PBMCs), and a dramatic apoptotic loss of the activated B cells (FIG. 2*b*). These data indicate that antigen-independent activated B cells in HIV disease initially activate NK cells.

Example 4: Antigen-independent B Cell Activation Results in NK Cell Activity

Elements of HIV infection that provide an antigen-independent activation signal to B cells that results in NK cell activation and polyclonal B cell activation are examined.

Antigen-independent activation of B cells: Human B cells: PBMCs are prepared from 5 normal and 5 HIV-infected adult donors using standard Ficoll-Hypaque density-gradient techniques. Irradiated (75 Gy) human CD40L-transfected murine fibroblasts (LTK-CD40L), are plated in six-well plates (BD Bioscience, Franklin Lakes, N.J.) at a concentration of 0.1×106 cells/well, in RPMI complete medium and cultured overnight at 37° C., 5% CO2. After washing twice with PBS, 2×106 cells/mL PBMC are co-cultured with LTK-CD40L cells in the presence of recombinant human interleukin-4 (rhIL-4; 4 ng/mL; Peprotech, Rocky Hill, N.J.) or with purified HIV derived gp 120 protein in complete Dulbecco's medium (Invitrogen), supplemented with 10% human AB serum (Gemini Bio-Product, Woodland, Calif.) Cultured cells are transferred to new plates with freshly prepared, irradiated LTK-CD40L cells every 3 to 5 days. Before use, dead cells are removed from the CD40-B cells by Ficoll density centrifugation, followed by washing twice with PBS. The viability of this fraction is expected to be >99%, and >95% of the cells, using this protocol, have been shown to be B cells that are more than 95% pure CD19+ and CD20+ after 2 weeks of culture. This protocol yields a viability of >99%, and >95% of the cells have been shown to be B cells that are more than 95% pure CD19+ and CD20+ after 2 weeks of culture.

The activated B cells are co-cultured with autologous PBMC at a ratio of 1:10 and cultured for five days. Harvested cells are stained with fluorochrome-conjugated antibodies (BD Pharmingen) to CD56, CD3, CD19, CD4, and CD8. Cells are analyzed flow cytometrically to determine the percentage of NK cells (Percent CD56+, CD3−) resulting from co-culture comparing non-infected to infected samples. NK cells are counter-stained for NK killing ligand KIR3DS1, NKG2D, FaL, or PD1. Similarly the percent surviving large and small C19+ cells are quantitated flow cytometrically.

B cell activation in HIV: To determine if activated NK or CD3 T cells promote polyclonal B cell activation, we perform reciprocal co-culture experiments in which we purposely activate NKs or CD3+ T cells and co-culture 1:10 in PBMC from the autologous donors. PBMCs are prepared from HIV infected or uninfected adult donors using standard Ficoll-Hypaque density-gradient techniques. To activate NKs and CD3+T cells, PBMCs are cultured in RPMI with 10% FCS, 1 mM penicillin, 1 mM Glutamax, and 1% W/V glucose at 2.0-4.0×106/mL for 3 days with 1:40,000 OKT3, 100U/mL IL-2, or no stimulation (resting). After 3 days stimulation, non-adherent PBMCs are gently harvested and immune cell subsets are purified by MACS technology according to manufacturers protocol (Miltenyi Biotec, Auburn Calif.). In brief, NK cells are first selected using the CD56+ multisort kit, followed by bead release, and depletion with anti-CD3 beads. T cells are obtained by depleting non-adherent PBMCs with CD56 beads with or without anti-CD4 or anti-CD8 beads for isolation of each individual subset. Purity of cell fractions are confirmed for each experiment by flow cytometry using CD56, CD3, CD4, CD8 and CD14 antibodies. Following culture for 5 days, we use flow cytometry to determine relative changes in CD19+, CD4, CD8, NK, CD3, and CD69 as a marker for activation.

We examine the NK cells from the co-culture experiments for KIR3DS1 and other killer cell ligands including NKG2D ligand, PD1, and FasL that are indicative of killer cell functions.

Antigen-independent activation of mouse B cells. Mouse spleens are removed from C57B16 mice, red cells are removed using buffered ammonium chloride, T cells are depleted with an anti-T cell antibody cocktail (HO13, GK1.5 and 30H12) and complement. T depleted splenocytes are washed and fractionated using Percoll density gradient centrifugation. We isolate the B cells at the 1.079/1.085 g/ml density interface (resting B cells) and wash to remove residual Percoll. The cells are cultured in the presence of LPS or tri-palmitoyl-S-glyceryl-cysteinyl N-terminus (Pam (3)Cys), agonists of TLR2, on B cells. The activated B cells are co-cultured with total spleen cells at a ratio of 1:10 B cell:total spleen cells. After five days in culture, the remaining cells are analyzed for expansion of cell subsets including those expressing mouse CD56, CD3, B220, CD4 and CD8. These cell surface molecules are analyzed flow cytometrically. CD56+CD3− cells are counterstained for NKG2D and other death-inducing receptors.

Example 5: NK Cells Kill Activated CD4+ T Cells

The ability of NK cells to lyse activated CD4 T cells as targets as a result of NK cell activation and changes in the CD4 T cell target is examined.

Activation of Human NK and CD3+ T cells: PBMCs are prepared from HIV infected or uninfected adult donors using standard Ficoll-Hypaque density-gradient techniques. NKs and CD3+ T cells are activated and isolated as disclosed herein. T cells and NK cells are routinely between 80-95% pure with less than 1% monocyte contamination. T cell activation in OKT3-stimulated PBMCs is confirmed by assays using 3H-thymidine incorporation. NK cell activation is confirmed by increase in size and granularity by flow cytometry, by staining for CD56+ and CD3− fow cytometrically, and by lytic activity as measured by chromium release of well-established NK targets. We load well-established NK cell targets or the non-specifically activated B cells as disclosed herein with 51-Chromium. We use chromium release as a measurement of target cell death.

Activation of mouse NK and CD3+ T cells: We isolate splenocytes as disclosed herein. The red blood cell-depleted spleen cells are cultured in recombinant mouse IL-2 or with 145.2C11 (anti-mouse CD3, Pharmingen) for 3 days. After stimulation, the cells are harvested and purified using Cellect Isolation kits for either NK, CD4, or CD8+ T cells. The cells are then co-cultured with 51-Chromium-labelled, well-established NK cell targets or with 51-Chromium-labelled non-specifically activated B cells as disclosed herein.

Example 6: Chronically Activated HIV Infected (or HIV-specific CD4 T Cells) are the Intercellular Targets of Activated Killer Cells Chronically activated CD4+ T cells become particularly susceptible to killer cells as a consequence of the chronic immune stimulation resulting from HIV infection.

We isolate NK cells from uninfected or HIV-infected individuals using the CD56+multisort kit as disclosed herein. We activate the cells in IL-2 as disclosed herein. We perform co-culture experiments with these cells added back to PBMC at a 1:10 ratio from autologous donors. Prior to co-culture we examine the NK cells from HIV infected and uninfected donors for deat-inducing receptor: ligand pairs killer, including KIR3DS1, FasL, and NKG2D ligands that are indicative of killer cell functions. In parallel, we stain pre- and post-coculture PBMCs from the autologous donors of HIV infected or uninfected donors.

Example 7: TNP MIXTURE Displaces CLIP from Model B Cell Lines

Kinetics of CLIP displacement from the surface of model B cells lines (Daudi and Raji) in response to thymic nuclear protein mixture was determined.

Results were expressed in histogram analyses (FIG. 3). The Y axis represents cell number of the 5000 live cells versus the X axis which is a reflection of relative Fitc fluorescence. The distance between the histogram from the isotype control staining versus the histogram reflecting the specific stain is a measure of level of cell surface CLIP on a population of live Raji or Daudi cells as indicated.

At three hours, on both cell lines, we see evidence by diminished ratio of Isotype to CLIP staining, that the TNP mixtures at 200 microgram/ml cause a reduction in detectable cell surface CLIP.

At 24 hours, the effect was less, and may have caused an increase in detectable CLIP. Noticeably at 24 hours, the TNP mixture caused death of the B cell lines at the 200 microgram/mL concentrations and by 48 hours all of the cells treated with 200 micrograms were dead and the 50 microgram concentrations also resulted in significant toxicity.

At 3 hours, treatment with 200 micrograms TNP/ml, there was 2.5 times the number of dead cells as determined by Trypan blue exclusion. Cell death in the flow cytometric experiments was, determined by forward versus side scatter changes (decreased forward scatter, increased side scatter).

Materials and Methods

Cell Culture Conditions: The Raji and Daudi cell lines were purchased from American Type Culture Collection, were thawed, and grown in RPMI 1640 medium supplemented with standard supplements, including 10% fetal calf serum, gentamycin, penicillin, streptomycin, sodium pyruvate, HEPES buffer, 1-glutamine, and 2-ME.

Protocol: Cells were plated into a 12 well plate with 3 mls total volume containing approximately 0.5×106/well for Daudi cells and 1.0×106/well for. Raji cells. Treatment groups included no treatment as control; 50 micrograms/ml TNP mixture; 200-micrograms/ml TNP mixture; 50 micrograms of control bovine albumin; or 200 micrograms/ml bovine albumin as protein controls.

The cells were incubated at 37° C. in an atmosphere containing 5% CO2 and approximately 92% humidity. The cells were incubated for 3, 24, and 48 hours. At each time point, the cells from that experimental time were harvested and stained for flow cytometric analysis of cell surface expression of CLIP (MHC Class II invariant peptide, human) by using the commercially available (Becton/Dickinson/PHarmingen) anti-human CLIP Fitc. Catalogue #555981.

Harvested cells were stained using standard staining procedure that called for a 1:100 dilution of Fitc-anti-human CLIP or isotype control. Following staining on ice for 25 minutes, cells were washed with PBS/FCS and resuspended in 100 microliters and added to staining tubes containing 400 microliters of PBS. Samples were acquired and analyzed on a Coulter Excel Flow Cytometer.

Example 8: MKN1 (bioCLIP) Alters Cell Surface CLIP and CD74 Levels

The ability of MKN1 (bioCLIP) to alter cell surface CLIP and CD74 levels was determined using Raji or Daudi cells.

Data were analyzed by histogram with Y axis represents cell number of the 5000 live cells versus the X axis which is a reflection of relative FITC fluorescence with either antibodies to CLIP or CD74. The distance between the histogram from the isotype control staining versus the histogram reflecting the specific stain and is a measure of level of cell surface CLIP or CD74 when staining a population of live Raji or Daudi cells.

Our results show that treatment with MKN1 (bioCLIP) alters cell surface CLIP and CD74 levels.

Materials and Methods:

Cell Culture Conditions: The Raji and Daudi cell lines were purchased from American Type Culture Collection, were thawed, and grown in RPMI 1640 medium supplemented with standard supplements, including 10% fetal calf serum, gentamycin, penicillin, streptomycin, sodium pyruvate, HEPES buffer, 1-glutamine, and 2-ME.

Protocol: Cells were plated into a 12 well plate with 3 mls total volume containing approximately 0.5×106/mL for Daudi cells and 0.5×106/mL for Raji cells. Treatment groups included no treatment as control; MKN 3 and MKN 5 at 50 microMolar final concentration based on the reported molarity of the synthesized compounds.

Peptide 1: MKN.1 (19 mer) Biotin at N-Terminal=Biotinylated CLIP

SGG GSK MRM ATP LLM QAL Y (SEQ ID NO: 5)

5-10 mg Obtained @>95% purity (ELIM Pharmaceuticals)

The cells were incubated at 37° C. in an atmosphere containing 5% CO2 and approximately 92% humidity. The cells were incubated for 24 and 48 hours. At each time point, the cells from that experimental time were harvested and stained for flow cytometric analysis of cell surface expression of CLIP (MHC Class II invariant peptide, human) by using the commercially available (Becton/Dickinson/Pharmingen) anti-human CLIP Fitc. Catalogue #555981 versus Streptavidin and for CD74 using the commercially available (Becton/Dickinson/Pharmingen) anti-human CC74 Fitc antibody.

Harvested cells were stained using standard staining procedure that called for a 1:100 dilution of Fitc-anti-human CLIP or CD74 antibody (Fitc, Pharmingen, Cat #554647) or isotype control. Following staining on ice for 25 minutes, cells were washed with PBS/FCS and resuspended in 100 microliters and added to staining tubes containing 400 microliters of PBS. Samples were acquired and analyzed on a Coulter Excel Flow Cytometer.

Example 9: 2-Deoxyglucose and Dichloroacetate Cause Removal of B Cell Surface CLIP The ability of 2-Deoxyglucose and dichloroacetate affect B cell surface CLIP was determined.

Figure 4:
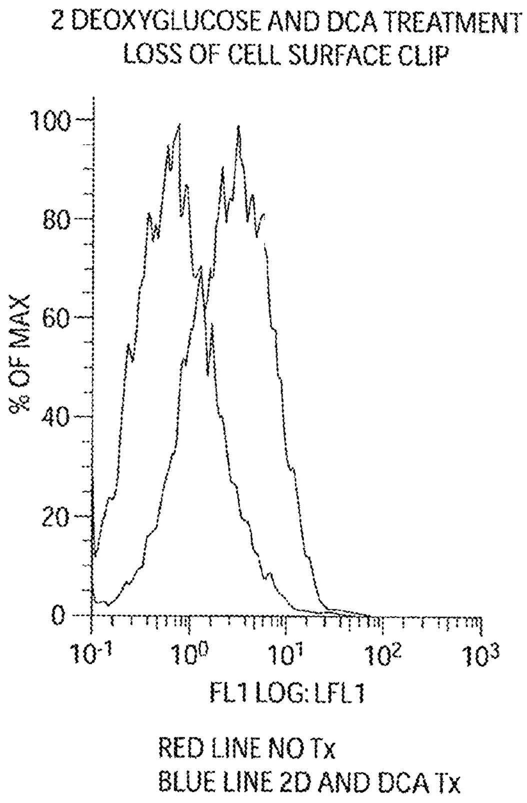
FIG. 4 depicts that 2-Deoxyglucose and dichloroacetate affects B cell surface CLIP.
Figure 5A:
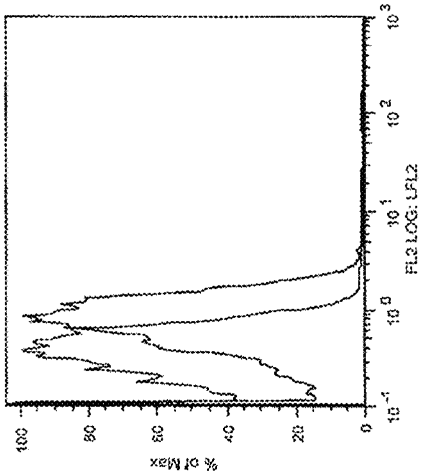
FIGS. 5A-5D depict CLIP displacement from the surface of Raji B cells lines in response to no treatment (FIGS. 5A and 5C) or treatment with MKN.5 (FIGS. 5B and 5D) for 4 (FIGS. 5A and 5B) and 24 hours (FIGS. 5C and 5D).
Figure 5B:
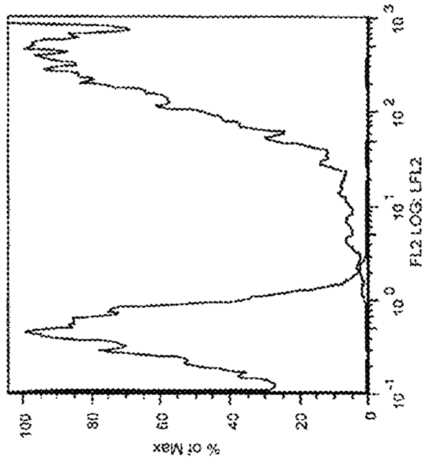
Figure 5C:
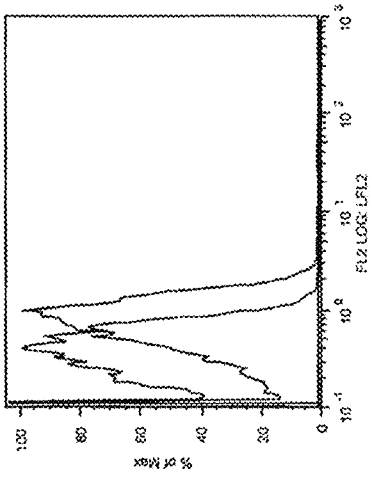
Figure 5D:
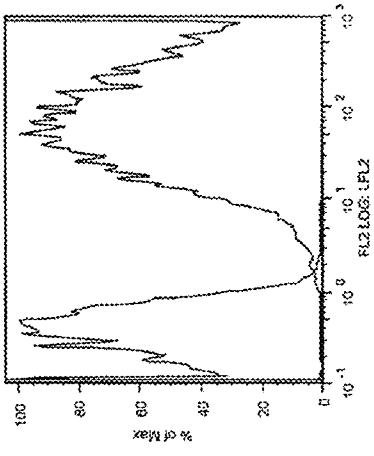
Figure 6B:
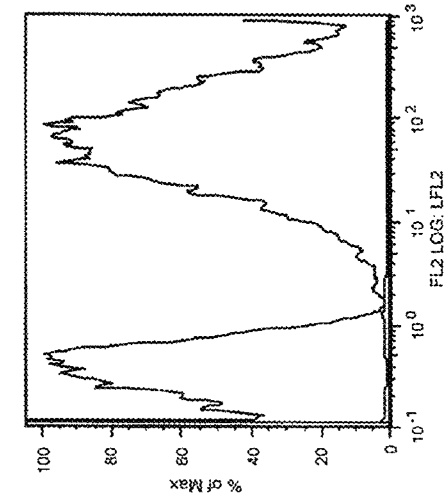
FIGS. 6A-6D depict CLIP displacement from the surface of Daudi B cells lines in response to no treatment (FIGS. 6A and 6C) or treatment with MKN.5 (FIGS. 6B and 6D) for 4 (FIGS. 6A and 6B) and 24 hours (FIGS. 6C and 6D).
Figure 6D:
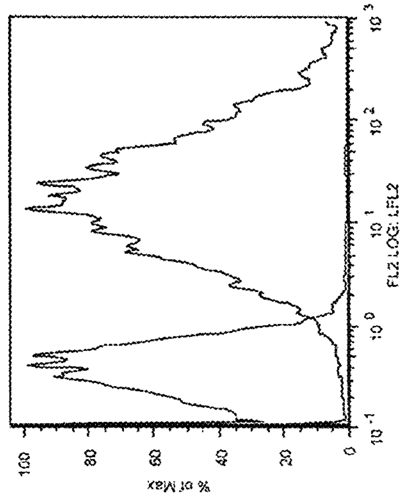
Figure 6A:
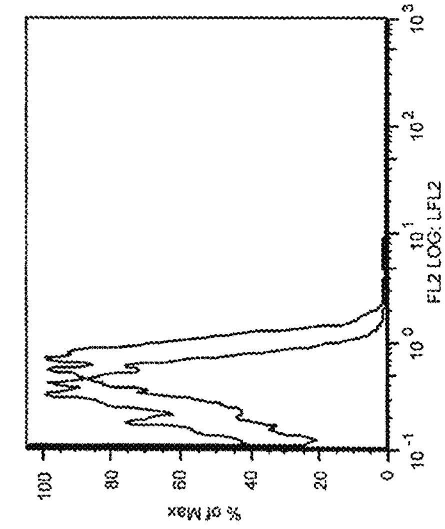
Figure 6C:
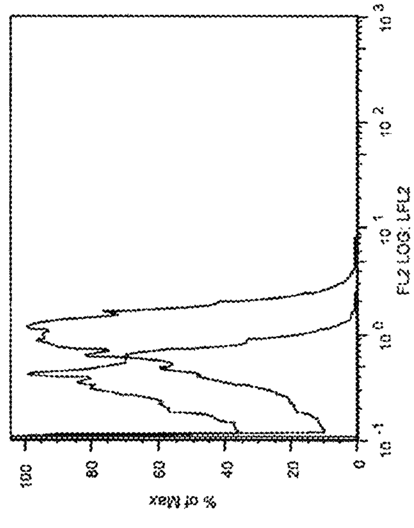
Figure 7B:
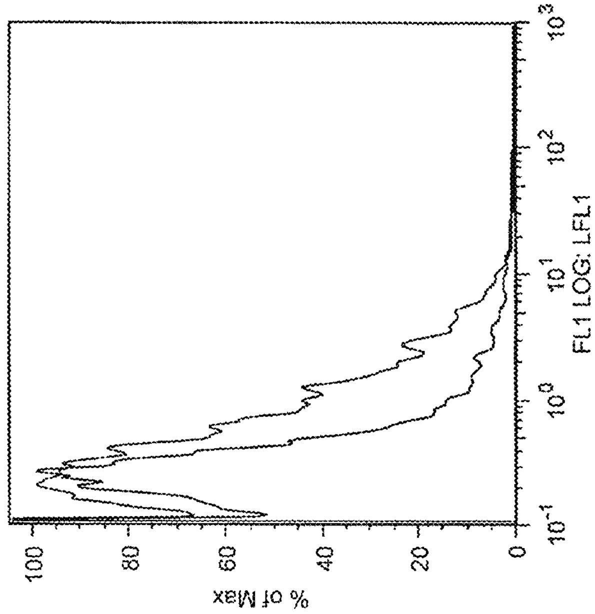
FIGS. 7A and 7B depict CLIP displacement from the surface of Raji (FIG. 7B) or Daudi (FIG. 7A) B cells lines in response to treatment with FRIMAVLAS (SEQ ID NO: 2) for 24 hours.
Figure 7A:
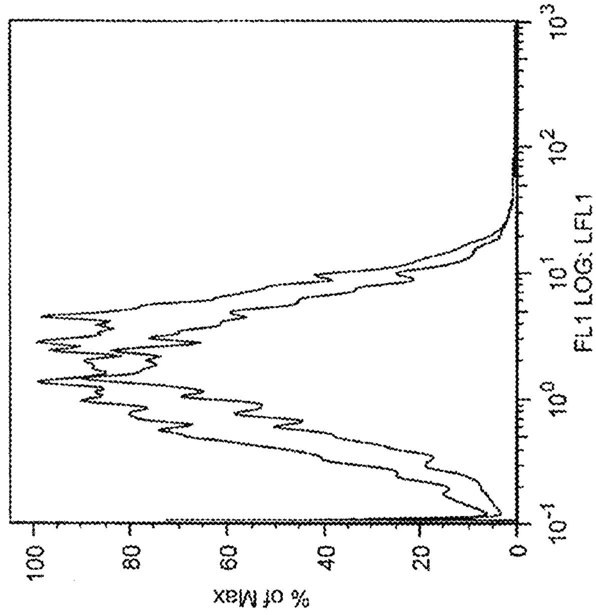
Figure 8A:
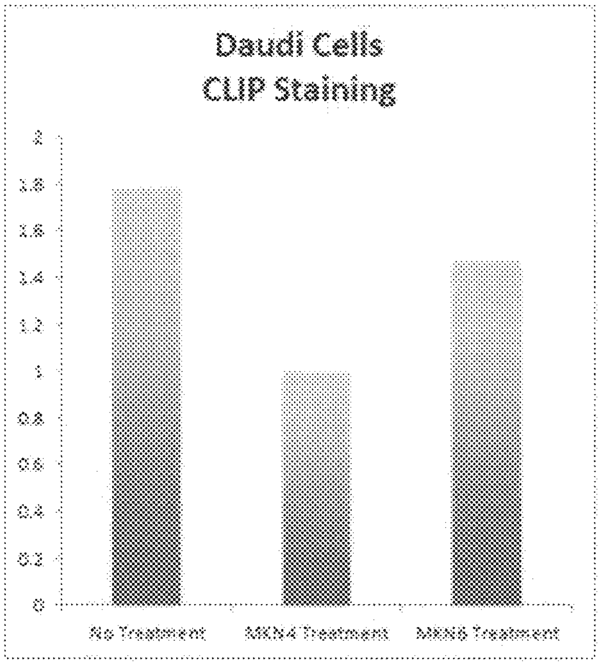
FIGS. 8A and 8B are a set of bar graphs depicting CLIP (FIG. 8A), HLA DR, DP,DQ (FIG. 8B) staining on the surface of Daudi cells in response to no treatment, or treatment with MKN.4 or MKN.6.
Figure 8B:
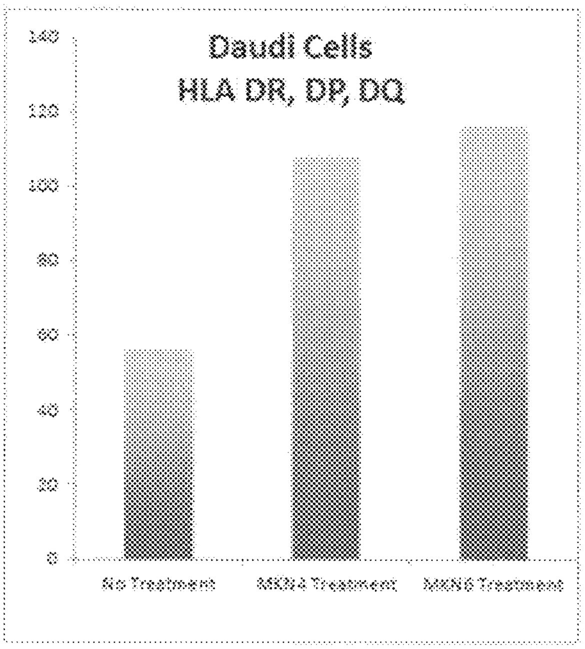
Figure 9A:
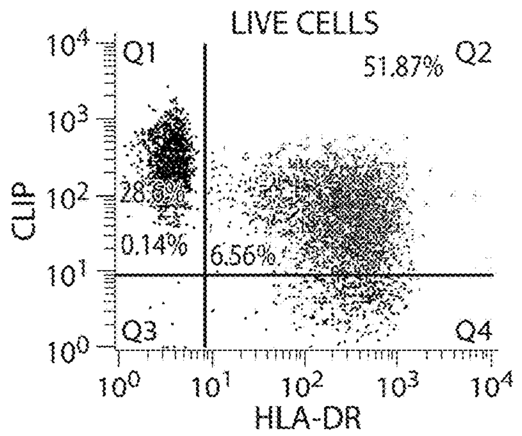
FIGS. 9A-9C depict CLIP (y-axis) and HLA DR (x-axis) staining on the surface of B cells in response to no treatment (FIG. 9A), or treatment with MKN.4 (FIG. 9B) or MKN.10 (FIG. 9C).
Figure 9B:
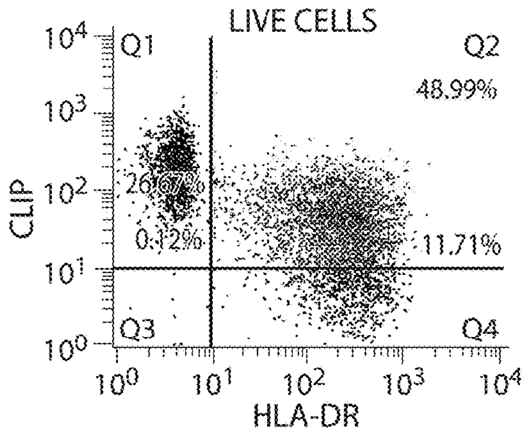
Figure 9C:
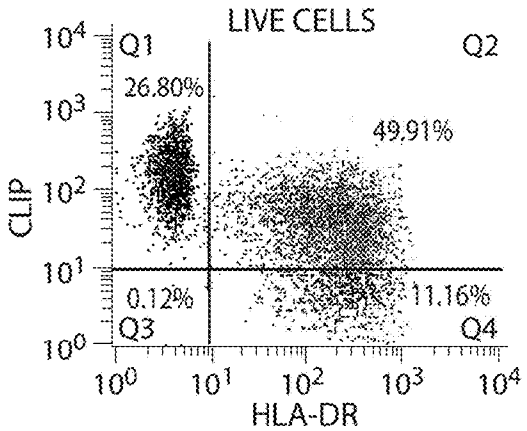
Figure 10A:
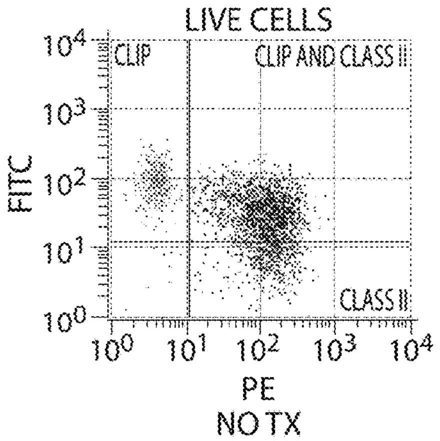
FIGS. 10A-10G depict CLIP (y-axis) and HLA DR (x-axis) staining on the surface of B cells in response to no treatment (FIG. 10A) or DMSO (FIG. 10G), or treatment with MKN.3 (FIG. 10B), MKN5 (FIG. 10C), MKN6 (FIG. 10D), MKN.8 (FIG. 10E) or MKN.10 (FIG. 10F).
Figure 10B:
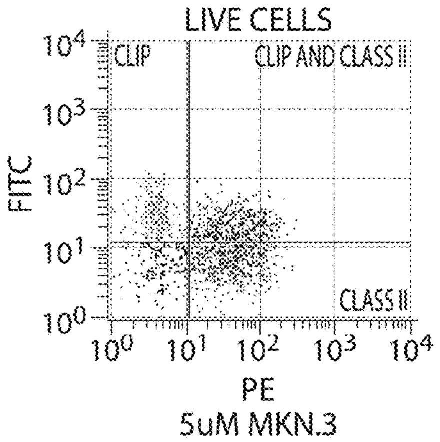
Figure 10C:
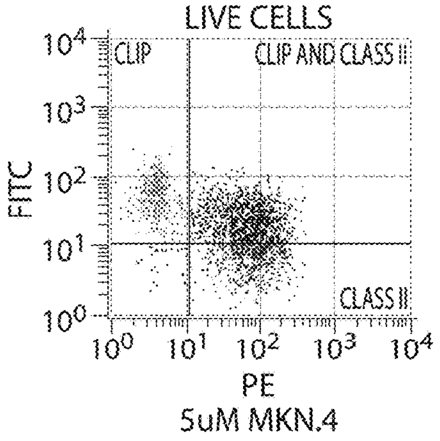
Figure 10D:
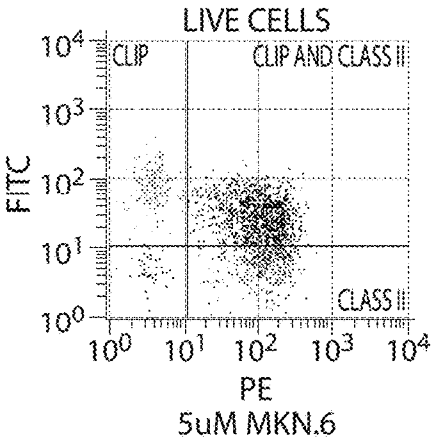
Figure 10E:
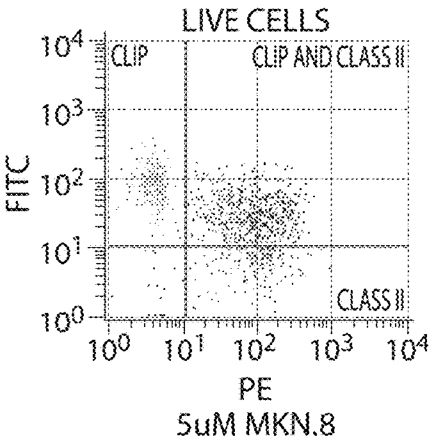
Figure 10F:
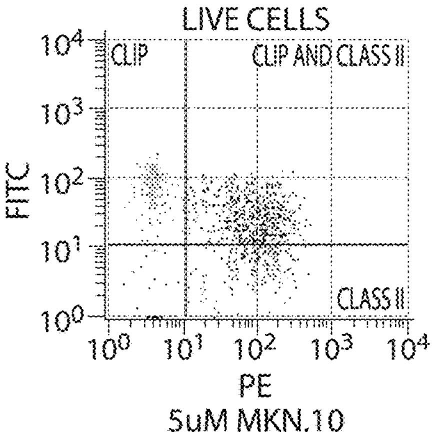
Figure 10G:
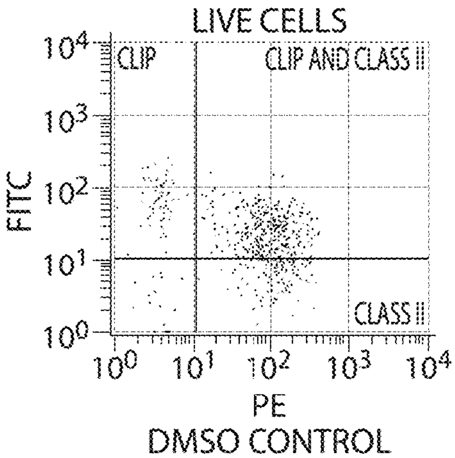

Results are expressed in histogram analyses (FIG. 4). The Y axis represents cell number of the 5000 live cells versus the X axis which is a reflection of relative Fitc fluorescence with either antibodies to CLIP. The distance between the histogram from the isotype control staining versus the histogram reflecting the specific stain and is a measure of level of cell surface CLIP when staining a population of live Raji or Daudi cells as indicated.

Our results show that treatment equimolar amounts of 2-deoxyglucose and dichloroacetate decrease (remove) cell surface CLIP from both B cell lines optimally at 48 hours.

Materials and Methods:

Cell Culture Conditions: The Raji and Daudi cell lines were purchased from American Type Culture Collection, were thawed, and grown in RPMI 1640 medium supplemented with standard supplements, including 10% fetal calf serum, gentamycin, penicillin, streptomycin, sodium pyruvate, HEPES buffer, 1-glutamine, and 2-ME.

Protocol: Cells were plated into a 12 well plate with 3 mls total volume containing approximately 0.5×106/ml for Daudi cells and 0.5×106/ml for Raji cells. Treatment groups included no treatment as control; MKN 3 and MKN 5 at 50 microMolar final concentration based on the reported molarity of the synthesized compounds.

The cells were incubated at 37° C. in an atmosphere containing 5% CO2 and approximately 92% humidity. The cells were incubated for 4, 24 and 48 hours with or without 2 deoxyglucose and dichloroacetate at 1 mg/ml of each compound. At each time point, the cells from that experimental time were harvested and stained for flow cytometric analysis of cell surface expression of CLIP (MHC Class II invariant peptide, human) by using the commercially available (Becton/Dickinson/PHarmingen) anti-human CLIP Fitc. Catalogue #555981.

Harvested cells were stained using standard staining procedure that called for a 1:100 dilution of Fitc-anti-human CLIP (Fitc, Pharmingen, Cat #555981) or isotype control. Following staining on ice for 25 minutes, cells were washed with PBS/FCS and resuspended in 100 microliters and added to staining tubes containing 400 microliters of PBS. Samples were acquired and Analyzed on a Coulter Excel Flow Cytometer.

Example 10: Competing Peptides Induce Cell Surface Expression of CD1d

The ability of synthetic peptides to compete with binding of CLIP peptides and result in the cell surface expression of CD1d was determined.

Results: The results shown in FIG. 5 are expressed in histogram analyses. The Y axis represents cell number of the 5000 live cells versus the X axis which is a reflection of relative Fitc fluorescence versus Streptavidin-PE (eBioscience, Cat. #12-4317) that will bind with high affinity to cell-bound biotinylated peptides. The distance between the histogram from the isotype control staining versus the histogram reflecting the specific stain and is a measure of level of cell surface CD1d.

At four hours, on both cell lines, significant evidence that the biotinylated synthetic peptide bound with high affinity to the human B cell lines, Raji and Daudi, at 4 hours was observed. Less binding is observed at 24 hours. The cells were counter-stained the cells with FITC-Anti-CD1d and found that treatment and binding of Biotinylated FRIMAVLAS (SEQ ID NO: 2) resulted in cell surface expression of CD1d on both cell lines, marginally at 4 hours and slightly more at 24.

Methods:

Cell Culture Conditions: The Raji and Daudi cell lines were purchased from American Type Culture Collection, were thawed, and grown in RPMI 1640 medium supplemented with standard supplements, including 10% fetal calf serum, gentamycin, penicillin, streptomycin, sodium pyruvate, HEPES buffer, 1-glutamine, and 2-ME.

Protocol: Cells were plated into a 12 well plate with 3 mls total volume containing approximately $1.5\times10^6$/well for Daudi cells and $3.0\times10^6$/well for Raji cells. Treatment groups included no treatment as control and biotinylated FRIMVALAS (SEQ ID NO: 2) (also referred to as MKN 5) at 50 microMolar final concentration based on the reported molarity of the synthesized compounds.

The cells were incubated at 37° C. in an atmosphere containing 5% CO2 and approximately 92% humidity. The cells were incubated for 4 and 24 hours. At each time point, the cells from that experimental time were harvested and stained for flow cytometric analysis of cell surface expression of CD1d by staining with PE anti-human CD1d (eBioscience, clone 51.5, cat. #12-00016-71).

Harvested cells were stained using standard staining procedure that called for a 1:100 dilution of PE anti-CD1d. Following staining on ice for 25 minutes, cells were washed with PBS/FCS and resuspended in 100 microliters and added to staining tubes containing 400 microliters of PBS. Samples were acquired and analyzed on a Coulter Excel Flow Cytometer.

Example 11: CLIP Inhibitor Peptide Binding to MHC Class II

Several of the peptides that were identified using the computational model described above were analyzed for binding to MHC class II.

Methods:

Cell Culture Conditions: The Raji and Daudi cell lines were purchased from American Type Culture Collection, were thawed, and grown in RPMI 1640 medium supplemented with standard supplements, including 10% fetal calf serum, gentamycin, penicillin, streptomycin, sodium pyruvate, HEPES buffer, 1-glutamine, and 2-ME.

Protocol: Cells were plated into a 12 well plate with 3 mls total volume containing approximately 0.5×106/well for Daudi cells and 1.0×106/well for Raji cells. Treatment groups included no treatment as control; 5 microMolar synthetic peptide as described in the figure legend and in each figure.

The cells were incubated at 37° C. in an atmosphere containing 5% CO2 and approximately 92% humidity. The cells were incubated for 24 hours. At that time point, the cells were harvested and stained for flow cytometric analysis of cell surface expression of CLIP (MHC Class II invariant peptide, human) and were counterstained with fluorochrome conjugated antibody to MHC class II/HLA-DR by using the commercially available (Becton/Dickinson/PHarmingen) anti-human CLIP Fitc. Catalogue #555981 and antibody to Human HLA-DR.

Harvested cells were stained using standard staining procedure that called for a 1:100 dilution of Fitc-anti-human CLIP, and anti-human HLA-DR or their respective isotype controls. Following staining on ice for 25 minutes, cells were washed with PBS/FCS and resuspended in 100 microliters in a 96 well plate. Samples were acquired and analyzed on a Beckman Coulter Quanta flow cytometer.

Results:

The data is shown in FIG. 10. 10A and 10G are controls involving no treatment (10A) or DMSO (10G). FIG. 10B involved treatment with 5 uM MKN.3 FIG. 10C involved treatment with 5 uM MKN.4 FIG. 10D involved treatment with 5 uM MKN.6. FIG. 10E involved treatment with 5 uM MKN.8. FIG. 10F involved treatment with 5 uM MKN.10.

The data in FIG. 10A through 10G illustrate competitive inhibition of cell surface binding of CLIP versus HLA-DR. In each figure the upper right dot plot represents cells expressing both HLA-DR and CLIP. In the lower right quadrant, the figure represents cells positive for HLA-DR, but negative for CLIP. In each figure the lower left quadrant represents cells negative for both stains. In the upper left quadrant of each dot plot are cells positive for CLIP, but negative for HLA-DR. In all cases, the percentage of cells in each quadrant can be calculated. In each case, after treatment with the appropriate peptides, the percentage of cells bearing HLA-DR (lower right quadrant) increases subsequent to peptide treatment.

Example 12: Treg Activation by CLIP Inhibitor Peptide and TNP Extract

A peptide that was identified using the computational model described above and TNP extract were analyzed for Treg activation.

Methods:

Cell Culture. All tumor cells were grown in culture in complete RPMI medium (supplemented with 10% Fetal calf serum, glutamine, beta-mercapto-ethanol, and antibiotics).

Flow Cytometry and Cell Surface Staining: Cells were harvested, counted, and resuspended at $10^6$ cells/100 μl in preparation for flow cytometric analysis. Cells were stained for cell surface CLIP using a 1:100 dilution of Anti-Human CLIP (Pharmingen). Cells were also stained for cell surface HLA-DR using a 1:100 dilution of Anti-Human HLA-DR antibody (Pharmingen). Briefly, cells were incubated with either of the above antibodies alone or together for 30 minutes on ice and in the dark. They were washed once in PBS containing 5% fetal calf serum and analyzed flow cytometrically. Data were acquired on the Beckman Coulter Quanta MPL (Coulter, Hialeah, Fla.) and analyzed with FlowJo software, (Tree Star Inc., California). The Quanta MPL flow cytometer has a single excitation wavelength (488 nm) and band filters for PE (575 nm) and FITC (525 nm) that were used to analyze the stained cells. Each sample population was classified for cell size (electronic volume, EV) and complexity (side scatter, SS), gated on a population of interest and evaluated using 10,000 cells. Each figure describing flow cytometric data represents one of at least four replicate experiments.

Cell Counting: Cells were harvested and resuspended in 1 mL of RPMI medium. A 1:20 dilution of the cell suspension was made by using 50 μL of trypan blue (Sigma chemicals), 45 μL of Phosphate Buffered Saline (PBS) supplemented with 2% FBS, and 5 μL of the cell suspension. Live cells were counted using a hemacytometer and the following calculation was used to determine cell number: Average # of Cells x Dilution x $10^4$.

Preparation of Cell for Staining: For staining protocols, between $0.5\times10^6$ and $1.0\times10^6$ cells were used; all staining was done in a 96-well U-bottom staining plate. Cells were harvested by centrifugation for 5 minutes at 300×g, washed with PBS/2% FBS, and resuspended into PBS/2% FBS for staining. Cells were plated into wells of a labeled 96-well plate in 100 μL of PBS/2% FBS.

Statistical Analysis, Percents, and Geometric Mean Values:

Percents: Gating is a tool provided by Cell Quest software and allows for the analysis of a certain population of cells. Gating around both the live and dead cell populations gave a percent of the cell numbers that was in each population. After the gates were drawn, a percent value of dead cells was calculated by taking the number of dead cells divided by the number of total cells and multiplying by one hundred.

Standard Error: When experiments were done in triplicate, a standard error of the mean value was determined using the Excel program (Microsoft). This identified the value given for the error bars seen on some figures.

Geometric Mean Fluorescence: When analyzing data on Cell Quest software, a geometric mean value will be given for each histogram plotted. Once the stained sample was plotted against the control (isotype or unstained), geometric mean fluorescence values were obtained for both histogram peaks. The stained control sample value was subtracted from sample to identify the actual fluorescence of the stained sample over that of the control.

Figure 11A:
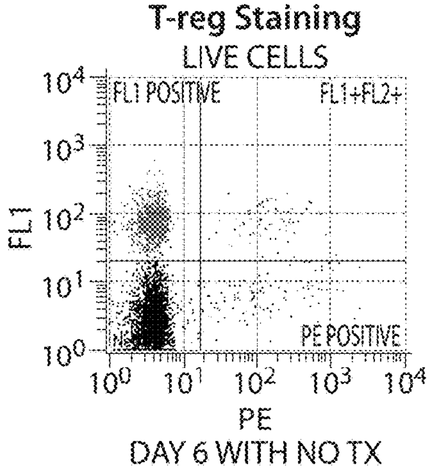
FIGS. 11A-11C depict Treg in response to no treatment (FIG. 11A), or treatment with MKN.6 (FIG. 11B) or TNP (FIG. 11C).
Figure 11B:
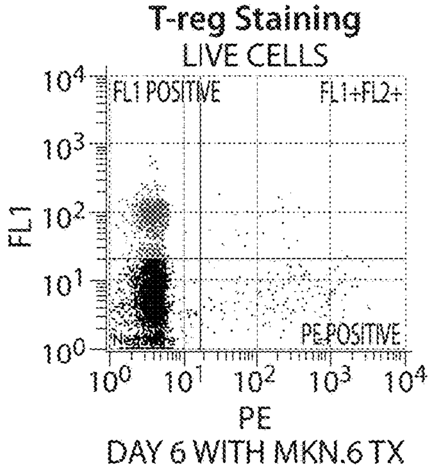
Figure 11C:
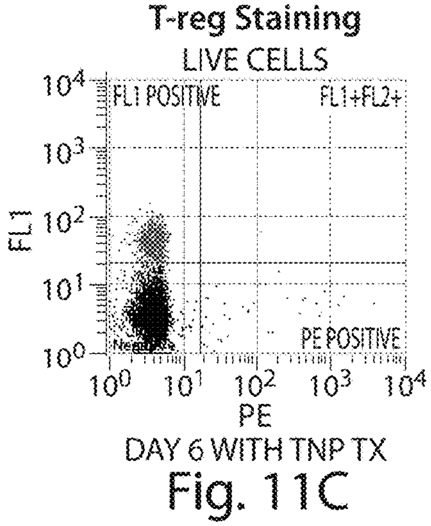

Results:

The data is shown in FIG. 11. The test peptides demonstrated Treg activation.

Example 13: TLR Activators Promote CLIP-MHC HLA Association and CLIP Inhibitor Peptides Reduce and TLR Activator Promoted CLIP-MHC HLA Association Methods Preparation of Cells: Mice were sacrificed by cervical dislocation. Spleens and lymph nodes were removed; the tissues were minced through cell strainers to create single cell suspensions; red cells were lysed using buffered ammonium chloride followed by addition of phosphate buffered saline and centrifugation to wash out the ammonium chloride; and the cells were counted using trypan blue exclusion to determine live versus dead cell discrimination and to determine the number of cells per tissue.

Treatments: The spleen or lymph node cells were treated in vitro with various stimuli (TLR activators: CpG ODN (Alexis), LPS (Sigma), PolyI:C (BD Pharmagen), Pam3Cys (Genway); IL-4 (BD Pharmagen), anti-CD40 monoclonal antibody(BD Pharmagen), both IL-4 and anti-CD40 antibody and OspA and Osp C (Genway) and the cells were cultured for the indicated time periods. The cells were grown in RPMI 1640 medium supplemented with standard supplements, including 10% fetal calf serum, gentamycin, penicillin, streptomycin, sodium pyruvate, HEPES buffer, 1-glutamine, and 2-ME as well as (where indicated) the stimuli listed above. The cells were incubated at 37° C. in an atmosphere containing 5% CO2 and approximately 92% humidity. The cells were incubated for 3, 24, and 48 hours. At each time point, the cells from that experimental time were harvested and stained for flow cytometric analysis of cell surface expression of CLIP (MHC Class II invariant peptide/IAb, Santa Cruz) by using the commercially available anti-mouse CLIP/IAb peptide, anti-mouse B220, anti-mouse CD4, anti-mouse CD8, and anti-mouse FoxP3 (all commercially available from Becton Dickinson/Pharmingen). Harvested cells were stained using standard staining procedure that called for a 1:100 dilution of Fitc-anti-mouse CLIP/IAb or isotype control. Following staining on ice for 25 minutes, cells were washed with PBS/FCS and resuspended in 100 microliters and added to staining tubes containing 400 microliters of PBS. Samples were acquired and analyzed on a Coulter Excel Flow Cytometer. The data were analyzed using FloJo software.

Results

Figure 12:
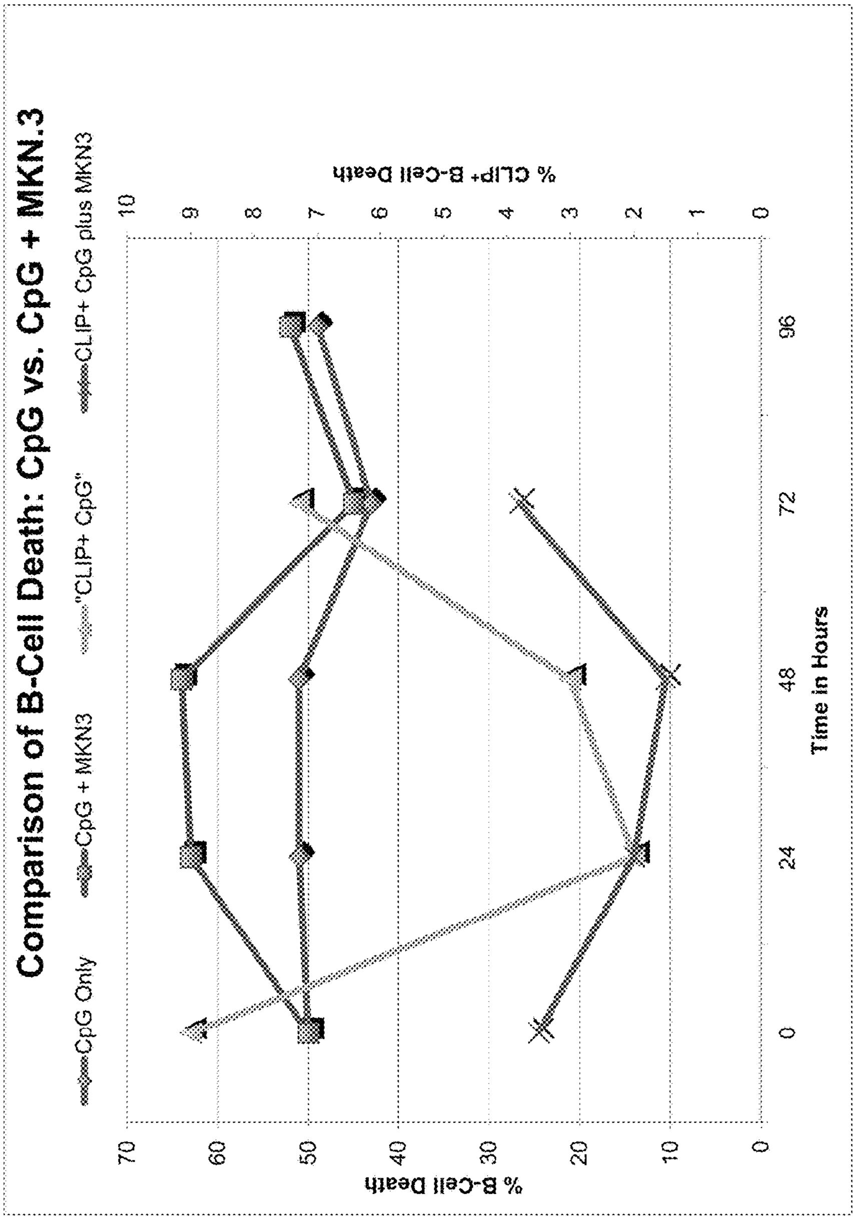
FIG. 12 demonstrates that TLR activators promote CLIP-MHC HLA association and CLIP Inhibitor peptides reduce and TLR activator promoted CLIP-MHC HLA association.

B cell death, including total B cell death and % CLIP positive B cell death in cells treated with a TLR activator (CpG ODN) alone or in combination with MKN3 in the presence or absence of CLIP was assessed. The results are shown in FIG. 12. FIG. 12 is a line graph having a double Y axis, on one side depicting % total B cell death (diamonds, representing CpG ODN alone and squares representing CpG ODN+MKN3) and on the other side depicting % CLIP+ B cell death (triangles, representing CpG ODN and CLIP alone and Xs representing CpG ODN+MKN3 and CLIP). The data reveal that CpG ODN cause an initial increase in B cell death which after 72 hours appears to level off. The CpG ODN+MKN3 data demonstrate that MKN3 is capable of preventing the increase in B cell death.

Figure 13:
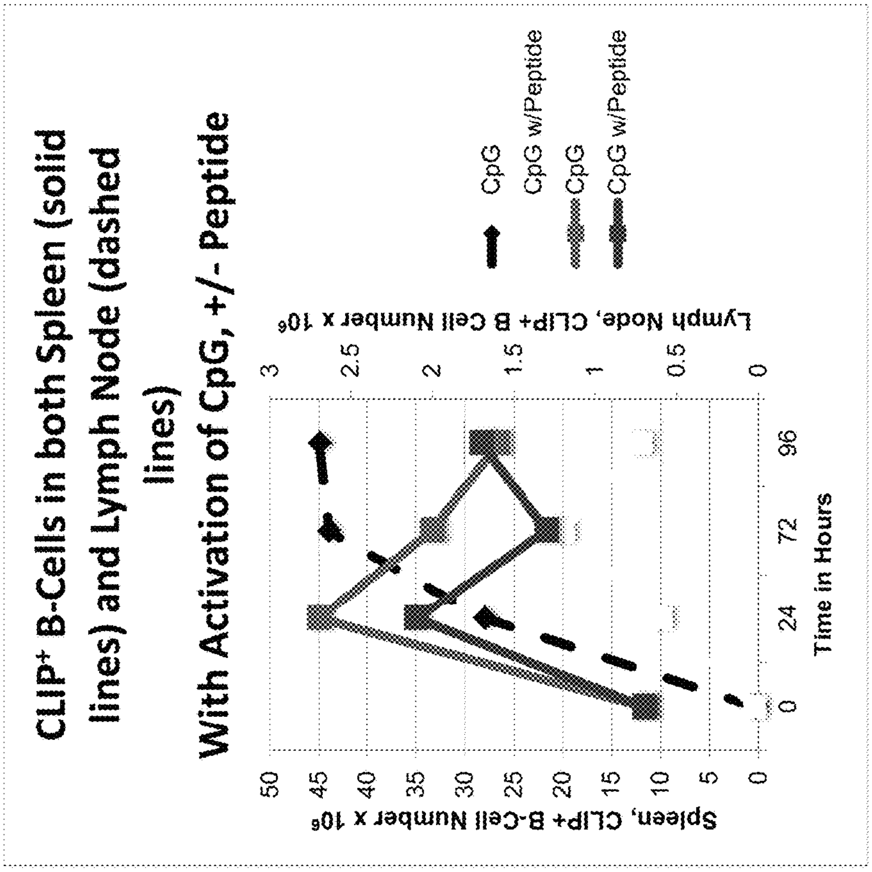
FIG. 13 demonstrates changes in CLIP positive B cells in spleen versus lymph nodes.

Changes in CLIP positive B cells in spleen versus lymph nodes were also assessed. FIG. 13 is a line graph having a double Y axis, on one side depicting % CLIP+ B cell numbers in spleen (light gray square with solid lines representing CpG ODN alone and dark gray square with solid lines representing CpG ODN+MKN3) and on the other side depicting % CLIP+ B cell numbers in lymph nodes (diamonds with dashed lines representing CpG ODN alone and light gray square with dashed lines representing CpG ODN+MKN3). In both spleen and lymph nodes the addition of the peptide to the cells with CpG ODN resulted in less CLIP positive B cells.

Figure 14C:
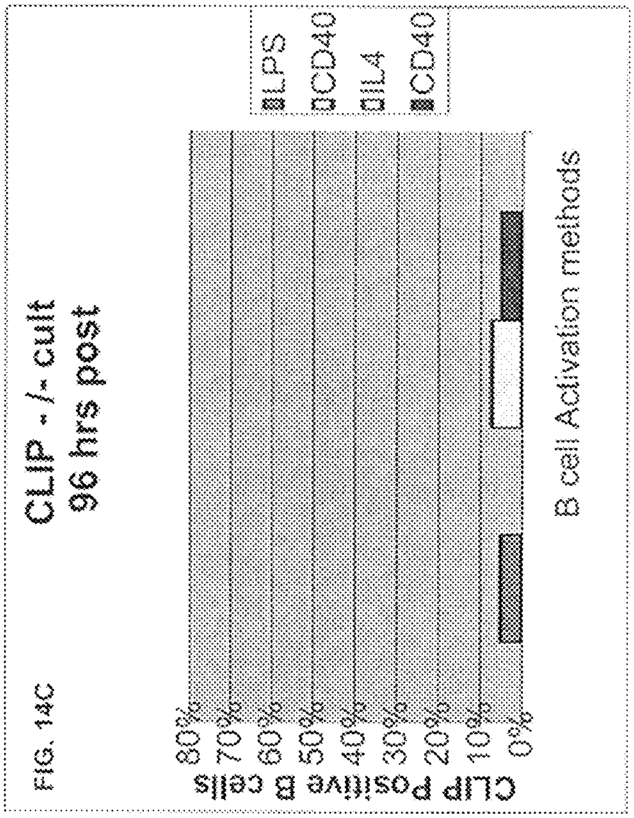
FIGS. 14A-14C are a set of graphs examining CLIP positive B6.129 cultured B cells (H-2b haplotype) and H2M−/− (from C3H HeJ mice) cultured B cells in the presence or absence of treatment with a number of different TLR activators, wherein FIG. 14A uses treatments with LPS, CD40, IL4, CD40+IL4, non-activated, and TLR3, FIG. 14B uses treatments with LPS, CD40, IL4 and FIG. 14C uses treatments with LPS, IL4 and CD40.
Figure 14A:
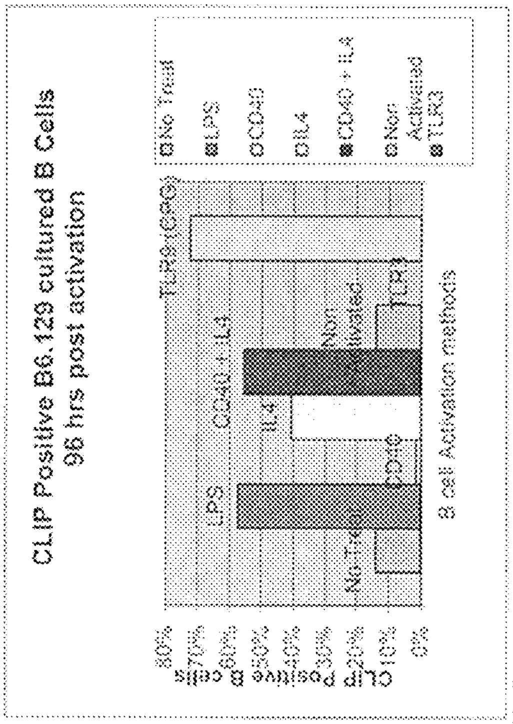
Figure 14B:
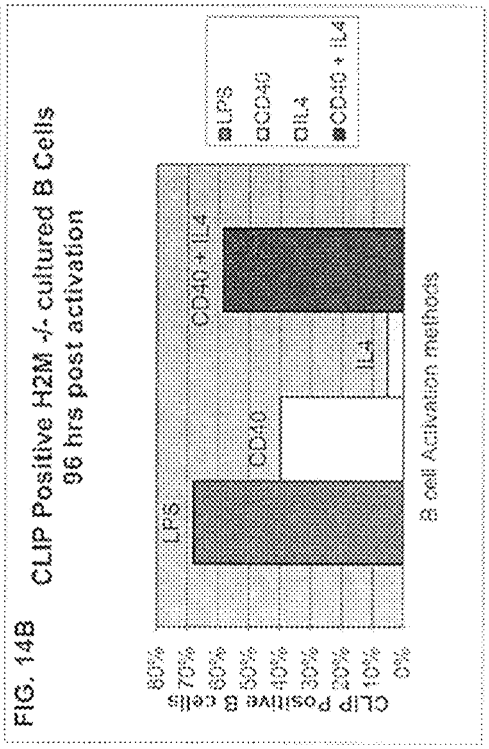

CLIP positive B6.129 cultured B cells (H-2b haplotype) and H2M−/− (from C3H HeJ mice) cultured B cells were also examined in the presence or absence of treatment with a number of different TLR activators. The data is shown in FIGS. 14A and 14B. As shown in the Figures, several TLR activators were able to induce levels of CLIP+ B cells.

Example 14: CD20+, CLIP+ B Cells in Peripheral Blood and Lymph Nodes of HIV Infected Humans Methods: Peripheral blood samples were obtained from 3 normal (HIV negative) and 4 HIV positive human subjects.

Figure 15A:
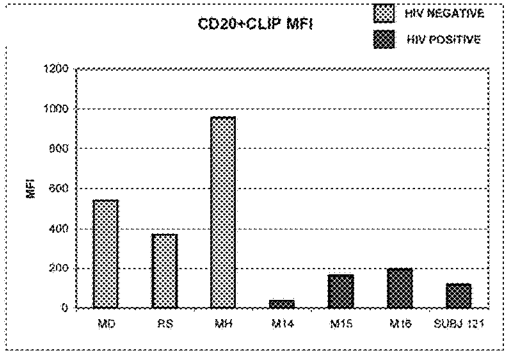
FIGS. 15A-15C are a table and a set of graphs showing the types of cells present in peripheral blood and lymph nodes of HIV infected humans. The characteristics of the subject are shown in the table on FIG. 15.
Figure 15B:
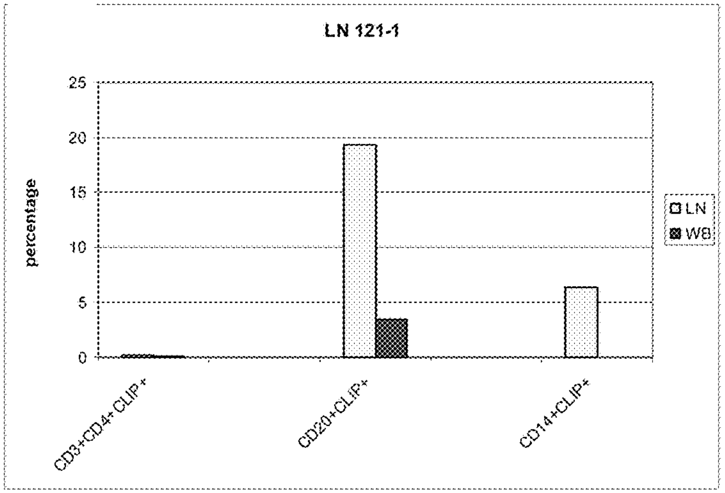
Figure 15C:
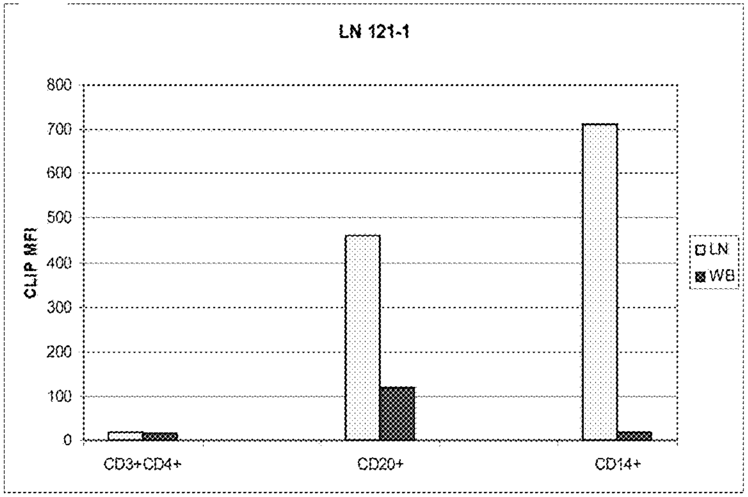

Results: The characteristics of the subject are shown in the table on FIG. 15. FIG. 15A is a line graph depicting the amount of CD20+ CLIP+ B cells as mean fluoresce intensity. FIGS. 15B and 15C are bar graphs depicting the percentage of different types of CLIP+ cells in lymph nodes (LN) or peripheral blood (WB) of the patient designated as SUB 121 in FIG. 15A (121-1). More CLIP+ cells were found in the lymph node than peripheral blood.

Example 15: The Ability of HLA Alleles to Bind to CLIP and Resist being Replaced is Directly Proportional to the Rate of HIV Disease Progression Methods: A correlation between HLA alleles and rate of progression to AIDs was described in Borghans, J. A. M., HLA Alleles Associated with Slow Progression to AIDS; Truly Prefer to Present HIV-1 p24, 2007. Additionally Gao et al. describe the effects of amino acid changes in HLA alleles and the rate of progression to AIDs (NEJM 344:12). From these studies we selected all alleles having a p value less than 0.2 and a population frequency higher than 3.5%. A computer error prevented the use of HLA-Cw16. Thus 14 alleles were available for further analysis. Gau et al reported 2 digit allele names. To convert these into 4 digit names, the most common allele for each race was used, as had been done in Borghans. (Risk Factors are shown in the Table below).

Figure 16:
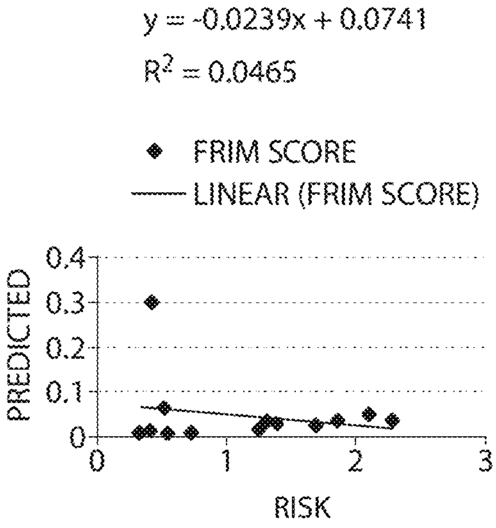
FIG. 16 is a graph depicting the risk for quicker progression to AIDs based on affinity for FRMIAVLAS (SEQ ID NO 2). The x axis of FIG. 16 is risk factor and the y axis is predicted binding score (higher predicts a tighter binding interaction).
Figure 18:
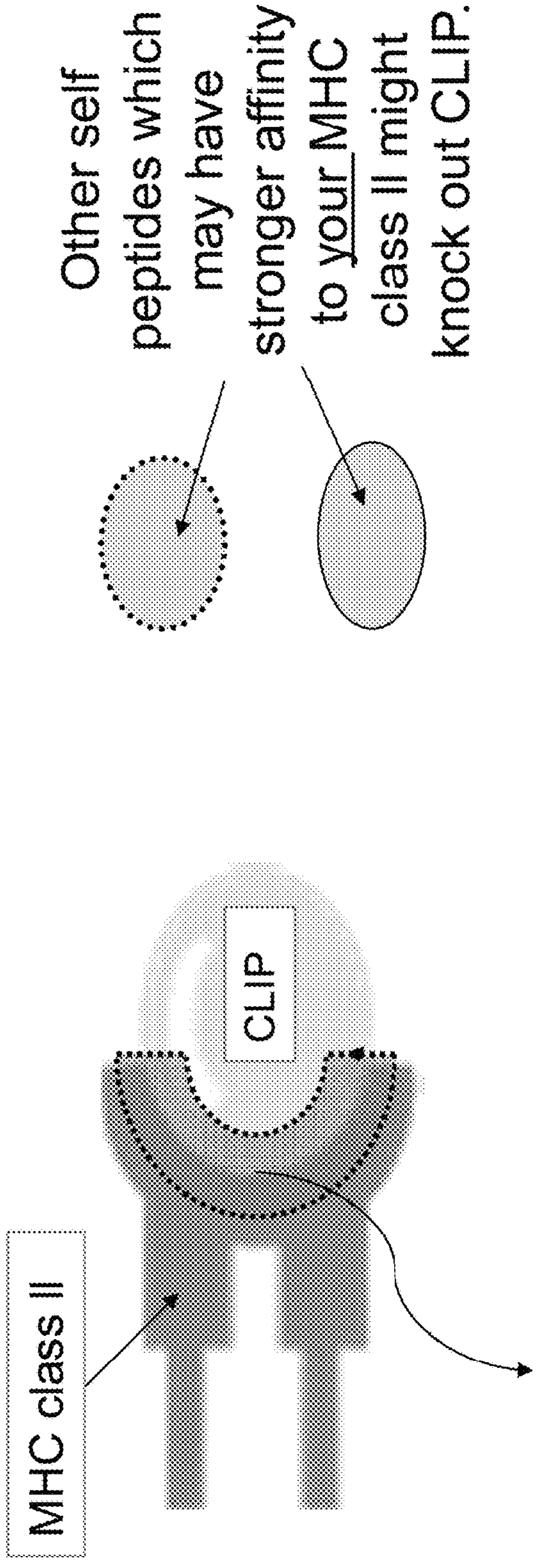
FIG. 18 is a schematic diagram of an MHC class II molecule with CLIP on the surface. The diagram depicts that some self peptides may have a stronger affinity for a Particular MHC class II and be more likely to known out CLIP. Some subjects have MHC class II that holds tightly to CLIP and thus are expected to have a faster disease progression to HIV and other that do not and are expected to have a lower disease progression to HIV.

NetMHCpan (www.cbs.dtu.dk/services/) which can predict any allele based on its amino acid sequence) was then used to predict the binding affinities of each peptide as described below. Other programs can also be used. The sequences inputted were: 1. human CLIP, 2. Human invariant chain, 3. frimavlas (SEQ ID NO 2) and the entire sequence of the TNP mixture. The program evaluates every possible consecutive 9 amino acids and gives a score for each allele. A higher score indicates a tighter predicted binding. The data is shown in the Table below labeled Best Predictors. For each of the 14 subject alleles, the score from the best 9 amino acid peptide versus the HIV progression risk factor were plotted. Then the plot was fit to a line using excel (FIG. 16).

Next, the analysis was limited only to HLA-B alleles (data not shown). For CLIP the slope is −0.15, with a Standard Error of 0.13. The main contribution is strong predicted strong binding (high score predicts better binding) to B2705. The classical CLIP register (MRMATPLLM) is the best binder in this case and its better than any other possible peptide in Invariant chain. To further investigate this, two specific CLIP registers were compared: MRM . . . and MATP . . . These 9mers were analyzed separately and plotted separately (not shown).

The Risk Factors characteristics are shown in the following Table

| Allele | freq. | RH | p | Race |
|---|---|---|---|---|
| A*01 | 17.20% | 1.25 | 0.09 | Cauc |
| A*02 | 28.90% | 0.91 | 0.41 | Cauc |
| A*03 | 12.30% | 0.97 | 0.84 | Cauc |
| A*11 | 6.20% | 0.73 | 0.11 | Cauc |
| A*23 | 2.10% | 1.24 | 0.47 | Cauc |
| A*24 | 8.90% | 1.15 | 0.38 | Cauc |
| A*25 | 2.20% | 0.91 | 0.75 | Cauc |
| A*26 | 3.20% | 0.57 | 0.07 | Cauc |
| A*29 | 3.50% | 1.39 | 0.15 | Cauc |
| A*30 | 2.60% | 1.01 | 0.96 | Cauc |
| A*31 | 2.80% | 0.93 | 0.79 | Cauc |
| A*32 | 3.90% | 0.89 | 0.61 | Cauc |
| A*33 | 1.40% | 1.2 | 0.64 | Cauc |
| A*34 | 0.10% | . | . | Cauc |
| A*36 | 0.10% | . | . | Cauc |
| A*66 | 0.30% | 4.39 | 0.01 | Cauc |
| A*68 | 3.50% | 1.31 | 0.2 | Cauc |
| A*69 | 0.40% | 0.47 | 0.45 | Cauc |
| A*74 | 0.30% | 2.15 | 0.29 | Cauc |
| Cw*01 | 3.60% | 1.21 | 0.45 | Cauc |
| Cw*02 | 5.70% | 0.52 | 0.004 | Cauc |
| Cw*03 | 12.70% | 1.05 | 0.72 | Cauc |
| Cw*04 | 11.20% | 1.7 | 0.0002 | Cauc |
| Cw*05 | 7.30% | 0.88 | 0.49 | Cauc |
| Cw*06 | 10.80% | 0.93 | 0.63 | Cauc |
| Cw*07 | 29.70% | 0.95 | 0.67 | Cauc |
| Cw*08 | 3.20% | 0.7 | 0.2 | Cauc |
| Cw*12 | 6.50% | 0.88 | 0.51 | Cauc |
| Cw*14 | 1.70% | 0.6 | 0.15 | Cauc |
| Cw*15 | 3.20% | 1.16 | 0.55 | Cauc |

-continued

| Allele | freq. | RH | p | Race |
|---|---|---|---|---|
| Cw*16 | 3.40% | 1.24 | 0.36 | Cauc |
| Cw*17 | 0.80% | 1.03 | 0.97 | Cauc |
| B*07 | 12.50% | 1.06 | 0.68 | Cauc |
| B*08 | 10.70% | 0.97 | 0.82 | Cauc |
| B*13 | 3.00% | 0.75 | 0.29 | Cauc |
| B*14 | 3.20% | 0.7 | 0.2 | Cauc |
| B*15 | 7.50% | 1.04 | 0.83 | Cauc |
| B*18 | 4.80% | 0.81 | 0.32 | Cauc |
| B*27 | 5.20% | 0.43 | 0.001 | Cauc |
| B*35 | 8.30% | 1.87 | 8.00E−05 | Cauc |
| B*37 | 1.90% | 1.42 | 0.22 | Cauc |
| B*38 | 2.40% | 0.8 | 0.42 | Cauc |
| B*39 | 1.90% | 1.86 | 0.02 | Cauc |
| B*40 | 6.30% | 0.95 | 0.77 | Cauc |
| B*41 | 0.70% | 1.22 | 0.73 | Cauc |
| B*42 | 0.20% | . | . | Cauc |
| B*44 | 11.90% | 1.09 | 0.57 | Cauc |
| B*45 | 0.50% | 2.18 | 0.12 | Cauc |
| B*48 | 0.00% | . | . | Cauc |
| B*49 | 1.80% | 1.17 | 0.61 | Cauc |
| B*50 | 0.80% | 1.3 | 0.57 | Cauc |
| B*51 | 5.90% | 0.85 | 0.41 | Cauc |
| B*52 | 0.90% | 0.24 | 0.16 | Cauc |
| B*53 | 0.80% | 1.7 | 0.25 | Cauc |
| B*55 | 2.50% | 1.29 | 0.33 | Cauc |
| B*56 | 0.60% | 1.32 | 0.59 | Cauc |
| B*57 | 4.10% | 0.55 | 0.04 | Cauc |
| B*58 | 0.80% | 0.36 | 0.08 | Cauc |
| B*67 | 0.00% | . | . | Cauc |
| B*78 | 0.00% | . | . | Cauc |
| B*81 | 0.00% | . | . | Cauc |
| A*01 | 3.70% | 1.24 | 0.69 | African |
| A*02 | 19.40% | 0.78 | 0.42 | African |
| A*03 | 7.50% | 0.42 | 0.1 | African |
| A*11 | 1.80% | 0 | 0.06 | African |
| A*23 | 10.00% | 1.15 | 0.7 | African |
| A*24 | 2.10% | 0.48 | 0.48 | African |
| A*25 | 0.50% | . | . | African |
| A*26 | 1.80% | 1.04 | 0.96 | African |
| A*29 | 2.50% | 2.57 | 0.06 | African |
| A*30 | 13.50% | 0.63 | 0.24 | African |
| A*31 | 2.30% | 0.63 | 0.53 | African |
| A*32 | 1.60% | 0 | 0.07 | African |
| A*33 | 7.10% | 1.07 | 0.88 | African |
| A*34 | 3.70% | 1.03 | 0.96 | African |
| A*36 | 2.50% | 3.57 | 0.02 | African |
| A*66 | 2.10% | 2.1 | 0.23 | African |

-continued

| Allele | freq. | RH | p | Race |
|---|---|---|---|---|
| A*68 | 10.70% | 2.29 | 0.01 | African |
| A*69 | 0.20% | . | . | African |
| A*74 | 6.80% | 1.01 | 0.99 | African |
| Cw*01 | 0.90% | 2.42 | 0.39 | African |
| Cw*02 | 6.20% | 1.59 | 0.27 | African |
| Cw*03 | 11.20% | 0.84 | 0.65 | African |
| Cw*04 | 22.10% | 1.17 | 0.62 | African |
| Cw*05 | 2.50% | 1.56 | 0.47 | African |
| Cw*06 | 8.00% | 1.5 | 0.3 | African |
| Cw*07 | 19.90% | 0.77 | 0.42 | African |
| Cw*08 | 3.40% | 0 | 0.01 | African |
| Cw*12 | 1.60% | 0.63 | 0.65 | African |
| Cw*14 | 4.10% | 0.64 | 0.47 | African |
| Cw*15 | 2.70% | 0.51 | 0.36 | African |
| Cw*16 | 9.80% | 1.61 | 0.19 | African |
| Cw*17 | 5.50% | 0.94 | 0.91 | African |
| B*07 | 10.30% | 0.66 | 0.34 | African |
| B*08 | 3.40% | 0.49 | 0.35 | African |
| B*13 | 0.50% | . | . | African |
| B*14 | 2.30% | 0 | 0.03 | African |
| B*15 | 14.40% | 0.98 | 0.96 | African |
| B*18 | 2.30% | 0.91 | 0.89 | African |
| B*27 | 0.70% | . | . | African |
| B*35 | 9.60% | 0.84 | 0.66 | African |
| B*37 | 0.00% | . | . | African |
| B*38 | 0.20% | . | . | African |
| B*39 | 1.10% | 0.76 | 0.78 | African |
| B*40 | 2.10% | 0.97 | 0.97 | African |
| B*41 | 1.40% | 3.59 | 0.04 | African |
| B*42 | 4.30% | 0.62 | 0.51 | African |
| B*44 | 7.10% | 1.42 | 0.35 | African |
| B*45 | 5.00% | 0.68 | 0.52 | African |
| B*48 | 0.00% | . | . | African |
| B*49 | 2.50% | 1.73 | 0.37 | African |
| B*50 | 2.10% | 1.1 | 0.9 | African |
| B*51 | 2.50% | 1.57 | 0.41 | African |
| B*52 | 2.30% | 1.03 | 0.97 | African |
| B*53 | 12.30% | 2.11 | 0.02 | African |
| B*55 | 0.50% | . | . | African |
| B*56 | 0.20% | . | . | African |
| B*57 | 5.90% | 0.33 | 0.13 | African |
| B*58 | 5.30% | 1.08 | 0.88 | African |
| B*67 | 0.00% | . | . | African |
| B*78 | 0.50% | . | . | African |
| B*81 | 1.40% | 0 | 0.07 | African |

Best Predictors

| Allele | Freq. | RH | P | Race | | Most common 4 digit | Best li score | Best Clip score | Frim score | Best tnp score | MRMATPLLM | MATPLLMQA |
|---|---|---|---|---|---|---|---|---|---|---|---|---|
| A*01 | 17.20% | 1.25 | 0.09 | Cauc | A0101 | HLA-A0101 | 0.3628 | 0.1096 | 0.0156 | 0.4658 | 0.1096 | 0.1003 |
| A*03 | 7.50% | 0.42 | 0.1 | African | A0301 | HLA-A0301 | 0.5444 | 0.2397 | 0.013 | 0.663 | 0.1128 | 0.0773 |
| A*11 | 6.20% | 0.73 | 0.11 | Cauc | A1101 | HLA-A1101 | 0.6589 | 0.156 | 0.0079 | 0.8146 | 0.0984 | 0.1047 |
| A*29 | 3.50% | 1.39 | 0.15 | Cauc | A2902 | HLA-A2902 | 0.6339 | 0.2729 | 0.0272 | 0.8274 | 0.2729 | 0.1084 |
| A*68 | 3.50% | 1.31 | 0.2 | Cauc | A6801 | HLA-A6801 | 0.7964 | 0.2169 | 0.0313 | 0.8874 | 0.0936 | 0.2169 |
| A*68 | 10.70% | 2.29 | 0.01 | African | A6802 | HLA-A6802 | 0.6642 | 0.6155 | 0.0334 | 0.83 | 0.1118 | 0.6155 |
| B*27 | 5.20% | 0.43 | 0.001 | Cauc | B2705 | HLA-B2705 | 0.7494 | 0.7494 | 0.297 | 0.7647 | 0.7494 | 0.0186 |
| B*35 | 8.30% | 1.87 | 8.00E−05 | Cauc | B3503 | HLA-B3503 | 0.3364 | 0.1025 | 0.0338 | 0.3711 | 0.1025 | 0.096 |
| B*53 | 12.30% | 2.11 | 0.02 | African | B5301 | HLA-B5301 | 0.6593 | 0.2996 | 0.048 | 0.6528 | 0.2996 | 0.1545 |
| B*57 | 5.90% | 0.33 | 0.13 | African | B5701 | HLA-B5701 | 0.369 | 0.3089 | 0.007 | 0.6148 | 0.1222 | 0.0796 |
| B*57 | 4.10% | 0.55 | 0.04 | Cauc | B5701 | HLA-B5701 | 0.369 | 0.3089 | 0.007 | 0.6148 | 0.1222 | 0.0796 |
| Cw*02 | 5.70% | 0.52 | 0.004 | Cauc | C0202 | HLA-C0202 | 0.3421 | 0.2231 | 0.062 | 0.4085 | 0.2231 | 0.1887 |
| Cw*04 | 11.20% | 1.7 | 0.0002 | Cauc | C0401 | HLA-C0401 | 0.2683 | 0.2061 | 0.0242 | 0.2647 | 0.165 | 0.097 |
| Cw*16 | 9.80% | 1.61 | 0.19 | African | C1601 | HLA-C1601 | | | | | | |

Results

FIG. 16 is a graph depicting the risk for quicker progression to AIDs based on affinity for FRMIAVLAS (SEQ ID NO 2). The x axis of FIG. 16 is risk factor and the y axis is predicted binding score (higher predicts a tighter binding interaction). A positive slope means that fast disease progression correlates with tight binding. A negative slope means that tight binding correlates with slower disease progression.

Example 16: In Vivo Study to Assess the Spleen Versus Lymph Node Cellularity and CLIP+ B Cells Upon Activation with TLR Ligands Methods In vivo experiments. B6.129 mice (H-2b haplotype) or C3H HeJ mice (H-2k) mice were injected peritoneally with various toll ligands as indicated on the figures (CpG ODN, Poly I:C, LPS, Pam3Cys, OspA, or OspC—all of which were used at concentrations to approximate 5 micrograms/25 g mouse). Peptides were injected simultaneously at a concentration of 5 micrograms per mouse). Spleens and lymph nodes were harvested at the indicated times after injection, processed through cell strainers as described above, and stained as described above.

Results

FIG. 17 is a set of line graphs depicting the results of in vivo administered TLR ligands (data for CpG ODN shown, other data not shown) alone or in the presence of MKN3 peptide. The data demonstrates that in vivo, like the in vitro data, TLR activators produce higher levels of spleen and lymph node cellularity as well as CLIP+B cells and that the presence of peptide reduces the cellularity and CLIP+ B cells.

In view of the data described herein it is believed that when HIV infects CD4 cells, the cells become CLIP positive. It is known that a significant portion of viral replication occurs in the lymph nodes.

TABLE 4

Appendix A

Virtual Matrix for HLA-DRB_10101

| Amino acid | P1 | P2 | P3 | P4 | P5 | P6 | P7 | P8 | P9 |
|---|---|---|---|---|---|---|---|---|---|
| | Position | | | | | | | | |
| A: | −999.00 | 0.00 | 0.00 | 0.00 | — | 0.00 | 0.00 | — | 0.00 |
| D: | −999.00 | −1.30 | −1.30 | −2.40 | — | −2.70 | −2.00 | — | −1.90 |
| E: | −999.00 | 0.10 | −1.20 | −0.40 | — | −2.40 | −0.60 | — | −1.90 |
| F: | 0.00 | 0.80 | 0.80 | 0.08 | — | −2.10 | 0.30 | — | −0.40 |
| G: | −999.00 | 0.50 | 0.20 | −0.70 | — | −0.30 | −1.10 | — | −0.80 |
| H: | −999.00 | 0.80 | 0.20 | −0.70 | — | −2.20 | 0.10 | — | −1.10 |
| I: | −1.00 | 1.10 | 1.50 | 0.50 | — | −1.90 | 0.60 | — | 0.70 |
| K: | −999.00 | 1.10 | 0.00 | −2.10 | — | −2.00 | −0.20 | — | −1.70 |
| L: | −1.00 | 1.00 | 1.00 | 0.90 | — | −2.00 | 0.30 | — | 0.50 |
| M: | −1.00 | 1.10 | 1.40 | 0.80 | — | −1.80 | 0.09 | — | 0.08 |
| N: | −999.00 | 0.80 | 0.50 | 0.04 | — | −1.10 | 0.10 | — | −1.20 |
| P: | −999.00 | −0.50 | 0.30 | −1.90 | — | −0.20 | 0.07 | — | −1.10 |
| Q: | −999.00 | 1.20 | 0.00 | 0.10 | — | −1.80 | 0.20 | — | −1.60 |
| R: | −999.00 | 2.20 | 0.70 | −2.10 | — | −1.80 | 0.09 | — | −1.00 |
| S: | −999.00 | −0.30 | 0.20 | −0.70 | — | −0.60 | −0.20 | — | −0.30 |
| T: | −999.00 | 0.00 | 0.00 | −1.00 | — | −1.20 | 0.09 | — | −0.20 |
| V: | −1.00 | 2.10 | 0.50 | −0.05 | — | −1.10 | 0.70 | — | 0.30 |
| W: | 0.00 | −0.10 | 0.00 | −1.80 | — | −2.40 | −0.08 | — | −1.40 |
| Y: | 0.00 | 0.90 | 0.80 | −1.10 | — | −2.00 | 0.50 | — | −0.90 |
| Percent Threshold | 1% 2% | 3% | 4% | 5% | 6% | 7% | 8% | 9% | 10% |
| Numerical Score | 1.24 0.6 | 0.14 | −0.2 | −0.5 | −0.76 | −1 | −1.2 | −1.4 | −1.6 |

Virtual Matrix for HLA-DRB1_0102

| Amino acid | P1 | P2 | P3 | P4 | P5 | P6 | P7 | P8 | P9 |
|---|---|---|---|---|---|---|---|---|---|
| | Position | | | | | | | | |
| A: | −999.00 | 0.00 | 0.00 | 0.00 | — | 0.00 | 0.00 | — | 0.00 |
| D: | −999.00 | −1.30 | −1.30 | −2.40 | — | −2.70 | −2.00 | — | −1.90 |
| E: | −999.00 | 0.10 | −1.20 | −0.40 | — | −2.40 | −0.60 | — | −1.90 |
| F: | 0.00 | 0.80 | 0.80 | 0.08 | — | −2.10 | 0.30 | — | −0.40 |
| G: | −999.00 | 0.50 | 0.20 | −0.70 | — | −0.30 | −1.10 | — | −0.80 |
| H: | −999.00 | 0.80 | 0.20 | −0.70 | — | −2.20 | 0.10 | — | −1.10 |
| I: | 0.00 | 1.10 | 1.50 | 0.50 | — | −1.90 | 0.60 | — | 0.70 |
| K: | −999.00 | 1.10 | 0.00 | −2.10 | — | −2.00 | −0.20 | — | −1.70 |
| L: | 0.00 | 1.00 | 1.00 | 0.90 | — | −2.00 | 0.30 | — | 0.50 |
| M: | 0.00 | 1.10 | 1.40 | 0.80 | — | −1.80 | 0.09 | — | 0.08 |
| N: | −999.00 | 0.80 | 0.50 | 0.04 | — | −1.10 | 0.10 | — | −1.20 |
| P: | −999.00 | −0.50 | 0.30 | −1.90 | — | −0.20 | 0.07 | — | −1.10 |
| Q: | −999.00 | 1.20 | 0.00 | 0.10 | — | −1.80 | 0.20 | — | −1.60 |
| R: | −999.00 | 2.20 | 0.70 | −2.10 | — | −1.80 | 0.09 | — | −1.00 |
| S: | −999.00 | −0.30 | 0.20 | −0.70 | — | −0.60 | −0.20 | — | −0.30 |
| T: | −999.00 | 0.00 | 0.00 | −1.00 | — | −1.20 | 0.09 | — | −0.20 |
| V: | 0.00 | 2.10 | 0.50 | −0.05 | — | −1.10 | 0.70 | — | 0.30 |

TABLE 4-continued

Appendix A

| | | | | | | | | | | |
|---|---|---|---|---|---|---|---|---|---|---|
| W: | −1.00 | −0.10 | 0.00 | −1.80 | — | −2.40 | −0.08 | — | −1.40 | |
| Y: | −1.00 | 0.90 | 0.80 | −1.10 | — | −2.00 | 0.50 | — | −0.90 | |
| Percent Threshold | 1% | 2% | 3% | 4% | 5% | 6% | 7% | 8% | 9% | 10% |
| Numerical Score | 1.9 | 1.18 | 0.7 | 0.4 | 0.1 | −0.2 | −0.4 | −0.6 | −0.8 | −0.91 |

Virtual Matrix for HLA-DRB1__0301

| Amino acid | Position P1 | P2 | P3 | P4 | P5 | P6 | P7 | P8 | P9 | |
|---|---|---|---|---|---|---|---|---|---|---|
| A: | −999.00 | 0.00 | 0.00 | 0.00 | — | 0.00 | 0.00 | — | 0.00 | |
| D: | −999.00 | −1.30 | −1.30 | 2.30 | — | −2.40 | −0.60 | — | −0.60 | |
| E: | −999.00 | 0.10 | −1.20 | −1.00 | — | −1.40 | −0.20 | — | −0.30 | |
| F: | −1.00 | 0.80 | 0.80 | −1.00 | — | −1.40 | 0.50 | — | 0.90 | |
| G: | −999.00 | 0.50 | 0.20 | 0.50 | — | −0.70 | 0.10 | — | 0.40 | |
| H: | −999.00 | 0.80 | 0.20 | 0.00 | — | −0.10 | −0.80 | — | −0.50 | |
| I: | 0.00 | 1.10 | 1.50 | 0.50 | — | 0.70 | 0.40 | — | 0.60 | |
| K: | −999.00 | 1.10 | 0.00 | −1.00 | — | 1.30 | −0.90 | — | −0.20 | |
| L: | 0.00 | 1.00 | 1.00 | 0.00 | — | 0.20 | 0.20 | — | −0.04 | |
| M: | 0.00 | 1.10 | 1.40 | 0.00 | — | −0.90 | 1.10 | — | 1.10 | |
| N: | −999.00 | 0.80 | 0.50 | 0.20 | — | −0.60 | −0.09 | — | −0.60 | |
| P: | −999.00 | −0.50 | 0.30 | −1.00 | — | 0.50 | 0.70 | — | −0.30 | |
| Q: | −999.00 | 1.20 | 0.00 | 0.00 | — | −0.30 | −0.10 | — | −0.20 | |
| R: | −999.00 | 2.20 | 0.70 | −1.00 | — | 1.00 | −0.90 | — | 0.50 | |
| S: | −999.00 | −0.30 | 0.20 | 0.70 | — | −0.10 | 0.07 | — | 1.10 | |
| T: | −999.00 | 0.00 | 0.00 | −1.00 | — | 0.80 | −0.10 | — | −0.50 | |
| V: | 0.00 | 2.10 | 0.50 | 0.00 | — | 1.20 | 0.20 | — | 0.30 | |
| W: | −1.00 | −0.10 | 0.00 | −1.00 | — | −1.40 | −0.60 | — | −1.00 | |
| Y: | −1.00 | 0.90 | 0.80 | −1.00 | — | −1.40 | −0.05 | — | 0.30 | |
| Percent Threshold | 1% | 2% | 3% | 4% | 5% | 6% | 7% | 8% | 9% | 10% |
| Numerical Score | 4.03 | 3.3 | 2.96 | 2.6 | 2.4 | 2.17 | 1.96 | 1.73 | 1.5 | 1.3 |

Virtual Matrix for HLA-DRB1__0305

| Amino acid | Position P1 | P2 | P3 | P4 | P5 | P6 | P7 | P8 | P9 | |
|---|---|---|---|---|---|---|---|---|---|---|
| A: | −999.00 | 0.00 | 0.00 | 0.00 | — | 0.00 | 0.00 | — | 0.00 | |
| D: | −999.00 | −1.30 | −1.30 | 2.30 | — | −2.40 | −0.60 | — | −1.70 | |
| E: | −999.00 | 0.10 | −1.20 | −1.00 | — | −1.40 | −0.20 | — | −1.70 | |
| F: | 0.00 | 0.80 | 0.80 | −1.00 | — | −1.40 | 0.50 | — | −1.00 | |
| G: | −999.00 | 0.50 | 0.20 | 0.50 | — | −0.70 | 0.10 | — | −1.00 | |
| H: | −999.00 | 0.80 | 0.20 | 0.00 | — | −0.10 | −0.80 | — | 0.08 | |
| I: | −1.00 | 1.10 | 1.50 | 0.50 | — | 0.70 | 0.40 | — | −0.30 | |
| K: | −999.00 | 1.10 | 0.00 | −1.00 | — | 1.30 | −0.90 | — | −0.30 | |
| L: | −1.00 | 1.00 | 1.00 | 0.00 | — | 0.20 | 0.20 | — | −1.00 | |
| M: | −1.00 | 1.10 | 1.40 | 0.00 | — | −0.90 | 1.10 | — | −0.40 | |
| N: | −999.00 | 0.80 | 0.50 | 0.20 | — | −0.60 | −0.09 | — | −1.40 | |
| P: | −999.00 | −0.50 | 0.30 | −1.00 | — | 0.50 | 0.70 | — | −1.30 | |
| Q: | −999.00 | 1.20 | 0.00 | 0.00 | — | −0.30 | −0.10 | — | 0.50 | |
| R: | −999.00 | 2.20 | 0.70 | −1.00 | — | 1.00 | −0.90 | — | −1.00 | |
| S: | −999.00 | −0.30 | 0.20 | 0.70 | — | −0.10 | 0.07 | — | 0.70 | |
| T: | −999.00 | 0.00 | 0.00 | −1.00 | — | 0.80 | −0.10 | — | −1.20 | |
| V: | −1.00 | 2.10 | 0.50 | 0.00 | — | 1.20 | 0.20 | — | −0.70 | |
| W: | 0.00 | −0.10 | 0.00 | −1.00 | — | −1.40 | −0.60 | — | −1.00 | |
| Y: | 0.00 | 0.90 | 0.80 | −1.00 | — | −1.40 | −0.05 | — | −1.00 | |
| Percent Threshold | 1% | 2% | 3% | 4% | 5% | 6% | 7% | 8% | 9% | 10% |
| Numerical Score | 2.7 | 2.1 | 1.7 | 1.4 | 1.1 | 0.87 | 0.61 | 0.45 | 0.30 | 0.10 |

Virtual Matrix for HLA-DRB1__0306

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | 2.30 | — | −2.40 | −0.30 | — | −1.70 |
| E: | −999.00 | 0.10 | −1.20 | −1.00 | — | −1.40 | 0.20 | — | −1.70 |
| F: | −1.00 | 0.80 | 0.80 | −1.00 | — | −1.40 | −1.00 | — | −1.00 |
| G: | −999.00 | 0.50 | 0.20 | 0.50 | — | −0.70 | −1.30 | — | −1.00 |

TABLE 4-continued

Appendix A

| | | | | | | | | | |
|---|---|---|---|---|---|---|---|---|---|
| H: | −999.00 | 0.80 | 0.20 | 0.00 | — | −0.10 | 0.00 | — | 0.08 |
| I: | 0.00 | 1.10 | 1.50 | 0.50 | — | 0.70 | 0.08 | — | −0.30 |
| K: | −999.00 | 1.10 | 0.00 | −1.00 | — | 1.30 | −0.30 | — | −0.30 |
| L: | 0.00 | 1.00 | 1.00 | 0.00 | — | 0.20 | 0.70 | — | −1.00 |
| M: | 0.00 | 1.10 | 1.40 | 0.00 | — | −0.90 | 0.80 | — | −0.40 |
| N: | −999.00 | 0.80 | 0.50 | 0.20 | — | −0.60 | 0.60 | — | −1.40 |
| P: | −999.00 | −0.50 | 0.30 | −1.00 | — | 0.50 | −0.70 | — | −1.30 |
| Q: | −999.00 | 1.20 | 0.00 | 0.00 | — | −0.30 | 0.00 | — | 0.50 |
| R: | −999.00 | 2.20 | 0.70 | −1.00 | — | 1.00 | −1.20 | — | −1.00 |
| S: | −999.00 | −0.30 | 0.20 | 0.70 | — | −0.10 | −0.20 | — | 0.70 |
| T: | −999.00 | 0.00 | 0.00 | −1.00 | — | 0.80 | −0.10 | — | −1.20 |
| V: | 0.00 | 2.10 | 0.50 | 0.00 | — | 1.20 | 0.08 | — | −0.70 |
| W: | −1.00 | −0.10 | 0.00 | −1.00 | — | −1.40 | −1.40 | — | −1.00 |
| Y: | −1.00 | 0.90 | 0.80 | −1.00 | — | −1.40 | −1.20 | — | −1.00 |
| Percent Threshold | 1% | 2% | 3% | 4% | 5% | 6% | 7% | 8% | 9% | 10% |
| Numerical Score | 3.1 | 2.5 | 2.08 | 1.7 | 1.48 | 1.2 | 1.0 | 0.8 | 0.6 | 0.4 |

Virtual Matrix for HLA-DRB1_0307

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | 2.30 | — | −2.40 | −0.30 | — | −1.70 |
| E: | −999.00 | 0.10 | −1.20 | −1.00 | — | −1.40 | 0.20 | — | −1.70 |
| F: | −1.00 | 0.80 | 0.80 | −1.00 | — | −1.40 | −1.00 | — | −1.00 |
| G: | −999.00 | 0.50 | 0.20 | 0.50 | — | −0.70 | −1.30 | — | −1.00 |
| H: | −999.00 | 0.80 | 0.20 | 0.00 | — | −0.10 | 0.00 | — | 0.08 |
| I: | 0.00 | 1.10 | 1.50 | 0.50 | — | 0.70 | 0.08 | — | −0.30 |
| K: | −999.00 | 1.10 | 0.00 | −1.00 | — | 1.30 | −0.30 | — | −0.30 |
| L: | 0.00 | 1.00 | 1.00 | 0.00 | — | 0.20 | 0.70 | — | −1.00 |
| M: | 0.00 | 1.10 | 1.40 | 0.00 | — | −0.90 | 0.80 | — | −0.40 |
| N: | −999.00 | 0.80 | 0.50 | 0.20 | — | −0.60 | 0.60 | — | −1.40 |
| P: | −999.00 | −0.50 | 0.30 | −1.00 | — | 0.50 | −0.70 | — | −1.30 |
| Q: | −999.00 | 1.20 | 0.00 | 0.00 | — | −0.30 | 0.00 | — | 0.50 |
| R: | −999.00 | 2.20 | 0.70 | −1.00 | — | 1.00 | −1.20 | — | −1.00 |
| S: | −999.00 | −0.30 | 0.20 | 0.70 | — | −0.10 | −0.20 | — | 0.70 |
| T: | −999.00 | 0.00 | 0.00 | −1.00 | — | 0.80 | −0.10 | — | −1.20 |
| V: | 0.00 | 2.10 | 0.50 | 0.00 | — | 1.20 | 0.08 | — | −0.70 |
| W: | −1.00 | −0.10 | 0.00 | −1.00 | — | −1.40 | −1.40 | — | −1.00 |
| Y: | −1.00 | 0.90 | 0.80 | −1.00 | — | −1.40 | −1.20 | — | −1.00 |
| Percent Threshold | 1% | 2% | 3% | 4% | 5% | 6% | 7% | 8% | 9% | 10% |
| Numerical Score | 3.1 | 2.5 | 2.08 | 1.7 | 1.48 | 1.2 | 1.0 | 0.8 | 0.6 | 0.4 |

Virtual Matrix for HLA-DRB1_0308

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | 2.30 | — | −2.40 | −0.30 | — | −1.70 |
| E: | −999.00 | 0.10 | −1.20 | −1.00 | — | −1.40 | 0.20 | — | −1.70 |
| F: | −1.00 | 0.80 | 0.80 | −1.00 | — | −1.40 | −1.00 | — | −1.00 |
| G: | −999.00 | 0.50 | 0.20 | 0.50 | — | −0.70 | −1.30 | — | −1.00 |
| H: | −999.00 | 0.80 | 0.20 | 0.00 | — | −0.10 | 0.00 | — | 0.08 |
| I: | 0.00 | 1.10 | 1.50 | 0.50 | — | 0.70 | 0.08 | — | −0.30 |
| K: | −999.00 | 1.10 | 0.00 | −1.00 | — | 1.30 | −0.30 | — | −0.30 |
| L: | 0.00 | 1.00 | 1.00 | 0.00 | — | 0.20 | 0.70 | — | −1.00 |
| M: | 0.00 | 1.10 | 1.40 | 0.00 | — | −0.90 | 0.80 | — | −0.40 |
| N: | −999.00 | 0.80 | 0.50 | 0.20 | — | −0.60 | 0.60 | — | −1.40 |
| P: | −999.00 | −0.50 | 0.30 | −1.00 | — | 0.50 | −0.70 | — | −1.30 |
| Q: | −999.00 | 1.20 | 0.00 | 0.00 | — | −0.30 | 0.00 | — | 0.50 |
| R: | −999.00 | 2.20 | 0.70 | −1.00 | — | 1.00 | −1.20 | — | −1.00 |
| S: | −999.00 | −0.30 | 0.20 | 0.70 | — | −0.10 | −0.20 | — | 0.70 |
| T: | −999.00 | 0.00 | 0.00 | −1.00 | — | 0.80 | −0.10 | — | −1.20 |
| V: | 0.00 | 2.10 | 0.50 | 0.00 | — | 1.20 | 0.08 | — | −0.70 |
| W: | −1.00 | −0.10 | 0.00 | −1.00 | — | −1.40 | −1.40 | — | −1.00 |
| Y: | −1.00 | 0.90 | 0.80 | −1.00 | — | −1.40 | −1.20 | — | −1.00 |

TABLE 4-continued

Appendix A

| Percent Threshold | 1% | 2% | 3% | 4% | 5% | 6% | 7% | 8% | 9% | 10% |
|---|---|---|---|---|---|---|---|---|---|---|
| Numerical Score | 3.1 | 2.5 | 2.08 | 1.7 | 1.48 | 1.2 | 1.0 | 0.8 | 0.6 | 0.4 |

Virtual Matrix for HLA-DRB1_0309

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | 2.30 | — | −2.40 | −0.60 | — | −0.60 |
| E: | −999.00 | 0.10 | −1.20 | −1.00 | — | −1.40 | −0.20 | — | −0.30 |
| F: | 0.00 | 0.80 | 0.80 | −1.00 | — | −1.40 | 0.50 | — | 0.90 |
| G: | −999.00 | 0.50 | 0.20 | 0.50 | — | −0.70 | 0.10 | — | 0.40 |
| H: | −999.00 | 0.80 | 0.20 | 0.00 | — | −0.10 | −0.80 | — | −0.50 |
| I: | −1.00 | 1.10 | 1.50 | 0.50 | — | 0.70 | 0.40 | — | 0.60 |
| K: | −999.00 | 1.10 | 0.00 | −1.00 | — | 1.30 | −0.90 | — | −0.20 |
| L: | −1.00 | 1.00 | 1.00 | 0.00 | — | 0.20 | 0.20 | — | −0.04 |
| M: | −1.00 | 1.10 | 1.40 | 0.00 | — | −0.90 | 1.10 | — | 1.10 |
| N: | −999.00 | 0.80 | 0.50 | 0.20 | — | −0.60 | −0.09 | — | −0.60 |
| P: | −999.00 | −0.50 | 0.30 | −1.00 | — | 0.50 | 0.70 | — | −0.30 |
| Q: | −999.00 | 1.20 | 0.00 | 0.00 | — | −0.30 | −0.10 | — | −0.20 |
| R: | −999.00 | 2.20 | 0.70 | −1.00 | — | 1.00 | −0.90 | — | 0.50 |
| S: | −999.00 | −0.30 | 0.20 | 0.70 | — | −0.10 | 0.07 | — | 1.10 |
| T: | −999.00 | 0.00 | 0.00 | −1.00 | — | 0.80 | −0.10 | — | −0.50 |
| V: | −1.00 | 2.10 | 0.50 | 0.00 | — | 1.20 | 0.20 | — | 0.30 |
| W: | 0.00 | −0.10 | 0.00 | −1.00 | — | −1.40 | −0.60 | — | −1.00 |
| Y: | 0.00 | 0.90 | 0.80 | −1.00 | — | −1.40 | −0.05 | — | 0.30 |

| Percent Threshold | 1% | 2% | 3% | 4% | 5% | 6% | 7% | 8% | 9% | 10% |
|---|---|---|---|---|---|---|---|---|---|---|
| Numerical Score | 3.47 | 2.8 | 2.4 | 2.1 | 1.86 | 1.6 | 1.4 | 1.2 | 1.06 | 0.9 |

Virtual Matrix for HLA-DRB1_0311

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | 2.30 | — | −2.40 | −0.30 | — | −1.70 |
| E: | −999.00 | 0.10 | −1.20 | −1.00 | — | −1.40 | 0.20 | — | −1.70 |
| F: | −1.00 | 0.80 | 0.80 | −1.00 | — | −1.40 | −1.00 | — | −1.00 |
| G: | −999.00 | 0.50 | 0.20 | 0.50 | — | −0.70 | −1.30 | — | −1.00 |
| H: | −999.00 | 0.80 | 0.20 | 0.00 | — | −0.10 | 0.00 | — | 0.08 |
| I: | 0.00 | 1.10 | 1.50 | 0.50 | — | 0.70 | 0.08 | — | −0.30 |
| K: | −999.00 | 1.10 | 0.00 | −1.00 | — | 1.30 | −0.30 | — | −0.30 |
| L: | 0.00 | 1.00 | 1.00 | 0.00 | — | 0.20 | 0.70 | — | −1.00 |
| M: | 0.00 | 1.10 | 1.40 | 0.00 | — | −0.90 | 0.80 | — | −0.40 |
| N: | −999.00 | 0.80 | 0.50 | 0.20 | — | −0.60 | 0.60 | — | −1.40 |
| P: | −999.00 | −0.50 | 0.30 | −1.00 | — | 0.50 | −0.70 | — | −1.30 |
| Q: | −999.00 | 1.20 | 0.00 | 0.00 | — | −0.30 | 0.00 | — | 0.50 |
| R: | −999.00 | 2.20 | 0.70 | −1.00 | — | 1.00 | −1.20 | — | −1.00 |
| S: | −999.00 | −0.30 | 0.20 | 0.70 | — | −0.10 | −0.20 | — | 0.70 |
| T: | −999.00 | 0.00 | 0.00 | −1.00 | — | 0.80 | −0.10 | — | −1.20 |
| V: | 0.00 | 2.10 | 0.50 | 0.00 | — | 1.20 | 0.08 | — | −0.70 |
| W: | −1.00 | −0.10 | 0.00 | −1.00 | — | −1.40 | −1.40 | — | −1.00 |
| Y: | −1.00 | 0.90 | 0.80 | −1.00 | — | −1.40 | −1.20 | — | −1.00 |

| Percent Threshold | 1% | 2% | 3% | 4% | 5% | 6% | 7% | 8% | 9% | 10% |
|---|---|---|---|---|---|---|---|---|---|---|
| Numerical Score | 3.1 | 2.5 | 2.08 | 1.7 | 1.48 | 1.2 | 1.0 | 0.8 | 0.6 | 0.4 |

Virtual Matrix for HLA-DRB1_0401

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | 1.40 | — | −1.10 | −0.30 | — | −1.70 |
| E: | −999.00 | 0.10 | −1.20 | 1.50 | — | −2.40 | 0.20 | — | −1.70 |
| F: | 0.00 | 0.80 | 0.80 | −0.90 | — | −1.10 | −1.00 | — | −1.00 |
| G: | −999.00 | 0.50 | 0.20 | −1.60 | — | −1.50 | −1.30 | — | −1.00 |
| H: | −999.00 | 0.80 | 0.20 | 1.10 | — | −1.40 | 0.00 | — | 0.08 |
| I: | −1.00 | 1.10 | 1.50 | 0.80 | — | −0.10 | 0.08 | — | −0.30 |

TABLE 4-continued

Appendix A

| | | | | | | | | | | |
|---|---|---|---|---|---|---|---|---|---|---|
| K: | −999.00 | 1.10 | 0.00 | −1.70 | — | −2.40 | −0.30 | — | −0.30 | |
| L: | −1.00 | 1.00 | 1.00 | 0.80 | — | −1.10 | 0.70 | — | −1.00 | |
| M: | −1.00 | 1.10 | 1.40 | 0.90 | — | −1.10 | 0.80 | — | −0.40 | |
| N: | −999.00 | 0.80 | 0.50 | 0.90 | — | 1.30 | 0.60 | — | −1.40 | |
| P: | −999.00 | −0.50 | 0.30 | −1.60 | — | 0.00 | −0.70 | — | −1.30 | |
| Q: | −999.00 | 1.20 | 0.00 | 0.80 | — | −1.50 | 0.00 | — | 0.50 | |
| R: | −999.00 | 2.20 | 0.70 | −1.90 | — | −2.40 | −1.20 | — | −1.00 | |
| S: | −999.00 | −0.30 | 0.20 | 0.80 | — | 1.00 | −0.20 | — | 0.70 | |
| T: | −999.00 | 0.00 | 0.00 | 0.70 | — | 1.90 | −0.10 | — | −1.20 | |
| V: | −1.00 | 2.10 | 0.50 | −0.90 | — | 0.90 | 0.08 | — | −0.70 | |
| W: | 0.00 | −0.10 | 0.00 | −1.20 | — | −1.00 | −1.40 | — | −1.00 | |
| Y: | 0.00 | 0.90 | 0.80 | −1.60 | — | −1.50 | −1.20 | — | −1.00 | |
| Percent Threshold | 1% | 2% | 3% | 4% | 5% | 6% | 7% | 8% | 9% | 10% |
| Numerical Score | 2.7 | 2.0 | 1.48 | 1.1 | 0.7 | 0.48 | 0.2 | −0.099 | −0.3 | −0.5 |

Virtual Matrix for HLA-DRB1_0402

| | Position | | | | | | | | | |
|---|---|---|---|---|---|---|---|---|---|---|
| Amino acid | P1 | P2 | P3 | P4 | P5 | P6 | P7 | P8 | P9 | |
| A: | −999.00 | 0.00 | 0.00 | 0.00 | — | 0.00 | 0.00 | — | 0.00 | |
| D: | −999.00 | −1.30 | −1.30 | −2.30 | — | −1.10 | −2.10 | — | −1.70 | |
| E: | −999.00 | 0.10 | −1.20 | −2.30 | — | −2.40 | −1.20 | — | −1.70 | |
| F: | −1.00 | 0.80 | 0.80 | 0.30 | — | −1.10 | 0.50 | — | −1.00 | |
| G: | −999.00 | 0.50 | 0.20 | −0.70 | — | −1.50 | −2.10 | — | −1.00 | |
| H: | −999.00 | 0.80 | 0.20 | 1.20 | — | −1.40 | 0.50 | — | 0.08 | |
| I: | 0.00 | 1.10 | 1.50 | 0.08 | — | −0.10 | 0.50 | — | −0.30 | |
| K: | −999.00 | 1.10 | 0.00 | 0.10 | — | −2.40 | 0.00 | — | −0.30 | |
| L: | 0.00 | 1.00 | 1.00 | −0.60 | — | −1.10 | 1.00 | — | −1.00 | |
| M: | 0.00 | 1.10 | 1.40 | 0.60 | — | −1.10 | 0.80 | — | −0.40 | |
| N: | −999.00 | 0.80 | 0.50 | −0.40 | — | 1.30 | 0.60 | — | −1.40 | |
| P: | −999.00 | −0.50 | 0.30 | −1.30 | — | 0.00 | −1.00 | — | −1.30 | |
| Q: | −999.00 | 1.20 | 0.00 | −0.40 | — | −1.50 | 1.10 | — | 0.50 | |
| R: | −999.00 | 2.20 | 0.70 | 1.00 | — | −2.40 | 1.70 | — | −1.00 | |
| S: | −999.00 | −0.30 | 0.20 | −1.00 | — | 1.00 | −0.40 | — | 0.70 | |
| T: | −999.00 | 0.00 | 0.00 | −0.50 | — | 1.90 | 0.10 | — | −1.20 | |
| V: | 0.00 | 2.10 | 0.50 | −0.70 | — | 0.90 | 0.20 | — | −0.70 | |
| W: | −1.00 | −0.10 | 0.00 | 1.60 | — | −1.00 | 1.40 | — | −1.00 | |
| Y: | −1.00 | 0.90 | 0.80 | −0.40 | — | −1.50 | 0.90 | — | −1.00 | |
| Percent Threshold | 1% | 2% | 3% | 4% | 5% | 6% | 7% | 8% | 9% | 10% |
| Numerical Score | 2.9 | 2.3 | 1.8 | 1.38 | 1.1 | 0.8 | 0.5 | 0.2 | 0 | −0.2 |

Virtual Matrix for HLA-DRB1_0404

| | Position | | | | | | | | | |
|---|---|---|---|---|---|---|---|---|---|---|
| Amino acid | P1 | P2 | P3 | P4 | P5 | P6 | P7 | P8 | P9 | |
| A: | −999.00 | 0.00 | 0.00 | 0.00 | — | 0.00 | 0.00 | — | 0.00 | |
| D: | −999.00 | −1.30 | −1.30 | −1.10 | — | −1.10 | −1.20 | — | −1.70 | |
| E: | −999.00 | 0.10 | −1.20 | −1.10 | — | −2.40 | −0.70 | — | −1.70 | |
| F: | −1.00 | 0.80 | 0.80 | 1.00 | — | −1.10 | −0.05 | — | −1.00 | |
| G: | −999.00 | 0.50 | 0.20 | −2.40 | — | −1.50 | −1.20 | — | −1.00 | |
| H: | −999.00 | 0.80 | 0.20 | −1.00 | — | −1.40 | −0.40 | — | 0.08 | |
| I: | 0.00 | 1.10 | 1.50 | 1.10 | — | −0.10 | 0.08 | — | −0.30 | |
| K: | −999.00 | 1.10 | 0.00 | −1.50 | — | −2.40 | −1.30 | — | −0.30 | |
| L: | 0.00 | 1.00 | 1.00 | 1.00 | — | −1.10 | 0.30 | — | −1.00 | |
| M: | 0.00 | 1.10 | 1.40 | 1.80 | — | −1.10 | 0.70 | — | −0.40 | |
| N: | −999.00 | 0.80 | 0.50 | −0.70 | — | 1.30 | 0.70 | — | −1.40 | |
| P: | −999.00 | −0.50 | 0.30 | −1.30 | — | 0.00 | −1.00 | — | −1.30 | |
| Q: | −999.00 | 1.20 | 0.00 | 0.00 | — | −1.50 | −0.20 | — | 0.50 | |
| R: | −999.00 | 2.20 | 0.70 | −2.40 | — | −2.40 | −0.90 | — | −1.00 | |
| S: | −999.00 | −0.30 | 0.20 | −0.70 | — | 1.00 | 0.50 | — | 0.70 | |
| T: | −999.00 | 0.00 | 0.00 | −0.90 | — | 1.90 | 0.40 | — | −1.20 | |
| V: | 0.00 | 2.10 | 0.50 | 0.50 | — | 0.90 | −0.10 | — | −0.70 | |
| W: | −1.00 | −0.10 | 0.00 | −0.05 | — | −1.00 | −0.70 | — | −1.00 | |
| Y: | −1.00 | 0.90 | 0.80 | −0.40 | — | −1.50 | −0.20 | — | −1.00 | |
| Percent Threshold | 1% | 2% | 3% | 4% | 5% | 6% | 7% | 8% | 9% | 10% |
| Numerical Score | 3.1 | 2.3 | 1.8 | 1.3 | 1.0 | 0.7 | 0.4 | 0.2 | 0.0 | −0.2 |

TABLE 4-continued

Appendix A

Virtual Matrix for HLA-DRB1_0405

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.10 | — | −1.10 | −1.20 | — | 1.00 |
| E: | −999.00 | 0.10 | −1.20 | −1.10 | — | −2.40 | −0.70 | — | 1.30 |
| F: | 0.00 | 0.80 | 0.80 | 1.00 | — | −1.10 | −0.05 | — | −0.10 |
| G: | −999.00 | 0.50 | 0.20 | −2.40 | — | −1.50 | −1.20 | — | 0.30 |
| H: | −999.00 | 0.80 | 0.20 | −1.00 | — | −1.40 | −0.40 | — | 1.30 |
| I: | −1.00 | 1.10 | 1.50 | 1.10 | — | −0.10 | 0.08 | — | −0.10 |
| K: | −999.00 | 1.10 | 0.00 | −1.50 | — | −2.40 | −1.30 | — | −1.00 |
| L: | −1.00 | 1.00 | 1.00 | 1.00 | — | −1.10 | 0.30 | — | 0.00 |
| M: | −1.00 | 1.10 | 1.40 | 1.80 | — | −1.10 | 0.70 | — | 0.70 |
| N: | −999.00 | 0.80 | 0.50 | −0.70 | — | 1.30 | 0.70 | — | 0.60 |
| P: | −999.00 | −0.50 | 0.30 | −1.30 | — | 0.00 | −1.00 | — | −0.90 |
| Q: | −999.00 | 1.20 | 0.00 | 0.00 | — | −1.50 | −0.20 | — | 1.30 |
| R: | −999.00 | 2.20 | 0.70 | −2.40 | — | −2.40 | −0.90 | — | −1.00 |
| S: | −999.00 | −0.30 | 0.20 | −0.70 | — | 1.00 | 0.50 | — | 0.70 |
| T: | −999.00 | 0.00 | 0.00 | −0.90 | — | 1.90 | 0.40 | — | −0.30 |
| V: | −1.00 | 2.10 | 0.50 | 0.50 | — | 0.90 | −0.10 | — | −0.40 |
| W: | 0.00 | −0.10 | 0.00 | −0.05 | — | −1.00 | −0.70 | — | −0.10 |
| Y: | 0.00 | 0.90 | 0.80 | −0.40 | — | −1.50 | −0.20 | — | 0.10 |
| Percent Threshold | 1% | 2% | 3% 4% | 5% | 6% | 7% | 8% | 9% | 10% |
| Numerical Score | 3.2 | 2.5 | 2.0 1.65 | 1.3 | 1.0 | 0.7 | 0.45 | 0.2 | 0.0 |

Virtual Matrix for HLA-DRB1_0408

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.10 | — | −1.10 | −1.20 | — | −1.70 |
| E: | −999.00 | 0.10 | −1.20 | −1.10 | — | −2.40 | −0.70 | — | −1.70 |
| F: | 0.00 | 0.80 | 0.80 | 1.00 | — | −1.10 | −0.05 | — | −1.00 |
| G: | −999.00 | 0.50 | 0.20 | −2.40 | — | −1.50 | −1.20 | — | −1.00 |
| H: | −999.00 | 0.80 | 0.20 | −1.00 | — | −1.40 | −0.40 | — | 0.08 |
| I: | −1.00 | 1.10 | 1.50 | 1.10 | — | −0.10 | 0.08 | — | −0.30 |
| K: | −999.00 | 1.10 | 0.00 | −1.50 | — | −2.40 | −1.30 | — | −0.30 |
| L: | −1.00 | 1.00 | 1.00 | 1.00 | — | −1.10 | 0.30 | — | −1.00 |
| M: | −1.00 | 1.10 | 1.40 | 1.80 | — | −1.10 | 0.70 | — | −0.40 |
| N: | −999.00 | 0.80 | 0.50 | −0.70 | — | 1.30 | 0.70 | — | −1.40 |
| P: | −999.00 | −0.50 | 0.30 | −1.30 | — | 0.00 | −1.00 | — | −1.30 |
| Q: | −999.00 | 1.20 | 0.00 | 0.00 | — | −1.50 | −0.20 | — | 0.50 |
| R: | −999.00 | 2.20 | 0.70 | −2.40 | — | −2.40 | −0.90 | — | −1.00 |
| S: | −999.00 | −0.30 | 0.20 | −0.70 | — | 1.00 | 0.50 | — | 0.70 |
| T: | −999.00 | 0.00 | 0.00 | −0.90 | — | 1.90 | 0.40 | — | −1.20 |
| V: | −1.00 | 2.10 | 0.50 | 0.50 | — | 0.90 | −0.10 | — | −0.70 |
| W: | 0.00 | −0.10 | 0.00 | −0.05 | — | −1.00 | −0.70 | — | −1.00 |
| Y: | 0.00 | 0.90 | 0.80 | −0.40 | — | −1.50 | −0.20 | — | −1.00 |
| Percent Threshold | 1% 2% | 3% | 4% | 5% | 6% | 7% | 8% | 9% | 10% |
| Numerical Score | 2.4 1.7 | 1.2 | 0.8 | 0.48 | 0.2 | −0.1 | −0.3 | −0.52 | −0.8 |

Virtual Matrix for HLA-DRB1_0410

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.10 | — | −1.10 | −1.20 | — | 1.00 |
| E: | −999.00 | 0.10 | −1.20 | −1.10 | — | −2.40 | −0.70 | — | 1.30 |
| F: | −1.00 | 0.80 | 0.80 | 1.00 | — | −1.10 | −0.05 | — | −0.10 |
| G: | −999.00 | 0.50 | 0.20 | −2.40 | — | −1.50 | −1.20 | — | 0.30 |
| H: | −999.00 | 0.80 | 0.20 | −1.00 | — | −1.40 | −0.40 | — | 1.30 |
| I: | 0.00 | 1.10 | 1.50 | 1.10 | — | −0.10 | 0.08 | — | −0.10 |
| K: | −999.00 | 1.10 | 0.00 | −1.50 | — | −2.40 | −1.30 | — | −1.00 |
| L: | 0.00 | 1.00 | 1.00 | 1.00 | — | −1.10 | 0.30 | — | 0.00 |
| M: | 0.00 | 1.10 | 1.40 | 1.80 | — | −1.10 | 0.70 | — | 0.70 |
| N: | −999.00 | 0.80 | 0.50 | −0.70 | — | 1.30 | 0.70 | — | 0.60 |
| P: | −999.00 | −0.50 | 0.30 | −1.30 | — | 0.00 | −1.00 | — | −0.90 |

TABLE 4-continued

Appendix A

| | | | | | | | | | |
|---|---|---|---|---|---|---|---|---|---|
| Q: | −999.00 | 1.20 | 0.00 | 0.00 | — | −1.50 | −0.20 | — | 1.30 |
| R: | −999.00 | 2.20 | 0.70 | −2.40 | — | −2.40 | −0.90 | — | −1.00 |
| S: | −999.00 | −0.30 | 0.20 | −0.70 | — | 1.00 | 0.50 | — | 0.70 |
| T: | −999.00 | 0.00 | 0.00 | −0.90 | — | 1.90 | 0.40 | — | −0.30 |
| V: | 0.00 | 2.10 | 0.50 | 0.50 | — | 0.90 | −0.10 | — | −0.40 |
| W: | −1.00 | −0.10 | 0.00 | −0.05 | — | −1.00 | −0.70 | — | −0.10 |
| Y: | −1.00 | 0.90 | 0.80 | −0.40 | — | −1.50 | −0.20 | — | 0.10 |
| Percent Threshold | 1% | 2% | 3% | 4% | 5% | 6% | 7% | 8% | 9% | 10% |
| Numerical Score | 3.85 | 3.1 | 2.6 | 2.2 | 1.88 | 1.5 | 1.3 | 1.0 | 0.8 | 0.58 |

Virtual Matrix for HLA-DRB1_0423

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.10 | — | −1.10 | −1.20 | — | −1.70 |
| E: | −999.00 | 0.10 | −1.20 | −1.10 | — | −2.40 | −0.70 | — | −1.70 |
| F: | −1.00 | 0.80 | 0.80 | 1.00 | — | −1.10 | −0.05 | — | −1.00 |
| G: | −999.00 | 0.50 | 0.20 | −2.40 | — | −1.50 | −1.20 | — | −1.00 |
| H: | −999.00 | 0.80 | 0.20 | −1.00 | — | −1.40 | −0.40 | — | 0.08 |
| I: | 0.00 | 1.10 | 1.50 | 1.10 | — | −0.10 | 0.08 | — | −0.30 |
| K: | −999.00 | 1.10 | 0.00 | −1.50 | — | −2.40 | −1.30 | — | −0.30 |
| L: | 0.00 | 1.00 | 1.00 | 1.00 | — | −1.10 | 0.30 | — | −1.00 |
| M: | 0.00 | 1.10 | 1.40 | 1.80 | — | −1.10 | 0.70 | — | −0.40 |
| N: | −999.00 | 0.80 | 0.50 | −0.70 | — | 1.30 | 0.70 | — | −1.40 |
| P: | −999.00 | −0.50 | 0.30 | −1.30 | — | 0.00 | −1.00 | — | −1.30 |
| Q: | −999.00 | 1.20 | 0.00 | 0.00 | — | −1.50 | −0.20 | — | 0.50 |
| R: | −999.00 | 2.20 | 0.70 | −2.40 | — | −2.40 | −0.90 | — | −1.00 |
| S: | −999.00 | −0.30 | 0.20 | −0.70 | — | 1.00 | 0.50 | — | 0.70 |
| T: | −999.00 | 0.00 | 0.00 | −0.90 | — | 1.90 | 0.40 | — | −1.20 |
| V: | 0.00 | 2.10 | 0.50 | 0.50 | — | 0.90 | −0.10 | — | −0.70 |
| W: | −1.00 | −0.10 | 0.00 | −0.05 | — | −1.00 | −0.70 | — | −1.00 |
| Y: | −1.00 | 0.90 | 0.80 | −0.40 | — | −1.50 | −0.20 | — | −1.00 |
| Percent Threshold | 1% | 2% | 3% | 4% | 5% | 6% | 7% | 8% | 9% | 10% |
| Numerical Score | 2.9 | 2.1 | 1.68 | 1.3 | 0.9 | 0.68 | 0.4 | 0.18 | −0.1 | −0.3 |

Virtual Matrix for HLA-DRB1_0426

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | 1.40 | — | −1.10 | −0.30 | — | −1.70 |
| E: | −999.00 | 0.10 | −1.20 | 1.50 | — | −2.40 | 0.20 | — | −1.70 |
| F: | 0.00 | 0.80 | 0.80 | −0.90 | — | −1.10 | −1.00 | — | −1.00 |
| G: | −999.00 | 0.50 | 0.20 | −1.60 | — | −1.50 | −1.30 | — | −1.00 |
| H: | −999.00 | 0.80 | 0.20 | 1.10 | — | −1.40 | 0.00 | — | 0.08 |
| I: | −1.00 | 1.10 | 1.50 | 0.80 | — | −0.10 | 0.08 | — | −0.30 |
| K: | −999.00 | 1.10 | 0.00 | −1.70 | — | −2.40 | −0.30 | — | −0.30 |
| L: | −1.00 | 1.00 | 1.00 | 0.80 | — | −1.10 | 0.70 | — | −1.00 |
| M: | −1.00 | 1.10 | 1.40 | 0.90 | — | −1.10 | 0.80 | — | −0.40 |
| N: | −999.00 | 0.80 | 0.50 | 0.90 | — | 1.30 | 0.60 | — | −1.40 |
| P: | −999.00 | −0.50 | 0.30 | −1.60 | — | 0.00 | −0.70 | — | −1.30 |
| Q: | −999.00 | 1.20 | 0.00 | 0.80 | — | −1.50 | 0.00 | — | 0.50 |
| R: | −999.00 | 2.20 | 0.70 | −1.90 | — | −2.40 | −1.20 | — | −1.00 |
| S: | −999.00 | −0.30 | 0.20 | 0.80 | — | 1.00 | −0.20 | — | 0.70 |
| T: | −999.00 | 0.00 | 0.00 | 0.70 | — | 1.90 | −0.10 | — | −1.20 |
| V: | −1.00 | 2.10 | 0.50 | −0.90 | — | 0.90 | 0.08 | — | −0.70 |
| W: | 0.00 | −0.10 | 0.00 | −1.20 | — | −1.00 | −1.40 | — | −1.00 |
| Y: | 0.00 | 0.90 | 0.80 | −1.60 | — | −1.50 | −1.20 | — | −1.00 |
| Percent Threshold | 1% | 2% | 3% | 4% | 5% | 6% | 7% | 8% | 9% | 10% |
| Numerical Score | 2.8 | 2.1 | 1.6 | 1.2 | 0.9 | 0.6 | 0.4 | 0.18 | −0.1 | −0.3 |

TABLE 4-continued

Appendix A

Virtual Matrix for HLA-DRB1_0701

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.60 | — | −2.50 | −1.30 | — | −1.20 |
| E: | −999.00 | 0.10 | −1.20 | −1.40 | — | −2.50 | 0.90 | — | −0.30 |
| F: | 0.00 | 0.80 | 0.80 | 0.20 | — | −0.80 | 2.10 | — | 2.10 |
| G: | −999.00 | 0.50 | 0.20 | −1.10 | — | −0.60 | 0.00 | — | −0.60 |
| H: | −999.00 | 0.80 | 0.20 | 0.10 | — | −0.80 | 0.90 | — | −0.20 |
| I: | −1.00 | 1.10 | 1.50 | 1.10 | — | −0.50 | 2.40 | — | 3.40 |
| K: | −999.00 | 1.10 | 0.00 | −1.30 | — | −1.10 | 0.50 | — | −1.10 |
| L: | −1.00 | 1.00 | 1.00 | −0.80 | — | −0.90 | 2.20 | — | 3.40 |
| M: | −1.00 | 1.10 | 1.40 | −0.40 | — | −0.80 | 1.80 | — | 2.00 |
| N: | −999.00 | 0.80 | 0.50 | −1.10 | — | −0.60 | 1.40 | — | −0.50 |
| P: | −999.00 | −0.50 | 0.30 | −1.20 | — | −0.50 | −0.20 | — | −0.60 |
| Q: | −999.00 | 1.20 | 0.00 | −1.50 | — | −1.10 | 1.10 | — | −0.90 |
| R: | −999.00 | 2.20 | 0.70 | −1.10 | — | −1.10 | 0.70 | — | −0.80 |
| S: | −999.00 | −0.30 | 0.20 | 1.50 | — | 0.60 | 0.40 | — | −0.30 |
| T: | −999.00 | 0.00 | 0.00 | 1.40 | — | −0.08 | 0.90 | — | 0.40 |
| V: | −1.00 | 2.10 | 0.50 | 0.90 | — | 0.10 | 1.60 | — | 2.00 |
| W: | 0.00 | −0.10 | 0.00 | −1.10 | — | −0.90 | 1.40 | — | 0.80 |
| Y: | 0.00 | 0.90 | 0.80 | −0.90 | — | −1.00 | 1.70 | — | 1.10 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 5.6 | 4.7 | 4.1 | 3.62 | 3.2 | 2.8 | 2.5 | 2.1 | 1.9 | 1.6 |

Virtual Matrix for HLA-DRB1_0703

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.60 | — | −2.50 | −1.30 | — | −1.20 |
| E: | −999.00 | 0.10 | −1.20 | −1.40 | — | −2.50 | 0.90 | — | −0.30 |
| F: | 0.00 | 0.80 | 0.80 | 0.20 | — | −0.80 | 2.10 | — | 2.10 |
| G: | −999.00 | 0.50 | 0.20 | −1.10 | — | −0.60 | 0.00 | — | −0.60 |
| H: | −999.00 | 0.80 | 0.20 | 0.10 | — | −0.80 | 0.90 | — | −0.20 |
| I: | −1.00 | 1.10 | 1.50 | 1.10 | — | −0.50 | 2.40 | — | 3.40 |
| K: | −999.00 | 1.10 | 0.00 | −1.30 | — | −1.10 | 0.50 | — | −1.10 |
| L: | −1.00 | 1.00 | 1.00 | −0.80 | — | −0.90 | 2.20 | — | 3.40 |
| M: | −1.00 | 1.10 | 1.40 | −0.40 | — | −0.80 | 1.80 | — | 2.00 |
| N: | −999.00 | 0.80 | 0.50 | −1.10 | — | −0.60 | 1.40 | — | −0.50 |
| P: | −999.00 | −0.50 | 0.30 | −1.20 | — | −0.50 | −0.20 | — | −0.60 |
| Q: | −999.00 | 1.20 | 0.00 | −1.50 | — | −1.10 | 1.10 | — | −0.90 |
| R: | −999.00 | 2.20 | 0.70 | −1.10 | — | −1.10 | 0.70 | — | −0.80 |
| S: | −999.00 | −0.30 | 0.20 | 1.50 | — | 0.60 | 0.40 | — | −0.30 |
| T: | −999.00 | 0.00 | 0.00 | 1.40 | — | −0.08 | 0.90 | — | 0.40 |
| V: | −1.00 | 2.10 | 0.50 | 0.90 | — | 0.10 | 1.60 | — | 2.00 |
| W: | 0.00 | −0.10 | 0.00 | −1.10 | — | −0.90 | 1.40 | — | 0.80 |
| Y: | 0.00 | 0.90 | 0.80 | −0.90 | — | −1.00 | 1.70 | — | 1.10 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 5.5 | 4.6 | 4.0 | 3.5 | 3.12 | 2.8 | 2.5 | 2.2 | 2.0 | 1.7 |

Virtual Matrix for HLA-DRB1_0801

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.00 | — | −2.40 | −2.40 | — | 1.00 |
| E: | −999.00 | 0.10 | −1.20 | −1.00 | — | −1.40 | −2.40 | — | 1.30 |
| F: | 0.00 | 0.80 | 0.80 | 0.50 | — | −1.40 | −0.90 | — | −0.10 |
| G: | −999.00 | 0.50 | 0.20 | −1.00 | — | −0.70 | −0.50 | — | 0.30 |
| H: | −999.00 | 0.80 | 0.20 | −1.00 | — | −0.10 | −0.90 | — | 1.30 |
| I: | −1.00 | 1.10 | 1.50 | 0.30 | — | 0.70 | −0.80 | — | −0.10 |
| K: | −999.00 | 1.10 | 0.00 | 2.30 | — | 1.30 | −0.80 | — | −1.00 |
| L: | −1.00 | 1.00 | 1.00 | 0.70 | — | 0.20 | −0.30 | — | 0.00 |
| M: | −1.00 | 1.10 | 1.40 | 1.40 | — | −0.90 | −0.30 | — | 0.70 |
| N: | −999.00 | 0.80 | 0.50 | 0.00 | — | −0.60 | −1.30 | — | 0.60 |
| P: | −999.00 | −0.50 | 0.30 | −1.00 | — | 0.50 | −1.20 | — | −0.90 |

TABLE 4-continued

Appendix A

| | | | | | | | | | | |
|---|---|---|---|---|---|---|---|---|---|---|
| Q: | −999.00 | 1.20 | 0.00 | −1.00 | — | −0.30 | −1.20 | — | 1.30 | |
| R: | −999.00 | 2.20 | 0.70 | 2.30 | — | 1.00 | −0.60 | — | −1.00 | |
| S: | −999.00 | −0.30 | 0.20 | −1.00 | — | −0.10 | −1.30 | — | 0.70 | |
| T: | −999.00 | 0.00 | 0.00 | −1.00 | — | 0.80 | −2.40 | — | −0.30 | |
| V: | −1.00 | 2.10 | 0.50 | 0.30 | — | 1.20 | −1.10 | — | −0.40 | |
| W: | 0.00 | −0.10 | 0.00 | 0.00 | — | −1.40 | −1.20 | — | −0.10 | |
| Y: | 0.00 | 0.90 | 0.80 | 2.20 | — | −1.40 | −1.10 | — | 0.10 | |
| Percent Threshold | 1% | 2% | 3% | 4% | 5% | 6% | 7% | 8% | 9% | 10% |
| Numerical Score | 2.9 | 2.3 | 1.8 | 1.4 | 1.1 | 0.8 | 0.6 | 0.4 | 0.2 | −0.1 |

Virtual Matrix for HLA-DRB_0802

| | Position | | | | | | | | | |
|---|---|---|---|---|---|---|---|---|---|---|
| Amino acid | P1 | P2 | P3 | P4 | P5 | P6 | P7 | P8 | P9 | |
| A: | −999.00 | 0.00 | 0.00 | 0.00 | — | 0.00 | 0.00 | — | 0.00 | |
| D: | −999.00 | −1.30 | −1.30 | −1.00 | — | −2.40 | −2.40 | — | −1.70 | |
| E: | −999.00 | 0.10 | −1.20 | −1.00 | — | −1.40 | −2.40 | — | −1.70 | |
| F: | 0.00 | 0.80 | 0.80 | 0.50 | — | −1.40 | −0.90 | — | −1.00 | |
| G: | −999.00 | 0.50 | 0.20 | −1.00 | — | −0.70 | −0.50 | — | −1.00 | |
| H: | −999.00 | 0.80 | 0.20 | −1.00 | — | −0.10 | −0.90 | — | 0.08 | |
| I: | −1.00 | 1.10 | 1.50 | 0.30 | — | 0.70 | −0.80 | — | −0.30 | |
| K: | −999.00 | 1.10 | 0.00 | 2.30 | — | 1.30 | −0.80 | — | −0.30 | |
| L: | −1.00 | 1.00 | 1.00 | 0.70 | — | 0.20 | −0.30 | — | −1.00 | |
| M: | −1.00 | 1.10 | 1.40 | 1.40 | — | −0.90 | −0.30 | — | −0.40 | |
| N: | −999.00 | 0.80 | 0.50 | 0.00 | — | −0.60 | −1.30 | — | −1.40 | |
| P: | −999.00 | −0.50 | 0.30 | −1.00 | — | 0.50 | −1.20 | — | −1.30 | |
| Q: | −999.00 | 1.20 | 0.00 | −1.00 | — | −0.30 | −1.20 | — | 0.50 | |
| R: | −999.00 | 2.20 | 0.70 | 2.30 | — | 1.00 | −0.60 | — | −1.00 | |
| S: | −999.00 | −0.30 | 0.20 | −1.00 | — | −0.10 | −1.30 | — | 0.70 | |
| T: | −999.00 | 0.00 | 0.00 | −1.00 | — | 0.80 | −2.40 | — | −1.20 | |
| V: | −1.00 | 2.10 | 0.50 | 0.30 | — | 1.20 | −1.10 | — | −0.70 | |
| W: | 0.00 | −0.10 | 0.00 | 0.00 | — | −1.40 | −1.20 | — | −1.00 | |
| Y: | 0.00 | 0.90 | 0.80 | 2.20 | — | −1.40 | −1.10 | — | −1.00 | |
| Percent Threshold | 1% | 2% | 3% | 4% | 5% | 6% | 7% | 8% | 9% | 10% |
| Numerical Score | 2.3 | 1.5 | 1.0 | 0.6 | 0.3 | 0.0 | −0.3 | −0.5 | −0.7 | −0.9 |

Virtual Matrix for HLA-DRB1_0804

| | Position | | | | | | | | | |
|---|---|---|---|---|---|---|---|---|---|---|
| Amino acid | P1 | P2 | P3 | P4 | P5 | P6 | P7 | P8 | P9 | |
| A: | −999.00 | 0.00 | 0.00 | 0.00 | — | 0.00 | 0.00 | — | 0.00 | |
| D: | −999.00 | −1.30 | −1.30 | −1.00 | — | −2.40 | −2.40 | — | −1.70 | |
| E: | −999.00 | 0.10 | −1.20 | −1.00 | — | −1.40 | −2.40 | — | −1.70 | |
| F: | −1.00 | 0.80 | 0.80 | 0.50 | — | −1.40 | −0.90 | — | −1.00 | |
| G: | −999.00 | 0.50 | 0.20 | −1.00 | — | −0.70 | −0.50 | — | −1.00 | |
| H: | −999.00 | 0.80 | 0.20 | −1.00 | — | −0.10 | −0.90 | — | 0.08 | |
| I: | 0.00 | 1.10 | 1.50 | 0.30 | — | 0.70 | −0.80 | — | −0.30 | |
| K: | −999.00 | 1.10 | 0.00 | 2.30 | — | 1.30 | −0.80 | — | −0.30 | |
| L: | 0.00 | 1.00 | 1.00 | 0.70 | — | 0.20 | −0.30 | — | −1.00 | |
| M: | 0.00 | 1.10 | 1.40 | 1.40 | — | −0.90 | −0.30 | — | −0.40 | |
| N: | −999.00 | 0.80 | 0.50 | 0.00 | — | −0.60 | −1.30 | — | −1.40 | |
| P: | −999.00 | −0.50 | 0.30 | −1.00 | — | 0.50 | −1.20 | — | −1.30 | |
| Q: | −999.00 | 1.20 | 0.00 | −1.00 | — | −0.30 | −1.20 | — | 0.50 | |
| R: | −999.00 | 2.20 | 0.70 | 2.30 | — | 1.00 | −0.60 | — | −1.00 | |
| S: | −999.00 | −0.30 | 0.20 | −1.00 | — | −0.10 | −1.30 | — | 0.70 | |
| T: | −999.00 | 0.00 | 0.00 | −1.00 | — | 0.80 | −2.40 | — | −1.20 | |
| V: | 0.00 | 2.10 | 0.50 | 0.30 | — | 1.20 | −1.10 | — | −0.70 | |
| W: | −1.00 | −0.10 | 0.00 | 0.00 | — | −1.40 | −1.20 | — | −1.00 | |
| Y: | −1.00 | 0.90 | 0.80 | 2.20 | — | −1.40 | −1.10 | — | −1.00 | |
| Percent Threshold | 1% | 2% | 3% | 4% | 5% | 6% | 7% | 8% | 9% | 10% |
| Numerical Score | 2.7 | 2.1 | 1.6 | 1.2 | 0.88 | 0.5 | 0.3 | 0.1 | −0.1 | −0.3 |

TABLE 4-continued

Appendix A

Virtual Matrix for HLA-DRB1_0806

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.00 | — | −2.40 | −2.40 | — | 1.00 |
| E: | −999.00 | 0.10 | −1.20 | −1.00 | — | −1.40 | −2.40 | — | 1.30 |
| F: | −1.00 | 0.80 | 0.80 | 0.50 | — | −1.40 | −0.90 | — | −0.10 |
| G: | −999.00 | 0.50 | 0.20 | −1.00 | — | −0.70 | −0.50 | — | 0.30 |
| H: | −999.00 | 0.80 | 0.20 | −1.00 | — | −0.10 | −0.90 | — | 1.30 |
| I: | 0.00 | 1.10 | 1.50 | 0.30 | — | 0.70 | −0.80 | — | −0.10 |
| K: | −999.00 | 1.10 | 0.00 | 2.30 | — | 1.30 | −0.80 | — | −1.00 |
| L: | 0.00 | 1.00 | 1.00 | 0.70 | — | 0.20 | −0.30 | — | 0.00 |
| M: | 0.00 | 1.10 | 1.40 | 1.40 | — | −0.90 | −0.30 | — | 0.70 |
| N: | −999.00 | 0.80 | 0.50 | 0.00 | — | −0.60 | −1.30 | — | 0.60 |
| P: | −999.00 | −0.50 | 0.30 | −1.00 | — | 0.50 | −1.20 | — | −0.90 |
| Q: | −999.00 | 1.20 | 0.00 | −1.00 | — | −0.30 | −1.20 | — | 1.30 |
| R: | −999.00 | 2.20 | 0.70 | 2.30 | — | 1.00 | −0.60 | — | −1.00 |
| S: | −999.00 | −0.30 | 0.20 | −1.00 | — | −0.10 | −1.30 | — | 0.70 |
| T: | −999.00 | 0.00 | 0.00 | −1.00 | — | 0.80 | −2.40 | — | −0.30 |
| V: | 0.00 | 2.10 | 0.50 | 0.30 | — | 1.20 | −1.10 | — | −0.40 |
| W: | −1.00 | −0.10 | 0.00 | 0.00 | — | −1.40 | −1.20 | — | −0.10 |
| Y: | −1.00 | 0.90 | 0.80 | 2.20 | — | −1.40 | −1.10 | — | 0.10 |
| Percent Threshold | 1% | 2% | 3% 4% | 5% | 6% | 7% | 8% | 9% | 10% |
| Numerical Score | 3.4 | 2.8 | 2.4 2.0 | 1.7 | 1.4 | 1.2 | 0.9 | 0.7 | 0.5 |

Virtual Matrix for HLA-DRB1_0813

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.00 | — | −2.40 | −1.20 | — | −1.70 |
| E: | −999.00 | 0.10 | −1.20 | −1.00 | — | −1.40 | −0.70 | — | −1.70 |
| F: | 0.00 | 0.80 | 0.80 | 0.50 | — | −1.40 | −0.05 | — | −1.00 |
| G: | −999.00 | 0.50 | 0.20 | −1.00 | — | −0.70 | −1.20 | — | −1.00 |
| H: | −999.00 | 0.80 | 0.20 | −1.00 | — | −0.10 | −0.40 | — | 0.08 |
| I: | −1.00 | 1.10 | 1.50 | 0.30 | — | 0.70 | 0.08 | — | −0.30 |
| K: | −999.00 | 1.10 | 0.00 | 2.30 | — | 1.30 | −1.30 | — | −0.30 |
| L: | −1.00 | 1.00 | 1.00 | 0.70 | — | 0.20 | 0.30 | — | −1.00 |
| M: | −1.00 | 1.10 | 1.40 | 1.40 | — | −0.90 | 0.70 | — | −0.40 |
| N: | −999.00 | 0.80 | 0.50 | 0.00 | — | −0.60 | 0.70 | — | −1.40 |
| P: | −999.00 | −0.50 | 0.30 | −1.00 | — | 0.50 | −1.00 | — | −1.30 |
| Q: | −999.00 | 1.20 | 0.00 | −1.00 | — | −0.30 | −0.20 | — | 0.50 |
| R: | −999.00 | 2.20 | 0.70 | 2.30 | — | 1.00 | −0.90 | — | −1.00 |
| S: | −999.00 | −0.30 | 0.20 | −1.00 | — | −0.10 | 0.50 | — | 0.70 |
| T: | −999.00 | 0.00 | 0.00 | −1.00 | — | 0.80 | 0.40 | — | −1.20 |
| V: | −1.00 | 2.10 | 0.50 | 0.30 | — | 1.20 | −0.10 | — | −0.70 |
| W: | 0.00 | −0.10 | 0.00 | 0.00 | — | −1.40 | −0.70 | — | −1.00 |
| Y: | 0.00 | 0.90 | 0.80 | 2.20 | — | −1.40 | −0.20 | — | −1.00 |
| Percent Threshold | 1% | 2% | 3% 4% | 5% | 6% | 7% | 8% | 9% | 10% |
| Numerical Score | 3.1 | 2.4 | 1.9 1.5 | 1.2 | 1.0 | 0.7 | 0.5 | 0.3 | 0.1 |

Virtual Matrix for HLA-DRB1_0817

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.00 | — | −2.40 | −2.70 | — | 1.00 |
| E: | −999.00 | 0.10 | −1.20 | −1.00 | — | −1.40 | −1.30 | — | 1.30 |
| F: | 0.00 | 0.80 | 0.80 | 0.50 | — | −1.40 | −0.40 | — | −0.10 |
| G: | −999.00 | 0.50 | 0.20 | −1.00 | — | −0.70 | −0.40 | — | 0.30 |
| H: | −999.00 | 0.80 | 0.20 | −1.00 | — | −0.10 | −0.20 | — | 1.30 |
| I: | −1.00 | 1.10 | 1.50 | 0.30 | — | 0.70 | 0.80 | — | −0.10 |
| K: | −999.00 | 1.10 | 0.00 | 2.30 | — | 1.30 | −0.20 | — | −1.00 |
| L: | −1.00 | 1.00 | 1.00 | 0.70 | — | 0.20 | 1.50 | — | 0.00 |
| M: | −1.00 | 1.10 | 1.40 | 1.40 | — | −0.90 | 1.30 | — | 0.70 |
| N: | −999.00 | 0.80 | 0.50 | 0.00 | — | −0.60 | −1.00 | — | 0.60 |
| P: | −999.00 | −0.50 | 0.30 | −1.00 | — | 0.50 | −0.05 | — | −0.90 |

TABLE 4-continued

| Appendix A | | | | | | | | | |
|---|---|---|---|---|---|---|---|---|---|
| Q: | −999.00 | 1.20 | 0.00 | −1.00 | — | −0.30 | −1.10 | — | 1.30 |
| R: | −999.00 | 2.20 | 0.70 | 2.30 | — | 1.00 | −0.40 | — | −1.00 |
| S: | −999.00 | −0.30 | 0.20 | −1.00 | — | −0.10 | −1.30 | — | 0.70 |
| T: | −999.00 | 0.00 | 0.00 | −1.00 | — | 0.80 | −1.30 | — | −0.30 |
| V: | −1.00 | 2.10 | 0.50 | 0.30 | — | 1.20 | −0.60 | — | −0.40 |
| W: | 0.00 | −0.10 | 0.00 | 0.00 | — | −1.40 | −0.40 | — | −0.10 |
| Y: | 0.00 | 0.90 | 0.80 | 2.20 | — | −1.40 | −0.40 | — | 0.10 |
| Percent Threshold | 1% | 2% | 3% | 4% | 5% | 6% | 7% | 8% | 9% 10% |
| Numerical Score | 4.0 | 3.3 | 2.8 | 2.4 | 2.1 | 1.8 | 1.5 | 1.3 | 1.1 0.9 |

Virtual Matrix for HLA-DRB1__1101

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | −1.70 | — | −2.40 | −2.70 | — | −1.70 |
| E: | −999.00 | 0.10 | −1.20 | −1.70 | — | −1.40 | −1.30 | — | −1.70 |
| F: | 0.00 | 0.80 | 0.80 | 0.40 | — | −1.40 | −0.40 | — | −1.00 |
| G: | −999.00 | 0.50 | 0.20 | −1.70 | — | −0.70 | −0.40 | — | −1.00 |
| H: | −999.00 | 0.80 | 0.20 | −0.60 | — | −0.10 | −0.20 | — | 0.08 |
| I: | −1.00 | 1.10 | 1.50 | 0.90 | — | 0.70 | 0.80 | — | −0.30 |
| K: | −999.00 | 1.10 | 0.00 | −0.50 | — | 1.30 | −0.20 | — | −0.30 |
| L: | −1.00 | 1.00 | 1.00 | 1.10 | — | 0.20 | 1.50 | — | −1.00 |
| M: | −1.00 | 1.10 | 1.40 | 1.00 | — | −0.90 | 1.30 | — | −0.40 |
| N: | −999.00 | 0.80 | 0.50 | 0.00 | — | −0.60 | −1.00 | — | −1.40 |
| P: | −999.00 | −0.50 | 0.30 | −1.70 | — | 0.50 | −0.05 | — | −1.30 |
| Q: | −999.00 | 1.20 | 0.00 | −0.40 | — | −0.30 | −1.10 | — | 0.50 |
| R: | −999.00 | 2.20 | 0.70 | −0.70 | — | 1.00 | −0.40 | — | −1.00 |
| S: | −999.00 | −0.30 | 0.20 | −0.70 | — | −0.10 | −1.30 | — | 0.70 |
| T: | −999.00 | 0.00 | 0.00 | −0.60 | — | 0.80 | −1.30 | — | −1.20 |
| V: | −1.00 | 2.10 | 0.50 | 0.40 | — | 1.20 | −0.60 | — | −0.70 |
| W: | 0.00 | −0.10 | 0.00 | −0.10 | — | −1.40 | −0.40 | — | −1.00 |
| Y: | 0.00 | 0.90 | 0.80 | −0.70 | — | −1.40 | −0.40 | — | −1.00 |
| Percent Threshold | 1% | 2% 3% | 4% | 5% | 6% | 7% | 8% | 9% | 10% |
| Numerical Score | 2.3 | 1.6 1.1 | 0.7 | 0.4 | 0.1 | −0.1 | −0.3 | −0.6 | −0.8 |

Virtual Matrix for HLA-DRB1__1102

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | −1.40 | — | −2.40 | −1.50 | — | −1.70 |
| E: | −999.00 | 0.10 | −1.20 | −1.10 | — | −1.40 | −1.00 | — | −1.70 |
| F: | −1.00 | 0.80 | 0.80 | 0.80 | — | −1.40 | 0.60 | — | −1.00 |
| G: | −999.00 | 0.50 | 0.20 | −1.50 | — | −0.70 | −1.50 | — | −1.00 |
| H: | −999.00 | 0.80 | 0.20 | 1.50 | — | −0.10 | 0.30 | — | 0.08 |
| I: | 0.00 | 1.10 | 1.50 | −0.60 | — | 0.70 | −0.50 | — | −0.30 |
| K: | −999.00 | 1.10 | 0.00 | 0.80 | — | 1.30 | 0.00 | — | −0.30 |
| L: | 0.00 | 1.00 | 1.00 | 0.40 | — | 0.20 | 0.40 | — | −1.00 |
| M: | 0.00 | 1.10 | 1.40 | 0.80 | — | −0.90 | 0.00 | — | −0.40 |
| N: | −999.00 | 0.80 | 0.50 | 0.10 | — | −0.60 | 0.10 | — | −1.40 |
| P: | −999.00 | −0.50 | 0.30 | −1.50 | — | 0.50 | −0.50 | — | −1.30 |
| Q: | −999.00 | 1.20 | 0.00 | 0.60 | — | −0.30 | −0.40 | — | 0.50 |
| R: | −999.00 | 2.20 | 0.70 | 0.20 | — | 1.00 | 1.20 | — | −1.00 |
| S: | −999.00 | −0.30 | 0.20 | −0.60 | — | −0.10 | −0.90 | — | 0.70 |
| T: | −999.00 | 0.00 | 0.00 | −1.10 | — | 0.80 | −0.90 | — | −1.20 |
| V: | 0.00 | 2.10 | 0.50 | −0.90 | — | 1.20 | −0.10 | — | −0.70 |
| W: | −1.00 | −0.10 | 0.00 | 0.70 | — | −1.40 | 0.40 | — | −1.00 |
| Y: | −1.00 | 0.90 | 0.80 | 0.40 | — | −1.40 | −0.20 | — | −1.00 |
| Percent Threshold | 1% | 2% | 3% 4% | 5% | 6% | 7% | 8% | 9% | 10% |
| Numerical Score | 2.8 | 2.2 1.8 | 1.5 | 1.2 | 1.0 | 0.8 | 0.6 | 0.4 | 0.2 |

TABLE 4-continued

Appendix A

Virtual Matrix for HLA-DRB1_1104

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | −1.70 | — | −2.40 | −2.70 | — | −1.70 |
| E: | −999.00 | 0.10 | −1.20 | −1.70 | — | −1.40 | −1.30 | — | −1.70 |
| F: | −1.00 | 0.80 | 0.80 | 0.40 | — | −1.40 | −0.40 | — | −1.00 |
| G: | −999.00 | 0.50 | 0.20 | −1.70 | — | −0.70 | −0.40 | — | −1.00 |
| H: | −999.00 | 0.80 | 0.20 | −0.60 | — | −0.10 | −0.20 | — | 0.08 |
| I: | 0.00 | 1.10 | 1.50 | 0.90 | — | 0.70 | 0.80 | — | −0.30 |
| K: | −999.00 | 1.10 | 0.00 | −0.50 | — | 1.30 | −0.20 | — | −0.30 |
| L: | 0.00 | 1.00 | 1.00 | 1.10 | — | 0.20 | 1.50 | — | −1.00 |
| M: | 0.00 | 1.10 | 1.40 | 1.00 | — | −0.90 | 1.30 | — | −0.40 |
| N: | −999.00 | 0.80 | 0.50 | 0.00 | — | −0.60 | −1.00 | — | −1.40 |
| P: | −999.00 | −0.50 | 0.30 | −1.70 | — | 0.50 | −0.05 | — | −1.30 |
| Q: | −999.00 | 1.20 | 0.00 | −0.40 | — | −0.30 | −1.10 | — | 0.50 |
| R: | −999.00 | 2.20 | 0.70 | −0.70 | — | 1.00 | −0.40 | — | −1.00 |
| S: | −999.00 | −0.30 | 0.20 | −0.70 | — | −0.10 | −1.30 | — | 0.70 |
| T: | −999.00 | 0.00 | 0.00 | −0.60 | — | 0.80 | −1.30 | — | −1.20 |
| V: | 0.00 | 2.10 | 0.50 | 0.40 | — | 1.20 | −0.60 | — | −0.70 |
| W: | −1.00 | −0.10 | 0.00 | −0.10 | — | −1.40 | −0.40 | — | −1.00 |
| Y: | −1.00 | 0.90 | 0.80 | −0.70 | — | −1.40 | −0.40 | — | −1.00 |
| Percent Threshold | 1% | 2% 3% | 4% | 5% | 6% | 7% | 8% | 9% | 10% |
| Numerical Score | 3.3 | 2.4 2.0 | 1.6 | 1.3 | 1.0 | 0.75 | 0.5 | 0.3 | 0.0 |

Virtual Matrix for HLA-DRB1_1106

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | −1.70 | — | −2.40 | −2.70 | — | −1.70 |
| E: | −999.00 | 0.10 | −1.20 | −1.70 | — | −1.40 | −1.30 | — | −1.70 |
| F: | −1.00 | 0.80 | 0.80 | 0.40 | — | −1.40 | −0.40 | — | −1.00 |
| G: | −999.00 | 0.50 | 0.20 | −1.70 | — | −0.70 | −0.40 | — | −1.00 |
| H: | −999.00 | 0.80 | 0.20 | −0.60 | — | −0.10 | −0.20 | — | 0.08 |
| I: | 0.00 | 1.10 | 1.50 | 0.90 | — | 0.70 | 0.80 | — | −0.30 |
| K: | −999.00 | 1.10 | 0.00 | −0.50 | — | 1.30 | −0.20 | — | −0.30 |
| L: | 0.00 | 1.00 | 1.00 | 1.10 | — | 0.20 | 1.50 | — | −1.00 |
| M: | 0.00 | 1.10 | 1.40 | 1.00 | — | −0.90 | 1.30 | — | −0.40 |
| N: | −999.00 | 0.80 | 0.50 | 0.00 | — | −0.60 | −1.00 | — | −1.40 |
| P: | −999.00 | −0.50 | 0.30 | −1.70 | — | 0.50 | −0.05 | — | −1.30 |
| Q: | −999.00 | 1.20 | 0.00 | −0.40 | — | −0.30 | −1.10 | — | 0.50 |
| R: | −999.00 | 2.20 | 0.70 | −0.70 | — | 1.00 | −0.40 | — | −1.00 |
| S: | −999.00 | −0.30 | 0.20 | −0.70 | — | −0.10 | −1.30 | — | 0.70 |
| T: | −999.00 | 0.00 | 0.00 | −0.60 | — | 0.80 | −1.30 | — | −1.20 |
| V: | 0.00 | 2.10 | 0.50 | 0.40 | — | 1.20 | −0.60 | — | −0.70 |
| W: | −1.00 | −0.10 | 0.00 | −0.10 | — | −1.40 | −0.40 | — | −1.00 |
| Y: | −1.00 | 0.90 | 0.80 | −0.70 | — | −1.40 | −0.40 | — | −1.00 |
| Percent Threshold | 1% | 2% 3% | 4% | 5% | 6% | 7% | 8% | 9% | 10% |
| Numerical Score | 3.3 | 2.4 2.0 | 1.6 | 1.3 | 1.0 | 0.75 | 0.5 | 0.3 | 0.0 |

Virtual Matrix for HLA-DRB1_1107

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | 2.30 | — | −2.40 | −0.60 | — | −1.70 |
| E: | −999.00 | 0.10 | −1.20 | −1.00 | — | −1.40 | −0.20 | — | −1.70 |
| F: | −1.00 | 0.80 | 0.80 | −1.00 | — | −1.40 | 0.50 | — | −1.00 |
| G: | −999.00 | 0.50 | 0.20 | 0.50 | — | −0.70 | 0.10 | — | −1.00 |
| H: | −999.00 | 0.80 | 0.20 | 0.00 | — | −0.10 | −0.80 | — | 0.08 |
| I: | 0.00 | 1.10 | 1.50 | 0.50 | — | 0.70 | 0.40 | — | −0.30 |
| K: | −999.00 | 1.10 | 0.00 | −1.00 | — | 1.30 | −0.90 | — | −0.30 |
| L: | 0.00 | 1.00 | 1.00 | 0.00 | — | 0.20 | 0.20 | — | −1.00 |
| M: | 0.00 | 1.10 | 1.40 | 0.00 | — | −0.90 | 1.10 | — | −0.40 |
| N: | −999.00 | 0.80 | 0.50 | 0.20 | — | −0.60 | −0.09 | — | −1.40 |
| P: | −999.00 | −0.50 | 0.30 | −1.00 | — | 0.50 | 0.70 | — | −1.30 |

TABLE 4-continued

Appendix A

| | | | | | | | | | |
|---|---|---|---|---|---|---|---|---|---|
| Q: | −999.00 | 1.20 | 0.00 | 0.00 | — | −0.30 | −0.10 | — | 0.50 |
| R: | −999.00 | 2.20 | 0.70 | −1.00 | — | 1.00 | −0.90 | — | −1.00 |
| S: | −999.00 | −0.30 | 0.20 | 0.70 | — | −0.10 | 0.07 | — | 0.70 |
| T: | −999.00 | 0.00 | 0.00 | −1.00 | — | 0.80 | −0.10 | — | −1.20 |
| V: | 0.00 | 2.10 | 0.50 | 0.00 | — | 1.20 | 0.20 | — | −0.70 |
| W: | −1.00 | −0.10 | 0.00 | −1.00 | — | −1.40 | −0.60 | — | −1.00 |
| Y: | −1.00 | 0.90 | 0.80 | −1.00 | — | −1.40 | −0.05 | — | −1.00 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 3.3 | 2.5 | 2.1 | 1.8 | 1.5 | 1.3 | 1.1 | 0.9 | 0.7 | 0.5 |

Virtual Matrix for HLA-DRB1_1114

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | −1.40 | — | −2.40 | −1.50 | — | −1.70 |
| E: | −999.00 | 0.10 | −1.20 | −1.10 | — | −1.40 | −1.00 | — | −1.70 |
| F: | 0.00 | 0.80 | 0.80 | 0.80 | — | −1.40 | 0.60 | — | −1.00 |
| G: | −999.00 | 0.50 | 0.20 | −1.50 | — | −0.70 | −1.50 | — | −1.00 |
| H: | −999.00 | 0.80 | 0.20 | 1.50 | — | −0.10 | 0.30 | — | 0.08 |
| I: | −1.00 | 1.10 | 1.50 | −0.60 | — | 0.70 | −0.50 | — | −0.30 |
| K: | −999.00 | 1.10 | 0.00 | 0.80 | — | 1.30 | 0.00 | — | −0.30 |
| L: | −1.00 | 1.00 | 1.00 | 0.40 | — | 0.20 | 0.40 | — | −1.00 |
| M: | −1.00 | 1.10 | 1.40 | 0.80 | — | −0.90 | 0.00 | — | −0.40 |
| N: | −999.00 | 0.80 | 0.50 | 0.10 | — | −0.60 | 0.10 | — | −1.40 |
| P: | −999.00 | −0.50 | 0.30 | −1.50 | — | 0.50 | −0.50 | — | −1.30 |
| Q: | −999.00 | 1.20 | 0.00 | 0.60 | — | −0.30 | −0.40 | — | 0.50 |
| R: | −999.00 | 2.20 | 0.70 | 0.20 | — | 1.00 | 1.20 | — | −1.00 |
| S: | −999.00 | −0.30 | 0.20 | −0.60 | — | −0.10 | −0.90 | — | 0.70 |
| T: | −999.00 | 0.00 | 0.00 | −1.10 | — | 0.80 | −0.90 | — | −1.20 |
| V: | −1.00 | 2.10 | 0.50 | −0.90 | — | 1.20 | −0.10 | — | −0.70 |
| W: | 0.00 | −0.10 | 0.00 | 0.70 | — | −1.40 | 0.40 | — | −1.00 |
| Y: | 0.00 | 0.90 | 0.80 | 0.40 | — | −1.40 | −0.20 | — | −1.00 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 2.4 | 1.8 | 1.3 | 1.0 | 0.7 | 0.5 | 0.3 | 0.1 | −0.1 | −0.3 |

Virtual Matrix for HLA-DRB1_1120

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | −1.40 | — | −2.40 | −1.50 | — | −0.60 |
| E: | −999.00 | 0.10 | −1.20 | −1.10 | — | −1.40 | −1.00 | — | −0.30 |
| F: | 0.00 | 0.80 | 0.80 | 0.80 | — | −1.40 | 0.60 | — | 0.90 |
| G: | −999.00 | 0.50 | 0.20 | −1.50 | — | −0.70 | −1.50 | — | 0.40 |
| H: | −999.00 | 0.80 | 0.20 | 1.50 | — | −0.10 | 0.30 | — | −0.50 |
| I: | −1.00 | 1.10 | 1.50 | −0.60 | — | 0.70 | −0.50 | — | 0.60 |
| K: | −999.00 | 1.10 | 0.00 | 0.80 | — | 1.30 | 0.00 | — | −0.20 |
| L: | −1.00 | 1.00 | 1.00 | 0.40 | — | 0.20 | 0.40 | — | −0.04 |
| M: | −1.00 | 1.10 | 1.40 | 0.80 | — | −0.90 | 0.00 | — | 1.10 |
| N: | −999.00 | 0.80 | 0.50 | 0.10 | — | −0.60 | 0.10 | — | −0.60 |
| P: | −999.00 | −0.50 | 0.30 | −1.50 | — | 0.50 | −0.50 | — | −0.30 |
| Q: | −999.00 | 1.20 | 0.00 | 0.60 | — | −0.30 | −0.40 | — | −0.20 |
| R: | −999.00 | 2.20 | 0.70 | 0.20 | — | 1.00 | 1.20 | — | 0.50 |
| S: | −999.00 | −0.30 | 0.20 | −0.60 | — | −0.10 | −0.90 | — | 1.10 |
| T: | −999.00 | 0.00 | 0.00 | −1.10 | — | 0.80 | −0.90 | — | −0.50 |
| V: | −1.00 | 2.10 | 0.50 | −0.90 | — | 1.20 | −0.10 | — | 0.30 |
| W: | 0.00 | −0.10 | 0.00 | 0.70 | — | −1.40 | 0.40 | — | −1.00 |
| Y: | 0.00 | 0.90 | 0.80 | 0.40 | — | −1.40 | −0.20 | — | 0.30 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 3.1 | 2.5 | 2.1 | 1.8 | 1.5 | 1.3 | 1.1 | 0.9 | 0.7 | 0.5 |

TABLE 4-continued

Appendix A

Virtual Matrix for HLA-DRB1_1121

| Amino acid | P1 | P2 | P3 | P4 | P5 | P6 | P7 | P8 | P9 |
|---|---|---|---|---|---|---|---|---|---|
| | Position | | | | | | | | |
| A: | −999.00 | 0.00 | 0.00 | 0.00 | — | 0.00 | 0.00 | — | 0.00 |
| D: | −999.00 | −1.30 | −1.30 | −1.40 | — | −2.40 | −1.50 | — | −1.70 |
| E: | −999.00 | 0.10 | −1.20 | −1.10 | — | −1.40 | −1.00 | — | −1.70 |
| F: | −1.00 | 0.80 | 0.80 | 0.80 | — | −1.40 | 0.60 | — | −1.00 |
| G: | −999.00 | 0.50 | 0.20 | −1.50 | — | −0.70 | −1.50 | — | −1.00 |
| H: | −999.00 | 0.80 | 0.20 | 1.50 | — | −0.10 | 0.30 | — | 0.08 |
| I: | 0.00 | 1.10 | 1.50 | −0.60 | — | 0.70 | −0.50 | — | −0.30 |
| K: | −999.00 | 1.10 | 0.00 | 0.80 | — | 1.30 | 0.00 | — | −0.30 |
| L: | 0.00 | 1.00 | 1.00 | 0.40 | — | 0.20 | 0.40 | — | −1.00 |
| M: | 0.00 | 1.10 | 1.40 | 0.80 | — | −0.90 | 0.00 | — | −0.40 |
| N: | −999.00 | 0.80 | 0.50 | 0.10 | — | −0.60 | 0.10 | — | −1.40 |
| P: | −999.00 | −0.50 | 0.30 | −1.50 | — | 0.50 | −0.50 | — | −1.30 |
| Q: | −999.00 | 1.20 | 0.00 | 0.60 | — | −0.30 | −0.40 | — | 0.50 |
| R: | −999.00 | 2.20 | 0.70 | 0.20 | — | 1.00 | 1.20 | — | −1.00 |
| S: | −999.00 | −0.30 | 0.20 | −0.60 | — | −0.10 | −0.90 | — | 0.70 |
| T: | −999.00 | 0.00 | 0.00 | −1.10 | — | 0.80 | −0.90 | — | −1.20 |
| V: | 0.00 | 2.10 | 0.50 | −0.90 | — | 1.20 | −0.10 | — | −0.70 |
| W: | −1.00 | −0.10 | 0.00 | 0.70 | — | −1.40 | 0.40 | — | −1.00 |
| Y: | −1.00 | 0.90 | 0.80 | 0.40 | — | −1.40 | −0.20 | — | −1.00 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 2.8 | 2.2 | 1.8 | 1.5 | 1.2 | 1.0 | 0.8 | 0.6 | 0.4 | 0.2 |

Virtual Matrix for HLA-DRB1_1128

| Amino acid | P1 | P2 | P3 | P4 | P5 | P6 | P7 | P8 | P9 |
|---|---|---|---|---|---|---|---|---|---|
| | Position | | | | | | | | |
| A: | −999.00 | 0.00 | 0.00 | 0.00 | — | 0.00 | 0.00 | — | 0.00 |
| D: | −999.00 | −1.30 | −1.30 | −1.70 | — | −2.40 | −2.70 | — | −0.60 |
| E: | −999.00 | 0.10 | −1.20 | −1.70 | — | −1.40 | −1.30 | — | −0.30 |
| F: | 0.00 | 0.80 | 0.80 | 0.40 | — | −1.40 | −0.40 | — | 0.90 |
| G: | −999.00 | 0.50 | 0.20 | −1.70 | — | −0.70 | −0.40 | — | 0.40 |
| H: | −999.00 | 0.80 | 0.20 | −0.60 | — | −0.10 | −0.20 | — | −0.50 |
| I: | −1.00 | 1.10 | 1.50 | 0.90 | — | 0.70 | 0.80 | — | 0.60 |
| K: | −999.00 | 1.10 | 0.00 | −0.50 | — | 1.30 | −0.20 | — | −0.20 |
| L: | −1.00 | 1.00 | 1.00 | 1.10 | — | 0.20 | 1.50 | — | −0.04 |
| M: | −1.00 | 1.10 | 1.40 | 1.00 | — | −0.90 | 1.30 | — | 1.10 |
| N: | −999.00 | 0.80 | 0.50 | 0.00 | — | −0.60 | −1.00 | — | −0.60 |
| P: | −999.00 | −0.50 | 0.30 | −1.70 | — | 0.50 | −0.05 | — | −0.30 |
| Q: | −999.00 | 1.20 | 0.00 | −0.40 | — | −0.30 | −1.10 | — | −0.20 |
| R: | −999.00 | 2.20 | 0.70 | −0.70 | — | 1.00 | −0.40 | — | 0.50 |
| S: | −999.00 | −0.30 | 0.20 | −0.70 | — | −0.10 | −1.30 | — | 1.10 |
| T: | −999.00 | 0.00 | 0.00 | −0.60 | — | 0.80 | −1.30 | — | −0.50 |
| V: | −1.00 | 2.10 | 0.50 | 0.40 | — | 1.20 | −0.60 | — | 0.30 |
| W: | 0.00 | −0.10 | 0.00 | −0.10 | — | −1.40 | −0.40 | — | −1.00 |
| Y: | 0.00 | 0.90 | 0.80 | −0.70 | — | −1.40 | −0.40 | — | 0.30 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 3.3 | 2.6 | 2.15 | 1.8 | 1.5 | 1.2 | 1.0 | 0.8 | 0.6 | 0.4 |

Virtual Matrix for HLA-DRB1_1301

| Amino acid | P1 | P2 | P3 | P4 | P5 | P6 | P7 | P8 | P9 |
|---|---|---|---|---|---|---|---|---|---|
| | Position | | | | | | | | |
| A: | −999.00 | 0.00 | 0.00 | 0.00 | — | 0.00 | 0.00 | — | 0.00 |
| D: | −999.00 | −1.30 | −1.30 | −1.40 | — | −2.40 | −1.50 | — | −0.60 |
| E: | −999.00 | 0.10 | −1.20 | −1.10 | — | −1.40 | −1.00 | — | −0.30 |
| F: | −1.00 | 0.80 | 0.80 | 0.80 | — | −1.40 | 0.60 | — | 0.90 |
| G: | −999.00 | 0.50 | 0.20 | −1.50 | — | −0.70 | −1.50 | — | 0.40 |
| H: | −999.00 | 0.80 | 0.20 | 1.50 | — | −0.10 | 0.30 | — | −0.50 |
| I: | 0.00 | 1.10 | 1.50 | −0.60 | — | 0.70 | −0.50 | — | 0.60 |
| K: | −999.00 | 1.10 | 0.00 | 0.80 | — | 1.30 | 0.00 | — | −0.20 |
| L: | 0.00 | 1.00 | 1.00 | 0.40 | — | 0.20 | 0.40 | — | −0.04 |
| M: | 0.00 | 1.10 | 1.40 | 0.80 | — | −0.90 | 0.00 | — | 1.10 |
| N: | −999.00 | 0.80 | 0.50 | 0.10 | — | −0.60 | 0.10 | — | −0.60 |
| P: | −999.00 | −0.50 | 0.30 | −1.50 | — | 0.50 | −0.50 | — | −0.30 |

TABLE 4-continued

Appendix A

| | | | | | | | | | |
|---|---|---|---|---|---|---|---|---|---|
| Q: | −999.00 | 1.20 | 0.00 | 0.60 | — | −0.30 | −0.40 | — | −0.20 |
| R: | −999.00 | 2.20 | 0.70 | 0.20 | — | 1.00 | 1.20 | — | 0.50 |
| S: | −999.00 | −0.30 | 0.20 | −0.60 | — | −0.10 | −0.90 | — | 1.10 |
| T: | −999.00 | 0.00 | 0.00 | −1.10 | — | 0.80 | −0.90 | — | −0.50 |
| V: | 0.00 | 2.10 | 0.50 | −0.90 | — | 1.20 | −0.10 | — | 0.30 |
| W: | −1.00 | −0.10 | 0.00 | 0.70 | — | −1.40 | 0.40 | — | −1.00 |
| Y: | −1.00 | 0.90 | 0.80 | 0.40 | — | −1.40 | −0.20 | — | 0.30 |
| Percent Threshold | 1% | 2% | 3% | 4% | 5% | 6% | 7% | 8% | 9% | 10% |
| Numerical Score | 3.5 | 2.96 | 2.6 | 2.26 | 2.0 | 1.76 | 1.5 | 1.36 | 1.2 | 1.0 |

Virtual Matrix for HLA-DRB1__1302

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | −1.40 | — | −2.40 | −1.50 | — | −0.60 |
| E: | −999.00 | 0.10 | −1.20 | −1.10 | — | −1.40 | −1.00 | — | −0.30 |
| F: | 0.00 | 0.80 | 0.80 | 0.80 | — | −1.40 | 0.60 | — | 0.90 |
| G: | −999.00 | 0.50 | 0.20 | −1.50 | — | −0.70 | −1.50 | — | 0.40 |
| H: | −999.00 | 0.80 | 0.20 | 1.50 | — | −0.10 | 0.30 | — | −0.50 |
| I: | −1.00 | 1.10 | 1.50 | −0.60 | — | 0.70 | −0.50 | — | 0.60 |
| K: | −999.00 | 1.10 | 0.00 | 0.80 | — | 1.30 | 0.00 | — | −0.20 |
| L: | −1.00 | 1.00 | 1.00 | 0.40 | — | 0.20 | 0.40 | — | −0.04 |
| M: | −1.00 | 1.10 | 1.40 | 0.80 | — | −0.90 | 0.00 | — | 1.10 |
| N: | −999.00 | 0.80 | 0.50 | 0.10 | — | −0.60 | 0.10 | — | −0.60 |
| P: | −999.00 | −0.50 | 0.30 | −1.50 | — | 0.50 | −0.50 | — | −0.30 |
| Q: | −999.00 | 1.20 | 0.00 | 0.60 | — | −0.30 | −0.40 | — | −0.20 |
| R: | −999.00 | 2.20 | 0.70 | 0.20 | — | 1.00 | 1.20 | — | 0.50 |
| S: | −999.00 | −0.30 | 0.20 | −0.60 | — | −0.10 | −0.90 | — | 1.10 |
| T: | −999.00 | 0.00 | 0.00 | −1.10 | — | 0.80 | −0.90 | — | −0.50 |
| V: | −1.00 | 2.10 | 0.50 | −0.90 | — | 1.20 | −0.10 | — | 0.30 |
| W: | 0.00 | −0.10 | 0.00 | 0.70 | — | −1.40 | 0.40 | — | −1.00 |
| Y: | 0.00 | 0.90 | 0.80 | 0.40 | — | −1.40 | −0.20 | — | 0.30 |
| Percent Threshold | 1% | 2% | 3% | 4% | 5% | 6% | 7% | 8% | 9% | 10% |
| Numerical Score | 3.1 | 2.5 | 2.1 | 1.8 | 1.5 | 1.3 | 1.1 | 0.9 | 0.7 | 0.5 |

Virtual Matrix for HLA-DRB1__1304

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | −1.40 | — | −2.40 | −1.50 | — | 1.00 |
| E: | −999.00 | 0.10 | −1.20 | −1.10 | — | −1.40 | −1.00 | — | 1.30 |
| F: | −1.00 | 0.80 | 0.80 | 0.80 | — | −1.40 | 0.60 | — | −0.10 |
| G: | −999.00 | 0.50 | 0.20 | −1.50 | — | −0.70 | −1.50 | — | 0.30 |
| H: | −999.00 | 0.80 | 0.20 | 1.50 | — | −0.10 | 0.30 | — | 1.30 |
| I: | 0.00 | 1.10 | 1.50 | −0.60 | — | 0.70 | −0.50 | — | −0.10 |
| K: | −999.00 | 1.10 | 0.00 | 0.80 | — | 1.30 | 0.00 | — | −1.00 |
| L: | 0.00 | 1.00 | 1.00 | 0.40 | — | 0.20 | 0.40 | — | 0.00 |
| M: | 0.00 | 1.10 | 1.40 | 0.80 | — | −0.90 | 0.00 | — | 0.70 |
| N: | −999.00 | 0.80 | 0.50 | 0.10 | — | −0.60 | 0.10 | — | 0.60 |
| P: | −999.00 | −0.50 | 0.30 | −1.50 | — | 0.50 | −0.50 | — | −0.90 |
| Q: | −999.00 | 1.20 | 0.00 | 0.60 | — | −0.30 | −0.40 | — | 1.30 |
| R: | −999.00 | 2.20 | 0.70 | 0.20 | — | 1.00 | 1.20 | — | −1.00 |
| S: | −999.00 | −0.30 | 0.20 | −0.60 | — | −0.10 | −0.90 | — | 0.70 |
| T: | −999.00 | 0.00 | 0.00 | −1.10 | — | 0.80 | −0.90 | — | −0.30 |
| V: | 0.00 | 2.10 | 0.50 | −0.90 | — | 1.20 | −0.10 | — | −0.40 |
| W: | −1.00 | −0.10 | 0.00 | 0.70 | — | −1.40 | 0.40 | — | −0.10 |
| Y: | −1.00 | 0.90 | 0.80 | 0.40 | — | −1.40 | −0.20 | — | 0.10 |
| Percent Threshold | 1% | 2% | 3% | 4% | 5% | 6% | 7% | 8% | 9% | 10% |
| Numerical Score | 3.7 | 3.0 | 2.6 | 2.3 | 2.1 | 1.8 | 1.6 | 1.4 | 1.2 | 1.0 |

TABLE 4-continued

Appendix A

Virtual Matrix for HLA-DRB1__1305

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.70 | — | −2.40 | −2.70 | — | −0.60 |
| E: | −999.00 | 0.10 | −1.20 | −1.70 | — | −1.40 | −1.30 | — | −0.30 |
| F: | 0.00 | 0.80 | 0.80 | 0.40 | — | −1.40 | −0.40 | — | 0.90 |
| G: | −999.00 | 0.50 | 0.20 | −1.70 | — | −0.70 | −0.40 | — | 0.40 |
| H: | −999.00 | 0.80 | 0.20 | −0.60 | — | −0.10 | −0.20 | — | −0.50 |
| I: | −1.00 | 1.10 | 1.50 | 0.90 | — | 0.70 | 0.80 | — | 0.60 |
| K: | −999.00 | 1.10 | 0.00 | −0.50 | — | 1.30 | −0.20 | — | −0.20 |
| L: | −1.00 | 1.00 | 1.00 | 1.10 | — | 0.20 | 1.50 | — | −0.04 |
| M: | −1.00 | 1.10 | 1.40 | 1.00 | — | −0.90 | 1.30 | — | 1.10 |
| N: | −999.00 | 0.80 | 0.50 | 0.00 | — | −0.60 | −1.00 | — | −0.60 |
| P: | −999.00 | −0.50 | 0.30 | −1.70 | — | 0.50 | −0.05 | — | −0.30 |
| Q: | −999.00 | 1.20 | 0.00 | −0.40 | — | −0.30 | −1.10 | — | −0.20 |
| R: | −999.00 | 2.20 | 0.70 | −0.70 | — | 1.00 | −0.40 | — | 0.50 |
| S: | −999.00 | −0.30 | 0.20 | −0.70 | — | −0.10 | −1.30 | — | 1.10 |
| T: | −999.00 | 0.00 | 0.00 | −0.60 | — | 0.80 | −1.30 | — | −0.50 |
| V: | −1.00 | 2.10 | 0.50 | 0.40 | — | 1.20 | −0.60 | — | 0.30 |
| W: | 0.00 | −0.10 | 0.00 | −0.10 | — | −1.40 | −0.40 | — | −1.00 |
| Y: | 0.00 | 0.90 | 0.80 | −0.70 | — | −1.40 | −0.40 | — | 0.30 |
| Percent Threshold | 1% | 2% 3% | 4% | 5% | 6% | 7% | 8% | 9% | 10% |
| Numerical Score | 3.4 | 2.7 2.2 | 1.9 | 1.55 | 1.2 | 1.0 | 0.7 | 0.56 | 0.3 |

Virtual Matrix for HLA-DRB1__1307

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.70 | — | −2.40 | −2.40 | — | −1.70 |
| E: | −999.00 | 0.10 | −1.20 | −1.70 | — | −1.40 | −2.40 | — | −1.70 |
| F: | 0.00 | 0.80 | 0.80 | 0.40 | — | −1.40 | −0.90 | — | −1.00 |
| G: | −999.00 | 0.50 | 0.20 | −1.70 | — | −0.70 | −0.50 | — | −1.00 |
| H: | −999.00 | 0.80 | 0.20 | −0.60 | — | −0.10 | −0.90 | — | 0.08 |
| I: | −1.00 | 1.10 | 1.50 | 0.90 | — | 0.70 | −0.80 | — | −0.30 |
| K: | −999.00 | 1.10 | 0.00 | −0.50 | — | 1.30 | −0.80 | — | −0.30 |
| L: | −1.00 | 1.00 | 1.00 | 1.10 | — | 0.20 | −0.30 | — | −1.00 |
| M: | −1.00 | 1.10 | 1.40 | 1.00 | — | −0.90 | −0.30 | — | −0.40 |
| N: | −999.00 | 0.80 | 0.50 | 0.00 | — | −0.60 | −1.30 | — | −1.40 |
| P: | −999.00 | −0.50 | 0.30 | −1.70 | — | 0.50 | −1.20 | — | −1.30 |
| Q: | −999.00 | 1.20 | 0.00 | −0.40 | — | −0.30 | −1.20 | — | 0.50 |
| R: | −999.00 | 2.20 | 0.70 | −0.70 | — | 1.00 | −0.60 | — | −1.00 |
| S: | −999.00 | −0.30 | 0.20 | −0.70 | — | −0.10 | −1.30 | — | 0.70 |
| T: | −999.00 | 0.00 | 0.00 | −0.60 | — | 0.80 | −2.40 | — | −1.20 |
| V: | −1.00 | 2.10 | 0.50 | 0.40 | — | 1.20 | −1.10 | — | −0.70 |
| W: | 0.00 | −0.10 | 0.00 | −0.10 | — | −1.40 | −1.20 | — | −1.00 |
| Y: | 0.00 | 0.90 | 0.80 | −0.70 | — | −1.40 | −1.10 | — | −1.00 |
| Percent Threshold | 1% | 2% 3% | 4% | 5% | 6% | 7% | 8% | 9% | 10% |
| Numerical Score | 1.7 | 1.0 0.6 | 0.2 | −0.1 | −0.4 | −0.6 | −0.9 | −1.0 | −1.2 |

Virtual Matrix for HLA-DRB1__1311

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.70 | — | −2.40 | −2.70 | — | −1.70 |
| E: | −999.00 | 0.10 | −1.20 | −1.70 | — | −1.40 | −1.30 | — | −1.70 |
| F: | −1.00 | 0.80 | 0.80 | 0.40 | — | −1.40 | −0.40 | — | −1.00 |
| G: | −999.00 | 0.50 | 0.20 | −1.70 | — | −0.70 | −0.40 | — | −1.00 |
| H: | −999.00 | 0.80 | 0.20 | −0.60 | — | −0.10 | −0.20 | — | 0.08 |
| I: | 0.00 | 1.10 | 1.50 | 0.90 | — | 0.70 | 0.80 | — | −0.30 |
| K: | −999.00 | 1.10 | 0.00 | −0.50 | — | 1.30 | −0.20 | — | −0.30 |
| L: | 0.00 | 1.00 | 1.00 | 1.10 | — | 0.20 | 1.50 | — | −1.00 |
| M: | 0.00 | 1.10 | 1.40 | 1.00 | — | −0.90 | 1.30 | — | −0.40 |
| N: | −999.00 | 0.80 | 0.50 | 0.00 | — | −0.60 | −1.00 | — | −1.40 |
| P: | −999.00 | −0.50 | 0.30 | −1.70 | — | 0.50 | −0.05 | — | −1.30 |

TABLE 4-continued

Appendix A

| | | | | | | | | | |
|---|---|---|---|---|---|---|---|---|---|
| Q: | −999.00 | 1.20 | 0.00 | −0.40 | — | −0.30 | −1.10 | — | 0.50 |
| R: | −999.00 | 2.20 | 0.70 | −0.70 | — | 1.00 | −0.40 | — | −1.00 |
| S: | −999.00 | −0.30 | 0.20 | −0.70 | — | −0.10 | −1.30 | — | 0.70 |
| T: | −999.00 | 0.00 | 0.00 | −0.60 | — | 0.80 | −1.30 | — | −1.20 |
| V: | 0.00 | 2.10 | 0.50 | 0.40 | — | 1.20 | −0.60 | — | −0.70 |
| W: | −1.00 | −0.10 | 0.00 | −0.10 | — | −1.40 | −0.40 | — | −1.00 |
| Y: | −1.00 | 0.90 | 0.80 | −0.70 | — | −1.40 | −0.40 | — | −1.00 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 3.3 | 2.4 | 2.0 | 1.6 | 1.3 | 1.0 | 0.75 | 0.5 | 0.3 | 0.0 |

Virtual Matrix for HLA-DRB1_1321

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | −1.70 | — | −2.40 | −2.70 | — | 1.00 |
| E: | −999.00 | 0.10 | −1.20 | −1.70 | — | −1.40 | −1.30 | — | 1.30 |
| F: | 0.00 | 0.80 | 0.80 | 0.40 | — | −1.40 | −0.40 | — | −0.10 |
| G: | −999.00 | 0.50 | 0.20 | −1.70 | — | −0.70 | −0.40 | — | 0.30 |
| H: | −999.00 | 0.80 | 0.20 | −0.60 | — | −0.10 | −0.20 | — | 1.30 |
| I: | −1.00 | 1.10 | 1.50 | 0.90 | — | 0.70 | 0.80 | — | −0.10 |
| K: | −999.00 | 1.10 | 0.00 | −0.50 | — | 1.30 | −0.20 | — | −1.00 |
| L: | −1.00 | 1.00 | 1.00 | 1.10 | — | 0.20 | 1.50 | — | 0.00 |
| M: | −1.00 | 1.10 | 1.40 | 1.00 | — | −0.90 | 1.30 | — | 0.70 |
| N: | −999.00 | 0.80 | 0.50 | 0.00 | — | −0.60 | −1.00 | — | 0.60 |
| P: | −999.00 | −0.50 | 0.30 | −1.70 | — | 0.50 | −0.05 | — | −0.90 |
| Q: | −999.00 | 1.20 | 0.00 | −0.40 | — | −0.30 | −1.10 | — | 1.30 |
| R: | −999.00 | 2.20 | 0.70 | −0.70 | — | 1.00 | −0.40 | — | −1.00 |
| S: | −999.00 | −0.30 | 0.20 | −0.70 | — | −0.10 | −1.30 | — | 0.70 |
| T: | −999.00 | 0.00 | 0.00 | −0.60 | — | 0.80 | −1.30 | — | −0.30 |
| V: | −1.00 | 2.10 | 0.50 | 0.40 | — | 1.20 | −0.60 | — | −0.40 |
| W: | 0.00 | −0.10 | 0.00 | −0.10 | — | −1.40 | −0.40 | — | −0.10 |
| Y: | 0.00 | 0.90 | 0.80 | −0.70 | — | −1.40 | −0.40 | — | 0.10 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 3.3 | 2.7 | 2.2 | 1.8 | 1.5 | 1.2 | 1.0 | 0.7 | 0.5 | 0.3 |

Virtual Matrix for HLA-DRB1_1322

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | −1.40 | — | −2.40 | −1.50 | — | −1.70 |
| E: | −999.00 | 0.10 | −1.20 | −1.10 | — | −1.40 | −1.00 | — | −1.70 |
| F: | −1.00 | 0.80 | 0.80 | 0.80 | — | −1.40 | 0.60 | — | −1.00 |
| G: | −999.00 | 0.50 | 0.20 | −1.50 | — | −0.70 | −1.50 | — | −1.00 |
| H: | −999.00 | 0.80 | 0.20 | 1.50 | — | −0.10 | 0.30 | — | 0.08 |
| I: | 0.00 | 1.10 | 1.50 | −0.60 | — | 0.70 | −0.50 | — | −0.30 |
| K: | −999.00 | 1.10 | 0.00 | 0.80 | — | 1.30 | 0.00 | — | −0.30 |
| L: | 0.00 | 1.00 | 1.00 | 0.40 | — | 0.20 | 0.40 | — | −1.00 |
| M: | 0.00 | 1.10 | 1.40 | 0.80 | — | −0.90 | 0.00 | — | −0.40 |
| N: | −999.00 | 0.80 | 0.50 | 0.10 | — | −0.60 | 0.10 | — | −1.40 |
| P: | −999.00 | −0.50 | 0.30 | −1.50 | — | 0.50 | −0.50 | — | −1.30 |
| Q: | −999.00 | 1.20 | 0.00 | 0.60 | — | −0.30 | −0.40 | — | 0.50 |
| R: | −999.00 | 2.20 | 0.70 | 0.20 | — | 1.00 | 1.20 | — | −1.00 |
| S: | −999.00 | −0.30 | 0.20 | −0.60 | — | −0.10 | −0.90 | — | 0.70 |
| T: | −999.00 | 0.00 | 0.00 | −1.10 | — | 0.80 | −0.90 | — | −1.20 |
| V: | 0.00 | 2.10 | 0.50 | −0.90 | — | 1.20 | −0.10 | — | −0.70 |
| W: | −1.00 | −0.10 | 0.00 | 0.70 | — | −1.40 | 0.40 | — | −1.00 |
| Y: | −1.00 | 0.90 | 0.80 | 0.40 | — | −1.40 | −0.20 | — | −1.00 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 2.8 | 2.2 | 1.8 | 1.5 | 1.2 | 1.0 | 0.8 | 0.6 | 0.4 | 0.2 |

TABLE 4-continued

Appendix A

Virtual Matrix for HLA-DRB1_1323

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.40 | — | −2.40 | −1.50 | — | −1.70 |
| E: | −999.00 | 0.10 | −1.20 | −1.10 | — | −1.40 | −1.00 | — | −1.70 |
| F: | 0.00 | 0.80 | 0.80 | 0.80 | — | −1.40 | 0.60 | — | −1.00 |
| G: | −999.00 | 0.50 | 0.20 | −1.50 | — | −0.70 | −1.50 | — | −1.00 |
| H: | −999.00 | 0.80 | 0.20 | 1.50 | — | −0.10 | 0.30 | — | 0.08 |
| I: | −1.00 | 1.10 | 1.50 | −0.60 | — | 0.70 | −0.50 | — | −0.30 |
| K: | −999.00 | 1.10 | 0.00 | 0.80 | — | 1.30 | 0.00 | — | −0.30 |
| L: | −1.00 | 1.00 | 1.00 | 0.40 | — | 0.20 | 0.40 | — | −1.00 |
| M: | −1.00 | 1.10 | 1.40 | 0.80 | — | −0.90 | 0.00 | — | −0.40 |
| N: | −999.00 | 0.80 | 0.50 | 0.10 | — | −0.60 | 0.10 | — | −1.40 |
| P: | −999.00 | −0.50 | 0.30 | −1.50 | — | 0.50 | −0.50 | — | −1.30 |
| Q: | −999.00 | 1.20 | 0.00 | 0.60 | — | −0.30 | −0.40 | — | 0.50 |
| R: | −999.00 | 2.20 | 0.70 | 0.20 | — | 1.00 | 1.20 | — | −1.00 |
| S: | −999.00 | −0.30 | 0.20 | −0.60 | — | −0.10 | −0.90 | — | 0.70 |
| T: | −999.00 | 0.00 | 0.00 | −1.10 | — | 0.80 | −0.90 | — | −1.20 |
| V: | −1.00 | 2.10 | 0.50 | −0.90 | — | 1.20 | −0.10 | — | −0.70 |
| W: | 0.00 | −0.10 | 0.00 | 0.70 | — | −1.40 | 0.40 | — | −1.00 |
| Y: | 0.00 | 0.90 | 0.80 | 0.40 | — | −1.40 | −0.20 | — | −1.00 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 2.4 | 1.8 | 1.3 | 1.0 | 0.7 | 0.5 | 0.3 | 0.1 | −0.1 | −0.3 |

Virtual Matrix for HLA-DRB1_1327

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.40 | — | −2.40 | −1.50 | — | −0.60 |
| E: | −999.00 | 0.10 | −1.20 | −1.10 | — | −1.40 | −1.00 | — | −0.30 |
| F: | −1.00 | 0.80 | 0.80 | 0.80 | — | −1.40 | 0.60 | — | 0.90 |
| G: | −999.00 | 0.50 | 0.20 | −1.50 | — | −0.70 | −1.50 | — | 0.40 |
| H: | −999.00 | 0.80 | 0.20 | 1.50 | — | −0.10 | 0.30 | — | −0.50 |
| I: | 0.00 | 1.10 | 1.50 | −0.60 | — | 0.70 | −0.50 | — | 0.60 |
| K: | −999.00 | 1.10 | 0.00 | 0.80 | — | 1.30 | 0.00 | — | −0.20 |
| L: | 0.00 | 1.00 | 1.00 | 0.40 | — | 0.20 | 0.40 | — | −0.04 |
| M: | 0.00 | 1.10 | 1.40 | 0.80 | — | −0.90 | 0.00 | — | 1.10 |
| N: | −999.00 | 0.80 | 0.50 | 0.10 | — | −0.60 | 0.10 | — | −0.60 |
| P: | −999.00 | −0.50 | 0.30 | −1.50 | — | 0.50 | −0.50 | — | −0.30 |
| Q: | −999.00 | 1.20 | 0.00 | 0.60 | — | −0.30 | −0.40 | — | −0.20 |
| R: | −999.00 | 2.20 | 0.70 | 0.20 | — | 1.00 | 1.20 | — | 0.50 |
| S: | −999.00 | −0.30 | 0.20 | −0.60 | — | −0.10 | −0.90 | — | 1.10 |
| T: | −999.00 | 0.00 | 0.00 | −1.10 | — | 0.80 | −0.90 | — | −0.50 |
| V: | 0.00 | 2.10 | 0.50 | −0.90 | — | 1.20 | −0.10 | — | 0.30 |
| W: | −1.00 | −0.10 | 0.00 | 0.70 | — | −1.40 | 0.40 | — | −1.00 |
| Y: | −1.00 | 0.90 | 0.80 | 0.40 | — | −1.40 | −0.20 | — | 0.30 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 3.5 | 2.96 | 2.6 | 2.26 | 2.0 | 1.76 | 1.5 | 1.36 | 1.2 | 1.0 |

Virtual Matrix for HLA-DRB1_1328

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.40 | — | −2.40 | −1.50 | — | −0.60 |
| E: | −999.00 | 0.10 | −1.20 | −1.10 | — | −1.40 | −1.00 | — | −0.30 |
| F: | −1.00 | 0.80 | 0.80 | 0.80 | — | −1.40 | 0.60 | — | 0.90 |
| G: | −999.00 | 0.50 | 0.20 | −1.50 | — | −0.70 | −1.50 | — | 0.40 |
| H: | −999.00 | 0.80 | 0.20 | 1.50 | — | −0.10 | 0.30 | — | −0.50 |
| I: | 0.00 | 1.10 | 1.50 | −0.60 | — | 0.70 | −0.50 | — | 0.60 |
| K: | −999.00 | 1.10 | 0.00 | 0.80 | — | 1.30 | 0.00 | — | −0.20 |
| L: | 0.00 | 1.00 | 1.00 | 0.40 | — | 0.20 | 0.40 | — | −0.04 |
| M: | 0.00 | 1.10 | 1.40 | 0.80 | — | −0.90 | 0.00 | — | 1.10 |
| N: | −999.00 | 0.80 | 0.50 | 0.10 | — | −0.60 | 0.10 | — | −0.60 |
| P: | −999.00 | −0.50 | 0.30 | −1.50 | — | 0.50 | −0.50 | — | −0.30 |

TABLE 4-continued

Appendix A

| | | | | | | | | | |
|---|---|---|---|---|---|---|---|---|---|
| Q: | −999.00 | 1.20 | 0.00 | 0.60 | — | −0.30 | −0.40 | — | −0.20 |
| R: | −999.00 | 2.20 | 0.70 | 0.20 | — | 1.00 | 1.20 | — | 0.50 |
| S: | −999.00 | −0.30 | 0.20 | −0.60 | — | −0.10 | −0.90 | — | 1.10 |
| T: | −999.00 | 0.00 | 0.00 | −1.10 | — | 0.80 | −0.90 | — | −0.50 |
| V: | 0.00 | 2.10 | 0.50 | −0.90 | — | 1.20 | −0.10 | — | 0.30 |
| W: | −1.00 | −0.10 | 0.00 | 0.70 | — | −1.40 | 0.40 | — | −1.00 |
| Y: | −1.00 | 0.90 | 0.80 | 0.40 | — | −1.40 | −0.20 | — | 0.30 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 3.5 | 2.96 | 2.6 | 2.26 | 2.0 | 1.76 | 1.5 | 1.36 | 1.2 | 1.0 |

Virtual Matrix for HLA-DRB1_1501

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | −0.40 | — | −0.40 | −0.70 | — | −1.90 |
| E: | −999.00 | 0.10 | −1.20 | −0.60 | — | −1.00 | −0.70 | — | −1.90 |
| F: | −1.00 | 0.80 | 0.80 | 2.40 | — | −0.30 | 1.40 | — | −0.40 |
| G: | −999.00 | 0.50 | 0.20 | 0.00 | — | 0.50 | 0.00 | — | −0.80 |
| H: | −999.00 | 0.80 | 0.20 | 1.10 | — | −0.50 | 0.60 | — | −1.10 |
| I: | 0.00 | 1.10 | 1.50 | 0.60 | — | 0.05 | 1.50 | — | 0.70 |
| K: | −999.00 | 1.10 | 0.00 | −0.70 | — | −0.30 | −0.30 | — | −1.70 |
| L: | 0.00 | 1.00 | 1.00 | 0.50 | — | 0.20 | 1.90 | — | 0.50 |
| M: | 0.00 | 1.10 | 1.40 | 1.00 | — | 0.10 | 1.70 | — | 0.08 |
| N: | −999.00 | 0.80 | 0.50 | −0.20 | — | 0.70 | 0.70 | — | −1.20 |
| P: | −999.00 | −0.50 | 0.30 | −0.30 | — | −0.20 | 0.30 | — | −1.10 |
| Q: | −999.00 | 1.20 | 0.00 | −0.80 | — | −0.80 | −0.30 | — | −1.60 |
| R: | −999.00 | 2.20 | 0.70 | 0.20 | — | 1.00 | −0.50 | — | −1.00 |
| S: | −999.00 | −0.30 | 0.20 | −0.30 | — | 0.60 | 0.30 | — | −0.30 |
| T: | −999.00 | 0.00 | 0.00 | −0.30 | — | −0.04 | 0.20 | — | −0.20 |
| V: | 0.00 | 2.10 | 0.50 | 0.20 | — | −0.30 | 0.30 | — | 0.30 |
| W: | −1.00 | −0.10 | 0.00 | 0.40 | — | −0.40 | 0.60 | — | −1.40 |
| Y: | −1.00 | 0.90 | 0.80 | 2.50 | — | 0.40 | 0.70 | — | −0.90 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 4.6 | 3.8 | 3.25 | 2.9 | 2.6 | 2.3 | 2.0 | 1.8 | 1.6 | 1.5 |

Virtual Matrix for HLA-DRB1_1502

| | Position | | | | | | | | |
|---|---|---|---|---|---|---|---|---|---|
| Amino acid | P1 | P2 | P3 | P4 | P5 | P6 | P7 | P8 | P9 |
| A: | −999.00 | 0.00 | 0.00 | 0.00 | — | 0.00 | 0.00 | — | 0.00 |
| D: | −999.00 | −1.30 | −1.30 | −0.40 | — | −0.40 | −0.70 | — | −1.90 |
| E: | −999.00 | 0.10 | −1.20 | −0.60 | — | −1.00 | −0.70 | — | −1.90 |
| F: | 0.00 | 0.80 | 0.80 | 2.40 | — | −0.30 | 1.40 | — | −0.40 |
| G: | −999.00 | 0.50 | 0.20 | 0.00 | — | 0.50 | 0.00 | — | −0.80 |
| H: | −999.00 | 0.80 | 0.20 | 1.10 | — | −0.50 | 0.60 | — | −1.10 |
| I: | −1.00 | 1.10 | 1.50 | 0.60 | — | 0.05 | 1.50 | — | 0.70 |
| K: | −999.00 | 1.10 | 0.00 | −0.70 | — | −0.30 | −0.30 | — | −1.70 |
| L: | −1.00 | 1.00 | 1.00 | 0.50 | — | 0.20 | 1.90 | — | 0.50 |
| M: | −1.00 | 1.10 | 1.40 | 1.00 | — | 0.10 | 1.70 | — | 0.08 |
| N: | −999.00 | 0.80 | 0.50 | −0.20 | — | 0.70 | 0.70 | — | −1.20 |
| P: | −999.00 | −0.50 | 0.30 | −0.30 | — | −0.20 | 0.30 | — | −1.10 |
| Q: | −999.00 | 1.20 | 0.00 | −0.80 | — | −0.80 | −0.30 | — | −1.60 |
| R: | −999.00 | 2.20 | 0.70 | 0.20 | — | 1.00 | −0.50 | — | −1.00 |
| S: | −999.00 | −0.30 | 0.20 | −0.30 | — | 0.60 | 0.30 | — | −0.30 |
| T: | −999.00 | 0.00 | 0.00 | −0.30 | — | −0.04 | 0.20 | — | −0.20 |
| V: | −1.00 | 2.10 | 0.50 | 0.20 | — | −0.30 | 0.30 | — | 0.30 |
| W: | 0.00 | −0.10 | 0.00 | 0.40 | — | −0.40 | 0.60 | — | −1.40 |
| Y: | 0.00 | 0.90 | 0.80 | 2.50 | — | 0.40 | 0.70 | — | −0.90 |

| | | | | | | | | | | |
|---|---|---|---|---|---|---|---|---|---|---|
| Percent Threshold | 1% | 2% | 3% | 4% | 5% | 6% | 7% | 8% | 9% | 10% |
| Numerical Score | 4.6 | 3.8 | 3.25 | 2.9 | 2.6 | 2.3 | 2.0 | 1.8 | 1.6 | 1.5 |

TABLE 4-continued

Appendix A

Virtual Matrix for HLA-DRB1__1506

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −0.40 | — | −0.40 | −0.70 | — | −1.90 |
| E: | −999.00 | 0.10 | −1.20 | −0.60 | — | −1.00 | −0.70 | — | −1.90 |
| F: | −1.00 | 0.80 | 0.80 | 2.40 | — | −0.30 | 1.40 | — | −0.40 |
| G: | −999.00 | 0.50 | 0.20 | 0.00 | — | 0.50 | 0.00 | — | −0.80 |
| H: | −999.00 | 0.80 | 0.20 | 1.10 | — | −0.50 | 0.60 | — | −1.10 |
| I: | 0.00 | 1.10 | 1.50 | 0.60 | — | 0.05 | 1.50 | — | 0.70 |
| K: | −999.00 | 1.10 | 0.00 | −0.70 | — | −0.30 | −0.30 | — | −1.70 |
| L: | 0.00 | 1.00 | 1.00 | 0.50 | — | 0.20 | 1.90 | — | 0.50 |
| M: | 0.00 | 1.10 | 1.40 | 1.00 | — | 0.10 | 1.70 | — | 0.08 |
| N: | −999.00 | 0.80 | 0.50 | −0.20 | — | 0.70 | 0.70 | — | −1.20 |
| P: | −999.00 | −0.50 | 0.30 | −0.30 | — | −0.20 | 0.30 | — | −1.10 |
| Q: | −999.00 | 1.20 | 0.00 | −0.80 | — | −0.80 | −0.30 | — | −1.60 |
| R: | −999.00 | 2.20 | 0.70 | 0.20 | — | 1.00 | −0.50 | — | −1.00 |
| S: | −999.00 | −0.30 | 0.20 | −0.30 | — | 0.60 | 0.30 | — | −0.30 |
| T: | −999.00 | 0.00 | 0.00 | −0.30 | — | −0.04 | 0.20 | — | −0.20 |
| V: | 0.00 | 2.10 | 0.50 | 0.20 | — | −0.30 | 0.30 | — | 0.30 |
| W: | −1.00 | −0.10 | 0.00 | 0.40 | — | −0.40 | 0.60 | — | −1.40 |
| Y: | −1.00 | 0.90 | 0.80 | 2.50 | — | 0.40 | 0.70 | — | −0.90 |
| Percent Threshold | 1% | 2% | 3% 4% | 5% | 6% | 7% | 8% | 9% | 10% |
| Numerical Score | 4.2 | 3.5 | 3.1 2.8 | 2.5 | 2.2 | 2.0 | 1.8 | 1.6 | 1.5 |

Virtual Matrix for HLA-DRB5__0101

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.90 | — | −2.00 | −1.50 | — | −1.50 |
| E: | −999.00 | 0.10 | −1.20 | −1.30 | — | −2.00 | −0.90 | — | −0.60 |
| F: | 0.00 | 0.80 | 0.80 | −0.60 | — | −1.70 | 1.50 | — | 1.20 |
| G: | −999.00 | 0.50 | 0.20 | −1.60 | — | −0.30 | 0.60 | — | 0.40 |
| H: | −999.00 | 0.80 | 0.20 | −1.40 | — | −1.20 | 1.20 | — | 1.00 |
| I: | −1.00 | 1.10 | 1.50 | 1.30 | — | −1.40 | 1.20 | — | 1.20 |
| K: | −999.00 | 1.10 | 0.00 | −1.70 | — | −1.50 | 0.90 | — | 2.70 |
| L: | −1.00 | 1.00 | 1.00 | 0.60 | — | −1.00 | 0.60 | — | 1.30 |
| M: | −1.00 | 1.10 | 1.40 | 1.70 | — | −1.50 | 0.40 | — | 0.50 |
| N: | −999.00 | 0.80 | 0.50 | −1.70 | — | −1.30 | 0.50 | — | 0.00 |
| P: | −999.00 | −0.50 | 0.30 | −1.50 | — | 0.20 | −0.60 | — | −0.80 |
| Q: | −999.00 | 1.20 | 0.00 | −0.70 | — | −1.40 | 0.70 | — | 0.70 |
| R: | −999.00 | 2.20 | 0.70 | −1.70 | — | −1.30 | 1.30 | — | 2.50 |
| S: | −999.00 | −0.30 | 0.20 | −0.50 | — | −0.50 | −0.20 | — | 0.70 |
| T: | −999.00 | 0.00 | 0.00 | 0.30 | — | −0.80 | 0.30 | — | −0.20 |
| V: | −1.00 | 2.10 | 0.50 | 1.10 | — | −1.30 | −0.30 | — | −0.20 |
| W: | 0.00 | −0.10 | 0.00 | −1.40 | — | −1.70 | 0.40 | — | −0.70 |
| Y: | 0.00 | 0.90 | 0.80 | −0.60 | — | −1.00 | 1.20 | — | 1.30 |
| Percent Threshold | 1% | 2% | 3% 4% | 5% | 6% | 7% | 8% | 9% | 10% |
| Numerical Score | 3.5 | 2.7 | 2.3 2.0 | 1.6 | 1.3 | 1.0 | 0.7 | 0.5 | 0.3 |

Virtual Matrix for HLA-DRB5__0105

| Amino acid | Position P1 | P2 | P3 | P4 | P5 | P6 | P7 | P8 | P9 |
|---|---|---|---|---|---|---|---|---|---|
| A: | −999.00 | 0.00 | 0.00 | 0.00 | — | 0.00 | 0.00 | — | 0.00 |
| D: | −999.00 | −1.30 | −1.30 | −1.90 | — | −2.00 | −1.50 | — | −1.50 |
| E: | −999.00 | 0.10 | −1.20 | −1.30 | — | −2.00 | −0.90 | — | −0.60 |
| F: | 0.00 | 0.80 | 0.80 | −0.60 | — | −1.70 | 1.50 | — | 1.20 |
| G: | −999.00 | 0.50 | 0.20 | −1.60 | — | −0.30 | 0.60 | — | 0.40 |
| H: | −999.00 | 0.80 | 0.20 | −1.40 | — | −1.20 | 1.20 | — | 1.00 |
| I: | −1.00 | 1.10 | 1.50 | 1.30 | — | −1.40 | 1.20 | — | 1.20 |
| K: | −999.00 | 1.10 | 0.00 | −1.70 | — | −1.50 | 0.90 | — | 2.70 |
| L: | −1.00 | 1.00 | 1.00 | 0.60 | — | −1.00 | 0.60 | — | 1.30 |
| M: | −1.00 | 1.10 | 1.40 | 1.70 | — | −1.50 | 0.40 | — | 0.50 |
| N: | −999.00 | 0.80 | 0.50 | −1.70 | — | −1.30 | 0.50 | — | 0.00 |
| P: | −999.00 | −0.50 | 0.30 | −1.50 | — | 0.20 | −0.60 | — | −0.80 |

TABLE 4-continued

| Appendix A | | | | | | | | | | |
|---|---|---|---|---|---|---|---|---|---|---|
| Q: | −999.00 | 1.20 | | 0.00 | −0.70 | — | −1.40 | 0.70 | — | 0.70 |
| R: | −999.00 | 2.20 | | 0.70 | −1.70 | — | −1.30 | 1.30 | — | 2.50 |
| S: | −999.00 | −0.30 | | 0.20 | −0.50 | — | −0.50 | −0.20 | — | 0.70 |
| T: | −999.00 | 0.00 | | 0.00 | 0.30 | — | −0.80 | 0.30 | — | −0.20 |
| V: | −1.00 | 2.10 | | 0.50 | 1.10 | — | −1.30 | −0.30 | — | −0.20 |
| W: | 0.00 | −0.10 | | 0.00 | −1.40 | — | −1.70 | 0.40 | — | −0.70 |
| Y: | 0.00 | 0.90 | | 0.80 | −0.60 | — | −1.00 | 1.20 | — | 1.30 |
| Percent Threshold | 1% | 2% | 3% | 4% | 5% | 6% | 7% | 8% | 9% | 10% |
| Numerical Score | 3.5 | 2.8 | 2.3 | 1.9 | 1.6 | 1.4 | 1.1 | 0.9 | 0.7 | 0.5 |

The threshold is defined as the ‘percentage of best scoring natural peptides’. For example, a threshold of 1% would predict peptides in any given protein sequence which belong to the 1% best scoring natural peptides. Peptides with score greater than or equal to corresponding threshold value will be predicted as binder

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A synthesized peptide comprising FRIM $X_4VLX_6S$ (SEQ ID NO: 6), wherein $X_4$ and $X_6$ are any amino acid, and wherein the peptide is a CLIP displacer, wherein the peptide has 9-20 amino acids.

2. The peptide of claim 1, wherein $X_4$ is Alanine.

3. The peptide of claim 1, wherein $X_6$ is Alanine.

4. The peptide of claim 1, wherein SEQ ID NO: 6 further comprises 1-5 amino acids at the N and/or C terminus.

5. The peptide of claim 4, wherein SEQ ID NO: 6 has 1-5 amino acids at the C terminus.

6. The peptide of claim 4, wherein SEQ ID NO: 6 has 1-5 amino acids at the N terminus.

7. The peptide of claim 1, wherein $X_4$ and $X_6$ are Alanine.

8. The peptide of claim 1, wherein the peptide comprises FRIMAVLAS (SEQ ID NO: 2).

9. The peptide of claim 1, wherein the peptide consists of FRIMAVLAS (SEQ ID NO: 2).

10. The peptide of claim 1, wherein the peptide comprises N-FRIMAVLAS-C (SEQ ID NO: 7).

11. An isolated peptide comprising FRIMAVLAS (SEQ ID NO: 2).

12. A composition comprising a peptide of claim 1 and a carrier.

* * * * *

SEQUENCE LISTING

```
<160> NUMBER OF SEQ ID NOS: 9

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1

Met Arg Met Ala Thr Pro Leu Leu Met
1               5


<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

Phe Arg Ile Met Ala Val Leu Ala Ser
1               5


<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa represents any amino acid
<220> FEATURE:
<221> NAME/KEY: misc_feature
<222> LOCATION: (3)..(6)
<223> OTHER INFORMATION: Xaa represents any amino acid
<220> FEATURE:
<221> NAME/KEY: misc_feature
<222> LOCATION: (3)..(4)
<223> OTHER INFORMATION: At least one Xaa represents methionine
<220> FEATURE:
<221> NAME/KEY: misc_feature
<222> LOCATION: (8)..(9)
<223> OTHER INFORMATION: Xaa represents any amino acid
<220> FEATURE:
<221> NAME/KEY: misc_feature
```

<222> LOCATION: (1)..(9)
<223> OTHER INFORMATION: The sequence is not N-MRMATPLLM-C

<400> SEQUENCE: 3

Xaa Arg Xaa Xaa Xaa Xaa Leu Xaa Xaa
1 5

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Free N-Terminal Methionine
<220> FEATURE:
<221> NAME/KEY: misc_feature
<222> LOCATION: (9)..(9)
<223> OTHER INFORMATION: Free C-Terminal Methionine

<400> SEQUENCE: 4

Met Arg Met Ala Thr Pro Leu Leu Met
1 5

<210> SEQ ID NO 5
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 5

Ser Gly Gly Gly Ser Lys Met Arg Met Ala Thr Pro Leu Leu Met Gln
1 5 10 15

Ala Leu Tyr

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (5)..(5)
<223> OTHER INFORMATION: Xaa represents any amino acid
<220> FEATURE:
<221> NAME/KEY: misc_feature
<222> LOCATION: (8)..(8)
<223> OTHER INFORMATION: Xaa represents any amino acid

<400> SEQUENCE: 6

Phe Arg Ile Met Xaa Val Leu Xaa Ser
1 5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Free N-Terminal Phenylalanine
<220> FEATURE:
<221> NAME/KEY: misc_feature
<222> LOCATION: (9)..(9)

```
<223> OTHER INFORMATION: Free C-Terminal Serine

<400> SEQUENCE: 7

Phe Arg Ile Met Ala Val Leu Ala Ser
1               5


<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa represents Ala, Phe, Met, Leu, Ile, Val,
      Pro, or Trp
<220> FEATURE:
<221> NAME/KEY: misc_feature
<222> LOCATION: (3)..(4)
<223> OTHER INFORMATION: Xaa represents Ala, Phe, Met, Leu, Ile, Val,
      Pro, or Trp
<220> FEATURE:
<221> NAME/KEY: misc_feature
<222> LOCATION: (5)..(5)
<223> OTHER INFORMATION: Xaa represents any amino acid
<220> FEATURE:
<221> NAME/KEY: misc_feature
<222> LOCATION: (6)..(6)
<223> OTHER INFORMATION: Xaa represents Ala, Phe, Met, Leu, Ile, Val,
      Pro, or Trp
<220> FEATURE:
<221> NAME/KEY: misc_feature
<222> LOCATION: (8)..(8)
<223> OTHER INFORMATION: Xaa represents any amino acid
<220> FEATURE:
<221> NAME/KEY: misc_feature
<222> LOCATION: (9)..(9)
<223> OTHER INFORMATION: Xaa represents Ala, Cys, Thr, Ser, Gly, Asn,
      Gln, Tyr

<400> SEQUENCE: 8

Xaa Arg Xaa Xaa Xaa Xaa Leu Xaa Xaa
1               5


<210> SEQ ID NO 9
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Free N-Terminal
<220> FEATURE:
<221> NAME/KEY: misc_feature
<222> LOCATION: (1)..(1)
<223> OTHER INFORMATION: Xaa represents any amino acid
<220> FEATURE:
<221> NAME/KEY: misc_feature
<222> LOCATION: (3)..(6)
<223> OTHER INFORMATION: Xaa represents any amino acid
<220> FEATURE:
<221> NAME/KEY: misc_feature
<222> LOCATION: (8)..(9)
<223> OTHER INFORMATION: Xaa represents any amino acid
<220> FEATURE:
<221> NAME/KEY: misc_feature
<222> LOCATION: (9)..(9)
<223> OTHER INFORMATION: Free C-Terminal
```

-continued

```
<400> SEQUENCE: 9

Xaa Arg Xaa Xaa Xaa Xaa Leu Xaa Xaa
1               5
```